United States Patent [19]

Tone et al.

[11] Patent Number: 5,238,938
[45] Date of Patent: Aug. 24, 1993

[54] INDOLE DERIVATIVES

[75] Inventors: Hitoshi Tone; Seiji Sato; Hideaki Sato; Katsumi Tamura; Shigeharu Tamada, all of Tokushima; Kazumi Kondo, Naruto; Tomoyuki Kawaguchi; Yoshimasa Nakano, both of Tokushima; Yasuyuki Kita, Kashiwara; Shuji Akai, Takatsuki; Hiromichi Fujioka, Minoo; Yasumitsu Tamura, Takarazuka; Katsuhide Matoba, Kawanishi; Youichi Taniguchi, Tokushima; Shinji Nishitani, Naruto; Satoshi Hayakawa, Nishinomiya; Toshinori Kaneyasu, Naruto; Yoshihiko Ito, Kyoto; Masahiro Murakami, Kyoto, all of Japan

[73] Assignee: Otsuka Pharmaceutical Co., Ltd., Tokyo, Japan

[21] Appl. No.: 857,726
[22] Filed: Mar. 26, 1992

Related U.S. Application Data

[63] Continuation of Ser. No. 582,230, Oct. 5, 1990, abandoned.

[30] Foreign Application Priority Data

Feb. 10, 1989 [JP] Japan ................................. 1-031579
Jul. 31, 1989 [JP] Japan ................................. 1-199771
Sep. 11, 1989 [JP] Japan ................................. 1-234978
Jan. 23, 1990 [JP] Japan ................................. 2-014551

[51] Int. Cl.$^5$ .................. A61K 31/495; C07D 403/06; C07D 209/04
[52] U.S. Cl. .................... 514/253; 514/254; 544/229; 544/357; 544/373; 544/405
[58] Field of Search ............... 544/373, 357, 229, 405; 514/254, 253

[56] References Cited

U.S. PATENT DOCUMENTS

| | | | |
|---|---|---|---|
| 3,388,127 | 6/1968 | Shen et al. | 260/250 |
| 4,806,538 | 2/1989 | Shimazaki et al. | 514/253 |
| 4,851,406 | 7/1989 | Mertens et al. | 544/405 |
| 4,940,709 | 7/1990 | Shimazaki et al. | 544/373 |

FOREIGN PATENT DOCUMENTS

| | | |
|---|---|---|
| 0072932 | 3/1983 | European Pat. Off. |
| 0181152 | 5/1986 | European Pat. Off. |
| 284337 | 9/1988 | European Pat. Off. ............ 544/373 |
| 0303250 | 2/1989 | European Pat. Off. |
| 61-112060 | 5/1986 | Japan |
| 1-131177 | 5/1989 | Japan |

OTHER PUBLICATIONS

Chemical Abstracts, vol. 95, (1981), 95:150589z.
Chemical Abstracts, vol. 82, (1975), 75:151872e.
Chemical Abstracts, vol. 102, (1985), 102:221162f.
Chem. Pharm. Bull. vol. 29, (6), pp. 1510–1517, (1981), by K. Arai et al.
The Journal of Antibiotics, vol. XXVII, (10), Oct. 1974, pp. 733–737, by K. Kakinuma et al.
Liebigs Ann. Chem., (1985), pp. 413–417, by Ulrich Schoelkopf et al.
J. Chem. Soc. Perkin Trans. I, No. 11, (1987) pp. 2481–2490.
J. Org. Chem., vol. 47, No. 11, (1982) pp. 2147–2154.
Chemical Abstracts, vol. 103, No. 3, (1985) 22519Y.
Chemical Abstracts, vol. 98, No. 3, (1983) 16659F.

Primary Examiner—Cecilia Tsang
Attorney, Agent, or Firm—Finnegan, Henderson, Farabow, Garrett & Dunner

[57] ABSTRACT

The novel indole derivatives and salts thereof represented by the general formula (1)

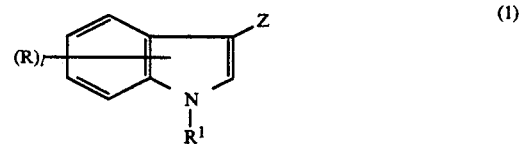

possess, for example, an inhibitory effect against superoxide ($O_2^-$) released from the macrophage cells of guinea pig by stimulation and an anti-albuminuria activity against Masugi nephritis, and are useful in various clinical fields as an agent for preventing and treating diseases and cases associated with the above superoxide radical, for example, autoimmune diseases (e.g. rheumatism), arteriosclerosis, ischemic disease, ischemic encephalopathia, hepatic insufficiency and renal insufficiency, and also as an agent for preventing and treating nephritis.

51 Claims, No Drawings

INDOLE DERIVATIVES

This application is a continuation of application Ser. No. 582,230, filed Oct. 5, 1990, now abandoned.

FIELD OF THE INVENTION

The present invention relates to novel indole derivatives and salts thereof. More particularly, the invention relates to said indole derivatives and salts thereof, processes for preparing said indole derivatives and salts thereof, and a pharmaceutical composition containing, as the active ingredient, said indole derivative or salt thereof.

PRIOR ART

There have been known NF-1616-904 compound of the formula (1a),

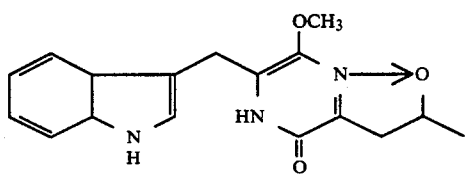

(cf. European Patent Publication No. 0303250, published on Feb. 15, 1989), said NF-1616-904 compound was prepared by hydrolyzing an intermediate compound of NF-1616-902 which had been isolated from a culture medium of *Thielavia minor* OFR-1561 (Deposition No. FERM BP-1908, deposited at the Fermentation Research Institute, Agency of Industrial Science and Technology, Ministry of International Trade and Industry), said microorganism had been isolated from a soil sampled in Iriomote-jima, Okinawa-ken, Japan. According to said fermentation method, it is required to keep the fermentation conditions constant, because the method uses the specific strain of microorganism, also it is required to use special and expensive apparatus for preparing said intermediate compound of NF-166-902 in a large quantity for an industrial scale production. In addition to the above, said intermediate compound of NF-1616-902 can hardly be obtained from a culture medium in a good yield, and also it can hardly be obtained said intermediate compound as highly purified product.

The chemical structure of said known NF-1616-904 compound of the formula (1a) resembles to the chemical structure of the indole derivatives represented by the general formula (1). As the result of an extensive research work made by the present inventors, they found methods for preparing the indole derivatives represented by the general formula (1), which will be shown later, by without using any strain of microorganism, and also by without using any troublesome separation method. Thus, the present invention had been successfully completed by the finding of methods for preparing the desired novel indole derivatives represented by the general formula (1) as highly purified product in a high yield.

SUMMARY OF THE INVENTION

An object of the present invention is to provide novel indole derivatives and salts thereof.

Another object of the presnet invention is to provide processes for preparing said indole derivatives and salts thereof.

Further object of the present invention is to provide a pharmaceutical composition containing, as the active ingredient, said indole derivative.or salt thereof.

DETAILED DESCRIPTION OF PREFERRED EMBODIMENTS

The novel indole derivatives and salts thereof of the present invention are represented by the general formula (1),

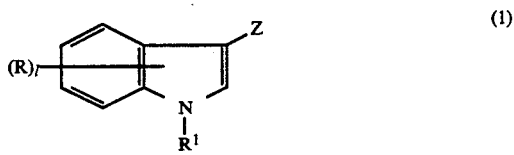

wherein R is a hydrogen atom, a cyano group, a phenyl-lower alkoxy group, a carboxy group, a phenyl group, a lower alkoxycarbonyl group, a lower alkyl group, a lower alkoxy group, a hydroxy group or a halogen atom;

l is an integer of 1 to 2;

$R^1$ is a hydrogen atom, a lower alkyl group, a phenyl-lower alkyl group, a lower alkanoyl group, a lower alkoxy-carbonyl group, a phenyl-lower alkoxycarbonyl group, a carboxy group, a group of the formula

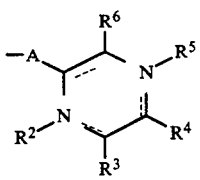

(wherein A is a single bond, a group of the formula

a group of the formula —CH=, a group of the formula

or a lower alkylene group;

$R^2$ is a hydrogen atom, a lower alkyl group, a hydroxy group or a lower alkoxy group;

$R^3$ is a hydrogen atom, an oxo group, a halogen atom, a lower alkoxy group, a lower alkanoyloxy group, a lower alkyl group, a silyloxy group having 1 to 3 substituents selected from the group consisting of a benzoyloxy group, a lower alkoxycarbonyloxy group, a lower alkyl group and a phenyl group, an unsubstituted phenyl-lower alkoxy group, a substituted phenyl-lower alkoxy group having substituents, on the phenyl ring, selected from the group consisting of a halogen atom, a lower alkyl group, a nitro group, an amino group and a lower alkoxy group, or a hydroxy group;

$R^4$ is a hydrogen atom, a lower alkyl group, a phenyl group, an unsubstituted phenyl-lower alkyl group, a substituted phenyl-lower alkyl group having substituents, on the phenyl ring, selected from the group consisting of a hydroxy group and a phenyl-lower alkoxy group, a cycloalkyl group, a cycloalkyl-lower alkyl group, an indolyl-lower alkyl group or a lower alkenylene group;

$R^5$ is a hydorgen atom, an oxo group, a hydroxy group, a phenyl-lower alkoxy group, a lower alkoxy group or a lower alkyl group;

$R^6$ is a lower alkoxy group, an oxo group, a hydrogen atom, a hydroxy group, a halogen atom, a lower alkyl group, an amino group, a substituted amino group having a lower alkanoyl group as the substituent, a lower alkylthio group, a lower alkylsulfinyl group, a lower alkylsulfonyl group, a cycloalkyloxy group or a phenyl-lower alkoxy group;

the bondings at 1-, 2-, 3-, 4-, 5- and 6-positions in the pyrazine ring are single bonds or double bonds); a benzoyl group, an unsubstituted phenylsulfonyl group or a substituted phenylsulfonyl group having lower alkyl groups as substituents on the phenyl ring;

Z is a hydorgen atom or a group of the formula

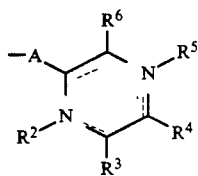

(wherein A, $R^2$, $R^3$, $R^4$, $R^5$ and $R^6$ are the same as defined the above, and the bondings at 1-, 2-, 3-, 4-, 5- and 6-positions in the pyrazine ring are single bonds or double bonds); provided that, (i) when A is a lower alkylene group, both $R^3$ and $R^6$ are oxo groups at the same time, and the bondings between 4- and 5-positions in hte piperazine ring is a single bond, then each one of $R^2$ and $R^5$ should be neither a hydrogen atom nor a lower alkyl group; .

(ii) when A is a methylene group, each one of R, $R^1$ and $R^2$ is a hydrogen atom, each one of $R^3$ and $R^5$ is an oxo group and $R^6$ is a methoxy group, then $R^4$ should not be an isobutyl group;

(iii) when $R^1$ is a group of the formula

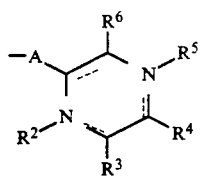

(wherein A, $R^2$, $R^3$, $R^4$, $R^5$ and $R^6$ are the same as defined the above, and the bondings at 1-, 2-, 3-, 4-, 5- and 6-positions in the pyrazine ring are single bonds or double bonds), then Z is a hydrogen atom;

(iv) both $R^1$ and Z should not be hydrogen atoms at the same time.

The indole derivatives and salts thereof represented by the general formula (1) of the present invention possess an inhibitory effect against superoxide radicals ($O_2^-$) released from the macrophage cells of guinea pig by stimulation, and also possess an anti-albuminuria activity in Masugi nephritis. Thus, the indole derivatives and salts thereof represented by the general formula (1) are useful agents for preventing and treating of various diseases caused by the above-mentioned superoxide radicals, for example diseases of autoimmune such as rheumatoid arthritis, arteriosclerosis, ischemic heart disease, transient cerebral ischematic attack, hepatic insufficiency, renal insufficiency and the like, as well as useful agents for preventing and treating the nephritis in various clinical fields.

In the present specification, various substituents represented by the symbols of R, $R^1$, $R^2$, $R^3$, $R^4$, $R^5$, $R^6$, A and Z shown in the general formula (1) are specifically exemplified as follows:

As to the lower alkylene group, a straight chain-or branched chain-alkylene group having 1 to 6 carbon atoms, such as methylene, ethylene, trimethylene, tetramethylene, 2-methyltrimethylene, 2,2-dimethyltrimethylene, 1-methyltrimethylene, methylmethylene, ethylmethylene, pentamethylene, and hexamethylene groups and the like can be exemplified.

As to the lower alkyl group, a straight chain- or branched chain-alkyl group having 1 to 6 carbon atoms, such as methyl, ethyl, propyl, isopropyl, butyl, tert-butyl, pentyl and hexyl groups and the like can be exemplified.

As to the unsubstituted phenyl-lower alkyl group, a phenylalkyl group in which the alkyl moiety thereof having a straight chain- or branched chain-alkyl group, such as benzyl, 2-phenylethyl, 1-phenylethyl, 3-phenylpropyl, 4-phenylbutyl, 1,1-dimethyl-2-phenylethyl, 5-phenylpentyl, 6-phenylhexyl, and 2-methyl-3-phenylpropyl groups and the like can be exemplified.

As to the substituted phenyl-lower alkyl group having substituents, on the phenyl ring, selected from the group consisting of a halogen atom, a lower alkyl group, a nitro group, an amino group and a lower alkoxy group, a phenylalkyl group in which the alkyl moiety thereof is a straight chain- or branched chain-alkyl group having 1 to 6 carbon atoms, and the phenyl ring thereof having 1 to 3 substituents selected from the group consisting of a halogen atom, a straight chain- or branched chain-alkyl group having 1 to 6 carbon atoms, a nitro group, an amino group and a straight chain- or branched chain-alkoxy group having 1 to 6 carbon atoms, and the examples are benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, 2-chlorobenzyl, 2-(3-chlorophenyl)ethyl, 1-(4-chlorophenyl)ethyl, 3-(2-fluorophenyl)propyl, 4-(3-fluorophenyl)butyl, 1,1-dimethyl-2-(4-fluorophenyl)ethyl, 5-(2-bromophenyl)-pentyl, 6-(3-bromophenyl)hexyl, 2-methyl-3-(4-bromophenyl)propyl, 3-iodobenzyl, 2-(4-iodophenyl)ethyl, 1-(3,5-dichlorophenyl)ethyl, 2-(3,4-dichlorophenyl)ethyl, 3-(2,6-dichlorophenyl)propyl, 4-(3,4-dichlorophenyl)butyl, 1,1-dimethyl-2-(3,4-difluorophenyl)ethyl, 5-(3,5-dibromophenyl)pentyl, 6-(3,4,5-trichlorophenyl)-hexyl, 4-methylbenzyl, 2-(2-methylphenyl)ethyl, 1-(3-methylphenyl)ethyl, 3-(3-ethylphenyl)propyl, 4-(2-ethylphenyl)butyl, 5-(4-ethylphenyl)pentyl, 6-(3-isopropylphenyl)hexyl, 2-methyl-3-(4-hexylphenyl)propyl, 2-(3,4-dimethylphenyl)ethyl, 2-(2,5-dimethylphenyl)ethyl, 2-(3,4,5-trimethylphenyl)ethyl, 4-methoxybenzyl, 3,4-dimethoxybenzyl, 3,4,5-trimethoxybenzyl, 1-(3-methoxyphenyl)ethyl, 2-(2-methoxyphenyl)ethyl, 3-(2-ethoxyphenyl)propyl, 4-(4-ethoxyphenyl)butyl, 5-(3-ethoxyphenyl)pentyl, 6-(4-isopropoxyphenyl(hexyl, 1,1-dimethyl-2-(4-hexyloxyphenyl)ethyl, 2-methyl-3-(3,4-dimethoxyphenyl)propyl, 2-(3,4-dimethoxyphenyl)ethyl, 2-(3,4-diethoxyphenyl- )ethyl, 2-(3,4,5-trimethoxyphenyl)ethyl, 1-(2,5-dimethoxyphenyl)ethyl, (2-chloro-4-methoxy)benzyl, 2-aminobenzyl, 1-(3-aminophenyl)ethyl, 1-(4-aminophenyl)propyl, 1-(2,3-diaminophenyl)butyl, 1-(2,3,4-triaminophenyl)pentyl, 1-(2,4-diaminophenyl)hexyl, 2-nitrobenzyl, 1-(3-nitrophenyl)ethyl, 1-(4-nitrophenyl)propyl, 1-(2,4-dinitorphenyl)butyl, 1-(2,4,6-trinitrophenyl)pentyl, 1-(2-chloro-4-nitrophenyl)hexyl and (3-methyl-4-amino)benzyl groups and the like.

As to the substituted phenyl-lower alkyl group having substituents, on the phenyl ring, selected from the group consisting of a hydroxy group and a phenyl-lower alkyl group, a phenyl alkyl group in which the alkyl moiety thereof is a straight chain- or branched chain-alkyl group having 1 to 6 carbon atoms, and the phenyl ring thereof having 1 to 3 substituents selected from the group consisting of a hydroxy group and a stright chain- or branched chain-alkoxy group having 1 to 6 carbon atoms, and the examples are, in addition to the above-mentioned substituted phenylalkyl groups, 4-hydroxybenzyl, 2-(3-hydroxyphenyl)ethyl, 1-(2-hydroxyphenyl)ethyl, 3-(2,4-dihydroxyphenyl)propyl, 4-(3,4-dihydroxyphenyl)butyl, 1,1-dimethyl-2-(2,3,4-trihydroxyphenyl)ethyl, 5-(4-hydroxy)pentyl, 6-(3-hydroxyphenyl)hexyl, 2-methyl-3-(2-hydroxyphenyl)propyl, 4-benzyloxybenzyl, 2-[3-(2-phenylethoxy)phenyl] ethyl, 1-[2-(1-phenylethoxy)phenyl]ethyl, 3-(2,4-dibenzyloxyphneyl)propyl, 4-(3,4-dibenzyloxyphenyl)butyl, 1,1-dimethyl-2-(2,3,4-tribenzyloxyphenyl)ethyl, 5- 4-(3-phenylpropoxy)phenyl pentyl, 6-[3-(4-phenylbutoxy)phenyl]-hexyl, 2-methyl-3-[2-(5-phenylpentyl)phenyl]propyl and 4-(6-phenylhexyloxy)benzyl groups and the like.

As to the lower alkanoyl group, a straight chain-or branched chain-alkanoyl group having 1 to 6 carbon atoms, and the examples are formyl, acetyl, propionyl, butyryl, isobutyryl, pentanoyl, tert-butylcarbonyl and hexanoyl groups and the like.

As to the lower alkoxycarbonyl group, a straight chain- or branched chain-alkoxycarbonyl group having 1 to 6 carbon atoms, the examples are methoxycarbonyl, ethoxycarbonyl, propoxycarbonyl, isopropoxycarbonyl, butoxycarbonyl, tert-butoxycarbonyl, pentyloxycarbonyl and hexyloxycarbonyl groups and the like.

As to the phenyl-lower alkoxycarbonyl group, a phenylalkoxycarbonyl group in which the alkoxy moiety is a straight chain- or branched chain-alkoxy group having 1 to 6 carbon atoms, and the examples are benzyloxycarbonyl, 2-phenylethoxycarbonyl, 1-phenylethoxycarbonyl, 3-phenylpropoxycarbonyl, 4-phenylbutoxycarbonyl, 1,1-dimethyl-2-phenylethoxycarbonyl, 5-phenylpentyloxycarbonyl, 6-phenylhexyloxycarbonyl and 2-methyl-3-phenylpropoxycarbonyl groups and the like.

As to the substituted phenylsulfonyl group having lower alkyl groups as substituents on the phenyl ring, a phenylaulfonyl group having a straight chain- or branched chain-alkyl group having 1 to 6 carbon atoms as substituents on the phenyl ring, the examples are 4-methylphenylsulfonyl, 3-ethylphneylsulfonyl, 2-propylphenylsulfonyl, 4-n-butylphenylsulfonyl, 3-pentylphenylsulfonyl and 2-hexylphenylsulfonyl groups and the like.

As to the lower alkoxy group, a straight chain-or branched chain-alkoxy group having 1 to 6 carbon atom, and the examples are methoxy, ethoxy, propoxy, isopropoxy, butoxy, tert-butoxy, pentyloxy and hexyloxy groups and the like.

As to the lower alkanoyloxy group, a straight chain- or branched chain-alkanoyloxy group having 1 to 6 carbon atoms, and the examples are formyloxy, acetyloxy, propionyloxy, butyryloxy, isobutyryloxy, pentanoyloxy, tert-butylcarbonyloxy and hexanoyloxy groups and the like.

As to the phenyl-lower alkoxy group, a phenylalkoxy group in which the alkoxy moiety is a straight chain- or branched chain-alkoxy group having 1 to 6 carbon atoms, and the examples are phenylmehtoxy, 2-phenylethoxy, 1-phenylethoxy, 3-phenylpropoxy, 4-phenylbutoxy, 1,1-dimethyl-2-phenylethoxy, 4-phenylpentyloxy, 6-phenylhexyloxy, and 2-methyl-3-phenylpropoxy groups and the like.

As to the lower alkenylene group, a straight chain- or branched chain-alkenylene group having 2 to 6 carbon atoms, and the examples are vinylene, 2-propenylene, 2-butenylene, 2-pentenylene, 3-pentenylene, 1-methyl-2-butenylene, 2-hexenylene, and 4-hexenylene group and the like.

As to the substituted amino group having a lower alkanoyl group as the substituent, an amino group having a straight chain- or branched chain-alkanoyl group as the substituent, and the examples are acetylamino, formylamino, propionylamino, butyrylamino, pentanoylamino, and hexanoylamino groups and the like.

As to the halogen atom, a chlorine atom, a bromine atom, an iodine atom and a fluorine atom can be exemplified.

As to the lower alkanesulfonyloxy group, the examples are methanesulfonyloxy, ethanesulfonyloxy, isopropanesulfonyloxy, propanesulfonyloxy, butanesulfonyloxy, tert-butanesulfonyloxy, pentanesulfonyloxy, and hexanesulfonyloxy groups and the like.

As to the arylsulfonyloxy group, a substituted-or unsubstituted-arylsulfonyloxy group, and the examples are phenylsulfonyloxy, 4-methylphenylsulfonyloxy, 2-methylphenylsulfonyloxy, 4-nitrophenylsulfonyloxy, 4-methoxyphenylsulfonyloxy, 3-chlorophenylsulfonyloxy, and -naphthylphenylsulfonyloxy groups and the like.

As to the aralkylsulfonyloxy group, a substituted-or unsubstituted-aralkylsulfonyloxy group, and the examples are benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, 3-chlorobenzylsulfonyloxy, and α-naphthylmethylsulfonyloxy groups and the like.

As to the cycloalkyl group, a cycloalkyl group having 3 to 8 carbon atoms, and the examples are cyclopropyl, cyclobutyl, cyclopentyl, cyclohexyl, cycloheptyl, and cyclooctyl groups and the like.

As to the cycloalkyl-lower alkyl group, a cycloalkylalkyl group in which the alkyl moiety is a straight chain- or branched chain-alkyl group having 1 to 6 carbon atoms, and the examples are cyclopropylmethyl, 2-cyclobutylethyl, 1-cyclopentylethyl, 3-cyclohexylpropyl, 4-cycloheptylbutyl, 6-cyclooctylhexyl, 5-cyclopropylpentyl, 1,1-dimethyl-2-cyclopropylethyl, 2-methyl-3-cyclohexylpropyl, and cyclohexylmethyl groups and the like.

As to the indolyl-lower alkyl group, an indolyalkyl group in which the alkyl moiety is a straight chain-or branched chain-alkyl group having 1 to 6 carbon atoms, and the examples are (3-indolyl)methyl, (1-indoly)methyl, 2-(2-indolyl)ethyl, 1-(4-indolyl)ethyl, 3-(5-indolyl)propyl, 4-(6-indolyl)butyl, 6-(7-indolyl)hexyl, 5-(3-indolyl)pentyl, 1,1-dimethyl-2-(2-indolyl)ethyl, and 2-methyl-3-(3-indolyl)propyl group, and the like.

As to the lower alkylthio group, a straight chain- or branched chain-alkylthio group having 1 to 6 carbon atoms, and the examples are methylthio, ethylthio, propylthio, isopropylthio, butylthio, tert-butylthio, pentylthio, and hexylthio groups and the like.

As to the lower-alkylsulfinyl group, a straight chain- or branched chain-slkylsulfinyl group having 1 to 6 carbon atom, and the examples are methylsulfinyl, ethylsulfinyl, propylsulfinyl, propylsulfinyl, isopropylsulfinyl, butylsulfinyl, tert-butylsulfinyl, pentylsulfinyl, and hexylsulfinyl groups and the like.

As to the lower alkylsulfonyl group, a straight chain- or branched chain-alkylsulfonyl group having 1 to 6 carbon atoms, and the examples are methylsulfonyl, ethylsulfonyl, propylsulfonyl, isopropylsulfonyl, butylsulfonyl, tert-butylsulfonyl, pentylsulfonyl, and hexylsulfonyl groups and the like.

As to the cycloalkyloxy group, a cycloalkyloxy group having 3 to 8 carbon atoms, and the examples are cyclopropyloxy, cyclobutyloxy, cyclopentyloxy, cyclohexyloxy, cycloheptyloxy, and cyclooctyloxy groups and the like.

As to the substituted phenyl-lower alkyl group having substituents, on the phenyl ring, selected from the group consisting of a hydroxy group and a phenyl-lower alkoxy group, a phenylalkyl group in which the alkyl moiety is a straight chain- or branched chain-alkyl group having 1 to 6 carbon atoms, and the phenyl ring thereof having substituents selected from the group consisting of a hydroxy group and an alkoxy group which is a straight chain or group and an alkoxy group which is a atraight chain- or branched chain alkoxy group having 1 to 6 carbon atom, and the examples are, in addition to the above-mentioned substituted phenyl-lower alkyl group, 4-hydroxybenzyl, 2-(3-hydorxyphenyl)ethy, 1-(2-hydroxyphenyl)ethyl, 3-(2,4-dihydroxyphenyl)propyl, 4-(3,4-dihydroxyphenyl)butyl, 1,1-dimethyl-2-(2,3,4-trihydroxyphenyl)ethyl, 5-(4-hydroxyphenyl)pentyl, 6-(3-hydorxyphenyl)hexyl, 2-methyl-3-(2-hydorxyphneyl)propyl, 4-benzyloxybenzyl, 2-[3-(2-phenylethoxy)phenyl]ethyl, 1-[2-(1-phneylethoxy)phenyl]ethyl, 3-(2,4-dibenzyloxyphenyl)-propyl, 4-(3,4-dibenzyloxyphenyl)butyl, 1,1-dimethyl-2-(2,3,4-tribenzyloxyphenyl)ethyl, 5-[4-(3-phenylpropoxy)phenyl]pentyl, 6-[3-(4-phenylbutoxy)phenyl]-hexyl, 2-methyl-3-[2-(5-phenylpentyl)phenyl]propyl, and 4-(6-phenylhexyloxy)benzyl groups and the like.

As to the lowe-alkoxycarbonyloxy group, a straight chain- or branched chain-alkoxycarbonyloxy group having 1 to 6 carbon atoms, and the examples are methoxycarbonyloxy, ethoxycarbonyloxy, propoxycarbonyloxy, isopropoxycarbonyloxy, butoxycarbonyloxy, tert-butoxycarbonyloxy, pentyloxycarbonyloxy, and hexyloxycarbonyloxy groups and the like.

The compounds of the present invention represented by the general formula (1) can be produced by various processes. A preferable example of the processes is shown as follows.

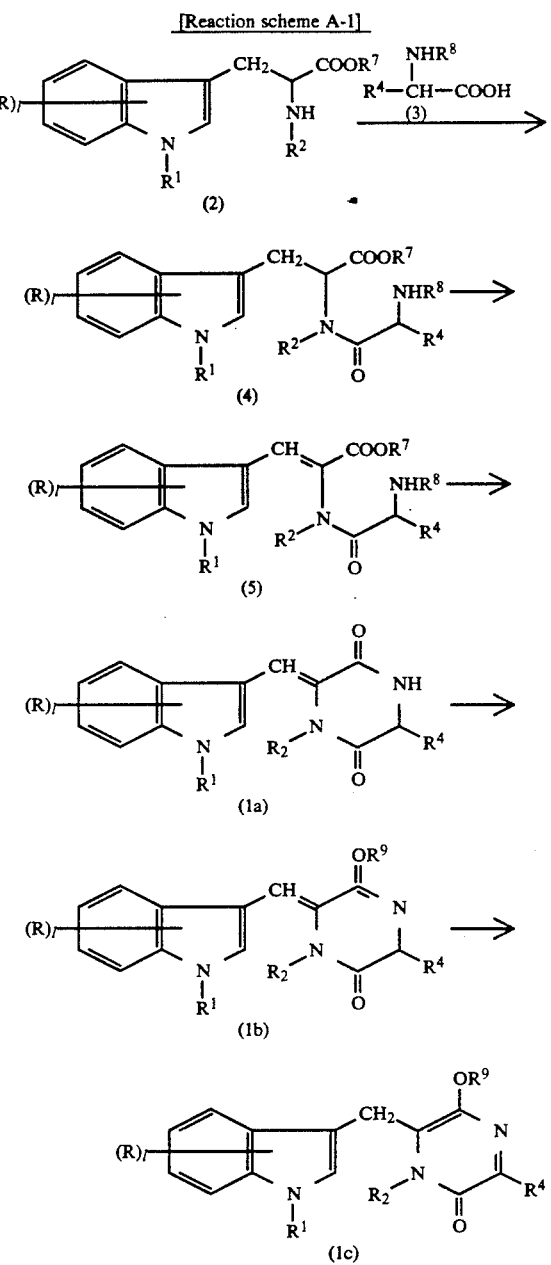

[in the formulas, R, l, $R^1$, $R^2$ and $R^4$ are the same as defined above; $R^7$ is a lower alkyl group; $R^8$ is a lower alkoxycarbonyl group or a phenyl-lower alkoxycarbonyl group; and $R^9$ is a lower alkyl group.]

In the reaction scheme A-1, the reaction between an amine represented by the general formula (2) and a carboxylic acid represented by the general formula (3) is carried out in accordance with an ordinary amide bond forming reaction. The amide bond forming reaction can be carried out by various known methods, for example, (a) a mixed acid anhydride method, for example, a method wherein a carboxylic acid (3) is reacted with an alkyl halocarboxylate and the resulting mixed acid anhydride is reacted with an amine (2); (b) an activated ester method, for example, a method wherein a carboxylic acid (3) is converted to an activated ester such as p-nitrophenyl ester, N-hydroxysuccinimide ester, 1-hydroxy-benzotriazole ester or the like and the activated ester is reacted with an amine (2); (c) a carbodiimide method, that is, a method wherein a carboxylic acid (3) is condensed with an amine (2) in the presence of an activating agent such as dicylcohexylcarbodiimide, carbonyldiimidazole or the like; (d) other methods, for example, a method wherein a carboxylic acid (3) is converted to a corresponding carboxylic acid anhydide with a dehydrating agent such as acetic anhydride or the like and the carboxylic acid anhydride is reacted with an amine (2), a method wherein an ester between a carboxylic acid (3) and a lower alcohol is reacted with an amine (2) under a high pressure and at a high temperature, and a method wherein an acid halide of a carboxylic acid (3), i.e. a carboxylic acid halide is reacted with an amine (2). The amide bond forming reaction can also be carried out by a method wherein a carboxylic acid (3) is activated by a phosphorus compound such as triphenylphosphine, diethyl chlorophosphate or the like and the activated carboxylic acid is reacted with an amine (2), a method wherein a carboxylic acid (3) is converted to N-carboxyaminoacid anhydride with phosgene, trichloromethyl chloroformate or the like and the anhydride is reacted with an amine (2), and so forth.

In the mixed acid anhydride method (a), the mixed acid anhydride used is obtained by an ordinary Schotten-Baumann reaction and is reacted with an amine (2) ordinarily without being isolated, whereby a compound of the general formula (4) can be produced. The Schotten-Baumann reaction is carried out in the presence of a basic compound. As to the basic compound, there are used compounds conventionally used in the Schotten-Baumann reaction. They are illustrated by, for example, organic bases such as triethylamine, trimethylamine, pyridine, picoline, dimethylaniline, N-methylmorpholine, 4-dimethylaminopyridine, 1,5-diazabicyclo[4,3,0]nonene-5 (DBN), 1,8-diazabicyclo[5,4,0]undecene-7 (DBU), 1,4-diazabicyclo[2,2,2]octane (DABCO) and the like, and inorganic bases such as potassium carbonate, sodium carbonate, potassium hydrogencarbonate, sodium hydrogencarbonate and the like. The reaction is carried out at about $-20°$ to $100°$ C., preferably $0°$ to $50°$ C. for about 5 minutes to 10 hours, preferably about 5 minutes to 2 hours. The reaction of the mixed acid anhydride obtained, with an amine (2) is carried out at about $-20°$ to $150°$ C., preferably $10°$ to $50°$ C. for about 5 minutes to 10 hours, preferably about 5 minutes to 5 hours. The mixed acid anhydride method is carried out generally in an appropriate solvent conventionally used in the method, such as halogenated hydrocarbon (e.g. methylene chloride, chloroform, dichloroethane), aromatic hydrocarbon (e.g. benzene, toluene, xylene), ether (e.g. diethyl ether, dioxane, diisopropyl ether, tetrahydrofuran, dimethoxyethane), ester (methyl acetate, ethyl acetate), aprotic polar solvent (e.g. 1,1,3,3-tetramethylurea, N,N-dimethylformamide, dimethyl sulfoxide, hexamethylphosphoric triamide) or the like, or in a mixed solvent or in the absence of any solvent. As to examples of the alkyl halocarboxylate used in the production of the mixed acid anhydride, there can be mentioned methyl chloroformate, methyl bromoformate, ethyl chloroformate, ethyl bromoformate and isobutyl chloroformate. The alkyl halocarboxylate is used in an amount of ordinarily at least 1 mole, preferably about 1 to 1.5 moles per mole of the amine (2). The preferable ratio of the carboxylic acid (3) used is ordinarily at least 1 mole, preferably about 1 to 1.5 moles per mole of the amine (2).

The activated ester method (b), when there is used, for example, N-hydroxysuccinimide ester, is carried out in an appropriate solvent giving no adverse effect to the reaction. As to the solvent, there can be specifically mentioned, for example, halogenated hydrocarbons such as methylene chloride, chloroform, dichloroethane and the like; aromatic hydrocarbons such as benzene, toluene, xylene and the like; ethers such as diethyl ether, tetrahydrofuran, dimethoxyethane and the like; esters such as methyl acetate, ethyl acetate and the like; and aprotic polar solvents such as N,N-dimethylformamide, dimethyl sulfoxide, hexamethylphosphoric triamide and the like. The reaction is completed in 5 to 30 hours at $0°$ to $150°$ C., preferably $10°$ to $100°$ C. The desirable proportions of the carboxylic acid (3) and the N-hydroxysuccinimide ester are such that the former is used in an amount of ordinarily at least one mole, preferably 1 to 2 moles per mole of the latter.

When there is used the method (d) wherein a carboxylic acid halide is reacted with an amine (2), the reaction is carried out in an appropriate solvent in the presence of a dehydrohalogenating agent. As to the dehydrohalogenating agent, there are used ordinary basic compounds. The basic compounds can be those known and widely used, for example, basic compounds used in the Schotten-Baumann reaction, sodium hydroxide, potassium hydroxide, sodium hydride and potassium hydride. As to the solvent, there can be mentioned not only those used in the mixed acid anhydride method but also solvents such as alcohols (e.g. methanol, ethanol, propanol, butanol, 3-methoxy-1-butanol, ethyl cellosolve, methyl cellosolve), pyridine, acetone, acetonitrile and mixtures of two or more of the above. The proportions of the amine (2) and the carboxylic acid halide are not particularly restricted and can vary over a wide range; however, it is desirable that the latter be used in an amount of ordinarily at least about one mole, preferably 1 to 5 moles per mole of the former. The reaction is carried out ordinarily at about $-20°$ to $180°$ C., preferably at about $0°$ to $150°$ C. and is completed generally in 5 minutes to 30 hours.

In the above, the carboxylic acid halide is produced, for example, by reacting a carboxylic acid (3) with a halogenating agent in the presence or absence of a solvent. The solvent can be any as long as it gives no adverse effect on the reaction, and there can be mentioned, for example, aromatic hydrocarbons such as benzene, toluene, xylene and the like, halogenated hydrocarbons such as chloroform, methylene chloride, carbon tetrachloride and the like, ethers such as dioxane, tetrahydrofuran, diethyl ether and the like, dimethylformamide and dimethyl sulfoxide. As to the halogenating agent, there can be used ordinary halogenating agents which can convert the hydroxy group of carboxy group to a halogen, and there can be mentioned, for example, thionyl chloride, phosphorus oxychloride, phosphorus oxybromide and phosphorus pentabromide. The proportions of the carboxylic acid (3) and the halogenating agent are not particularly restricted and can be selected appropriately; however, when the reaction is carried out in the absence of a solvent, the latter is used ordinarily in a large excess amount relative to the former and, when the reaction is carried out in a solvent, the latter is used in an amount of ordinarily at least about one mole, preferably 2–4 moles per mole of the former. The reaction temperature (and the reaction time) is (are) not particularly restricted, either, and the reaction is carried out ordinarily at about room temperature to 100° C., preferably 50°-80° C. for about 30 minutes to 6 hours.

The compound (4) can also be obtained by reacting an amine (2) and a carboxylic acid (3) in the presence of a condensing agent which is a phosphorus compound such as triphenylphosphine, diethyl chlorophosphate, diphenylphosphinyl chloride, phenyl N-phenylphosphoramide chloridate, diethyl cyanophosphate, bis(2-oxo-3-oxazolidinyl)phosphinic chloride or the like.

The reaction is carried out ordinarily at about −20° to 150° C., preferably 0° to 100° C. in the presence of the same solvent and basic compound as used in the above-mentioned method of reacting a carboxylic acid halide with an amine (2), and is completed generally in about 5 minutes to 30 hours. The preferable amounts of the condensing agent and carboxylic acid (3) used are each at least about 1 mole, preferably about 1 to 2 moles per mole of the amine (2).

The dehydrogenation reaction of the compound of the general formula (4) is carried out in a solvent in the presence of 2,3-dichloro-5,6-cyanobenzoquinone (DDQ). As to the solvent, there can be mentioned aromatic hydrocarbons (e.g. benzene, toluene, xylene), ethers [e.g. dioxane, tetrahydrofuran (THF), diethyl ether], dimethylformamide (DMF), dimethyl sulfoxide (DMSO), hexamethylphosphoric triamide (HMPA), etc. The amount of DDQ used is not particularly restricted and can be selected appropriately from a wide range, but is ordinarily at least 1 mole, preferably about 1 to 3 moles per mole of the compound (4). The reaction is carried out at a temperature of ordinarily about 0° to 150° C., preferably about 0° to 120° C. and is completed ordinarily in about 0.5 to 5 hours.

In effecting the cyclization of the compound of the general formula (5), first the compound (5) is hydrolyzed. The hydrolysis is carried out in a suitable solvent or in a solventless state in the presence of an acid or a basic compound. The solvent can be any as long as it gives no adverse effect on the reaction, and there can be mentioned, for example, water, halogenated hydrocarbons (e.g. dichloromethane, chloroform), lower alcohols (e.g. methanol, ethanol, isopropanol), ketones (e.g. acetone, methyl ethyl ketone), ethers (e.g. dioxane, tetrahydrofuran, ethylene glycol monomethyl ether, ethylene glycol dimethyl ether), fatty acids (e.g. formic acid), dimethylformamide and their mixed solvents. As to the acid, there can be mentioned, for example, mineral acids (e.g. hydrochloric acid, sulfuric acid, hydrobromic acid) and organic acids (e.g. formic acid, trifluoroacetic acid, acetic acid, aromatic sulfonic acids). As to the basic compound, there can be mentioned, for example, sodium carbonate, potassium carbonate, metal hydroxides (e.g. sodium hydroxide, potassium hydroxide, calcium hydroxide) and alkali metal alcoholates (e.g. sodium methylate, sodium ethylate). The amount of the acid or base used is not particularly restricted and can be selected appropriately from a wide range, but is ordinarily about 1 to 10 moles, preferably about 1 to 2 moles per mole of the compound (5). The reaction proceeds favorably ordinarily at about room temperature to 200° C., preferably at about room temperature to 150° C. and is completed ordinarily in about 5 minutes to 7 days.

Then, the hydrolyzate of the compound (5) is subjected to the same reaction as the reaction between the acid halide of the carboxylic acid (3) and the amine (2), whereby a compound of the general formula (1a) according to the present invention can be obtained. The compound (1a) can also be obtained by a reaction ordinarily at about room temperature to 250° C., preferably at about room temperature to 200° C. for about 1 to 10 hours in a solvent such as ether (e.g. dioxane, diethylene glycol dimethyl ether), aromatic hydrocarbon (e.g. toluene, xylene, benzene) or the like.

The alkylation reaction of the compound (1a) is carried out in a solvent in the presence of an alkylating agent. As to the alkylating agent, there can be mentioned lower alkyl sulfonates such as $FSO_3CH_3$, $CF_3SO_3CH_3$, $(CH_3)_2SO_4$ and the like; lower alkyloxonium halide chelates such as $(CH_3)_3O^\oplus BF_4^\ominus$, $(C_2H_5)_3O^\oplus BF_4^\ominus$ and the like; and so forth. The solvent can be any as long as it gives no adverse effect to the reaction, and there can be mentioned, for example, halogenated hydrocarbons such as dichloromethane, chloroform, carbon tetrachloride and the like. The amount of the alkylating agent used is not specifically restricted and can be selected appropriately from a wide range, but is ordinarily at least about 1 mole, preferably about 1 to 2 moles per mole of the compound (1a). The reaction is carried out ordinarily at about −30° to 100° C., preferably at about −20° to 70° C. and is completed generally in about 1 to 40 hours.

The isomerization reaction of the present compound of the general formula (1b) is carried out in a solvent in the presence of a basic compound. As to the solvent and basic compound, there can be used the same as used in the above-mentioned reaction between the acid halide of the carboxylic acid (3) and the amine (2). As to the basic compound, there can also be used alkali metal alcoholates such as potassium tert-butoxide, sodium methylate, sodium ethylate and the like; alkali metals such as sodium amide, n-butyllithium, methyllithium and the like; and so forth. The reaction is carried out ordinarily at about 0° to 100° C., preferably at about 0° to 70° C., and is completed ordinarily in about 1 to 50 hours.

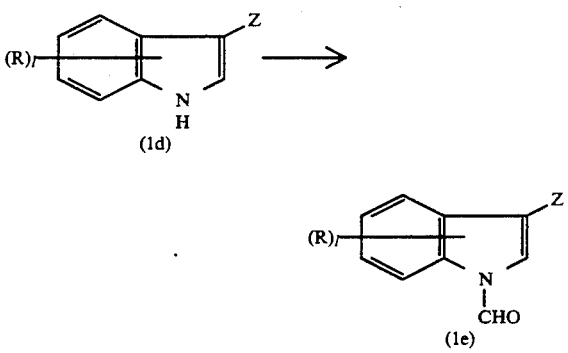

[in the formula, R, l, Z and the bonding states at 1-to 6-positions in the pyrazine ring are the same as defined above.]

The reaction for obtaining a present compound of the general formula (1e) is carried out in formic acid in the presence of a mineral acid such as hydrochloric acid, hydrobromic acid or the like. The reaction is carried out ordinarily at about 0° to 100° C., preferably at about 0° to 70° C., and is completed ordinarily in about 1 to 15 hours.

[Reaction scheme A-3]

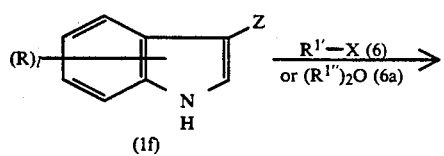

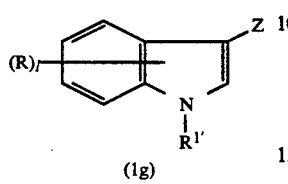

[in the formula, R, l, $R^2$, $R^3$, $R^4$, $R^5$, $R^6$, A, and the bonding states at 1- to 6-positions in the pyrazine ring are the same as defined above; $R^{1'}$ is a lower alkyl group, a phenyl-lower alkyl group, a lower alkanoyl group, a lower alkoxycarbonyl group, a phenyl-lower alkoxycarbonyl group, a group

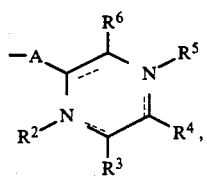

a benzoyl group or a phenylsulfonyl group which may have a lower alkyl group on the phenyl ring; X is a halogen atom; and $R^{1''}$ is a lower alkanoyl group, a lower alkoxycarbonyl group, a phenyl-lower alkoxycarbonyl group or a benzyl group.]

The reaction between the compound of the general formula (1f) and the compound of the general formula (6) or (6a) is carried out generally in a suitable inert solvent in the presence or absence of a basic compound. As to the inert solvent used, there can be mentioned, for example, halogenated hydrocarbons such as dichloromethane, chloroform, carbon tetrachloride and the like; aromatic hydrocarbons such as benzene, toluene, xylene and the like; ethers such as tetrahydrofuran, dioxane, diethylene glycol dimethyl ether and the like; lower alcohols such as methanol, ethanol, isopropanol, butanol and the like; acetic acid; ethyl acetate; acetonitrile; dimethyl sulfoxide; dimethylformamide; hexamethylphosphoric triamide; and their mixed solvents. As to the basic compound, there can be mentioned, for example, carbonates such as potassium carbonate, sodium hydrogencarbonate, potassium hydrogencarbonate and the like; metal hydroxides such as sodium hydroxide, potassium hydroxide and the like; sodium hydroxide; potassium; sodium; sodium amide; potassium amide; metal alcoholates such as sodium methylate, sodium ethylate, potassium tert-butoxide and the like; metal phenyl-lower alkoxides such as sodium benzyl oxide and the like; lower alkyl lithium compounds such as n-butyllithium, methyllithium and the like; organic bases such as sodium hydride, lithium diisopropylamide, pyridine, ethyldiisopropylamine, dimethylaminopyridine, triethylamine, DBN, DBU, DBACO and the like; and their mixtures. The proportions of the compound of the general formula (1f) and the compound of the general formula (6) or (6a) are not particularly restricted and can be selected suitably from wide ranges, and the latter can be used in an amount of ordinarily at least about 1 mole, preferably 1 to 5 moles per mole of the former. The reaction is carried out ordinarily at about 0° to 120° C., preferably at 0° to 100° C., and is completed generally in about 30 minutes to 30 hours. In the reaction, there may be added, for example, a phase transfer catalyst such as quaternary ammonium halide (e.g. tetra-n-butylammonium bromide, phenyltriethylammonium chloride), crown ether (e.g. 18-crown-6, benzo-18crown-6, dibenzo-18-crown-6, dicyclhexanocrown-6, 12-crown-4, 15-crown-5) or the like.

[Reaction scheme A-4]

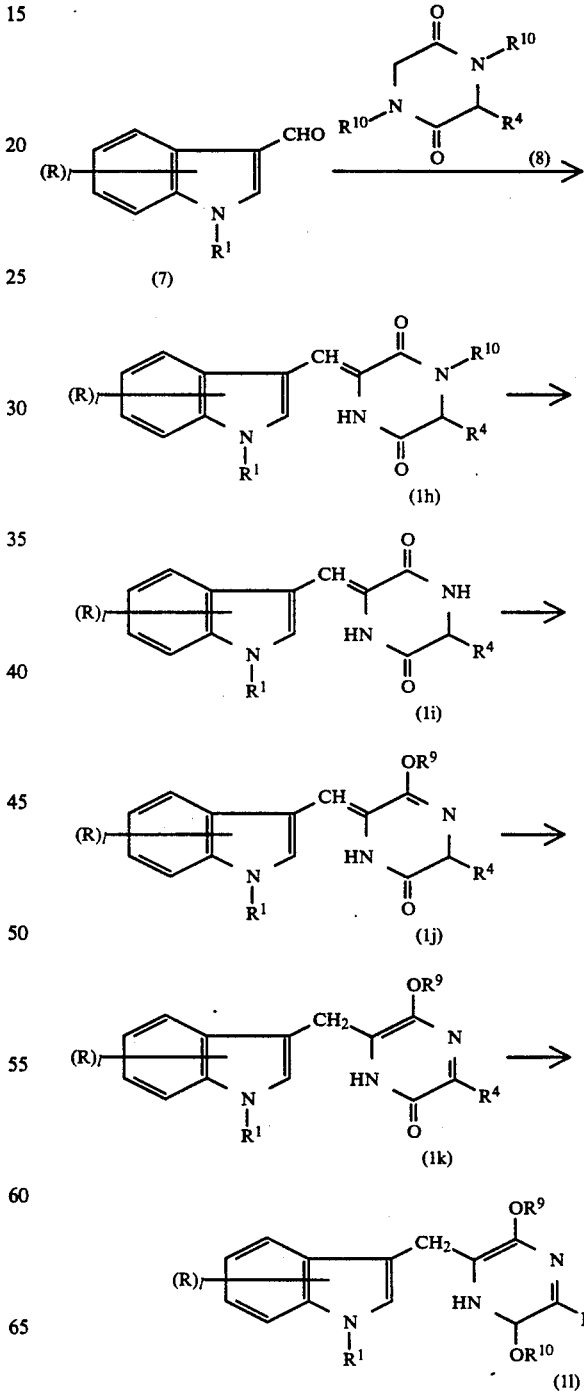

[in the formula, l, R, $R^1$, $R^4$ and $R^9$ are the same as defined above; $R^{10}$ is a silyl group having 1-3 groups selected from the group consisting of a lower alkanoyl group, a benzoyl group, a lower alkoxycarbonyl group, a lower alkyl group and a phenyl group, or a phenyl-lower alkyl group which may have, on the phenyl ring, substituents selected from the group consisting of a halogen atom, a lower alkyl group, a nitro group, an amino group and a lower alkoxy group.]

The reaction between the compound (7) and the compound (8) is carried out in a solvent in the presence of a basic compound. As to the solvent, there can be mentioned, for example, ethers such as THF, dioxane, diethyl ether and the like. As to the basic compound, there can be used the same compounds as used in the above-mentioned reaction for obtaining the compound (1c) from the compound (1c). There can also be used lower alkyllithium salts (e.g. n-butyllithium), etc. The amount of the compound (8) used is not particularly restricted and can be selected appropriately from a wide range, but is ordinarily at least about 1 mole, preferably 1 to 1.5 moles per mole of the compound (7). The reaction is carried out ordinarily at about −100° to 0° C., preferably at about −80° to 0° C., and is completed in about 1 to 5 hours.

The reaction for obtaining a compound (1i) is carried out in the same manner as in the above-mentioned hydrolysis reaction for obtaining the compound (1a) from the compound (5).

The reaction for obtaining a compound (1j) is carried out in the same manner as in the reaction for obtaining the compound (1b) from the compound (1a). In this reaction, there is obtained, in some cases, a compound wherein not only the 2-position but also the 5-position of the pyrazine ring have been alkylated; however, the compound can be separated easily.

The reaction for obtaining a compound (1k) is carried out in the same manner as in the reaction for obtaining the compound (c) from the compound (1b).

The reaction for obtaining a compound (1l) having, as the $R^{10}$, a benzoyl group, a lower alkoxycarbonyl group or a lower alkanoyl group is carried out by reacting the compound (1k) with an acrylating agent. The reaction is carried out in a solventless state or in an appropriate solvent, in the presence or absence of a basic compound, preferably in the presence of the basic compound. As to the acylating agent, there can be used, for example, acid anhydrides such as acetic anhydride, benzoic acid anhydride and the like, and acetyl chloride, benzoyl chloride, ethoxycarbonyl chloride and the like. As to the appropriate solvent, there can be used, for example, the above-mentioned aromatic hydrocarbons, lower alcohols (e.g. methanol, ethanol, propanol), DMF, DMSO, halogenated hydrocarbons (e.g. chloroform, methylene chloride), acetone and pyridine. As to the basic compound, there can be mentioned, for example, organic bases (e.g. triethylamine, pyridine, dimethylaminopyridine), sodium hydroxide, potassium hydroxide, sodium hydride and their mixtures. Alternatively, the compound (1k) may be reacted with an acylating agent in a solvent such as acetic acid or the like in the presence of a mineral acid such as sulfuric acid or the like. The amount of the acylating agent used is at least 1 mole, preferably 1 to 10 moles per mole of the compound (1k). The reaction is carried out ordinarily at about 0° to 200° C., preferably at about 0° to 150° C., and is completed in about 0.5 to 15 hours.

The reaction for obtaining a compound (1l) having, a substituted or unsubstituted phenyl-lower alkyl group as to the $R^{10}$, can be carried out under the conditions similar to those used in the reaction scheme A-27 between a compound (50) and a compound (52), described later.

The reaction for obtaining a compound (1l) having, a substituted or unsubstituted cyclooxy group as to the $R^{10}$, can be carried out by reacting the compound (1k) with a silylating agent such as alkylsilyl halide (e.g. tert-butylmethylsilyl chloride), alkylsilyl sulfonate (e.g. tert-butyldimethyltrifluoromethylsilyl sulfonate) or the like in a suitable solvent in the presence of a basic compound.

As to the basic compound used, there can be mentioned, for example, organic bases such as imidazole, triethylamine, dimethylaminopyridine, 2,6-lutidine, diisopropylethylamine, DBU, BBN and the like. As to the solvent used, there can be mentioned, for example, halogenated hydrocarbons (e.g. dichloromethane, chloroform), dimethylformamide, dimethyl sulfoxide and the like. The reaction is carried out ordinarily at 0° to 100° C., preferably about 0° to 70° C., and is completed in about 1 to 10 hours. The amount of the silylating agent used is at least 1 mole, preferably 1 to 3 moles per mole of the starting material.

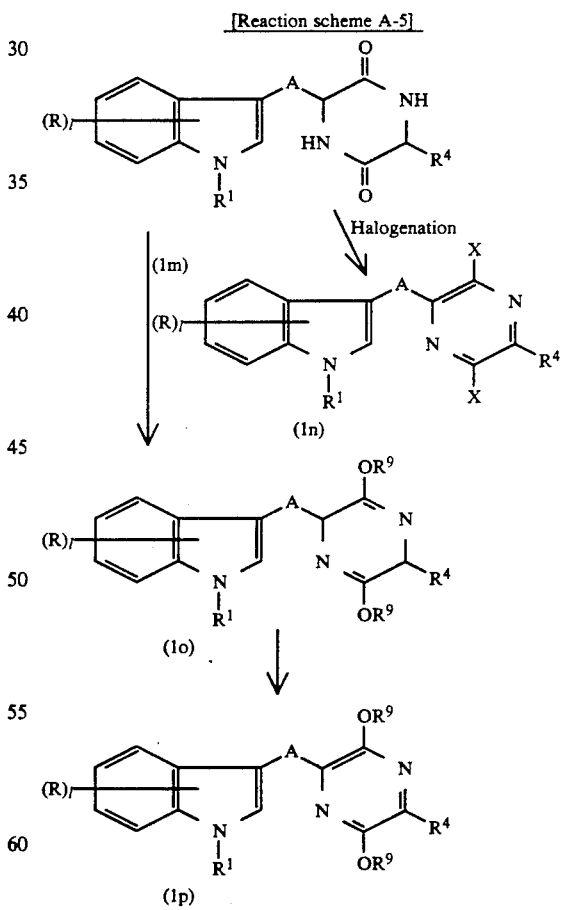

[Reaction scheme A-5]

[in the formula, R, l, $R^1$, $R^4$, A, X and $R^9$ are the same as defined above.]

The reaction for halogenating the compound (1m) to convert it to a compound (1n) can be carried out under any reaction conditions employed in an ordinary halogenation reaction for amido group. It is carried out, for example, by reacting the compound (1m) with a halogenating agent in an appropriate inert solvent or in a solventless state. As to the halogenating agent, there can be mentioned, for example, phosphorous or sulfur compounds such as phosphorous pentachloride, phosphorus pentabromide, phosphorus oxychloride, thionyl chloride and the like. As to the inert solvent, there can be mentioned, for example, ethers such as dioxane, tetrahydrofuran and the like; halogenated hydrocarbons such as chloroform, methylene chloride, carbon tetrachloride and the like; phosphorus oxychloride; etc. The ratio of amount of the compound (1m) to amount of the halogenating agent used are such that the amount of the latter is at least equimolar and ordinarily excessive to the former. The reaction is carried out ordinarily at about room temperature to 150° C., preferably at about room temperature to 80° C. for about 1 to 15 hours.

The reaction for obtaining a compound (1o) is carried out in the same manner as in the reaction for obtaining the compound (1b) from the compound (1a). However, the preferable amount of the alkylating agent used is ordinarily at least about 2 moles, preferably about 2–10 moles per mole of the compound (1m).

The reaction for obtaining a compound (1p) is carried out in the same manner as in the reaction for obtaining the compound (5) from the compound (4). In the halogenation conditions, there is obtained, in some cases, a monohalide compound formed by the halogenation of the compound (1m) at the 2- or 5-position; and, this compound can be separated easily. By reacting this monohalide compound under the same catalytic hydrogenation conditions as used for the conversion of compound (1s) to compound (1u), to be described later, there can be obtained a compound represented by the general formula

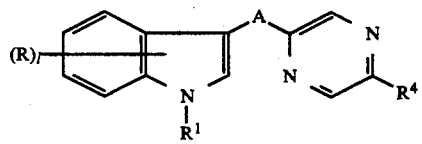

[in the formula, l, $R^1$, $R^4$, R and A are the same as defined above]. In carrying out the catalytic hydrogenation reaction, when a basic compound such as sodium acetate or the like is added to the reaction system, the reaction proceeds favorably.

[Reaction scheme A-6]

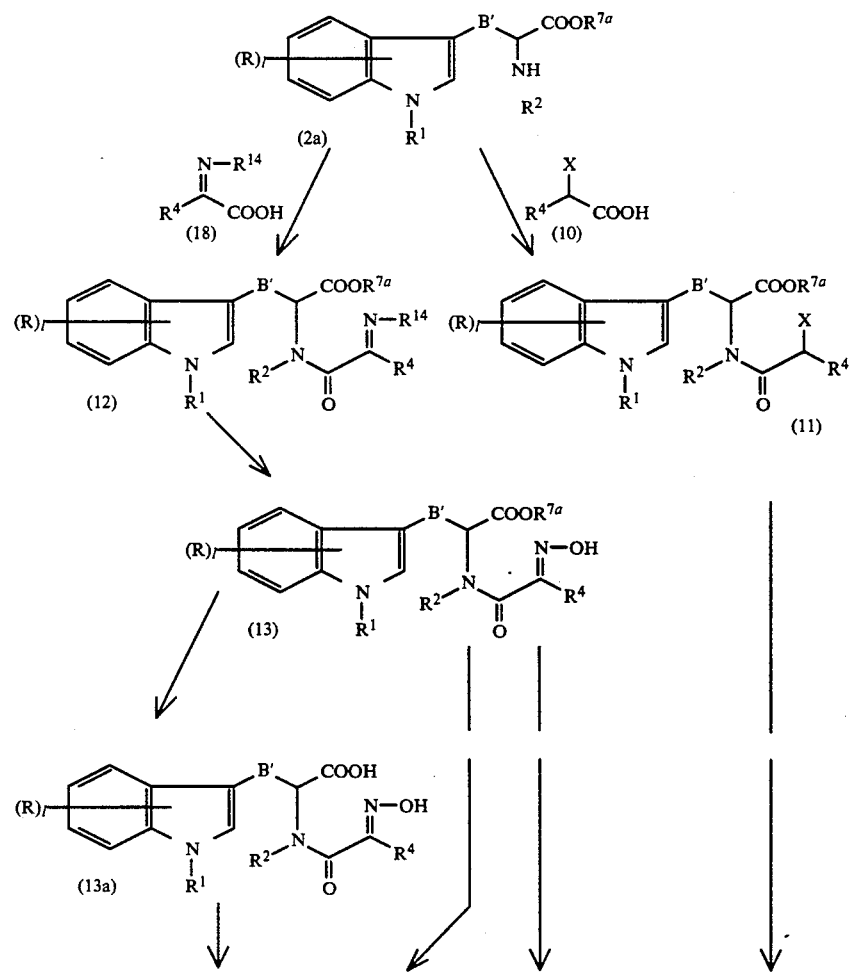

[Reaction scheme A-6]

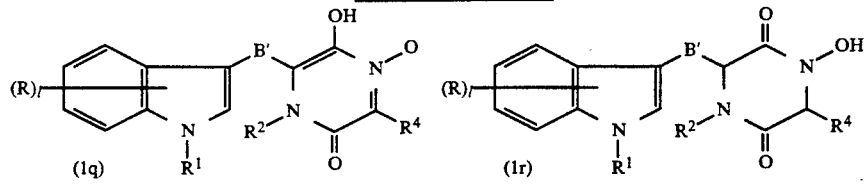

[in the formula, l, R, R¹, R², R⁴ and X are the same as defined above; R$^{7a}$ is a lower alkyl group or a phenyl-lower alkyl group which may have, on the phenyl ring, substitutents selected from the group consisting of a halogen atom, a lower alkyl group, a lower alkoxy group, a nitro group and a cyano group; B' is a single bond or a lower alkylene group; and R$^{14}$ is the same as defined later.]

The phenyl-lower alkoxy group which may have, on the phenyl ring, substitutents selected from the group consisting of a halogen atom, a lower alkyl group, a lower alkoxy group, a nitro group and an amino group, is a phenyl-lower alkoxy group whose alkoxy portion is a straight or branched chain of 1-6 carbon atoms and which may have, on the phenyl ring, 1-3 substitutents selected from the group consisting of a halogen atom, a straight or branched chain alkyl group of 1-6 carbon atoms, a nitro group, an amino group and a straight or branched chain alkoxy group, such as benzyloxy, 2-phenylethoxy, 1-phenylethoxy, 3-phenylpropoxy, 4-phenylbutoxy, 1,1-dimethyl-2-phenylethoxy, 5-phenylpentyloxy, 6phenylhexyloxy, 2-methyl-3-phenylpropoxy, 2-chlorobenzyloxy, 2-(3-chlorophenyl)ethoxy, 1-(4-chlorophenyl)ethoxy, 3-(2-fluorophenyl)propoxy, 4-(3-fluorophenyl)butoxy, 1,1-dimethyl-2-(4-fluorophenyl)ethoxy, 5-(2bromophenyl)pentyloxy, 6-(3-bromophenyl)hexyloxy, 2- methyl-3-(4-bromophenyl)propoxy, 3-iodobenzyloxy, 2-(4iodophenyl)ethoxy, 1-(3,5-dichlorophenyl)ethoxy, 2-(3,4-dichlorophenyl)ethoxy, 3-(2,6-dichlorophenyl)propoxy, 4-(3,4-dichlorophenyl)butoxy, 1,1-dimethyl-2-(3,4-difluorophenyl)ethoxy, 5-(3,5-dibromophenyl)pentyloxy, 6-(3,4,5-trichlorophenyl)hexyloxy, 4methylbenzyloxy, 2-(2-methylphenyl)ethoxy, 1-(3methylphenyl)ethoxy, 3-(3-ethylphenyl)propoxy, 4-(2ethylphenyl)butoxy, 5-(4-ethylphenyl)pentyloxy, 6-(3isopropylphenyl)hexyloxy, 2-methyl-3-(4-hexylphenyl)propoxy, 2-(3,4-dimethylphenyl)ethoxy, 2-(2,5dimethylphenyl)ethoxy, 2-(3,4,5-trimethylphenyl)ethoxy, 4-methoxybenzyloxy, 3,4-dimethoxybenzyloxy, 3,4,5-trimethoxybenzyloxy, 1-(3-methoxyphenyl)ethoxy, 2-(2-methoxyphenyl)ethoxy, 3-(2-ethoxyphenyl)propoxy, 4-(4-ethoxyphenyl)butoxy, 5-(3-ethoxyphenyl)pentyloxy, 6-(4-isopropoxyphenyl)hexyloxy, 1,1-dimethyl-2-(4hexyloxyphenyl)ethoxy, 2-methyl-3-(3,4-dimethoxyphenyl)propoxy, 2-(3,4-dimethoxyphenyl)ethoxy, 2-(3,4diethoxyphenyl)ethoxy, 2-(3,4,5-trimethoxyphenyl)ethoxy, 1-(2,5-dimethoxyphenyl)ethoxy, (2-chloro-4-methoxy)benzyloxy, 2-aminobenzyloxy, 1-(3-aminophenyl)ethoxy, 1-(4-aminophenyl)propoxy, 1-(2,3-diaminophenyl)butoxy, 1-(2,3,4-trimainophenyl)pentyloxy, 1-(2,4-diaminophenyl)hexyloxy, 2-nitrobenzyloxy, 1-(3-nitrophenyl)ethoxy, 1-(4-nitrophenyl)propoxy, 1-(2,4-dinitrophenyl)butoxy, 1-(2,4,6-trinitrophenyl)pentyloxy, 1-(2-chloro-4nitrophenyl)hexyloxy, (3-methyl-4-amino)benzyloxy, trityloxy, diphenylmethoxy or the like, and can be illustrated by phenylalkoxy groups having 1-3 substitutents on the phenyl ring. Of these, particularly preferable are phenyl-lower alkoxy groups having, on the 1-position of the alkyl portion, 1-3 substituted or unsubstituted phenyl groups as mentioned above, such as benzyloxy, 1-phenylethoxy, 1-(4-chlorophenyl)ethoxy, 1-(3,5-dichlorophenyl)ethoxy, 1-(3-methylphenyl)ethoxy, 1-(3-methoxyphenyl)ethoxy, 1-(2,5-dimethoxyphenyl)ethoxy, trityloxy, diphenylmethoxy and the like.

The silyloxy group having 1-3 groups selected from the group consisting of a lower alkyl group and a phenyl group can be illustrated by trialkylsilyloxy groups whose alkyl portion is a straight or branched chain alkyl group of 1-6 carbon atoms, such as trimethylsilyloxy, triethylsilyloxy, tripropylsilyloxy, tributylsilyloxy, tert-butyldimethylsilyloxy, tert-butyldiphenylsilyloxy, tripentylsilyloxy, trihexylsilyloxy, dimethylethylsilyloxy and the like.

The lower alkoxy-lower alkoxy group can be illustrated by alkoxyalkoxy groups whose alkoxy portion is a straight or branched chain alkoxy group of 1-6 carbon atoms, such as methoxymethoxy, 2-methoxyethoxy, 1-ethoxyethoxy, 3-propoxypropoxy, 4-butoxybutoxy, 5-pentyloxypentyloxy, 6-hexyloxyhexyloxy, 1,1-dimethyl-2-methoxyethoxy, 2-methyl-3-methoxypropoxy and the like. Of these, particularly preferable are 1-lower alkoxy-lower alkoxy groups such as methoxymethoxy, 1-ethoxyethoxy and the like.

The phenyl-lower alkyl group which may have, on the phenyl ring, substituents selected from the group consisting of a halogen atom, a lower alkyl group, a lower alkoxy group, a nitro group and a cyano group can be illustrated by phenylalkyl groups wherein the alkyl portion is a straight or branched chain alkyl group having 1-6 carbon atoms and has, as substitutents, 1-3 phenyl groups each having 1-3 substitutents selected from the group consisting of a halogen atom, a straight or branched chain alkyl group of 1-6 carbon atoms, a nitro group, a cyano group and a straight or branched chain alkoxy group of 1-6 carbon atoms, such as benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, 2-chlorobenzyl, 2-(3-chlorophenyl)ethyl, 1-(4-chlorophenyl)ethyl, 3-(2-fluorophenyl)propyl, 4-(3-flurophenyl)butyl, 1,1-dimethyl-2-(4-fluorophenyl)ethyl, 5-(2-bromophenyl)pentyl, 6-(3-bromophenyl)hexyl, 2-methyl-3-(4-bromophenyl)propyl, 3-iodobenzyl, 2-(4-iodophenyl)ethyl, 1-(3,5-dichlorophenyl)ethyl, 2-(3,4-dichlorophenyl)ethyl, 3-(2,6-dichlorophenyl)propyl, 4-(3,4-dichlorophenyl)butyl, 1,1-dimethyl-2-(3,4-difluorophenyl)ethyl, 5-(3,5dibromophenyl)pentyl, 6-(3,4,5-trichlorophenyl)hexyl, 4-methylbenzyl, 2-(2-methylphenyl)ethyl, 1-(3-methylphenyl)ethyl, 3-(3-ethylphenyl)propyl, 4-(2-ethylphenyl)butyl, 5-(4-ethylphenyl)pentyl, 6-(3-isopropylphenyl)hexyl, 2-methyl-3-(4-hexylphenyl)propyl, 2-(3,4-dimethylphenyl)-ethyl, 2-(2,5-dimethylphenyl)ethyl, 2-(3,4,5-trimethylphenyl)ethyl, 4-methoxybenzyl, 3,4-dimethoxybenzyl, 3,4,5-trimethoxybenzyl, 1-(3-methoxyphenyl)ethyl, 2-(2- methoxyphenyl)ethyl, 3-(2-ethoxyphenyl)propyl, 4-(4-ethoxyphenyl)butyl, 5-(3-ethoxyphenyl)pentyl, 6-(4-isopropoxyphenyl)hexyl, 1,1-dimethyl-2-(4hexyloxyphenyl)ethyl, 2-methyl-3-(3,4-dimethoxyphenyl)propyl, 2-(3,4-dimethoxyphenyl)ethyl, 2-(3,4-diethoxyphenyl)ethyl, 2-(3,4,5-trimethoxyphenyl)ethyl, 1-(2,5dimethoxyphenyl)ethyl, (2-chloro-4-methoxy)benzyl, 2-aminobenzyl, 1-(3-cyanophenyl)ethyl, 1-(4-cyanophenyl)propyl, 1-(2,3-dicyanophenyl)butyl, 1-(2,3,4-tricyanophenyl)pentyl, 1-(2,4-dicyanophenyl)hexyl, 2-nitrobenzyl, 1-(3-nitrophenyl)ethyl, 1-(4-nitrophenyl)propyl, 1-(2,4-dinotrophenyl)butyl, 1-(2,4,6-trinitrophenyl)pentyl, 1-(2-chloro-4-nitrophenyl)hexyl, (3-methyl-4-cyano)benzyl, trityl, diphenylmethyl and the like. Of these, particularly preferable are phenyl-lower alkyl groups wherein the 1-position of the alkyl group has, as substituents, 1-3 substituted or unsubstituted phenyl groups as mentioned above, such as 1-phenylethyl, 1-(4chlorophenyl)ethyl, 1-(3,5-dichlorophenyl)ethyl, 1-(3-methyphenyl)ethyl, 1-(3-methoxyphenyl)ethyl, 1-(2,5-dimethoxyphenyl)ethyl, trityl, diphenylmethyl and the like.

The reaction between the compound (2a) and the compound (10) and the reaction between the compound (2a) and the compound (18) are carried out according to an ordinary amide bond forming reaction. The amide bond forming reaction can be carried out by various known methods, for example, (a) a mixed acid anhydride method, for example, a method wherein a carboxylic acid (10) or (18) is reacted with an alkyl halocarboxylate and the resulting mixed acid anhydride is reacted with an amine (2a); (b) an activated ester method, for example, a method wherein a carboxylic acid (10) or (18) is converted to an activated ester such as p-nitrophenyl ester, N-hydroxysuccinimide ester, 1-hydroxybenzotriazole ester or the like and the activated ester is reacted with an amine (2a); (c) a carbodiimide method, that is, a method wherein a carboxylic acid (10) or (18) is condensed with an amine (4) in the presence of an activating agent such as dicyclohexylcarbodiimide, carbonyldiimidazole or the like; (d) other methods, for example, a method wherein a carboxylic acid (10) or (18) is converted to a corresponding carboxylic acid anhydride with a dehydrating agent such as acetic anhydride or the like and the carboxylic acid anhydride is reacted with an amine (2a), a method wherein an ester between a carboxylic acid (10) or (18) and a lower alcohol is reacted with an amine (2a) under a high pressure and at a high temperature, and a method wherein an acid halide of a carboxylic acid (10) or (18), i.e. a carboxylic acid halide is reacted with an amine (2a). The amide bond forming reaction can also be carried out by a method wherein a carboxylic acid (10) or (18) is activated by a phosphorus compound such as triphenylphosphine, diethyl chlorophosphate or the like and the activated carboxylic acid is reacted with an amine (2a), a method wherein a carboxylic acid (10) or (18) is converted to N-carboxyaminoacid anhydride with phosgene, trichloromethyl chloroformate or the like and the anhydride is reacted with an amine (2a), and so forth. The amide bond forming reaction can also be carried out by a method wherein a carboxylic acid (10) or (18) is activated with an acetylene compound such as trimethylsilylethoxyacetylene or the like and the resulting product is reacted with an amine (2a), and so forth.

In the mixed acid anhydride method (a), the mixed acid anhydride used is obtained by an ordinary Schotten-Baumann reaction and is reacted with an amine (2a) ordinarily without being isolated, whereby a compound of the general formula (12) or (11) can be produced. The schotten-Baumann reaction is carried out in the presence of a basic compound. As to the basic compound, there are used compounds conventionally used in the Schotten-Baumann reaction. They are illustrated by, for example, organic bases such as triethylamine, trimethylamine, pyridine, picoline, dimethylaniline, N-methylmorpholine, 4-dimethylaminopyridine, 1,5-diazabicyclo[4,3,0]nonene-5 (DBN), 1,8-diazabicyclo[5,4,0]undecene-7 (DBU), 1,4-diazabycyclo[2,2,2]octane (DABCO) and the like, and inorganic bases such as potassium carbonate, sodium carbonate, potassium hydrogencarbonate, sodium hydrogencarbonate and the like. The reaction is carried out at about −20° to 100° C., preferably 0° to 50° C. for about 5 minutes to 10 hours, preferably about 5 minutes to 2 hours. The reaction of the mixed acid anhydride obtained, with an amine (2a) is carried out at about −20° to 150° C., preferably 10° to 50° C. for about 5 minutes to 10 hours, preferably about 5 minutes to 5 hours. The mixed acid anhydride method is carried out generally in an appropriate solvent conventionally used in the method, such as halogenated hydrocarbon (e.g. methylene chloride, chloroform, dichloroethane), aromatic hydrocarbon (e.g. benzene, toluene, xylene), ether (e.g. diethyl ether, dioxane, diisopropyl ether, tetrahydrofuran, dimethoxyethane), ester (methyl acetate, ethyl acetate), aprotic polar solvent (e.g. 1,1,3,3-tetramethylurea, N,N-dimethylformamide, dimethyl sulfoxide, hexamethylphosphoric triamide) or the like, or in a mixed solvent or in the absence of any solvent. As to examples of the alkyl halocarboxylate used in the production of the mixed acid anhydride, there can be mentioned methyl chloroformate, methyl bromoformate, ethyl chloroformate, ethyl bromoformate and isobutyl chloroformate. The alkyl halocarboxylate is used in an amount of ordinarily at least 1 mole, preferably about 1 to 1.5 moles per mole of the amine (2a). The preferable proportion of the carboxylic acid (10) or (18) used is ordinarily at least 1 mole, preferably about 1 to 1.5 moles per mole of the amine (2a).

The activated ester method (b), when there is used, for example, N-hydroxysuccinimide ester, is carried out in a suitable solvent giving no adverse effect to the reaction, in the presence or absence of a basic compound. Into the reaction system may be added a condensing agent such as dicyclohexylcarbodiimide, carbonyldiimidazole, 1-ethyl-3-(3'-dimethylaminopropyl)-carbodiimide or the like. The basic compound can be any of the above-mentioned basic compounds used in the Schotten-Baumann reaction. The basic compound is further illustrated by alkali metal carboxylates such as sodium acetate, sodium benzoate, sodium formate, potassium acetate, lithium benzoate, cesium acetate and the like, and alkali metal halides such as potassium fluoride, cesium fluoride and the like. As to the solvent, there can be specifically mentioned, for example, halogenated hydrocarbons such as methylene chloride, chloroform, dichloroethane and the like; aromatic hydrocarbons such as benzene, toluene, xylene and the like; ethers such as diethyl ether, dioxane, tetrahydrofuran, dimethoxyethane and the like; esters such as methyl acetate, ethyl acetate and the like; aprotic polar solvents such as N,N'-dimethylformamide, dimethyl sulfoxide, hexamethylphosphoric triamide and the like; and their mixed solvents. The reaction is completed in 5 to 30 hours at 0° to 150° C., preferably at 10° to 100° C. The desirable ratio of the amount of the amine (2a) and to the amount of the N-hydroxysuccinimide ester used are ordinarily at least 1 mole, preferably 1 to 2 moles per mole of the compound (10) or (18). The compound (12) or (11) can also be obtained by reacting the amine (2a) and the carboxylic acid (10) or (18) in the presence of a condensing agent which is a phosphorus compound such as triphenylphosphine, triphenylphosphine-2,2'-dipyridyldisulfide, diethyl chlorophosphate, diphenylphosphinyl chloride, phenyl N-phenylphosphoramide chloridate, diethyl cyanophosphate, bis(2-oxo-3-oxazolidinyl)phosphinic chloride or the like.

The basic compound used can be various known compounds, and there can be mentioned, for example, the above-mentioned basic compounds used in the Schotten-Baumann reaction, sodium hydroxide, potassium hydroxide, etc. As the solvent, there can be mentioned, for example, the above-mentioned solvents used in the mixed acid anhydride method, pyridine, acetone, acetonitrile and mixed solvents consisting of two or more of them.

The reaction is carried out ordinarily at about $-20°$ to 150° C., preferably at about 0° to 100° C., and is completed generally in about 5 minutes to 30 hours. The amounts of the condensing agent and carboxylic acid (10) or (18) used are each at least about 1 mole, preferably about 1 to 2 moles per mole of the amine (2a).

The compound (12) or (11) can also be obtained by reacting the amine (2a) and the carboxylic acid (10) or (18) in the presence of a condensing agent. The reaction is carried out in an appropriate solvent in the presence or absence of a catalyst. The solvent can be illustrated by halogenated hydrocarbons such as dichloromethane, dichloroethane, chloroform, carbon tetrachloride and the like; acetonitrile; dimethylformamide; etc. The catalyst can be illustrated by organic bases such as dimethylaminopyridine, 4-piperidinopyridine and the like; salts such as pyridinium citrate and the like; camphorsulfonic acid; mercury oxide; etc. As to the condensing agent, there can be mentioned, for example, acetylene compounds such as trimethylsilylethoxyacetylene and the like. The desirable amount of the condensing agent used is ordinarily 1 to 10 moles, preferably 2 to 5 moles per mole of the amine (2a). The desirable amount of the carboxylic acid (10) or (18) used is ordinarily at least about 1 mole, preferably about 1 to 2 moles per mole of the amine (2a). The reaction is carried out ordinarily at about 0° to 150° C., preferably at about room temeprature to 100° C., and is completed generally in about 1 to 10 hours.

The reaction for converting the compound (12) to a compound (13) is carried out by reducing the compound (12), when is a phenyl-lower alkoxy group. This reduction reaction can be carried out, for exmaple, by catalytic hydrogenation in a suitable solvent in the presence of a catalyst. As to the solvent, there can be mentioned, for example, water; acetic acid; alcohols such as methanol, ethanol, isopropanol and the like; hydrocarbons such as hexane, cyclohexane and the like; ethers such as dioxane, tetrahydrofuran, diethyl ether, ethylene glycol dimethyl ether and the like; esters such as ethyl acetate, methyl acetate and the like; aprotic polar solvents such as dimethylformamide and the like; and their mixed solvents. As to the catalyst, there can be mentioned, for example, palladium, palladium-black, palladium-carbon, platinum, platinum oxide, copper chromite, Raney nickel and the like. The desirable amount of the catalyst used is generally about 0.02 to 1 time the amount of the compound (12). The desirable reaction temperature is ordinarily about $-20°$ to 100° C., preferably about 0° to 80° C.; the desirable hydrogen pressure is ordinarily 1 to 10 atm; and the reaction is completed generally in about 0.5 to 20 hours.

The reaction for converting the compound (12) to a compound (13) is carried out by hydrolysis of the compound (12), when $R^{14}$ is a tetrahydropyranyloxy group or a tri-lower alkylsilyloxy group. This hydrolysis is carried out in a suitable solvent or in the absence of a solvent in the presence of an acid. The solvent can be any as long as it gives no adverse effect on the reaction, and there can be mentioned, for example, water, halogenated hydrocarbons (e.g. dichloromethane, chloroform), lower alcohols (e.g. methanol, ethanol, isopropanol), ketones (e.g. acetone, methyl ethyl ketone), ethers (e.g. dioxane, tetrahydrofuran, ethylene glycol monomethyl ether, ethylene glycol dimethyl ether), fatty acids (e.g. formic acid, acetic acid) and mixed solvents thereof. As to the acid, there can be mentioned, for example, mineral acids such as hydrochloric acid, sulfuric acid, hydrobromic acid and the like, and organic acids such as formic acid, trifluoroacetic acid, acetic acid, aromatic sulfonic acid and the like. The amount of the acid used is not particularly restricted and can be selected from a wide range, but desirably is ordinarily about 1 to 10 moles, preferably about 1 to 2 moles per mole of the compound (12). The reaction proceeds favorably ordinarily at about 0° to 200° C., preferably at about room temperature to 150° C., and is completed ordinarily in about 5 to 15 hours. When $R^{14}$ is a tri-lower alkylsilyloxy group, the reaction may be carried out by using a fluorine compound such as tetra-n-butylammonium fluoride, hydrogen fluoride, cesium fluoride or the like.

When $R^{14}$ is a lower alkoxy-lower alkoxy group, the reaction for converting the compound (12) to a compound (13) is carried out by treating the compound (12) in a mixture of an mineral acid (e.g. hydrobromic acid, hydrochloric acid) or an organic acid (e.g. p-toluenesulfonic acid) and a solvent (e.g. water, methanol, ethanol, isopropanol) at 0° to 150° C., preferably room temperature to 120° C., or by hydrolyzing the compound (12). The hydrolysis is carried out in a suitable solvent in the presence of an acid. As to the solvent, there can be mentioned, for example, water; lower alcohols such as methanol, ethanol, isopropanol and the like; ethers such as dioxane, tetrahydrofuran and the like; halogenated hydrocarbons such as dichloromethane, chloroform, carbon tetrachloride and the like; polar solvents such as acetonitrile and the like; and their mixed solvents. As to the acid, there can be mentioned, for example, mineral acids such as hydrochloric acid, sulfuric acid, hydrobromic acid and the like; fatty acids such as formic acid, acetic acid and the like; Lewis acids such as boron trifluoride, aluminum chloride, boron tribromide and the like; iodides such as sodium iodide, potassium iodide and the like; and mixtures of the above Lewis acid and the above iodide. The reaction is generally carried out advantageously at 0° to 150° C., preferably at room temperature to 100° C., and is completed generally in about 0.5 to 15 hours.

The reaction for converting the compound (13) into a compound (13a) is carried out by hydrolyzing the compound (13) in the presence of a basic compound. The basic compound can be exemplified as sodium carbonate, potassium carbonate, sodium hydroxide, potassium hydroxide, barium hydroxide, etc. The desirable amount of the basic compound used is ordinarily about 1 to 15 moles, preferably about 1 to 10 moles. The solvent can be exemplified as water; alcohols such as methanol, ethanol, isopropanol and the like; ethers such as tetrahydrofuran, dioxane, dimethoxyethane and the like; dimethylformamide; dimethyl sulfoxide; hexamethylphosphoric triamide; and mixed solvents thereof. The reaction is carried out advantageously ordinarily at about 0° to 200° C., preferably at about room temperature to 150° C., and is completed generally in about 5 to 15 hours.

When the $R^{7a}$ of the compound (13) is a phenyl-lower alkyl group, the compound (13) can be converted into a compound (13a) by reducing the compound (13) under the same conditions as in the reduction reaction for converting the compound (12) into the compound (13).

In the process of the present invention, first the compound (13a or 13) obtained above is cyclized to obtained a compound (1q).

In the cyclization, there can be employed the same reaction conditions as in the reaction between the compound (2a) and the compound (18) in the above reaction scheme A-6. Particularly preferable is the method using a phosphorous compound such as triphenylphosphine-2,2'-dipyridyl sulfide or the like or an acetylene compound such as trimethylsilylethoxyacetylene or the like, or the method (b) using an activated ester such as N-hydroxysuccinimide ester, 1-hydroxybenzotriazole ester or the like. The basic compound used in this case is particularly preferably as alkali metal carboxylate, an alkali metal halide or the like.

The purity and stability of compound (13a) can be increased by forming its salt with an organic amine (e.g. DBU, DBN, diisopropylethylamine), an alkali metal (e.g. sodium, potassium) or the like, and the salt can be advantageously used in the subsequent reaction.

The reaction for obtaining a compound (1r) from the compound (11) is carried out in the presence of hydroxylamine in a solvent. As to the solvent, there can be used the same solvents as used in the reaction between the acid halide of carboxylic acid (3) and the amine (2). The reaction is carried out at about room temperature to 150° C., preferably at about room temperature to 100° C., and is completed generally in about 5 to 60 hours.

In obtaining a compound (1r) from the compound (13), first the compound (13) is reduced. The reducing reaction is carried out in a solvent in the presence of a reducing agent and a mineral acid. As to the reducing agent, there can be mentioned, for example, $BH_3 \cdot N(CH_3)_3$ and $BH_3 \cdot$pyridine; as the mineral acid, there can be mentioned, for example, hydrochloric acid and hydrobromic acid; as the solvent, there can be mentioned, for example, lower alcohols such as methanol, ethanol, propanol and the like. The reducing reaction is carried out ordinarily at about 0° to 100° C., preferably at about 0° to 70° C. for about 5 to 25 hours. Subsequently, the reduction product of the compound (13) is heated in a solvent to obtain a compound (1r). As to the solvent, there can be used the same solvents as used in the reaction between the acid halide of the carboxylic acid (3) and the amine (2). The heating reaction is carried out ordinarily at about room temperature to 150° C., preferably at about room temperature to 130° C. ordinarily for about 1 to 10 hours.

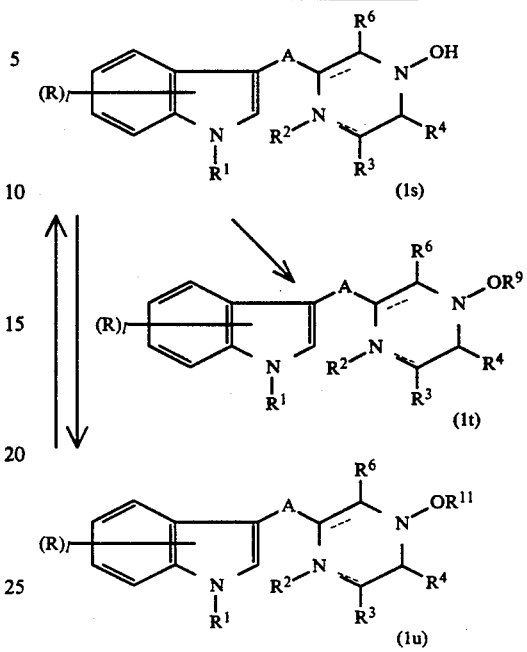

[Reaction scheme A-7]

[in the formula, R, l, $R^1$, $R^2$, $R^3$, $R^4$, $R^6$, $R^9$, A and the bonding states at 2-, 3-, 1- and 6-positions in the pyrazine ring are the same as defined above; and $R^{11}$ is a phenyl-lower alkyl group.]

The compound (1t) can be produced by reacting the compound (1s) with an alkylating agent in a solvent in the presence of a basic compound. As to the alkylating agent, there can be mentioned, for example, dialkyl sulfates (e.g. dimethyl sulfate), dialkoxy sulfuric acids (e.g. dimethoxy sulfuric acid), diazomethane and $R^9Y$ ($R^9$ is the same as defined above, and Y is a halogen atom). The solvent can be illustrated by, for exmaple, lower alcohols such as methanol, ethanol, propanol and the like; ethers such as diethyl ether, tetrahydrofuran, dioxane, ethylene glycol monomethyl ether and the like; halogenated hydrocarbons such as dichloromethane, chloroform, carbon tetrachloride and the like; aromatic hydrocarbons such as benzene, toluene, xylene and the like; esters such as methyl acetate, ethyl acetate and the like; ketones such as acetone, methyl ethyl ketone and the like; polar solvents such as acetonitrile, dimethylformamide, dimethyl sulfoxide, hexamethylphosphoric triamide and the like; and their mixed solvents. The basic compound can be illustrated by, for example, inorganic bases (e.g. sodium hydroxide, potassium hydroxide, sodium carbonate, potassium carbonate, sodium hydrogencarbonate, potassium hydrogencarbonate, sodium hydride), alkali metals (e.g. metallic sodium, metallic potassium), alkali metal alcoholates (e.g. sodium ethylate, sodium methylate) and organic bases (e.g. triethylamine, pyridine, N,N-dimethylaniline, N-methylmorpholine, 4-methylaminopyridine, DBN, DBU, DABCO).

The desirable amount of the alkylating agent used is at least 1 mole, preferably about 1 to 5 moles per mole of the compound (1s). The reaction is carried out ordinarily at 0° to 150° C., preferably about room temperature to 100° C., and is completed in about 0.5 to 20 hours.

When there is used a compound (1s) wherein $R^2$ is a hydroxy group, there is also obtained, in some cases, a product wherein the two hydroxy groups of the compound (1s) have been reacted with the lower alkyl group of the alkylating agent, and this product can be separated easily.

The reaction for obtaining a compound (1u) from the compound (1s) is carried out in the same manner as in the reaction between the compound (1f) and the compound (6).

It is also possible to obtain a compound (1s) by reducing the compound (1u). This reduction can be carried out, for example, by subjecting the compound (1u) to catalytic hydrogenation in an appropriate solvent in the presence of a catalyst. As to the solvent, there can be mentioned, for example, water; acetic acid; alcohols such as methanol, ethanol, isopropanol and the like; hydrocarbons such as hexane, cyclohexane and the like; ethers such as diethylene glycol dimethyl ether, dioxane, tetrahydrofuran, diethyl ether and the like; esters such as ethyl acetate, methyl acetate and the like; aprotic polar solvents such as dimethylformamide; and their mixed solvents. As to the catalyst, there can be mentioned, for example, palladium, palladium-black, palladium-carbon, platinum, platinum oxide, copper chromite and Raney nickel. The desirable amount of the catalyst used is generally about 0.02 to 1 time the amount of the compound (1s). The desirable reaction temperature is ordinarily about $-20°$ to $100°$ C., preferably about $0°$ to $80°$ C.; the desirable hydrogen pressure is ordinarily 1 to 10 atm; the reaction is completed generally in about 0.5 to 20 hours.

[Reaction scheme A-8]

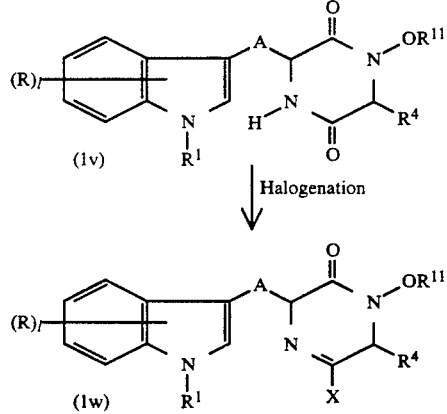

[in the formula, R, 1, $R^1$, $R^4$, $R^{11}$ and A are the same as defined above.]

The halogenation reaction for the compound (1v) is carried out in the same manner as in the reaction for obtaining the compound (1n) from the compound (1m). According to the reaction, there is also obtained, in some cases, a product wherein the 2-position of the indole ring as well has been halogenated; and this product can be separated easily.

[Reaction scheme A-9]

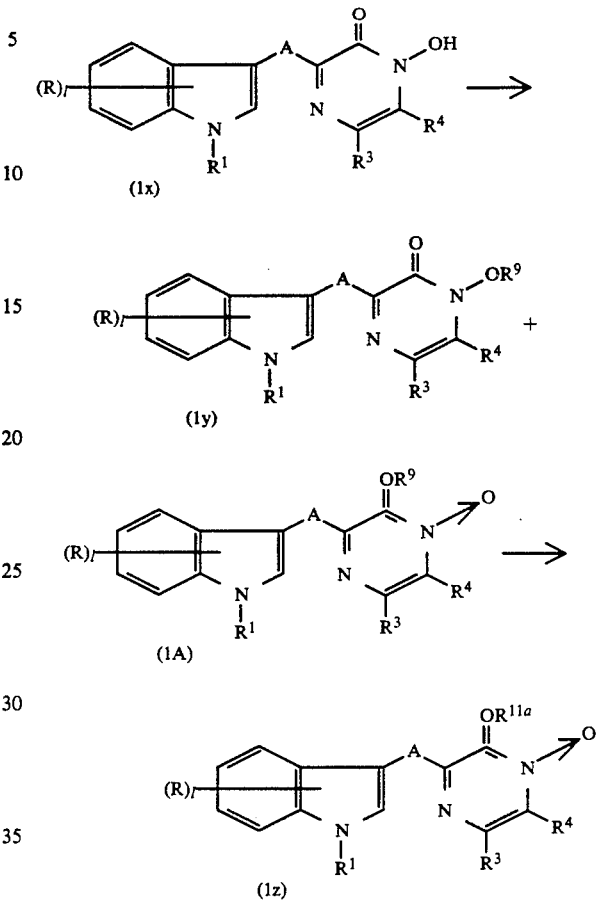

[in the formula, R, 1, $R^1$, $R^3$, $R^4$, $R^9$, $R^{11a}$ and A are the same as defined above.]

The compound (1x) is subjected to the same reaction as in obtaining a compound (1V) from a compound (1U) in the reaction scheme A-29 to be described later, whereby a compound (1y) and a compound (1A) can be obtained.

The reaction for obtaining a compound (1z) from the compound (1A) can be carried out by reacting the compound (1A) with $R^{11a}OM$ ($R^{11a}$ is a phenyl-lower alkyl group or a cycloalkyl group, and M is an alkali metal such as sodium, potassium or the like) in an appropriate solvent. The solvent can be exemplified by phenyl-lower alkyl alcohols (e.g. benzyl alcohol), dimethylformamide, dimethyl sulfoxide, hexamethylphosphoric triamide, etc. In this case, there may be added a phase transfer catalyst such as tetra-n-butylammonium bromide, 18-crown-6 or the like. The desirable amount of $R^{11a}OM$ used is ordinarily at least about 1 mole, preferably about 1 to 20 moles per mole of the compound (1A). The reaction is carried out ordinarily at about $0°$ to $150°$ C., preferably at about room temperature to $100°$ C., and is completed in about 5 minutes to 24 hours.

[Reaction scheme A-10]

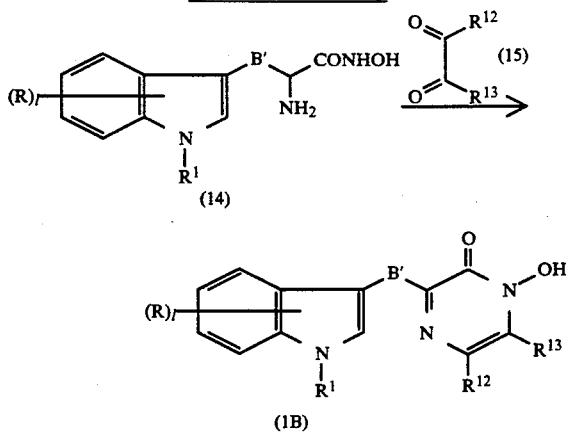

(1B)

[in the formula, R, l, $R^1$ and B' are the same as defined above; $R^{12}$ is a hydrogen atom or a lower alkyl group; and $R^{13}$ is a hydrogen atom, a lower alkyl group, a phenyl group or a phenyl-lower alkyl group which may have, on the phenyl ring, substituents selected from the group consisting of a hydroxy group and a phenyl-lower alkoxy group.]

The reaction between the compound (14) and the compound (15) is carried out in an appropriate solvent. As to the solvent, there can be used the same solvents as used in the reaction between the halide of the carboxylic acid (3) and the amine (2). The desirable amount of the compound (15) used is at least about 1 mole, preferably about 1 to 2 mole per mole of the compound (14). The reaction is carried out ordinarily at about 0° to 150° C., preferably at about 0° to 100° C., and is completed ordinarily in about 0.5 to 5 hours.

[Reaction scheme A-11]

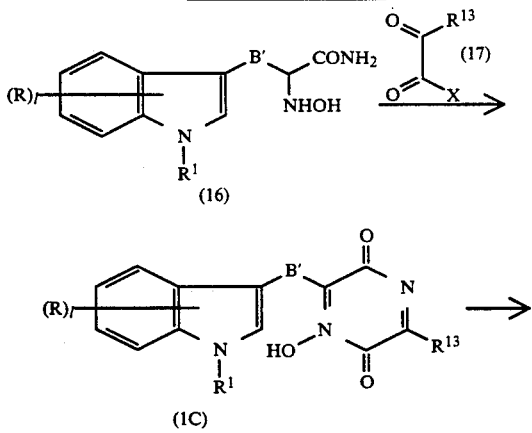

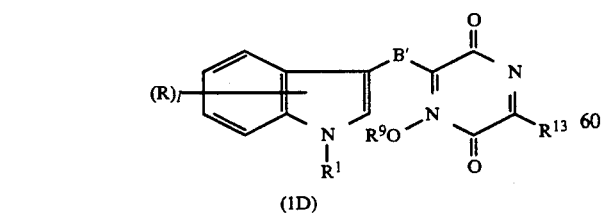

(1D)

[in the formula, R, l, $R^1$, $R^9$, $R^{13}$, X and B' are the same as defined above.]

The reaction between the compound (16) and the compound (17) is carried out in a solvent in the presence of a basic compound. As to the solvent and basic compound, there can be used the same as used in the reaction between the acid halide of the carboxylic acid (3) and the amine (2). The desirable amount of the compound (17) used is generally at least 1 mole, preferably 1 to 2 moles per mole of the compound (16). The reaction is carried out generally at about 0° to 100° C., preferably at about 0° to 70° C., and is completed generally in about 1 to 5 hours.

The reaction for obtaining a compound (1D) from the compound (1c) is carried out in the same manner as in the reaction for obtaining the compound (1t) from the compound (1s).

[Reaction scheme A-12]

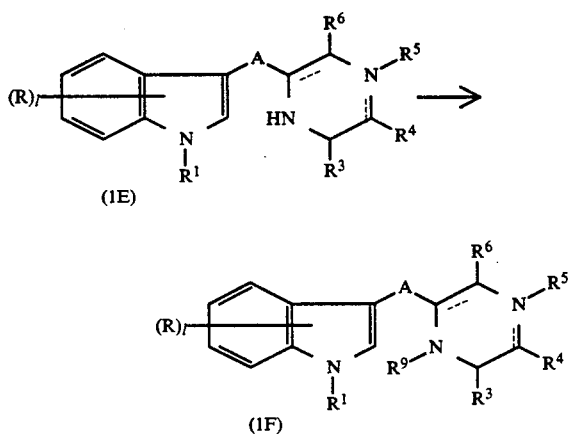

[in the formula, R, l, $R^1$, $R^3$, $R^4$, $R^5$, $R^6$, $R^9$, A and the bonding states at 2-, 3-, 4- and 5-positions in the pyrazine ring are the same as defined above.]

The reaction for obtaining a compound (1F) from the compound (1E) is carried out in the same manner as in the reaction for obtaining the compound (1t) from the compound (1s). In this reaction, there may be added a phase transfer catalyst such as tetra-n-butylammonium bromide, benzyltriethylammonium chloride, 18-crown-6- or the like. In this case, when there is used a compound (1E) wherein $R^3$ and/or $R^6$ is an oxo group and-/or $R^1$ is a hydrogen atom, there may be obtained, in some cases, a compound wherein said oxo group and/or the 1-position of the indole skeleton has been alkylated; and this compound can be separated easily.

[Reaction scheme A-13]

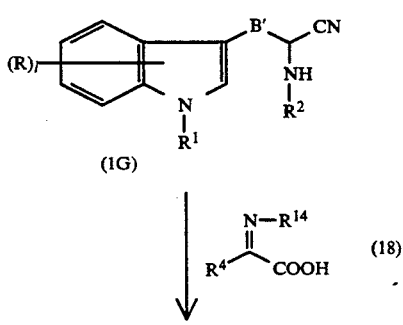

-continued
[Reaction scheme A-13]

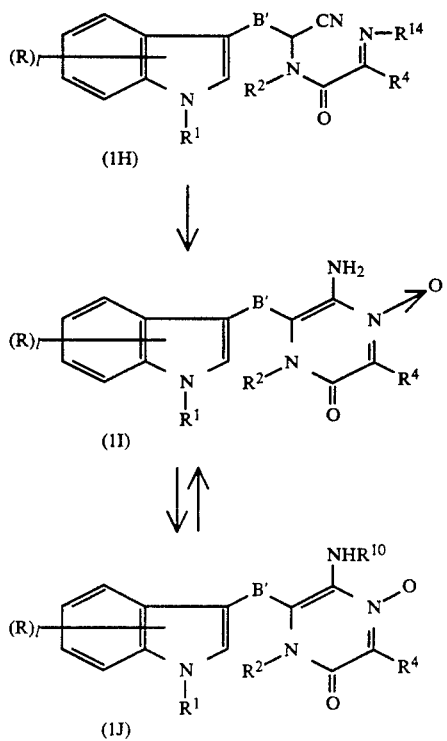

[in the formula, R, l, R$^1$, R$^2$, B', R$^4$ and R$^{10}$ are the same as defined above; and R$^{14}$ is a hydroxy group, a phenyl-lower alkoxy group which may have, on the phenyl ring, substituents selected from the group consisting of a halogen atom, a lower alkyl group, a lower alkoxy group, a nitro group and an amino group, a silyloxy group having 1-3 groups selected from the group consisting of a tetrahydropyranyloxy group, a lower alkyl group and a phenyl group, or a lower alkoxy-lower alkoxy group.]

The reaction between the compound (1G) and the compound (18) is carried out in the same manner as in the reaction between the compound (2) and the compound (3).

The reaction for obtaining a compound (1I) from the compound (1H) is carried out in acetic acid generally at about room temperature to 150° C., preferably at above room temperature to 100° C., and is completed generally in about 5–40 hours. In this case, a compound (1J) is formed as a by-product in some cases and it can be separated easily.

When there is used, as the compound (1H), a compound having, as the R$^{14}$, a tetrahydropyranyloxy group, first the compound is hydrolyzed under the same conditions as in the hydrolysis for obtaining the compound (1a) from the compound (5), to convert the R$^{14}$ to a hydroxy group, then the resulting product is subjected to the same reaction as in obtaining the compound (1I) from the compound (1H).

When there is used, as the compound (1H), a compound having, as the R$^{14}$, a phenyl-lower alkoxy group, the compound is reduced in the same manner as in the reduction reaction for obtaining the compound (1s) from the compound (1u), to convert the R$^{14}$ into a hydroxy group, then the resulting product is subjected to the same reaction as for obtaining the compound (1I) from the compound (1H).

The reaction for obtaining a compound (1J) from the compound (1I) is carried out in the same manner as in the reaction for obtaining the compound (1I) from the compound (1k).

In order to obtain the compound (1I) from the compound (1J), the compound (1J) is hydrolyzed under the same conditions as in the hydrolysis for obtaining the compound (1a) from the compound (5).

[Reaction scheme A-14]

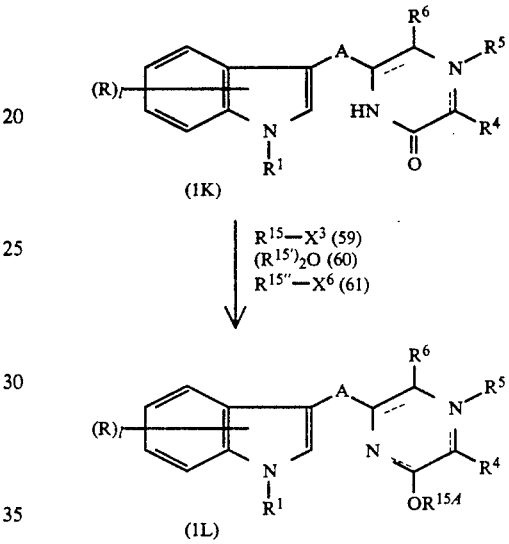

[in the formula, R, l, R$^1$, R$^2$, R$^4$, R$^5$, R$^6$, X$^3$, A and the bonding states at 2-, 3-, 4- and 5-positions in the pyrazine skeleton are the same as defined above; R$^{15}$ is a lower alkyl group, a phenyl-lower alkyl group which may have, on the phenyl ring, substitutents selected from the group consisting of a halogen atom, a lower alkyl group, a nitro group, an amino group and a lower alkoxy group, a lower alkanoyl group, a lower alkoxycarbonyl group or a benzoyl group; R$^{15'}$ is a benzoyl group, a lower alkanoyl group or a lower alkoxycarbonyl group; R$^{15''}$ is a silyl group having 1-3 groups selected from the group consisting of a lower alkyl group and a phenyl group; X$^6$ is a halogen atom or a lower alkyl-sulfonyloxy group which may have halogen atoms; and R$^{15A}$ is the above mentioned R$^{15}$ or R$^{15''}$.]

The reaction between the compound (1k) and the compound (59) or (60) is carried out in the same manner as in the reaction between the compound (1f) and the compound (6) or the reaction for obtaining the compound (1b) from the compound (1a). The reaction between the compound (11c) and the compound (61) can be carried out under the same conditions as in the reaction for obtaining a compound (1l) having, as the R$^{10}$, a substituted or unsubstituted silyloxy group in the reaction scheme-4.

[Reaction scheme A-15]

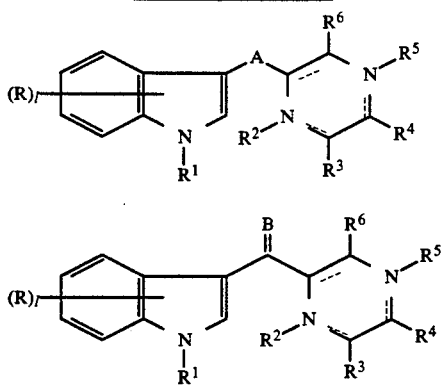

[in the formula, R, l, $R^1$, $R^2$, $R^3$, $R^4$, $R^5$, $R^6$ and the bonding states at 1-, 2-, 3-, 4-, 5- and 6-positions in the pyrazine ring are the same as defined above.]

The reaction for obtaining a compound (1N) from the compound (1M) is carried out in a solvent in the presence of an oxidizing agent. As the oxidizing agent, there can be mentioned, for example, selenium compounds such as DDQ, selenium dioxide and the like and cerium compounds such as cerium ammonium nitrate and the like. As to the solvent, there can be mentioned, for example, ethers such as THF, diethyl ether, dioxane and the like. The reaction is carried out generally at about 0° to 100° C., preferably at about room temperature to 70° C., and is completed generally in about 1 to 7 hours.

[Reaction scheme A-16]

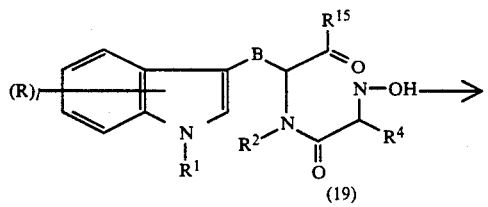

in the formula, R, l, $R^1$, $R^2$, $R^4$ and B are the same as defined above; and $R^{15}$ is a hydrogen atom or a lower alkyl group.]

The reaction for obtaining a compound (10) from the compound (19) is carried out in a solvent in the presence of an acid. As to the solvent, there can be used the same solvents as used in the reaction between the acid halide of the carboxylic acid (3) and the amine (2). As to the acid, there can be mentioned, for example, mineral acids such as hydrochloric acid, sulfuric acid, hydrobromic acid and the like; fatty acids such as formic acid, acetic acid and the like; sulfonic acids such as trifluoromethanesulfonic acid, p-toluenesulfonic acid and the like; boron trifluoride; and dimethyl etherate. The reaction is carried out generally at about 0° to 150° C., preferably at about room temperature to 100° C., and is completed generally in about 5 hours to 3 days.

In the reaction, there may be added an alkylsilyl halide such as trimethylsilyl chloride or the like.

The compound (19) used as a raw material compound in the reaction can be produced in accordance with, for exmaple, the following reaction formula A-17.

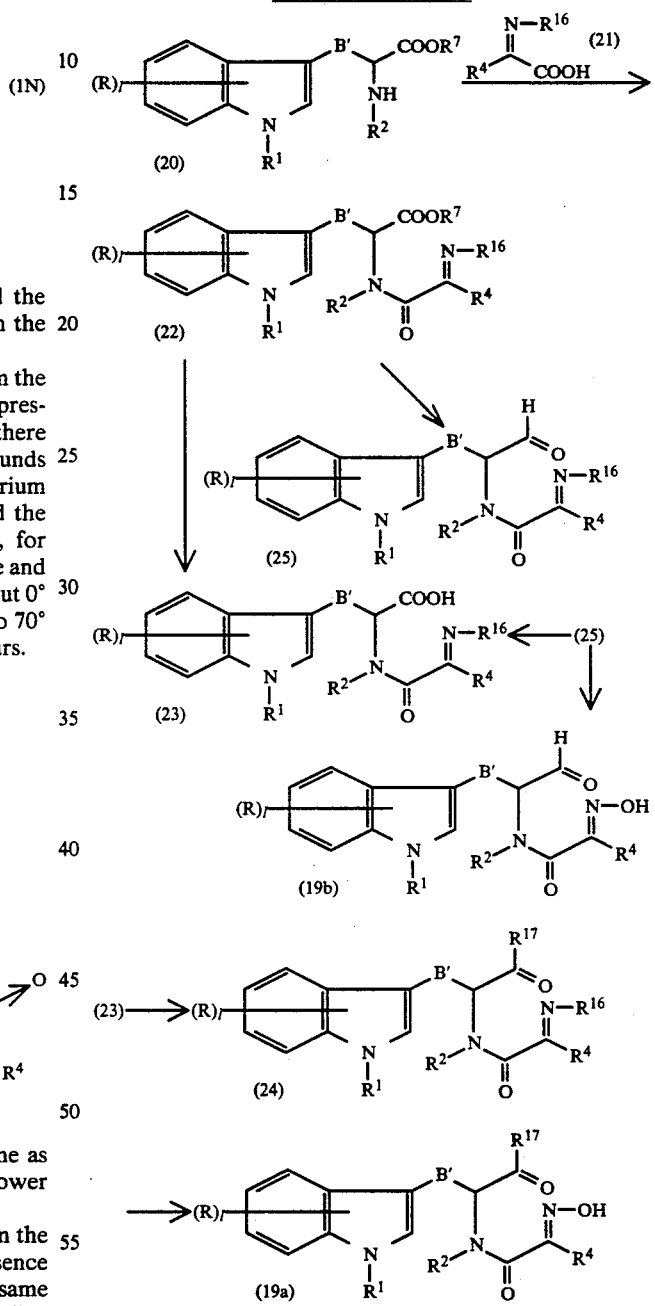

[in the formula, R, l, $R^1$, $R^2$, $R^4$, $R^7$ and B' are the same as defined above; $R^{16}$ is a phenyl-lower alkoxy group or a tetrahydropyranyloxy group; and $R^{17}$ is a lower alkyl group.]

The reaction between the compound (20) and the compound (21) is carried out in the same manner as in the reaction between the compound (2a) and the compound (18).

The reaction for obtaining a compound (23) from the compound (22) is carried out under the same conditions as in the hydrolysis for obtaining the compound pound (1a) from the compound (5).

The reaction for obtaining a compound (24) from the compound (23) is carried out in a solvent or in the absence of a solvent and in the presence of an acid anhydride and a basic compound. As to the acid anhydride, there can be mentioned, for example, a lower alkane acid anhydride such as acetic anhydride or the like. As the basic compound and solvent, there can be used the same as used in the reaction between the acid halide of the carboxylic acid (3) and the amine (2). The basic compound can also be illustrated by mixtures of the above-mentioned basic compounds. The desirable amount of the acid anhydride used is generally about 1 to 15 moles, preferably about 1 to 10 moles per mole of the compound (23). The reaction is carried out generally at about 0° to 150° C., preferably at about room temperature to 100° C., and is completed in about 1 to 20 hours.

The reaction for obtaining a compound (25) from the compound (22) is carried out in a solvent in the presence of a reducing agent. As to the solvent, there can be used, for example, ethers such as THF, diethyl ether, diglyme and the like; and halogenated hydrocarbons such as dichloromethane, chloroform and the like. As to the reducing agent, there can be used, for example, diisobutylaluminum hydride, lithium tri-tert-butoxyaluminum hydride, lithium triethoxyaluminum hydride and the like. The amount of the reducing agent used is not specifically restricted and can be selected suitably from a wide range, and desirably generally about 1 to 10 moles, preferably about 1 to 5 moles per mole of the compound (22) may be used. The reaction is carried out generally at about −150° to 0° C., preferably at about −120° to −20° C., and is completed generally in about 30 minutes to 20 hours.

In order to obtain a compound (19a) from the compound (24) and obtain a compound (19b) from the compound (25), there can be used the same method as used in converting the tetrahydropyranyloxy group ($R^{14}$) of the compound (1H) into a hydroxy group or in converting the phenyl-lower alkoxy group ($R^{14}$) of the compound (1H) into a hydroxy group.

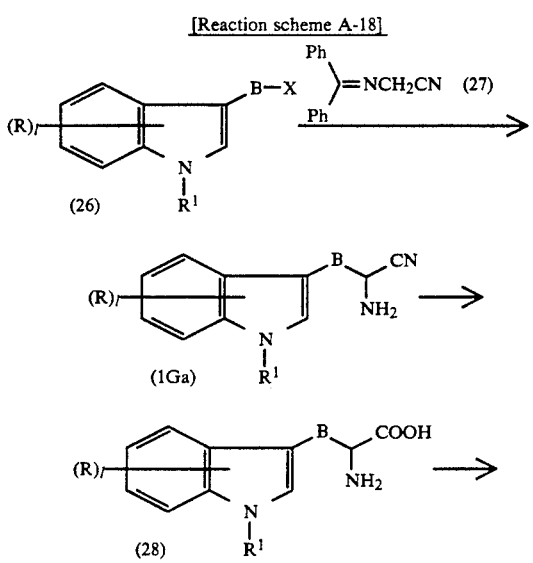

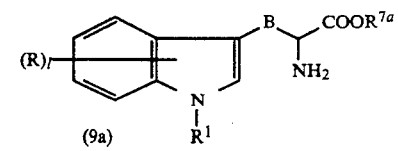

[in the formula, R, l, $R^1$, $R^{7a}$ and B are the same as defined above.]

The reaction between the compound (26) and the compound (27) is carried out in a solvent in the presence of a basic compound. As to the solvent and basic compound, there can be used the same as used in the reaction between the compound (1f) and the compound (6). The desirable amount of the compound (27) used is at least about 1 mole, preferably about 1 to 2 moles per mole of the compound (26). The reaction is carried out at a temperature of generally about 0° to 150° C., preferably about 0° to 100° C., and is completed generally in about 1 to 7 hours.

The hydrolysis reaction for the compound (1Ga) is carried out in a suitable solvent or in the absence of a solvent in the presence of a hydrolysis catalyst such as hydrohalogenic acid (e.g. hydrochloric acid, hydrobromic acid), mineral acid (e.g. sulfuric acid, phosphoric acid), alkali metal hydroxide (e.g. sodium hydroxide, potassium hydroxide), alkali metal carbonate or hydrogencarbonate (e.g. sodium carbonate, potassium carbonate, sodium hydrogencarbonate) or the like. As to the solvent, there can be mentioned, for example, water; alcohols such as methanol, ethanol and the like; and their mixed solvents. The reaction is completed in about 1 to 24 hours generally at about 50° to 150° C., preferably at about 70° to 100° C.

The esterification reaction for the compound (28) can be carried out by reacting the compound (28) with an alcohol such as methyl alcohol, ethyl alcohol, isopropyl alcohol, benzyl alcohol or the like in the presence of a mineral acid (e.g. hydrochloric acid, sulfuric acid) and a halogenating agent (e.g. thionyl chloride, phosphorus oxychloride, phosphorus pentachloride, phosphorus trichloride) generally at about 0° to 150° C., preferably at about 50° to 100° C. for about 1 to 10 hours.

The reaction on also be carried out under the same conditions as used in the alkylation reaction for converting the compound (1s) to the compound (1t) using an alkylating agent such as dialkyl sulfate (e.g. dimethyl sulfate), diazomethane or the like.

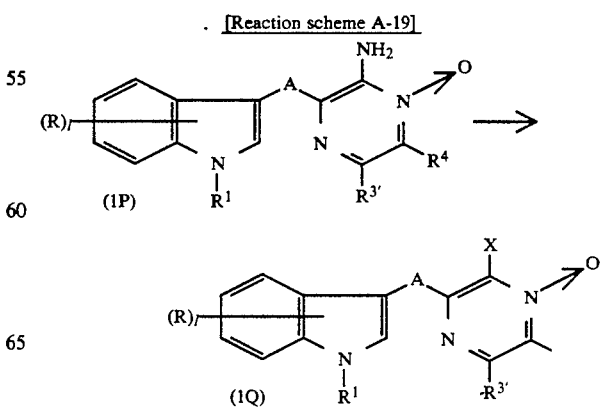

[in the formula, R, l, $R^1$, $R^4$, A and X are the same as defined above; and $R^{3'}$ is a hydrogen atom, a halogen atom, a lower alkoxy group, a lower alkanoyloxy group, a lower alkyl group, a phenyl-lower alkoxy group or a hydroxy group.]

The reaction for converting the compound (1P) to a compound (1Q) is carried out by reacting the compound (1P) with a metal nitrite such as sodium nitrite, potassium nitrite or the like in a solvent such as water or the like in the presence of an acid to obtain a diazonium salt or reacting the compound (1P) with a lower alkyl nitrite compound such as isoamyl nitrite or the like in a solvent such as acetonitrile or the like to obtain a diazonium salt, then heating the diazonium salt at about 50° to 200° C. or reacting the diazonium salt in the presence of a copper halide (e.g. cupric chloride, cupric bromide), cuprous bromide-hydrobromic acid, cuprous chloride-hydrochloric acid, or hydrobromic acid, potassium iodide, or an acid (e.g. hydrochloric acid) and a copper powder at about room temperature to 150° C. The acid can be illustrated by hydrochloric acid, hydrobromic acid, sulfuric acid, tetrafluoroboric acid, hexafluorophosphoric acid, etc. The desirable amounts of the acid and metal nitrite used are generally about 1 to 5 moles, preferably 1 to 3 moles (the former) and generally at least about 1 mole, preferably about 1 to 1.5 moles (the latter) per mole of the compound (1P).

The desirable amount of the copper halide to be reacted with the diazonium salt is generally at least about 1 mole, preferably about 1 to 5 moles per mole of the compound (1P).

[Reaction scheme A-20]

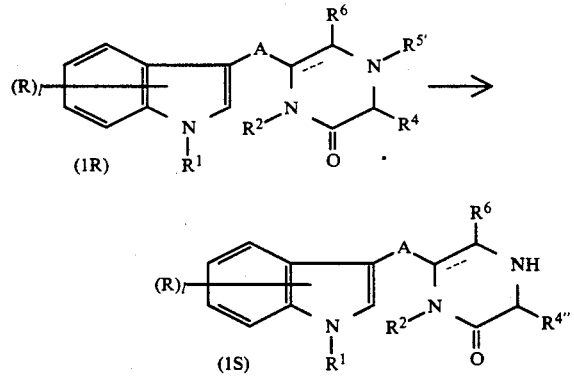

[in the formula, R, l, $R^1$, $R^2$, $R^6$, A and the bonding states at 2-, 3-, 1- and 6-positions in the pyrazine ring are the same as defined above; $R^{4'}$ is a lower (alkyl group; $R^{4''}$ is a lower alkylene group; and $R^{5'}$ is a lower alkoxy group.]

The reaction for converting the compound (1R) to a compound (1S) is carried out in the same solvent as used in the reaction for obtaining the compound (5) from the compound (4), in the presence of an inorganic base such as sodium amide, alkali metal alcoholate (e.g. sodium methylate, sodium ethylate), alkali metal (e.g. metallic sodium, metallic potassium), sodium hydride or the like, or an organic base such as DBN, DBU, DABCO or the like. The reaction is carried out generally at about room temperature to 200° C., preferably at about room temperature to 150° C., and is completed generally in about 10 minutes to 5 hours.

The compound of the general formula (1) wherein $R^1$ is a phenyl-lower alkoxycarbonyl group can be converted into a compound having a hydrogen atom as $R^1$, by reacting under the same conditions as in the reaction for converting the compound (1u) into the compound (1s), or by reacting in an alcohol such as ethanol, methanol, isopropanol or the like at about room temperature to 150° C., preferably at about room temperature to 100° C. for about 0.5 to 5 hours. When reacted under the same conditions as in the reaction for converting the compound (1u) into the compound (1s), there can be obtained, in some cases, a compound having a carboxy group as $R^1$, and this compound can be separated easily.

The compound of the general formula (1) wherein $R^1$ is a carboxyl group can be converted into a compound having a lower alkoxycarbonyl group as $R^1$, by reacting under the same conditions as in the reaction for converting the compound (28) to the compound (9a).

The compound of the general formula (1) wherein $R^6$ is an amino group having a lower alkanoyl group, can be converted into a compound having an amino $R^6$, in the same manner as in the reaction for converting the compound (1J) into the compound (1I).

The compound of the general formula (1) wherein $R^6$ is an amino group can be converted to a compound having, as $R^6$, an amino group having a lower alkanoyl group, in the same manner as in the reaction for converting the compound (1I) into the compound (1J).

The compound of the general formula (1) wherein $R^1$ is a lower alkoxycarbonyl group can be converted into a compound having hydrogen atom as $R^1$, by reacting under the same conditions as in the hydrolysis reaction for converting the compound (50) into the compound (1a), or by reacting in an alcohol such as ethanol, methanol, isopropanol or the like at about room temperature to 150° C., preferably at about room temperature to 100° C. for about 0.5 to 5 hours.

The compound (1) of the present invention wherein $R^3$ and/or $R^6$ is a substituted or unsubstituted phenyl-lower alkoxy group, can be converted into a compound having an oxo group as $R^3$ or/and $R^6$, by reduction.

The reducing reaction can be carried out by effecting, for example, catalytic hydrogenation in a suitable solvent in the presence of a catalyst. As to the solvent, there can be mentioned, for example, water; acetic acid; alcohols such as methanol, ethanol, isopropanol and the like; hydrocarbons such as hexane, cyclohexane and the like; ethers such as diethylene glycol dimethyl ether, dioxane, tetrahydrofuran, diethyl ether and the like; esters such as ethyl acetate, methyl acetate and the like; aprotic polar solvents such as dimethylformamide and the like; and mixed solvents thereof.

As to the catalyst, there can be mentioned, for example, palladium, palladium-black, palladium-carbon, platinum, platinum.oxide, copper chromite and Raney nickel. The desirable amount of the catalyst used is generally about 0.02 to 1 time the amount of the starting material. The desirable reaction temperature is generally about $-20°$ to $100°$ C., preferably about 0° to 80° C.; the desirable hydrogen pressure is generally 1 to 10 atm; and the reaction is completed generally in about 0.5 to 20 hours. To the reduction reaction system may be added a basic compound such as sodium hydroxide or the like. The compound (1R) can also be converted into a compound having an oxo group as $R^3$, by reacting the former compound under the same conditions as in the hydrolysis reaction for compound (54) in the reaction scheme A-27 to be described later. In the hydrolysis reaction, an organic acid such as trifluoroacetic acid or the like may be used.

The compound (1) of the present invention wherein R is a lower alkoxycarbonyl group can be converted to a compound having a carboxy group as R, by hydrolyzing the former compound under the same conditions as in the reaction for converting the compound (33) to the compound (34) in the reaction scheme A-23.

The compound (1) of the present invention wherein $R^6$ is a lower alkylthio group or a lower alkylsulfinyl group, can be converted into a compound having, as $R^6$, a lower alkylsulfinyl group or a lower alkylsulfonyl group, by reacting the former compound under the same conditions as in the reaction for converting a compound (31e) to a compound (31f) in the reaction formula A-28 to be described later.

The compound (1) of the present invention wherein $R^6$ is a lower alkylthio group, can be converted into a compound having a lower alkylsulfonyl group as $R^6$, by reacting the former compound under the same conditions as in the reaction for converting a compound (31e) into a compound (31g) in the reaction formula A-28 to be described later.

The compound (1) of the present invention wherein $R^5$ is a phenyl-lower alkoxy group, can be converted into a compound having a hydroxy group as $R^5$, by reducing the former compound under the same conditions as in the above-mentioned reduction reaction for the compound (1) of the present invention wherein $R^3$ is a phenyl-lower alkoxy group.

The compound (1) of the present invention wherein $R^4$ is a phenyl-lower alkyl group having at least one phenyl-lower alkoxy group, can be converted into a compound having, as $R^4$, a phenyl-lower alkyl group having at least one hydroxy group, by reducing the former compound under the same conditions as in the reduction reaction for the compound (1) of the present invention wherein $R^3$ is a phenyl-lower alkoxy group.

The compound (1) of the present invention wherein $R^3$ or/and $R^6$ is an oxo group, can be converted into a compound having a halogen atom as $R^3$ or/and $R^6$, by reacting the former compound under the same conditions as in the halogenation reaction for the compound (1v) in the reaction scheme A-8. Also, the compound (1) of the present invention wherein $R^6$ is an amino group, can be converted into a compound having a halogen atom as $R^6$, by reacting the former compound in the same manner as in the reaction for converting a compound (40) into a compound (41) in the reaction scheme A-24 to be described later.

The compound (1) of the present invention wherein $R^6$ is a phenyl-lower alkoxy group or a cycloalkyloxy group, can be obtained by reacting a compound having a hydroxy group as $R^6$, with $R^{22'}X^3$ ($R^{22'}$ is a phenyl-lower alkyl group or a cycloalkyl group and $X^3$ is the same as defined above) under the same conditions as in the reaction between a compound (33b) and a compound (49) in the reaction scheme A-26 to be described later.

The compound (1) of the present invention wherein $R^3$ is a lower alkanoyl-lower alkoxycarbonyloxy group, a benzoyloxy group or a lower alkoxycarbonyl group, or R is a lower alkanoyl group or a benzoyl group, can be subjected to hydrolysis. This hydrolysis is carried out under the same conditions as in the hydrolysis reaction for the compound (13), whereby a compound having an oxo group as $R^3$ can be obtained. The compound (1) of the present invention wherein $R^3$ is a silyloxy group having 1-3 groups selected from the group consisting of a lower alkyl group and a phenyl group, can be converted to a compound having an oxo group as $R^3$, by reacting the former compound in the presence of a desilylating agent such as tetraalkylammonium halide (e.g. tetrabutylammonium fluoride), fluoride (e.g. hydrofluoric acid, potassium fluoride, cesium fluoride, pyridinium hydrofluoride), mineral acid (e.g. hydrochloric acid, hydrobromic acid), organic acid (e.g. acetic acid), inorganic base (e.g. potassium carbonate, sodium hydroxide, potassium hydroxide) or the like in a solvent such as ether (e.g. tetrahydrofuran, diethyl ether, dioxane) or the like generally at about $-20°$ to $50°$ C., preferably at about $-20°$ C. to room temperature for about 10 minutes to 5 hours. The amount of the desilylating agent used can generally be a large excess relative to the starting material.

[Reaction scheme A-21]

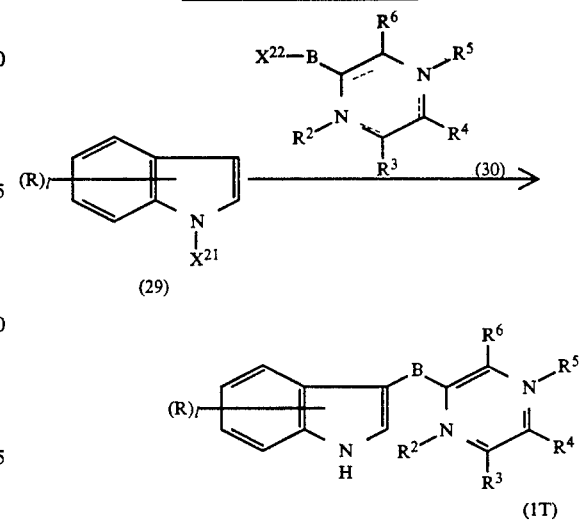

[in the formula, R, l, $R^1$, B, $R^2$, $R^3$, $R^4$, $R^5$, $R^6$ and the bonding states at 1-, 2-, 3-, 4-, 5- and 6-positions in the pyrazine ring are the same as defined above; $X^{21}$ is a hydrogen atom, a salt of an alkali metal such as lithium, sodium, potassium or the like, $MgX^3$ ($X^3$ is a halogen atom), $SnR^{18}$ ($R^{18}$ is a lower alkyl group) or $ZnX^3$ ($X^3$ is the same as defined above); and $X^{22}$ is a halogen atom, a lower alkanesulfonyloxy group, an arylsulfonyloxy group or an aralkylsulfonyloxy group.]

As to the specific examples of the lower alkanesulfonyloxy group, there can be exemplified methanesulfonyloxy, ethanesulfonyloxy, isopropanesulfonyloxy, propanesulfonyloxy, butanesulfonyloxy, tert-butanesulfonyloxy, pentanesulfonyloxy and hexanesulfonyloxy. As to the specific examples of the arylsulfonyloxy group, there can be mentioned substituted or unsubstituted arylsulfonyloxy groups such as phenylsulfonyloxy, 4-methylsulfonyloxy, 2-methylphenylsulfonyloxy, 4-nitrophenylsulfonyloxy, 4-methoxyphenylsulfonyloxy, 3-chlorophenylsulfonyloxy, α-naphthylphenylsulfonyloxy and the like. As to the specific examples of the aralkylsulfonyloxy group, there can be mentioned substituted or unsubstituted aralkylsulfonyloxy groups such as benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, 3-chlorobenzylsulfonyloxy and α-naphthylmethylsulfonyloxy and the like. $X^{21}$ is preferably a salt of an alkali metal (e.g. lithium, sodium, potassium), $ZnX^{31}$ or the like. This reaction is carried out generally in an appropriate solvent. As to the solvent, there can be mentioned aromatic hydrocarbons such as benzene, toluene, xylene and the like; ethers such as diethyl ether, tetrahydrofuran, dioxane, diethylene glycol dimethyl ether and the like; halogenated hydrocarbons such as chloroform, dichloromethane, carbon tetrachloride and the like; dimethyl sulfoxide; dimethylformamide; their mixed solvents; and so forth.

The reaction is completed for about 10 minutes to 50 hours generally at −30° to 150° C., preferably at about 10 minutes to 50 hours. The desirable amount of the compound (29) used is at least 1 mole, preferably 1 to 5 moles per mole of the compound (30).

[Reaction scheme A-22]

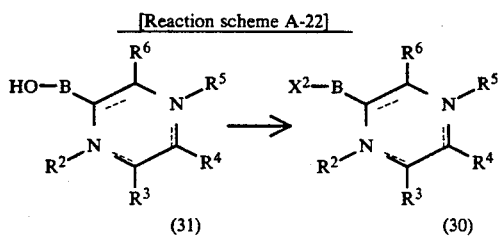

(31)            (30)

[in the formula, $R^2$, $R^3$, $R^4$, $R^5$, $R^6$, $X^3$, $X^2$ and the bonding states at 1-, 2-, 3-, 4-, 5- and 6-positions in the pyrazine ring are the same as defined above; and B is a lower alkylene group.]

The compound (30) wherein $X^2$ is a lower alkanesulfonyloxy group, an arylsulfonyloxy group or an aralkylsulfonyloxy group, can be produced by reacting the compound (31) with a compound (31) represented by the general formula (32)

$$R^{19}X^3 \qquad (32)$$

[in the formula, $R^{19}$ is a lower alkanesulfonyl group, an arylsulfonyl group or an aralkylsulfonyl group; and $X^3$ is the same as defined above.]

The reaction between the compound of the general formula (31) and the compound of the general formula (32) is carried out generally in a suitable inert solvent in the presence or absence of a basic compound. As to the inert solvent, there can be mentioned, for example, aromatic hydrocarbons such as benzene, toluene, xylene and the like; halogenated hdyrocarbons such as chloroform, dichloromethane, carbon tetrachloride and the like; ethers such as tetrahydrofuran, dioxane, diethylene glycol dimethyl ether and the like; acetic acid; ethyl acetate; acetone; acetonitrile; dimethyl sulfoxide; dimethylformamide; and hexamethylphosphoric triamide. As to the basic compound, there can be mentioned, for example, carbonates such as sodium carbonate, potassium carbonate, sodium hydrogencarbonate, potassium hydrogencarbonate and the like; metal hydroxides such as sodium hydroxide, potassium hydroxide and the like; sodium hydride; potassium; sodium; sodium amide; metal alcoholates such as sodium methylate, sodium ethylate and the like; and organic bases such as pyridine, ethyldiisopropylamine, dimethylaminopyridine, triethylamine, 1,5-diazabicyclo[4,3,0]nonene-5 (DBN), 1,8-diazabicyclo[5,4,0]undecene-7 (DBU), 1,4-diazabicyclo[2,2,2]octane (DABCO) and the like. The ratio of the amount of compound of the general formula (31) and the amount of compound of the general formula (32) used are not particularly restricted and can be selected from a wide range; and, desirably the latter is used at least about 1 mole, preferably about 1 to 1.5 moles per mole of the former. The reaction is carried out generally at about −78° to 100° C., preferably at about −30° to 70° C., and is completed generally in about 30 minutes to 30 hours.

The compound (30) wherein $X^2$ is a halogen atom, can also be obtained by reacting the compound (39) wherein $X^2$ is a lower alkanesulfonyloxy group, an arylsulfonyloxy group or an aralkylsulfonyloxy group, with a halogenating agent such as tetraalkylammonium halide (e.g. tetra-n-butylammonium iodide, tetra-n-butylammonium bromide), alkali metal halide (e.g. sodium iodide), phase transfer catalyst (e.g. alkali metal halide and 18-crown-6) or the like in a suitable solvent.

As to the solvent, there can be used any solvents used in the reaction between compound (31) and the compound (32). The desirable amount of the halogenating agent used is at least 1 mole, preferably about 1 mole to 2 moles per mole of the starting material. The reaction is carried out generally at 0° to 100° C., preferably at about 0 to 70° C, and is completed generally in about 10 minutes to 5 hours.

The compound (31) as the starting material which is a pyrazine derivative, can be produced by, for example, the following method.

[Reaction scheme A-23]

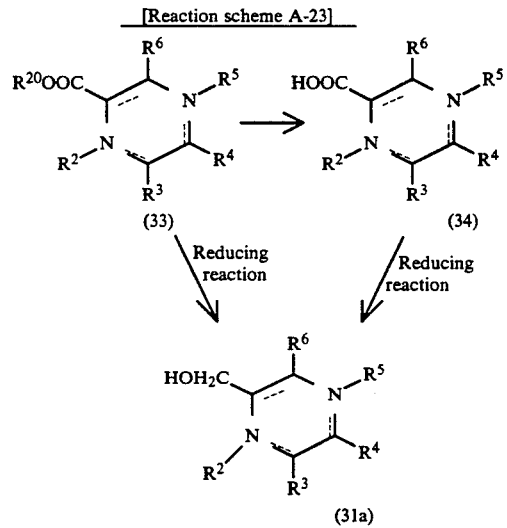

[in the formula, $R^2$, $R^3$, $R^4$, $R^5$, $R^6$ and the bonding states at 1-, 2-, 3-, 4-, 5- and 6-positions in the pyrazine ring are the same as defined above; and $R^{20}$ is a lower alkyl group, a lower alkanoyl group, a succinyl group, a lower alkoxycarbonyl group, a thiazolidinyl group which may have a thio group as a substituent, a methyleneiminium group which may have a lower alkyl group as a substituent, or a group —$SR^7$ ($R^7$ is a pyridyl group, a thiazolidinyl group, a lower alkyl group, a cycloalkyl group, a phenyl group or a phenyl-lower alkyl group).]

The reaction for converting the compound (33) into a compound (34) is carried out by hydrolysis. This hydrolysis reaction can be carried out under any conditions used in an ordinary hydrolysis reaction and is specifically carried out, for example, in the presence of a mineral acid (e.g. sulfuric acid, hydrochloric acid, nitric acid), an organic acid (e.g. acetic acid, aromatic sulfonic acid) or the like, or in the presence of a basic compound (e.g. sodium carbonate, potassium carbonate, sodium hydroxide, potassium hydroxide, barium hydroxide) in a solvent such as water, alcohol (e.g. methanol, ethanol, isopropyl alcohol), ketone (e.g. acetone, methyl ethyl ketone), ether (e.g. dioxane, ethylene glycol dimethyl ether), acetic acid or the like or their mixture. The reaction proceeds generally at 0° to 200° C., preferably at about room temperature to 150° C., and is completed generally in about 0.5 to 15 hours.

In the reducing reaction for the compound (33) and the compound (34), a reduction method using a hydrogenating reducing agent is employed preferably. As to the hydrogen reducing agent, there can be mentioned, for example, lithium aluminum hydride, sodium boron hydride, diisobutylaluminum hydride, diborane, lithium boron hydride and calcium boron hydride. The desirable amount of the hydrogen reducing agent used is at least 1 mole, preferably 1 to 5 moles per mole of the compound (33) or the compound (34).

The solvent can be illustrated by, for example, water, lower alcohols (e.g. methanol, ethanol, isopropyl alcohol), ethers (e.g. tetrahydrofuran, dioxane, diethyl ether, diglyme), halogenated hydrocarbons (e.g. dichloromethane, chloroform, carbon tetrachloride), acetonitrile, dimethylformamide and their mixed solvents. The reaction is carried out generally at −60° to 70° C., preferably at −30° to 50° C., and is completed in about 10 minutes to 20 hours. When lithium aluminum hydride or diborane is used as the reducing agent, it is preferable to use, as to the solvent, anhydrous diethyl ether, anhydrous tetrahydrofuran, anhydrous diglyme or the like. When there is used diisobutylaluminum hydride, there may be used, in place of the above ether type solvent, an aromatic hydrocarbon solvent such as benzene, toluene, xylene or the like.

The compound (31) or (33) used as a starting material can be produced by, for example, the following method.

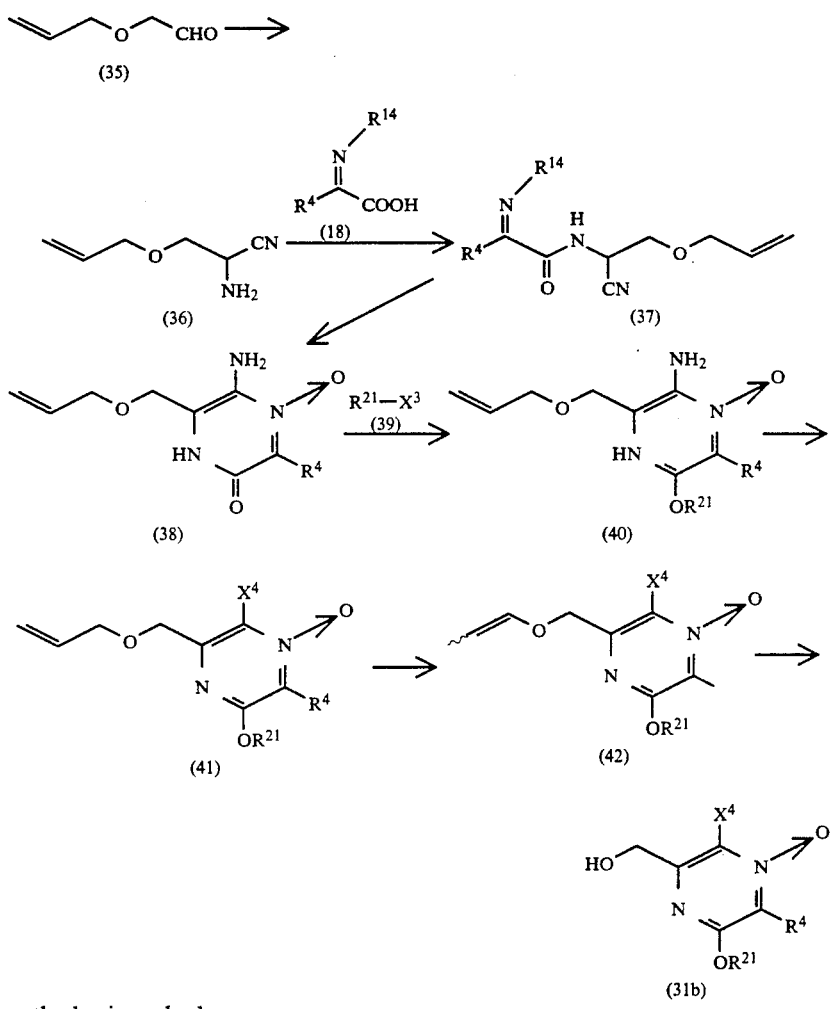

[in the formula, $R^4$, $R^{14}$ and $x^3$ are the same as defined above; $R^{21}$ is a lower alkyl group, a lower alkanoyl group or a phenyl-lower alkyl group; and $X^4$ is a halogen atom.]

The reaction for converting the compound (35) into a compound (36) is generally called the Strecker method, and the compound (36) can be obtained, for example, by reacting the compound (35) with an ammonium halide (e.g. ammonium chloride) and a metal cyanide (e.g. sodium cyanide, potassium cyanide) in water, an ether (e.g. diethyl ether, tetrahydrofuran, dioxane), an ammonium water or mixed solvents thereof. The desirable amounts of the ammonium halide and metal cyanide used are each at least 1 mole, preferably about 1 mole to 2 moles per mole of the compound (35). The reaction is carried out generally at 0° to 150° C., preferably at about 0° to 100° C., and is completed generally in about 5 to 80 hours.

The reaction between the compound (36) and the compound (18) is carried out according to a general amide bond forming reaction. The amide bond forming reaction can be carried out by various known methods, for example, (a) a mixed acid anhydride method, for example, a method wherein a carboxylic acid (18) is reacted with an alkyl halocarboxylate and the resulting mixed acid anhydride is reacted with an amine (36); (b) an activated ester method, for example, a method wherein a carboxylic acid (18) is converted to an activated ester such as p-nitrophenyl ester, N-hydroxysuccinimide ester, 1-hydroxybenzotriazole ester or the like and the activated ester is reacted with an amine (36); (c) a carbodiimide method, that is, a method wherein a carboxylic acid (18) is condensed with an amine (36) in the presence of an activating agent such as dicyclohexylcarbodiimide, carbonyldiimidazole or the like; (d) other methods, for example, a method wherein a carboxylic acid (18) is converted to a corresponding carboxylic acid anhydride with a dehydrating agent such as acetic anhydride or the like and the carboxylic acid anhydride is reacted with an amine (36), a method wherein an ester between a carboxylic acid (18) and a lower alcohol is reacted with an amine (36) under a high pressure and a high temperature, and a method wherein an acid halide of a carboxylic acid (18), i.e. a carboxylic acid halide is reacted with an amine (36). The amide bond forming reaction can also be carried out by a method wherein a carboxylic acid (18) is activated by a phosphorus compound such as triphenylphosphine, diethyl chlorophosphate or the like and the activated carboxylic acid is reacted with an amine (36), a method wherein a carboxylic acid (18) is converted to N-carboxyaminoacid anhydride with phosgene, trichloromethyl chloroformate or the like and the anhydride is reacted with an amine (36), and so forth.

In the mixed acid anhdyride method (a), the mixed acid anhydride used is obtained by an ordinary Schotten-Baumann reaction and is reacted with an amine (36) ordinarily without being isolated, whereby a compound of the general formula (4) can be produced. The Schotten-Baumann reaction is carried out in the presence of a basic compound. As to the basic compound, there are used compounds conventionally used in the Schotten-Baumann reaction. They are illustrated by, for example, organic bases such as triethylamine, trimethylamine, pyridine, dimethylaniline, N-methylmorpholine, 4-dimethylaminopyridine, 1,5-diazabicyclo[4,3,0]nonene-5 (DBN), 1,8-diazabicyclo[5,4,0]undecene-7 (DBU), 1,4-diazabicyclo[2,2,2]octane (DABCO) and the like, and inorganic bases such as potassium carbonate, sodium carbonate, potassium hydrogencarbonate, sodium hydrogencarbonate and the like. The reaction is carried out at about −20° to 100° C., preferably 0° to 50° C. for about 5 minutes to 10 hours, preferably about 5 minutes to 2 hours. The reaction of the mixed acid anhydride obtained, with an amine (36) is carried out at about −20° to 150° C., preferably 10° to 50° C. for about 5 minutes to 10 hours, preferably about 5 minutes to 5 hours. The mixed acid anhydride method is carried out generally in an appropriate solvent conventionally used in the method, such as halogenated hydrocarbon (e.g. methylene chloride, chloroform, dichloroethane), aromatic hydrocarbon (e.g. benzene, toluene, xylene), ether (e.g. diethyl ether, dioxane, diisopropyl ether, tetrahydrofuran, dimethoxyethane), ester (methyl acetate, ethyl acetate), aprotic polar solvent (e.g. 1,1,3,3-tetramethylurea, N,N-dimethylformamide, dimethyl sulfoxide, hexamethylphosphoric triamide) or the like, or in a mixed solvent or in the absence of any solvent. As to examples of the alkyl halocarboxylate used in the production of the mixed acid anhydride, there can be mentioned methyl chloroformate, methyl bromoformate, ethyl chloroformate, ethyl bromoformate and isobutyl chloroformate. The alkyl halocarboxylate is used in an amount of ordinarily at least 1 mole, preferably about 1 to 1.5 moles per mole of the amine (36). The preferable amount of the carboxylic acid (18) used is ordinarily at least 1 mole, preferably about 1 to 1.5 moles per mole of the amine (36).

The activated ester method (b), when there is used, for example, N-hydroxysuccinimide ester, is carried out in an appropriate solvent giving no adverse effect on the reaction, in the presence or absence of a basic compound. As to the basic compound, there can be used any basic compounds usable in the Schotten-Baumann reaction. As to the solvent, there can be specifically mentioned, for example, halogenated hydrocarbons such as methylene chloride, chloroform, dichloroethane and the like; aromatic hydrocarbons such as benzene, toluene, xylene and the like; ethers such as diethyl ether, dioxane, tetrahydrofuran, dimethoxyethane and the like; esters such as methyl acetate, ethyl acetate and the like; aprotic polar solvents such as N,N-dimethylformamide, dimethyl sulfoxide, hexamethylphosphoric triamide and the like; and their mixed solvents. The reaction is completed in 5 to 30 hours at 0° to 150° C., preferably 10° to 100° C. The desirable proportions of the amine (36) and N-hydroxysuccinimide ester used are each generally at least 1 mole, preferably 1 mole to 2 moles per mole of the compound (18). In the reaction, there may be added to the reaction system a condensing agent such as dicyclohexylcarbodiimide, carbonylimidazole or the like.

The compound (37) can also be obtained by reacting the amine (36) with the carboxylic acid (18) in the presence of a condensing agent which is a phosphorus compound such as triphenylphosphine, triphenylphosphine-2,2'-dipyridyl sulfide, diethyl chlorophosphate, diphenylphosphinyl chloride, phenyl N-phenylphosphoramide chloridate, diethyl cyanophosphate, bis(2-oxo-3-oxazolidinyl)phosphinic chloride or the like.

As the basic compound used in the above, there can be used various known basic compounds, and there can be mentioned, for example, the basic compounds used in the Schotten-Baumann reaction, sodium hydroxide and potassium hydroxide. As the solvent, there can be mentioned, for example, the solvents used in the above-mentioned mixed acid anhydride method; halogenated hydrocarbons such as dichloromethane, chloroform, carbon tetrachloride and the like; pyridine; acetone; acetonitrile; and mixed solvents consisting of two or more of the above.

The reaction is carried out generally at about −20° to 150° C., preferably at about 0° to 100° C., and is completed generally in about 5 minutes to 30 hours. The desirable amounts of the condensing agent and carboxylic acid (18) used are each at least about 1 mole, preferably about 1 mole to 2 moles per mole of the amine (36).

The reaction for converting the compound (37) to a compound (38) is carried out in acetic acid generally at about room temperature to 150° C., preferably at about room temperature to 100° C., and is completed generally in about 1 to 40 hours.

The reaction between the compound (38) and the compound (39) can be carried out under the same conditions as in the reaction between a compound (50) and a compound (52) in the reaction scheme A-27 to be described later.

The reaction for converting the compound (40) into a compound (41) is carried out by reacting the compound (40) with a metal nitrite such as sodium nitrite, potassium nitrite or the like in the presence of an acid in a solvent such as water or the like to obtain a diazonium salt or reacting the compound (40) with a lower alkyl nitrite compound such as tert-butyl nitrite, isoamyl nitrite or the like in a solvent such as acetonitrile or the like to obtain a diazonium salt, then heating the diazonium salt at about 150° to 200° C. or reacting the diazonium salt in the presence of a copper halide (e.g. cuprous chloride, cuprous bromide, cupric chloride, cupric bromide), a copper halide mixture (e.g. cupric chloride-cuprous chloride), cupric bromide-hydrobromic acid, cupric chloride-hydrochloric acid, hydrobromic acid, potassium iodide, or an acid (e.g. hydrochloric acid) and a copper powder at about room temperature to 150° C. for about 10 minutes to 5 hours. The acid can be illustrated by, for example, hydrochloric acid, hydrobromic acid, sulfuric acid, tetrafluoroboric acid and hexafluorophosphoric acid. The desirable amounts of the acid and metal nitrite used are generally about 1 to 5 moles, preferably about 1 to 3 moles (the former) and generally at least about 1 mole, preferably about 1 to 3 moles (the latter) per mole of the compound (40).

The desirable amount of the copper halide to be reacted with the diazonium salt is generally about at least 1 mole, preferably about 1 to 5 moles per mole of the compound (40). The reaction for converting the compound (41) to a compound (42) is carried out in the presence or absence of a basic compound in an appropriate solvent in the presence of a catalyst. The basic compound can be exemplified as organic bases such as triethylamine, trimethylamine, diisopropylamine, ethylamine, pyridine, dimethylaniline, N-methylmorpholine, 4-dimethylaminopyridine, DBN, DBU, DABCO and the like. The solvent can be illustrated by, for example, water, alcohols (e.g. ethanol, methanol, isopropyl alcohol) and their mixed solvents.

The catalyst can be exemplified as a Wilkinson complex

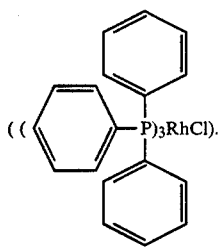

The desirable amount of the catalyst used is generally 0.1 to 1 time the weight of the compound (41).

The reaction is completed in about 1 to 5 hours generally at room temperature to 200° C., preferably at about room temperature to 150° C. The reaction for converting the compound (42) into a compound (31b) is carried out under the same conditions as in the hydrolysis reaction for the compound (54) having a tetrahydropyranyl group or a lower alkenyl group as $R^{23}$, in the reaction scheme A-27 to be described later.

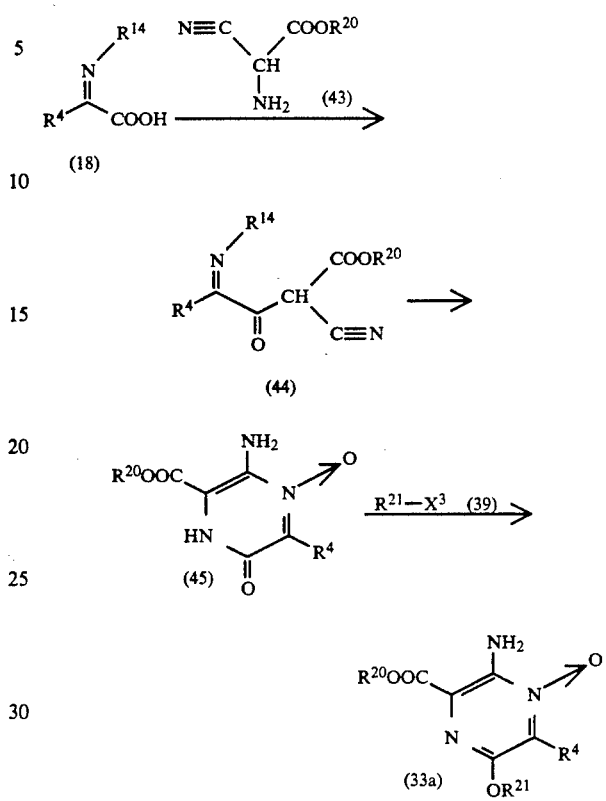

[in the formula, $R^4$, $R^{14}$, $R^{20}$, $X^3$ and $R^{21}$ are the same as defined above.]

The reaction between the compound (18) and the compound (43) is carried out under the same conditions as in the reaction between the compound (36) and the compound (18) in the reaction scheme A-24.

The reaction for converting the compound (44) to a compound (45) is carried out under the same conditions as in the reaction for converting the compound (37) to the compound (38) in the reaction scheme A-24.

The reaction between the compound (45) and the compound (39) is carried out under the same conditions as in the reaction between the compound (38) and the compound (39) in the reaction scheme A-24.

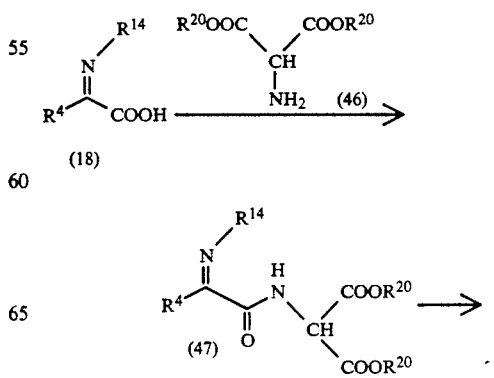

-continued
[Reaction scheme A-26]

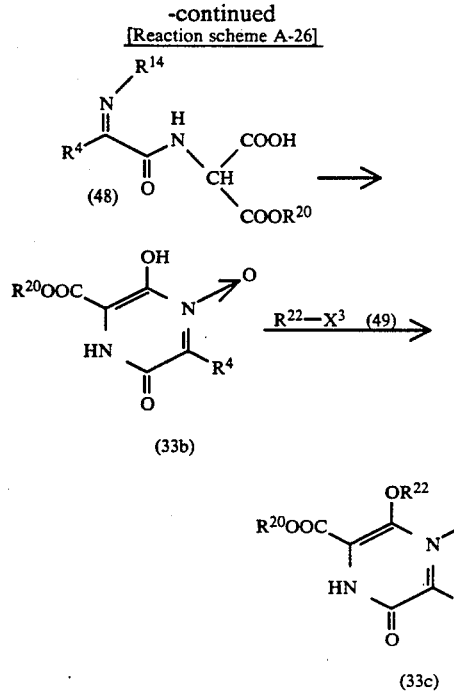

(33c)

[in the formula, $R^4$, $R^{14}$, $R^{20}$ and $X^3$ are the same as defined above; and $R^{22}$ is a lower alkyl group, a cycloalkyl group or a phenyl-lower alkyl group.]

The reaction between the compound (18) and the compound (46) is carried out under the same conditions as in the reaction between the compound (36) and the compound (18) in the reaction scheme A-24.

The reaction for converting the compound (47) into a compound (48) is carried out under the same conditions as in the reaction for converting the compound (33) to the compound (34) in the reaction scheme A-23.

The reaction for converting the compound (48) into a compound (33b) can be carried out under the same conditions as in the reaction between the compound (36) and the compound (18) in the reaction scheme A-24.

The reaction is carried out particularly preferably according to a method using a phosphorus compound such as triphenylphosphine-2,2'-dipyridyl disulfide or the like.

The reaction between the compound (33b) and the compound (49) can be carried out under the same conditions as in the reaction between the compound (38) and the compound (39) in the reaction scheme A-24.

The alkylation reaction for the compound (33b) can also be carried out by the use of other alkylating agent.

The reaction is carried out in a solvent in the presence or absence of a basic compound. As to the alkylating agent, there can be mentioned, for example, dimethyl sulfate; sulfonic acid esters such as methyl chlorosulfonate, methyl methanesulfonate, methyl trifluoromethanesulfonate and the like; trimethyloxonium tetrafluoroborate and diazomethane. As to the solvent, there can be mentioned, for example, lower alcohols such as methanol, ethanol, propanol and the like; ethers such as diethyl ether, tetrahydrofuran, dioxane, ethylene glycol monomethyl ether and the like; halogenated hydrocarbons such as dichloromethane, chloroform, carbon tetrachloride and the like; aromatic hydrocarbons such as benzene, toluene, xylene and the like; esters such as methyl acetate, ethyl acetate and the like; ketones such as acetone, methyl ethyl ketone and the like; polar solvents such as acetonitrile, dimethylformamide, dimethyl sulfoxide, hexamethylphosphoric triamide and the like; and their mixed solvents. The basic compound can be illustrated by, for example, inorganic bases such as sodium hydroxide, potassium hydroxide, sodium carbonate, potassium carbonate, sodium hydrogencarbonate, potassium hydrogencarbonate, sodium hydride and the like; alkali metals such as metallic sodium, metallic potassium and the like; alkali metal alcoholates such as sodium ethylate, sodium methylate and the like; and organic bases such as triethylamine, pyridine, N,N-dimethylaniline, N-methylmorpholine, diisopropylethylamine, 4-methylaminopyridine, DBN, DBU, DABCO and the like.

The desirable amount of the alkylating agent used is at least 1 mole, preferably about 1 to 5 moles per mole of the compound (33b). The reaction is carried out generally at $-30°$ to $150°$ C., preferably about $-20°$ to $100°$ C., and is completed in about 0.5 to 20 hours.

[Reaction scheme A-27]

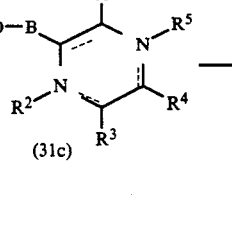

[in the formula, B, $R^2$, $R^3$, $R^4$, $R^5$, $X^4$ and the bondings at 1-, 2-, 3-, 4-, 5-, 6-positions in the pyrazine ring are the same as defined above; $R^{24}$ is a lower alkyl group, a cycloalkyl group or a phenyl-lower alkyl group; $R^{25}$ is a phenyl-lower alkyl group; M is a hydrogen atom or a salt of an alkali metal such as sodium, potassium or the like; and $R^{23}$ is a lower alkenyl group, a tetrahydropyranyl group or a lower alkoxy-lower alkyl group.]

The compound (50) wherein $R^{23}$ is a tetrahydropyranyl group can be produced by reacting the compound (31c) with dihydropyran in the presence of an acid in an appropriate solvent. The acid can be illustrated by, for example, mineral acids (e.g. hydrochloric acid, hydrobromic acid, sulfuric acid) and organic acids (e.g. p-toluenesulfonic acid). As to the solvent, there can be mentioned, for example, ethers such as dioxane, tetrahydrofuran and the like; halogenated hydrocarbons such as dichloromethane, chloroform, carbon tetrachloride and the like; polar solvents such as acetonitrile and the like; and their mixed solvents. The desirable amount of dihydropyran used is at least 1 mole, preferably 1 to 5 moles per mole of the compound (31c). The reaction proceeds favorably generally at −30° to 150° C., preferably at 0° to 100° C., and is completed generally in about 0.5 to 5 hours.

The compound (50) wherein $R^{23}$ is a lower alkenyl group or a lower alkoxy-lower alkyl group, can be produced by reacting the compound (31c) with a compound represented by the general formula $$R^{26}X^5 \qquad (55)$$

[in the formula, $R^{26}$ is a lower alkenyl group or a lower alkoxy-lower alkyl group; and $X^5$ is a halogen atom.]

The reaction between the compound (50) and the compound (52) is carried out generally in a suitable inert solvent in the presence or absence of a basic compound.

As to the basic compound and solvent, there can be used any basic compound and solvent mentioned in the reaction between the compound (31) and the compound (32) in the reaction scheme A-22. As to the solvent, there may also be used $R^{25}OH$ ($R^{25}$ is the same as defined above).

The desirable amount of the compound (52) used is at least 1 mole, preferably about 1 to 7 moles per mole of the compound (50). The reaction is carried out generally at 0° to 150° C., preferably at about 0 to 100° C., and is completed generally in about 10 minutes to 15 hours.

In the reaction, there may be added to the reaction system a phase transfer catalyst such as ammonium salt (e.g. tetra-n-butylammonium bromide, phenyltriethylammonium chloride), a crown ether (e.g. 18-crown-6-, benzo-18-crown-6, dibenzo-18-crown-6, dicyclohexano-18-crown-6, 12-crown-4, 15-crown-5) or the like.

The reaction between the compound (53) and the compound (51) or between the compound (50) and the compound (51) is carried out under the same conditions as in the reaction between the compound (50) and the compound (52).

The reaction for converting the compound (54) to a compound (31d) is carried out, when the $R^{23}$ of the compound (54) is a lower alkoxy-lower alkyl group, by treating the compound (54) in a mixture of a mineral acid (e.g. hydrobromic acid, hydrochloric acid) or an organic acid (e.g. p-toluenesulfonic acid) and a solvent (e.g. water, methanol, ethanol, isopropyl alcohol) generally at 0° to 150° C., preferably at room temperature to 120° C., or by hydrolyzing the compound (54).

This hydrolysis is carried out in a suitable solvent in the presence of an acid. As to the solvent, there can be mentioned, for example, water; lower alcohols such as methanol, ethanol, isopropyl alcohol and the like; ethers such as dioxane, tetrahydrofuran and the like; halogenated hydrocarbons such as dichloromethane, chloroform, carbon tetrachloride and the like; polar solvents such as acetonitrile and the like; and their mixed solvents. As the acid, there can be mentioned, for example, mineral acids such as hydrochloric acid, sulfuric acid, hydrobromic acid and the like; Lewis acids such as boron trifluoride, aluminum chloride, boron tribromide and the like; iodides such as sodium iodide, potassium iodide and the like; and mixtures of the above Lewis acid and the above iodide. The reaction proceeds favorably generally at 0° to 150° C., preferably at room temperature to 100° C., and is completed generally in about 0.5 to 15 hours.

The compound (54) wherein $R^3$ is a tetrahydropyranyl group or a lower alkenyl group, when hydrolyzed, can be converted into a compound (31d). The hydrolysis reaction can be carried out under any ordinary hydrolysis conditions. It is specifically carried out in the presence of a mineral acid (e.g. sulfuric acid, hydrochloric acid, nitric acid), an organic acid (e.g. acetic acid, aromatic sulfonic acid) or the like in a solvent such as water, alcohol (e.g. methanol, ethanol, isopropyl alcohol), ketone (e.g. acetone, methyl ethyl ketone), ether (e.g. dioxane, ethylene glycol diemthyl ether), acetic acid or their mixture. The reaction proceeds generally at 0 to 200° C., preferably at about room temperature to 150° C., and is completed generally in about 10 minutes to 15 hours.

[Reaction scheme A-28]

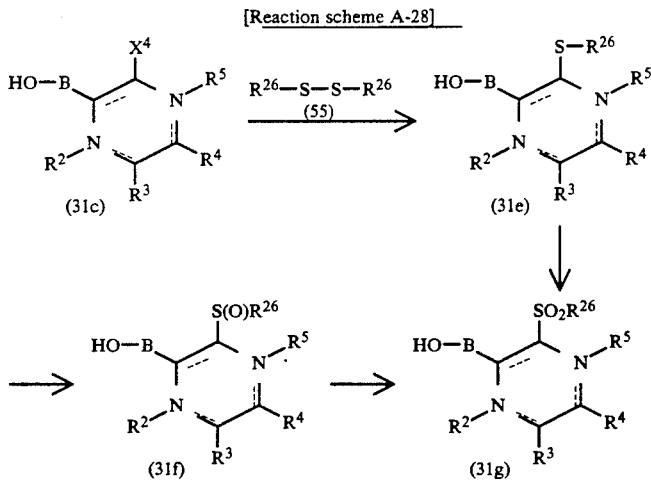

[in the formula, B, $R^2$, $R^3$, $R^4$, $R^5$, $X^4$ and the bonding states at 1-, 2-, 3-, 4-, 5- and 6-positions in the pyrazine ring are the same as defined above; and $R^{26}$ is a lower alkyl group.]

The reaction between the compound (31c) and the compound (55) can be carried out in a suitable solvent or in the absence of a solvent. As to the solvent, there can be used any solvent used in the reaction between the compound (1f) and the compound (6) in the reaction scheme A-3.

The reaction is completed in about 10 minutes to 5 hours generally at room temperature to 150° C., preferably at about room temperature to 100° C. The desirable amount of the compound (55) used is at least 1 mole, preferably 1 to 8 moles per mole of the compound (31c). The reaction for converting the compound (31e) into a compound (31f) and the compound (31f) into a compound (31g) is carried out in a suitable solvent in the presence of an oxidizing agent. The solvent can be illustrated by, for example, water; organic acids such as formic acid, acetic acid, trifluoroacetic acid and the like; alcohols such as methanol, ethanol and the like; halogenated hydrocarbons such as chloroform, dichloromethane and the like; and their mixed solvents. As the oxidizing agent, there can be mentioned, for example, peracids such as performic acid, peracetic acid, pertrifluoroacetic acid, permaleic acid, perbenzoic acid, m-chloroperbenzoic acid, o-carbonylperbenzoic acid and the like; hydrogen peroxide; sodium metaperiodate; dichromic acid; dichromates such as sodium dichromate, potassium dichromate and the like; permanganates such as potassium permanganate, sodium permanganate and the like; lead salts such as lead tetraacetate and the like; and sodium perboron hydride. The desirable amount of the oxidizing agent used is generally at least 1 mole, preferably 1 to 2 moles per mole of the starting material.

The reaction is carried out generally at −30° to 40° C., preferably at about −20° C. to room temperature, and is completed in about 10 minutes to 15 hours. In the reaction for converting the compound (31e) to a compound (31g), it is desirable that the oxidizing agent be used in an amount of at least 2 moles, preferably 2 to 4 moles per mole of the compound (31e). In other respects, the reaction can be carried out under the same conditions as in the reaction for converting the compound (31e) to the compound (31f).

[Reaction scheme A-29]

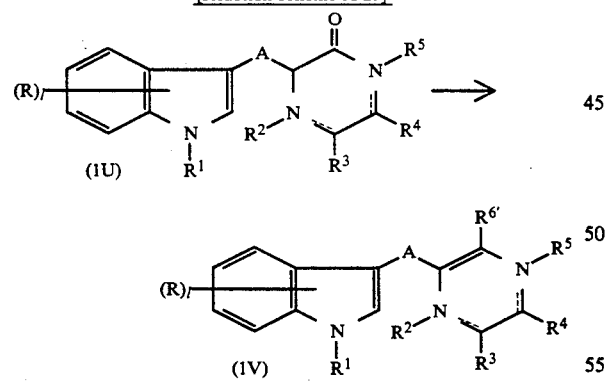

[in the formula, R, l, $R^1$, $R^2$, $R^3$, $R^4$, $R^5$ and A are the same as defined above; the bonding states at 1-, 2-, 3- and 4-positions in the pyrazine ring are single bonds or double bonds; and $R^{6'}$ is a lower alkoxy group.]

The reaction for converting the compound (1U) to a compound (1V) is carried out by reacting the above-formed compound with an alkylating agent in a suitable solvent in the presence or absence of a catalyst. As to the alkylating agent, there can be mentioned diazomethane; trimethylsilyldiazomethane; alkyl halides such as methyl iodide and the like; lower alkyl sulfonates such as $FSO_3CH_3$, $CF_3SO_3CH_3$, $(CH_3)_2SO_4$ and the like; lower alkyloxonium halide chelate salts such as $(CH_3)_3O^+BF_4^-$, $(C_2H_5)_3O^+BF_4^-$ and like; and lower alkoxy-oxonium halide chelate salts such as $(C_2H_5O)_3O^+BF_4^-$ and the like. The solvent can be illustrated by, for example, lower alcohols such as methanol, ethanol, propanol and the like; ethers such as dioxane, tetrahydrofuran, diethyl ether, ethylene glycol monomethyl ether and the like; halogenated hydrocarbons such as dichloromethane, chloroform, carbon tetrachloride and the like; and their mixed solvents. The catalyst can be illustrated by, for example, Lewis acids such as boron tribromide, boron trifluoride, diethyl ether and the like. The alkylating agent, when it is a diazomethane, is used generally in a large excess, preferably in about 10 to 20 equivalents relative to the raw material compound. The alkylating agent, when other compound is used, is used in an amount of at least 1 mole, preferably 1 to 3 moles per mole of the raw material compound. The reaction is carried out generally at about −30° to 100° C., preferably at about −20° to 70° C., and is completed generally in about 0.5 to 20 hours.

[Reaction scheme A-30]

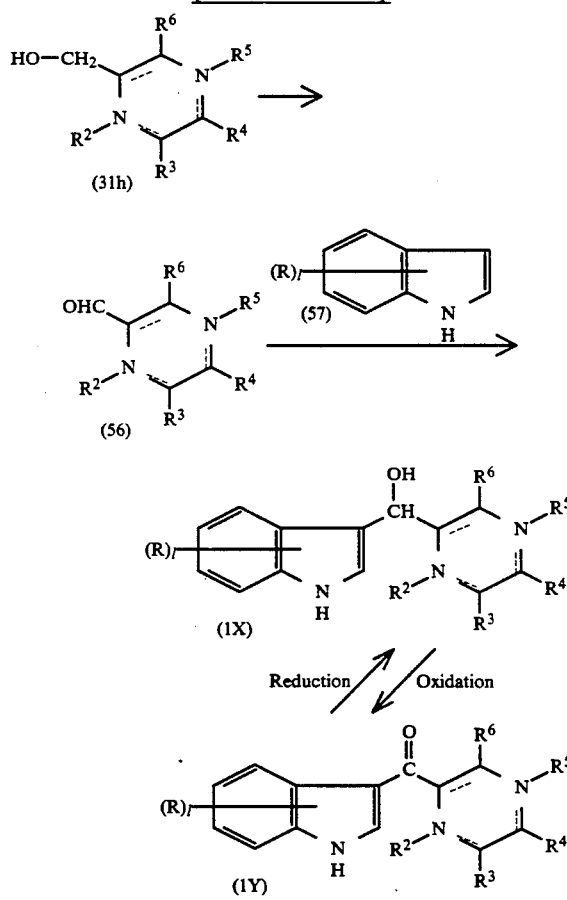

[in the formula, B, $R^2$, $R^3$, $R^4$, $R^5$, $R^6$, R, l and the bonding states at 1-, 2-, 3-, 4-, 5- and 6-positions in the pyrazine ring are the same as defined above.]

The reaction for converting the compound (31h) to a compound (56) can be carried out in an appropriate solvent in the presence of an oxidizing agent. The oxidizing agent can be illustrated by, for example, pyridinium chromates such as pyridinium chlorochromate, pyridinium dichrochromate and the like; dimethyl sulfoxide-oxalyl chloride; dichromic acid; dichroamtes such as sodium dichroamte, potassium dichromate and the like; permanganic acid; and permanganates such as potassium permanganate, sodium permanganate and the like.

The solvent can be illustrated by, for example, water; organic acids such as formic acid, acetic acid, trifluoroacetic acid and the like; alcohols such as methanol, ethanol and the like; halogenated hydrocarbons such as chloroform, dichloromethane and the like; ethers such as tetrahydrofuran, diethyl ether, dioxane and the like; dimethyl sulfoxide; dimethylformamide; and their mixed solvents. The desirable amount of the oxidizing agent used is generally at least 1 mole, preferably 1 to 2 moles per mole of the starting material. The reaction is completed in about 1 to 7 hours generally at about 0° to 100° C., preferably at about 0° to 70° C.

The reaction between the compound (56) and the compound (57) is carried out generally in a suitable inert solvent in the presence of a basic compound. As to the inert solvent, there can be mentioned, for example, aromatic hydrocarbons such as benzene, toluene, xylene and the like; ethers such as tetrahydrofuran, dioxane, diethylene glycol dimethyl ether and the like; lower alcohols such as methanol, ethanol, isopropanol and the like; acetic acid; ethyl acetate; acetone; acetonitrile; dimethyl sulfoxide; dimethylformamide; and hexamethylphosphoric triamide. As to the basic compound, there can be mentioned, for example, carbonates such as sodium carbonate, potassium carbonate, sodium hydrogencarbonate, potassium hydrogencarbonate and the like; metal hydroxides such as sodium hydroxide, potassium hydroxide and the like; potassium; sodium; metal alcoholates such as sodium methylate, sodium ethylate and the like; and organic bases such as pyridine, ethyldiisopropylamine, dimethylaminopyridine, triethylamine, 1,5-diazabicyclo[4,3,0]nonene-5 (BBN), 1,8-diazabicyclo[5,4,0]undecene-7 (DBU), 1,4-diazabicyclo[2,2,2]octane (DABCO) and the like. The proportions of the compound of the general formula (1h) and the compound of the general formula (11) used are not particularly restricted and can be selected suitably from a wide range; however, desirably the latter is used in an amount of at least about 1 mole, preferably about 1 to 5 moles per mole of the former. The reaction is carried out generally at about 0° to 200° C., preferably at about 0° to 170° C., and is completed generally in about 30 minutes to 30 hours.

The oxidation reaction for the compound (1X) can be carried out under the same conditions as in the oxidation reaction for converting the compound (31h) to the compound (56). As to the oxidizing agent used therein, there can be used DDQ, in addition to the oxidizing agents mentioned above.

In the reduction reaction for the compound (1Y), there can preferably be used a reduction method using a reducing agent for hydrogenation. As to the reducing agent for hydrogenation, there can be mentioned, for example, sodium boron hydride, lithium boron hydride, tetrabutylammonium boronhydride and calcium boron hydride. The amount of the reducing agent used is at least 1 mole, preferably 1 to 5 moles per mole of the raw material compound. This reduction reaction is carried out generally using a suitable solvent such as water, lower alcohol (e.g. methanol, ethanol, isopanol), ether (e.g. tetrahydrofuran, diethyl ether, diisopropyl ether, diglyme) or their mixture, generally at about −60 to 150° C., preferably at −30° to 100° C. in about 10 minutes to 5 hours.

The compound (1H) as a starting material can be produced in accordance with, for example, the following reaction scheme A-31.

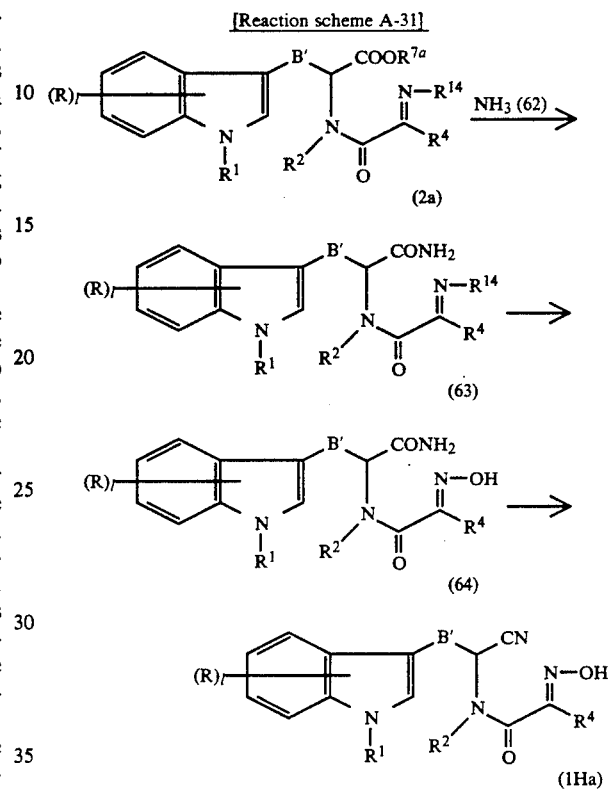

[Reaction scheme A-31]

[in the formula, R, l, R$^1$, B', R$^2$, R$^{14}$, l R$^4$ and R$^{7a}$ are the same as defined above.]

The reaction between the compound (2a) and the compound (62) can be carried out under the same conditions as in the reaction for reacting the compound (2) with the compound (3), i.e. the reaction of a carboxylic acid halide with an amine in the reaction scheme A-1. The reaction for converting the compound (63) into a compound (64) can be carried out under the same conditions as in the reaction for converting the compound (12) into the compound (13) in the reaction scheme A-6. The reaction for converting the compound (64) into a compound (1Ha) can be carried out in a suitable solvent in the presence of a dehydrating agent.

The solvent can be illustrated by halogenated hydrocarbons such as dichloromethane, chloroform and the like. The dehydrating agent can be illustrated by sulfonamides such as Et$_3$N$^+$SO$_2$N$^-$COOMe, ClSO$_2$NCO and the like. The desirable amount of the dehydrating agent used is at least 1 mole, preferably 1 to 5 moles per mole of the compound (64). The reaction is completed in about 1 to 10 hours generally at 0 to 100° C., preferably at about 0° to 70° C.

Specific examples of production according to the above reaction schemes A-1 to A-31 are described later in Reference Examples A-1 to A-25, Examples A-1 to A-59 and Reference Examples E-1 to E-30.

The known NF-1616-904 substance (201) which was the basis for development of the novel indole derivatives represented by the general formula (1) according to the present invention

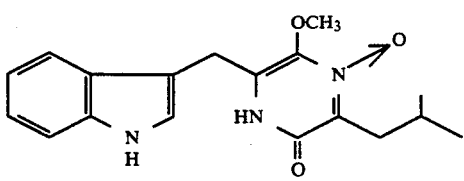
(201)

can be obtained according to the following method, at a high yield and a high purity on an industrial scale without using any troublesome separation method.

That is, the NF-1616-904 substance represented by the following formula

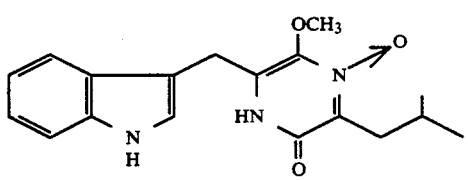
(201)

can be produced by reacting a pyrazine derivative represented by the general formula

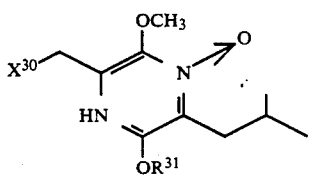
(202)

[in the formula, $R^{31}$ is a phenyl-lower alkyl group which may have, on the phenyl ring, substituents selected from the group consisting of a halogen atom, a lower alkyl group, a nitro group, an amino group and a lower alkoxy group; and $X^{30}$ is a halogen atom, a lower alkanesulfonyloxy group, an arylsulfonyloxy group or an aralkylsulfonyloxy group] with indole or its salt (203) to obtain an indole derivative represented by the general formula

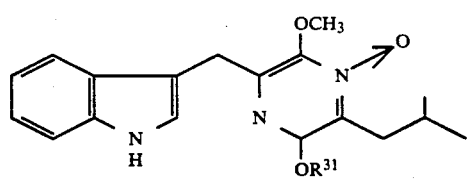
(204)

[in the formula, $R^{31}$ is the same as defined above], then reducing the indole derivative.

The pyrazine derivative of the general formula (202) used as a starting material in the above can be produced by the following method.

[Reaction scheme B-1]

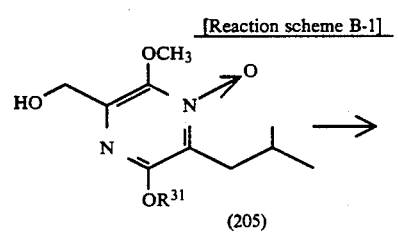
(205)

-continued
[Reaction scheme B-1]

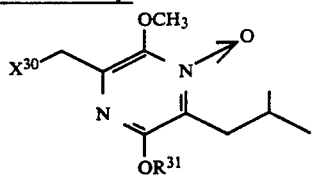
(202)

[in the formula, $R^{31}$ and $X^{30}$ are the same as defined above.]

The compound (202) wherein $X^{30}$ is a lower alkanesulfonyloxy group, an arylsulfonyloxy group or an aralkylsulfonyloxy group, can be produced by reacting the compound (205) with a compound represented by the general formula $$R^{32}X^{31} \qquad (206)$$

[in the formula, $R^{32}$ is a lower alkanesulfonyl group, an arylsulfonyl group or an aralkylsulfonyl group; and $X^{31}$ is a halogen atom].

The reaction between the compound of the general formula (205) and the compound (206) is carried out generally in an appropriate solvent in the presence or absence of a basic compound. As to the solvent, there can be mentioned, for example, aromatic hydrocarbons such as benzene, toluene, xylene and the like; halogenated hydrocarbons such as chloroform, dichloromethane, carbon tetrachloride and the like; ethers such as tetrahydrofuran, dioxane, diethylene glycol dimethyl ether and the like; acetic acid; ethyl acetate; acetone; acetonitrile; dimethyl sulfoxide; dimethylformamide; hexamethylphosphoric triamide and the like. As to the basic compound, there can be mentioned, for example, carbonates such as sodium carbonate, potassium carbonate, sodium hydrogencarbonate, potassium hydrogencarbonate and the like; metal hydroxides such as sodium hydroxide, potassium hydroxide and the like; sodium hydride; potassium; sodium; sodium amide; metal alcoholates such as sodium methylate, sodium ethylate and the like; and organic bases such as pyridine, ethyldiisopropylamine, diemthylaminopyridine, triethylamine, 1,5-diazabicyclo[4,3,0]nonene-5 (DBN), 1,8-diazabicyclo[5,4,0]undecene-7 (DBU), 1,4-diazabicyclo[2,2,2]octane (DABCO) and the like. The proportions of the compound of the general formula (205) and the compound of the general formula (206) are not particularly restricted and can be selected suitably from a wide range; however, desirably the latter is used in an amount of at least about 1 mole, preferably about 1 to 1.5 moles per mole of the former. The reaction is carried out generally at about $-78$ to $100°$ C., preferably at about $-30°$ to $70°$ C., and is completed generally in about 30 minutes to 30 hours.

The compound (202) wherein $X^{30}$ is a halogen atom, can also be obtained by reacting the compound (202) wherein $X^{30}$ is a lower alkanesulfonyloxy group, an arylsulfonyloxy group or an aralkylsulfonyloxy group, with a halogenating agent such as tetraalkylammonium halide (e.g. tetra-n-butylammonium iodide, tetra-n-butylammonium bromide), alkali metal halide (e.g. sodium iodide), alkali metal halide plus phase transfer catalyst (e.g. 18-crown-6), or the like in a suitable solvent.

As to the solvent, there can be used any solvents used in the reaction between the compound (205) and the compound (206). The desirable amount of the halogenating agent used is at least 1 mole, preferably about 1 to 2 moles per mole of the starting material. The reaction is carried out generally at 0 to 100° C., preferably at about 0° to 70° C., and is completed generally in about 10 minutes to 5 hours.

The compound (205) as a starting material which is a pyrazine derivative, can be produced by, for example, the following method.

100° C., and is completed generally in about 0.5 to 5 hours.

The compound (208) wherein $R^{33}$ is a lower alkenyl group or a lower alkoxy-lower alkyl group, can be produced by reacting the compound (207) with a compound represented by $$R^{35}X^{32} \qquad (211)$$

[in the formula, $R^{35}$ is a lower alkenyl group or a lower alkoxy-lower alkyl group; and $X^{32}$ is a halogen atom].

[Reaction scheme B-2]

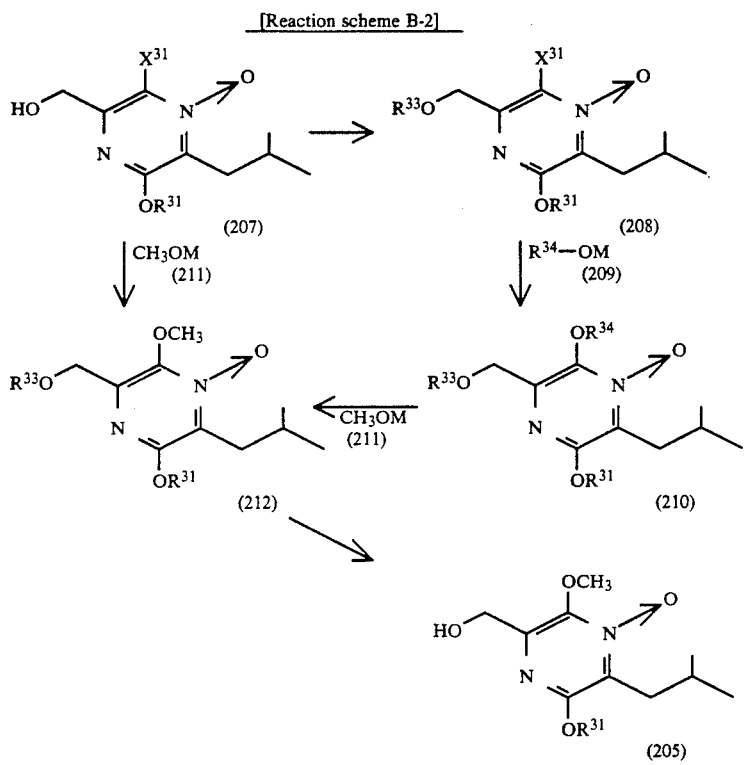

[in the formula, $R^{31}$ and $X^{31}$ are the same as defined above; $R^{33}$ is a lower alkenyl group, a tetrahydropyranyl group or a lower alkoxy-lower alkyl group; $R^{34}$ is a phenyl-lower alkyl group which may have, on the phenyl ring, substituents selected from the group consisting of a halogen atom, a lower alkyl group, a nitro group, an amino group and a lower alkoxy group; and M is a hydrogen atom or a salt of an alkali metal such as sodium, potassium or the like.]

The compound (208) wherein $R^{33}$ is a tetrahydropyranyl group, can be produced by reacting the compound (207) with dihydropyran in the presence of an acid in an appropriate solvent. The acid can be illustrated by, for example, mineral acids such as hydrochloric acid, hydrobromic acid, sulfuric acid and the like, and organic acids such as p-toluenesulfonic acid and the like. As to the solvent, there can be mentioned, for exmaple, ethers such as dioxane, tetrahydrofuran and the like; halogenated hydrocarbons such as dichloromethane, chloroform, carbon tetrachloride and the like; polar solvents such as acetonitrile and the like; and their mixed solvents. The desirable amount of the dihydropyran used is at least 1 mole, preferably 1 to 5 moles per mole of the compound (207). The reaction proceeds favorably generally at −30 to 150° C., preferably 0° to The reaction between the compound (207) and the compound (211) is carried out in a suitable solvent in the presence of a basic compound. The solvent can be illustrated by, for example, water; ethers such as diethyl ether, tetrahydrofuran, dioxane, ethylene glycol monomethyl ether and the like; aromatic hydrocarbons such as benzene, toluene, xylene and the like; esters such as methyl acetate, ethyl acetate and the like; ketones such as acetone, methyl ethyl ketone and the like; polar solvents such as acetonitrile, dimethylformamide, dimethyl sulfoxide, hexamethylphosphoric triamide and the like; and their mixed solvents. The basic compound can be illustrated by, for example, silver oxide; potassium fluoride; inorganic bases such as sodium hydride and the like; and organic bases such as triethylamine, diisopropylethylamine, pyridine, N,N-dimethylaniline, dimethylaminopyridine, N-methylmorpholine, 4-methylaminopyridine, 1,5-diazabicyclo[4,3,0]nonene-5 (DBN), 1,8-diazabicyclo[5,4,0]undecene-7 (DBU), 1,4-diazabicyclo[2,2,2]octane (DABCO) and the like. The compound (11) is used in an amount of generally 1 mole, preferably 1 to 10 moles per mole of the compound (207). The reaction is carried out generally at 0° to 150° C., preferably at about room temperature to 100° C., and is completed generally in about 0.5 to 80 hours.

The reaction between the compound (208) and the compound (209) is carried out generally in a suitable solvent in the presence or absence of a basic compound.

As to the basic compound and solvent, there can be used all the basic compounds and solvents mentioned with respect to the reaction between the compound (205) and the compound (206) in the reaction scheme B-1. As to the solvent, there may also be used $R^{34}OH$ ($R^{34}$ is the same as defined above).

The desirable amount of the compound (209) used is at least 1 mole, preferably 1 to 7 moles per mole of the compound (208). The reaction is carried out generally at 0° to 150° C., preferably at about 0° to 100° C., and is completed generally in about 10 minutes to 10 hours.

To the system of the above reaction may be added an ammonium salt such as tetra-n-butylammonium bromide, phenyltriethylammonium chloride or the like, or a phase transfer catalyst such as crown ether (e.g. 18-crown-6, benzo-18-crown-6, dibenzo-18-crown-6, dicyclohexano-18-crown-6, 12-crown-4, 15-crown-5) or the like.

The reaction between the compound (219) and the compound (211) or the reaction between the compound (208) and the compound (211) is carried out under the same conditions as in the reaction between the compound (208) and the compound (209).

The reaction for converting the compound (212) wherein $R^{33}$ is a lower alkoxy-lower alkyl group, to a compound (205) is carried out by treating the compound (212) in a mixture of a mineral acid (e.g. hydrobromic acid, hydrochloric acid) or an organic acid (e.g. p-toluenesulfonic acid) and a solvent (e.g. water, methanol, ethanol, isopropyl alcohol) generally at 0 to 150° C., preferably at room temperature to 120° C., or by hydrolyzing the compound (212).

This hydrolysis is carried out in an appropriate solvent in the presence of an acid. As to the solvent, these can be mentioned, for example, water; lower alcohols such as methanol, ethanol, isopropyl alcohol and the like; ethers such as dioxane, tetrahydrofuran and the like; halogenated hydrocarbons such as dichloromethane, chloroform, carbon tetrachloride and the like; polar solvents such as acetonitrile and the like; and their mixed solvents. As to the acid, there can be mentioned, for example, mineral acids such as hydrochloric acid, sulfuric acid, hydrobromic acid and the like; Lewis acids such as boron trifluoride, aluminum chloride, boron tribromide and the like; iodides such as sodium iodide, potassium iodide and the like; and mixtures of the above Lewis acid and the above iodide. The reaction proceeds favorably generally at 0° to 150° C., preferably at room temperature to 100° C., and is completed generally in about 0.5 to 15 hours.

The compound (212) wherein $R^{33}$ is a tetrahydropyranyl group or a lower alkenyl group, can be converted to a compound (205) by hydrolyzing the compound (212).

In this hydrolysis reaction there can be applied any reaction conditions used in ordinary hydrolysis. The reaction is specifically carried out in the presence of a mineral acid (e.g. sulfuric acid, hydrochloric acid, nitric acid), an organic acid (e.g. acetic acid, aromatic sulfonic acid) or the like in a solvent such as water, alcohol (e.g. methanol, ethanol, isopropyl alcohol), ketone (e.g. acetone, methyl ethyl ketone), ether (e.g. dioxane, ethylene glycol dimethyl ether), acetic acid or their mixed solvent. The reaction proceeds generally at 0° to 200° C., preferably at about room temperature to 150° C., and is completed in about 0.5 to 15 hours.

[Reaction scheme B-3]

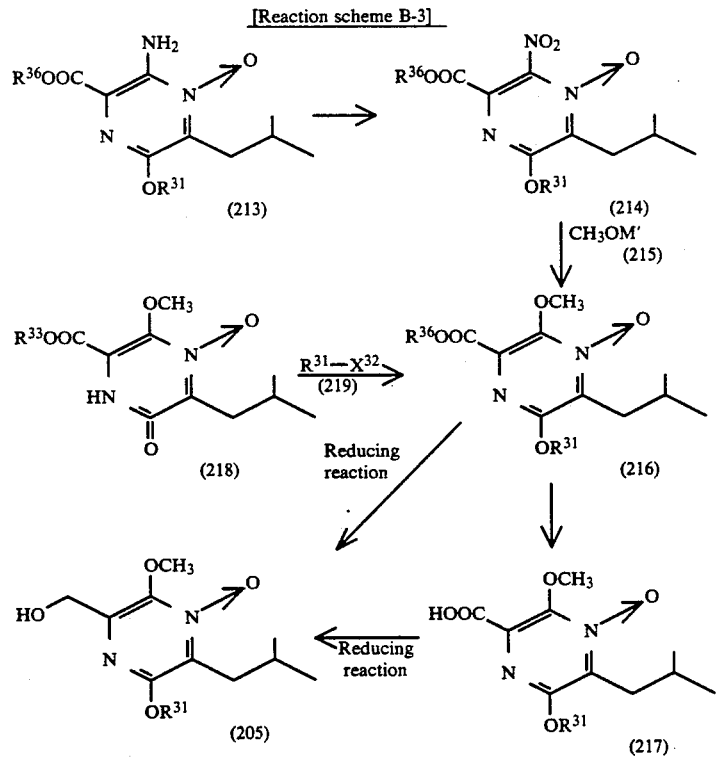

[in the formula, $R^{31}$ and $R^{32}$ are the same as defined above; $R^{36}$ is a lower alkyl group, a lower alkanoyl group, a succinimyl group, a lower alkoxycarbonyl group, a thiazolidinyl group which may have a thio group as a substituent, a methyleneiminium group having a lower alkyl group as a substituent, or a group —SR$^{37}$ (R$^{37}$ is a pyridyl group, a thiazolidinyl group, a lower alkyl group, a cycloalkyl group, a phenyl group or a phenyl-lower alkyl group); and M' is an alkali metal such as sodium, potassium or the like.]

The reaction for converting the compound (213) into a compound (214) is carried out in an appropriate solvent in the presence of an oxidizing agent.

As to the oxidizing agent, there can be mentioned, for example, peracids such as performic acid, permaleic acid, peracetic acid, pertrifluoroacetic acid and the like. The solvent can be illustrated by, for example, water; organic acids such as formic acid, acetic acid, trifluoroacetic acid and the like; halogenated hydrocarbons such as chloroform, dichloromethane and the like; and their mixed solvents. The desirable amount of the oxidizing agent used is at least equimolar, generally a large excess to the compound (213). The reaction is carried out generally at 0° to 150° C., preferably at about 0° to 100° C., and is completed generally in about 1 to 15 hours.

The reaction between the compound (214) and the compound (215) is carried out under the same conditions as in the reaction between the compound (208) and the compound (209) in the reaction scheme B-2.

The reaction for converting the compound (216) to a compound (217) is carried out under the same conditions as in the hydrolysis reaction for the compound (212) wherein R$^{33}$ is a tetrahydropyranyl group or a lower alkenyl group, in the reaction scheme B-2. The reaction may be carried out by using, besides the acid, a basic compound such as sodium carbonate, potassium carbonate, sodium hydroxide, potassium hydroxide, barium hydroxide or the like.

In the reduction reaction for the compound (216) or (217), there is preferably applied a reduction method using a reducing agent for hydrogenation. As to the reducing agent for hydrogenation, there can be mentioned, for example, lithium aluminum hydride, sodium boron hydride, diisobutylaluminum hydride, diborane, lithium boron hydride and calcium boron hydride. The desirable amount of the reducing agent used is generally at least 1 mole, preferably 1 to 5 moles per mole of the compound (216) or (217).

The solvent can be illustrated by, for example, water; lower alcohols such as methanol, ethanol, isopropyl alcohol and the like; ethers such as tetrahydrofuran, dioxane, diethyl ether, diglyme and the like; halogenated hydrocarbons such as dichloromethane, chloroform, carbon tetrachloride and the like; acetonitrile; dimethylformamide; and their mixed solvents. The reaction is carried out generally at —60° to 70° C., preferably at —30° to 50° C., and is completed in about 10 minutes to 20 hours. When there is used lithium aluminum hydride or diborane as the reducing agent, it is preferable to use an anhdyrous solvent such as diethyl ether, tetrahydrofuran, diglyme or the like. When there is used diisobutylaluminum hydride, there may be used, besides the above ether type solvent, an aromatic hydrocarbon such as benzene, toluene, xylene or the like.

The reaction between the compound (218) and the reaction (219) is carried out under the same conditions as in the reaction between the compound (208) and the compound (211) in the reaction scheme B-2.

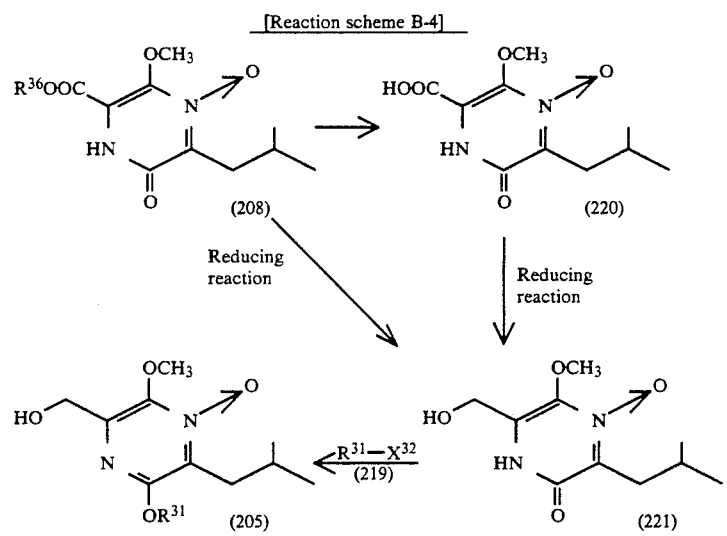

[Reaction scheme B-4]

[in the formula, R$^{31}$, X$^{32}$ and R$^{36}$ are the same as defined above.]

The reaction for converting the compound (218) into a compound (220) is carried out under the same conditions as in the reaction for converting the compound (216) into the compound (217), in the reaction scheme B-3.

The reducing reaction for the compound (218) or (220) is carried out under the same conditions as in the reduction reaction for the compound (216) or the compound (217) in the reaction scheme B-3.

The reaction between the compound (221) and the compound (219) is carried out under the same conditions as in the reaction between the compound (218) and the compound (219) in the reaction scheme B-3.

The compound (207) used as a starting material can be produced by, for example, the following method.

[Reaction scheme B-5]

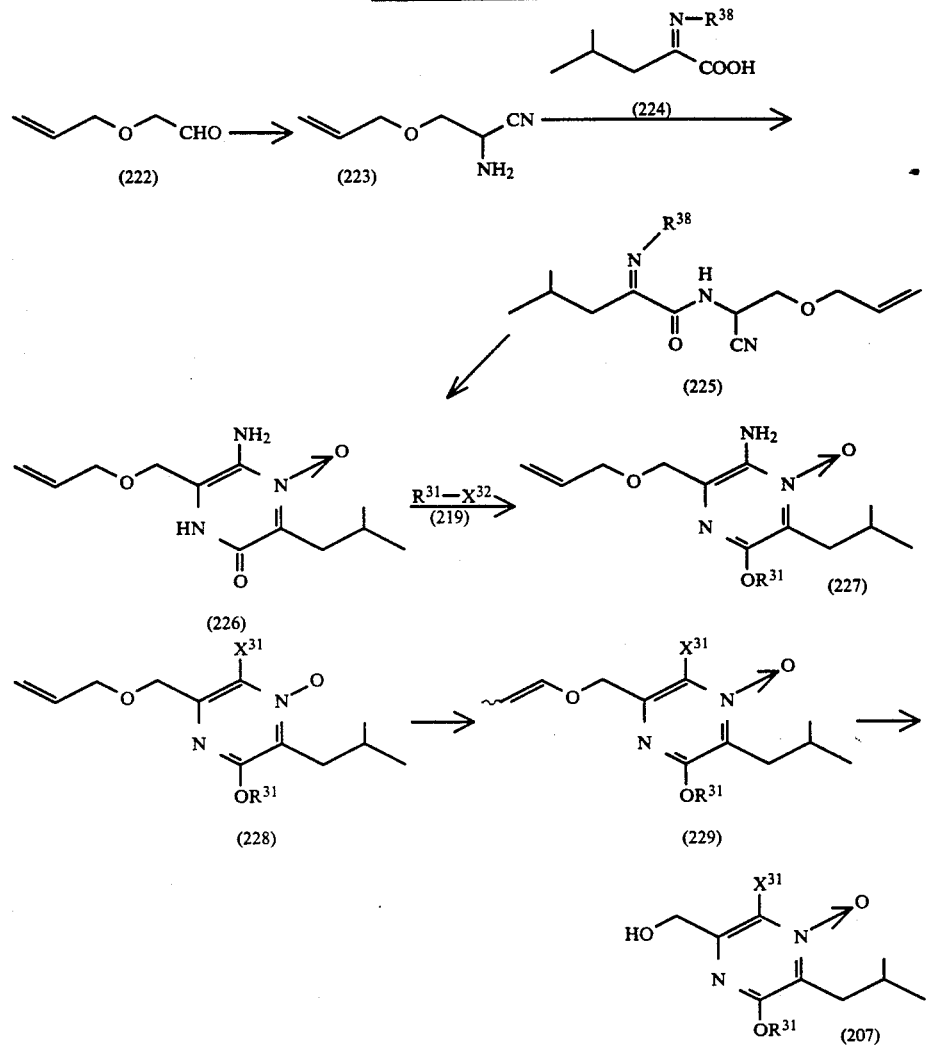

[in the formula, $R^{31}$, $X^{31}$ and $x^{32}$ are the same as defined above; and $R^{38}$ is a hydroxy group, a phenyl-lower alkoxy group, a tetrahydropyranyloxy group, a tri-lower alkylsilyloxy group or a lower alkoxy-lower alkoxy group.]

The reaction for converting the compound (222) into a compound (223) is generally called the strecker method, and the compound (223) can be obtained, for example, by reacting the compound (222) with an ammonium halide (e.g. ammonium chloride) and a metal cyanide (e.g. sodium cyanide, potassium cyanide) in a solvent such as water, ether (e.g. diethyl ether, tetrahydrofuran, dioxane), ammonium water or the like or their mixed solvent. The desirable amounts of the ammonium halide and metal cyanide used are each at least 1 mole, preferably about 1 to 2 moles per mole of the compound (222). The reaction is carried out generally at 0° to 150° C., preferably at about 0° to 100° C., and is completed in about 5 to 80 hours.

The reaction between the compound (223) and the compound (224) is carried out according to an ordinary amide bond forming reaction. The amide bond forming reaction can be carried out by various known methods, for example, (a) a mixed acid anhydride method, for example, a method wherein a carboxylic acid (224) is reacted with an alkyl halocarboxylate and the resulting mixed acid anhydride is reacted with an amine (223); (b) an activated ester method, for example, a method wherein a carboxylic acid (224) is converted to an activated ester such as p-nitrophenyl ester, N-hydroxysuccinimide ester, 1-hydroxybenzotriazole ester or the like and the activated ester is reacted with an amine (223); (c) a carbodiimide method, that is, a method wherein a carboxylic acid (224) is condensed with an amine (223) in the presence of an activating agent such as dicyclohexylcarbodiimide, carbonyldiimidazole or the like; (d) other methods, for example, a method wherein a carboxylic acid (224) is converted into a corresponding carboxylic acid anhydride with a dehydrating agent such as acetic anhydride or the like and the carboxylic acid anhydride is reacted with an amine (223), a method wherein an ester between a carboxylic acid (224) and a lower alcohol is reacted with an amine (223) under a high pressure and a high temperature, and a method wherein an acid halide of a carboxylic acid (224), i.e. a carboxylic acid halide is reacted with an amine (223). The amide bond forming reaction can also be carried out by a method wherein a carboxylic acid (224) is activated by a phosphorus compound such as triphenylphosphine, diethyl chlorophosphate or the like and the activated carboxylic acid is reacted with an amine (223), a method wherein a carboxylic acid (224) is converted to N-carboxyaminoacid anhdyride with phosgene, trichloromethyl chloroformate or the like and the anhydride is reacted with an amine (223), and so forth.

In the mixed acid anhydride method (a), the mixed acid anhydride used is obtained by an ordinary Schotten-Baumann reaction and is reacted with an amine (223) ordinarily without being isolated, whereby a compound of the general formula (225) can be produced. The Schotten-Baumann reaction is carried out in the presence of a basic compound. As the basic compound, there are used compounds conventionally used in the Schotten-Baumann reaction. They are illustrated by, for example, organic bases such as triethylamine, trimethylamine, pyridine, dimethylaniline, N-methylmorpholine, 4-dimethylaminopyridine, 1,5-diazabicyclo-[4,3,0]nonene-5 (DBN), 1,8-diazabicyclo[5,4,0]undecene-7 (DBU), 1,4-diazabicyclo[2,2,2]octane (DABCO) and the like, and inorganic bases such as potassium carbonate, sodium carbonate, potassium hydrogencarbonate, sodium hydrogen-carbonate and the like. The reaction is carried out at about −20° to 100° C., preferably 0° to 50° C. for about 5 minutes to 10 hours, preferably about 5 minutes to 2 hours. The reaction of the mixed acid anhydride obtained, with an amine (223) is carried out at about −20° to 150° C., preferably 10° to 50° C. for about 5 minutes to 10 hours, preferably about 5 minutes to 5 hours. The mixed acid anhydride method is carried out generally in a suitable solvent conventionally used in the method, such as halogenated hydrocarbon (e.g. methylene chloride, chloroform, dichloroethane, aromatic hydrocarbon (e.g. benzene, toluene, xylene), ether (e.g. diethyl ether, dioxane, diisopropyl ether, tetrahydrofuran, dimethoxyethane), ester (e.g. methyl acetate, ethyl acetate), aprotic polar solvent (e.g. 1,1,3,3-tetramethylurea, N,N-dimethylformamide, dimethyl sulfoxide, hexamethylphosphoric triamide) or the like, or in a mixed solvent or in the absence of any solvent. As to examples of the alkyl halocarboxylate used in the production of the mixed acid anhydride, there can be mentioned methyl chloroformate, methyl bromoformate, ethyl chloroformate, ethyl bromoformate and isobutyl chloroformate. The alkyl halocarboxylate is used in an amount of generally at least 1 mole, preferably about 1 to 1.5 moles per mole of the amine (223). The preferable proportion of the carboxylic acid (224) used is generally at least 1 mole, preferably about 1 to 1.5 moles per mole of the amine (223).

The activated ester method (b), when there is used, for example, N-hydroxysuccinimide ester, is carried out in an appropriate solvent giving no adverse effect on the reaction, in the presence or absence of a basic compound. As the basic compound, there can be used any basic compounds used in the Schotten-Baumann reaction. As to the solvent, there can be specifically mentioned, for example, halogenated hydrocarbons such as methylene chloride, chloroform, dichloroethane and the like; aromatic hydrocarbons such as benzene, toluene, xylene and the like; ethers such as diethyl ether, dioxane, tetrahydrofuran, dimethoxyethane and the like; esters such as methyl acetate, ethyl acetate and the like; aprotic polar solvents such as N,N-dimethylformamide, dimethyl sulfoxide, hexamethylphosphoric triamide and the like; and their mixed solvents. The reaction is completed in 5 to 30 hours at 0° to 150° C., preferably at 10° to 100° C. The desirable proportions of the amine (223) and N-hydroxysuccinimide ester used are each generally at least 1 mole, preferably 1 to 2 moles per mole of the compound (224). To the reaction system may be added a condensing agent such as dicyclohexylcarbodiimide, carbonylimidazole or the like.

The compound (225) can also be obtained by reacting the amine (223) with the carboxylic acid (224) in the presence of a condensing agent which is a phosphorus compound such as triphenylphosphine, triphenylphosphine-2,2′-dipyridyl sulfide, diethyl chlorophosphate, diphenylphosphinyl chloride, phenyl N-phenylphosphoramine chloridate, diethyl cyanophosphate, bis(2-oxo-2-oxazolidinyl)phsophinic chloride or the like.

As to the basic compound, there can be used various known basic compounds; and there can be mentioned, for example, not only those basic compounds used in the Schotten-Baumann reaction, but also sodium hydroxide and potassium hydroxide. As to the solvent, there can be mentioned, besides the solvents used in the above-mentioned mixed acid anhydride method, for example, halogenated hydrocarbons such as dichloromethane, chloroform, carbon tetrachloride and the like; pyridine; acetone; acetonitrile; and mixed solvents consisting of two or more of the above.

The reaction is carried out generally at about −20° to 150° C., preferably at about 0° to 100° C., and is completed generally in about 5 minutes to 30 hours. The desirable amounts of the condensing agent and carboxylic acid (224) are each at least 1 mole, preferably about 1 to 2 moles per mole of the amine (223).

The reaction for converting the compound (225) into a compound (226) is completed generally in about 1 to 40 hours generally at about room temperature to 150° C., preferably at about room temeprature to 100° C.

The reaction between the compound (226) and the compound (219) is carried out under the same conditions as in the reaction between the compound (208) and the compound (211) in the reaction scheme B-2.

The reaction for converting the compound (227) into a compound (228) is carried out by reacting the compound (227) with a metal nitrite such as sodium nitrite, potassium nitrite or the like in the presence of an acid in a solvent such as water or the like to obtain a diazonium salt or reacting the compound (227) with a lower alkyl nitrite such as tert-butyl nitrite, isoamyl nitrite or the like in a solvent such as acetonitrile or the like to obtain a diazonium salt, then heating the diazonium salt at about 150 to 200° C or reacting the diazonium salt at about room temeprature to 150° C for about 10 minutes to 5 hours in the presence of a copper halide (e.g. cupric chlroide, cupric bromide, cuprous chloride, cuprous bromide), a copper halide mixture (e.g. cupric chloride-cuprous chloride), cuprous bromide-hydrobromic acid, cuprous chloride-hydrochloric acid, hydrobromic acid, potassium iodide, or an acid (e.g. hydrochloric acid) and a copper powder. The acid can be illustrated by, for example, hydrochloric acid, hydrobromic acid, sulfuric acid, tetrafluoroboric acid and hexafluorophosphoric acid. The desirable amounts of the acid and metal nitrite used are generally about 1 to 5 moles, preferably about 1 to 3 moles (the former) and generally at least about 1 mole, preferably about 1 to 3 moles (the latter) per mole of the compound (227).

The desirable amount of the copper halide used to be reacted with the diazonium salt is generally at least about 1 mole, preferably about 1 to 5 moles per mole of the compound (227).

The reaction for converting the compound (228) into a compound (229) is carried out in the presence or absence of a basic compound in the presence of a catalyst in an appropriate solvent. The basic ompound can be illustrated by, for example, organic bases such as triethylamine, trimethylamine, diisopropylamine, ethylamine, pyridine, dimethylaniline, N-methylmorpholine, 4-dimethylaminopyridine, DBN, DBU, DABSCO and the like. The solvent can be illustrated by, for example, water, alcohols (e.g. ethanol, methanol, isopropyl alcohol) and their mixed solvents.

The catalyst can be illustrated by, for example, a Wilkinson complex represented by

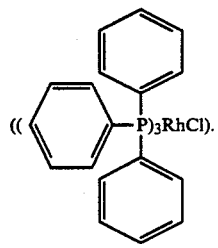

The desirable amount of the catalyst used is generally 0.1 to 1 time the weight of the compound (228).

The reaction is completed in about 1 to 5 hours generally at room temperature to 200° C., preferably at about room temperature to 150° C.

The reaction for converting the compound (229) into a compound (207) is carried out under the same conditions as in the hydrolysis reaction for the compound (212) wherein $R^{33}$ is a tetrahydropyranyl group or a lower alkenyl group, in the reaction scheme B-2.

tions as in the reaction for converting the compound (227) into the compound (228) in the reaction scheme B-5.

[Reaction scheme B-7]

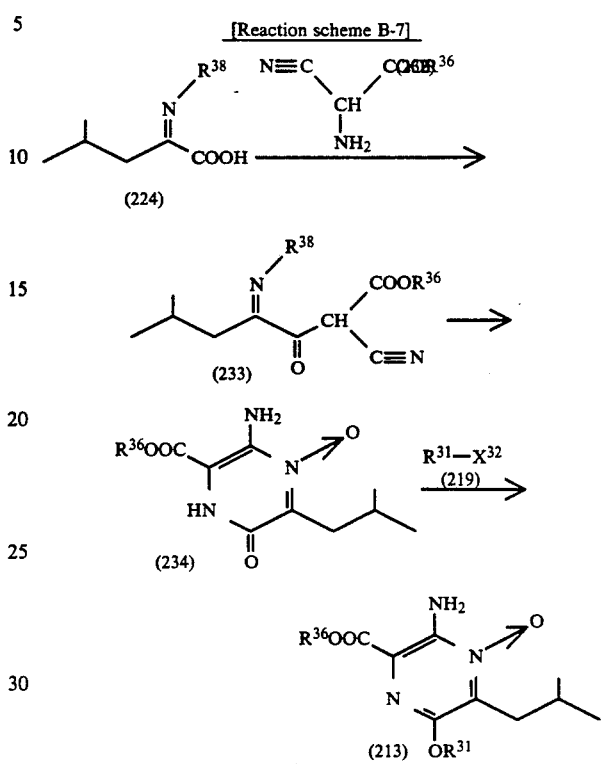

[in the formula, $R^{38}$, $R^{36}$, $X^{32}$ and $R^{31}$ are the same as defined above.]

The reaction between the compound (224) and the

[Reaction scheme B-6]

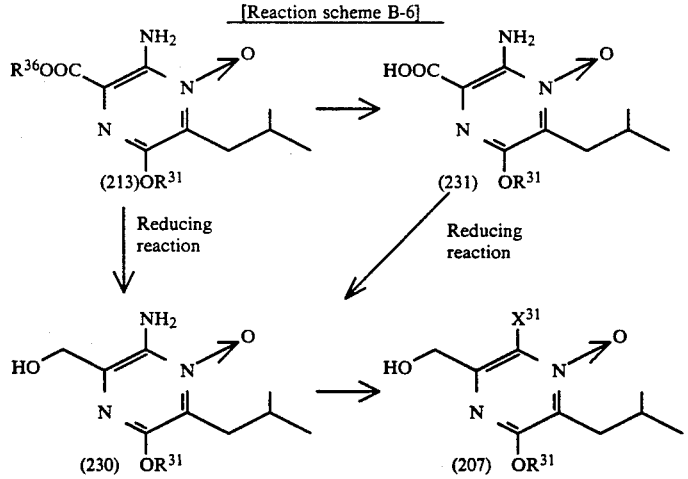

[in the formula, $R^{31}$, $R^{36}$ and $X^{31}$ are the same as defined above.]

The reducing reaction for the compound (213) or the compound (231) is carried out under the same conditions as in the reduction reaction for the compound (216) or (217) in the reaction scheme B-3.

The reaction for converting the compound (213) into the compound (231) is carried out under the same conditions as in the reaction for converting the compound (216) into the compound (217) in the reaction scheme B-3.

The reaction for converting the compound (230) into a compound (207) is carrie dout under the same condicompound (232) is carried out under the same conditions as in the reaction between the compound (223) and the compound (224) in the reaction scheme B-5.

The reaction for converting the compound (233) to a compound (234) is conducted under the same conditions as in the reaction for converting the compound (225) to the compound (226) in the reaction scheme B-5.

The reaction between the compound (234) and the compound (219) is carried out under the same conditions as in the reaction between the compound (208) and the compound (211) in the reaction scheme B-2.

The compound (218) used as a starting material can be produced by, for example, the following method.

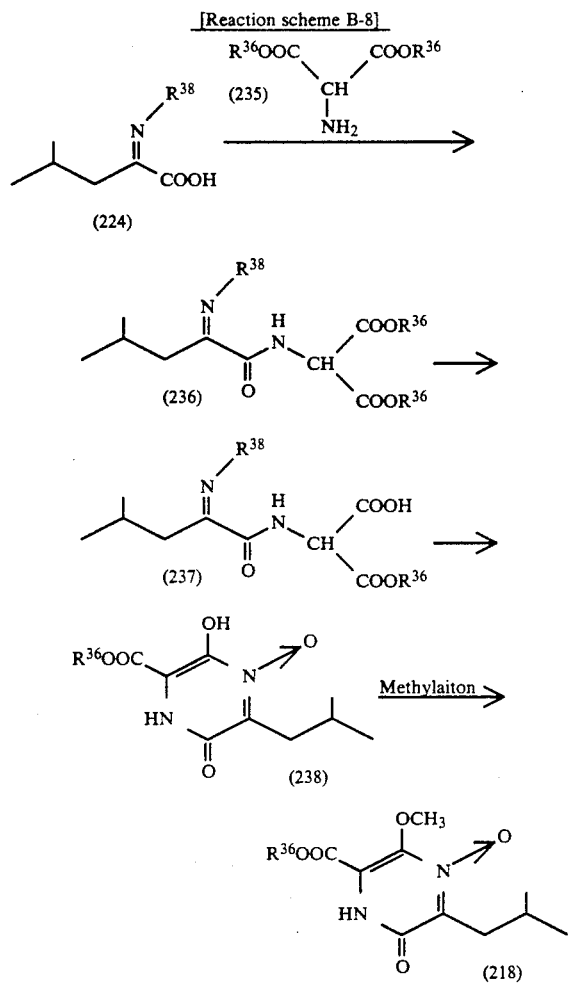

[Reaction scheme B-8]

[in the formula, $R^{38}$ and $R^{36}$ are the same as defined above.]

The reaction between the compound (224) and the compound (235) is carried out under the same conditions as in the reaction between the compound (223) and the compound (224) in the reaction scheme B-5.

The reaction for converting the compound (236) into a compound (237) is carried out under the same conditions as in the reaction for converting the compound (216) into the compound (127) in the reaction scheme B-3.

The reaction for converting the compound (237) into a compound (238) can be carried out under the same conditions as in the reaction between the compound (223) and the compound (224) in the reaction scheme B-5, and is preferably carried out by using a phosphorus compound such as triphenylphosphine-2,2'-dipyridyl sulfide or the like.

The methylation reaction for the compound (238) is carried out by reacting the compound (238) with a methylating agent in a solvent in the presence or absence of a basic compound. As to the methylating agent, there can be mentioned, for example, dimethyl sulfate; sulfonic acid esters such as methyl fluorosulfonate, methyl methanesulfonate, methyl trifluoromethanesulfonate and the like; trimethyloxonium tetrafluoroborate; diazomethane; and methyl halides such as methyl iodide and the like. The solvent can be illustrated by, for example, lower alcohols such as methanol, ethanol, propanol and the like; ethers such as diethyl ether, tetrahydrofuran, dioxane, ethylene glycol monomethyl ether and the like; halogenated hydrocarbons such as dichloromethane, chloroform, carbon tetrachloride and the like; aromatic hydrocarbons such as benzene, toluene, xylene and the like; esters such as methyl acetate, ethyl acetate and the like; ketones such as acetone, methyl ethyl ketone and the like; polar solvents such as acetonitrile, dimethyl formamide, dimethyl sulfoxide, hexamethylphosphoric triamide and the like; and their mixed solvents. The basic compound can be illustrated by, for example, inorganic bases such as sodium hydroxide, potassium hydroxide, sodium carbonate, potassium carbonate, sodium hydrogencarbonate, potassium hydrogencarbonate, sodium hydride and the like; alkali metals such as metallic sodium, metallic potassium and the like; alkali metal alcoholates such as sodium ethylate, sodium methylate and the like; and organic bases such as triethylamine, pyridine, N,N-dimethylaniline, N-methylmorpholine, diisopropylethylamine, 4-methylaminopyridine, DBN, DBU, DABCO and the like.

The desirable amount of the methylating agent used is at least 1 mole, preferably about 1 to 5 moles per mole of the compound (238). The reaction is carried out generally at $-30°$ to 150° C., preferably at about $-20°$ to 100° C., and is completed at about 0.5 to 20 hours.

In the process of the present invention, first the above-obtained compound (202) is reacted with an indole derivative and its salt, preferably the salt to obtain a compound (204). As to the salt of the indole derivative, there can be shown, for example, salts of an alkali metal such as lithium, sodium, potassium or the like; $MgX^{31}$ ($X^{31}$ is the same as defined above); $SnR^{39}$ ($R^{39}$ is a lower alkyl group); and $ZnX^{31}$ ($X^{31}$ is the same as defined above). Preferable salts are salts of an alkali metal such as lithium, sodium, potassium or the like; $ZnX^{31}$; and so forth. The reaction is carried out generally in an appropriate solvent. As to the solvent, there can be mentioned, for example, aromatic hydrocarbons such as benzene, toluene, xylene and the like; ethers such as diethyl ether, tetrahydrofuran, dioxane, diethylene glycol dimethyl ether and the like; and halogenated hydrocarbon such as chloroform, dichloromethane, carbon tetrachloride and the like.

The reaction is completed in about 10 minutes to 50 hours generally at $-30°$ to 150° C., preferably at about 0° to 100° C. The desirable amounts of the indole and its salt are at least 1 mole, preferably 1 to 5 moles per mole of the compound (202).

In the present invention, the compound (204) is then reduced. This reduction reaction can be carried out by, for example, catalytic hydrogenation in an appropriate solvent in the presence of a solvent. As to the solvent, there can be mentioned, for example, water; acetic acid; alcohols such as methanol, ethanol, isopropanol and the like; hydrocarbons such as hexane, cyclohexane and the like; ethers such as diethylene glycol diemthyl ether, dioxane, tetrahydrofuran, diethyl ether and the like; esters such as ethyl acetate, methyl acetate and the like; aprotic polar solvents such as dimethylformamide and the like; and their mixed solvents. As to the catalyst, there can be mentioned, for example, palladium, palladium-black, palladium-carbon, platinum, platinum oxide, copper chromite and Raney nickel. The desirable amount of the catalyst used is generally about 0.02 to 1 time the weight of the compound (204). The desirable reaction temperature is generally about −20° to 100° C., preferably about 0° to 80° C.; the desirable hydrogen pressure is generally 1 to 10 atm.; and the reaction is completed generally in about 0.5 to 20 hours. To the system of the reduction reaction may be added a basic compound such as sodium hydroxide or the like. Specific examples for production according to the above reaction schemes B-1 to B-8 are described in Reference Examples B-1 to B-36 and Examples B-1 to B-8 all to appear later.

The known NF-1616-904 substance represented by the following formula (301)

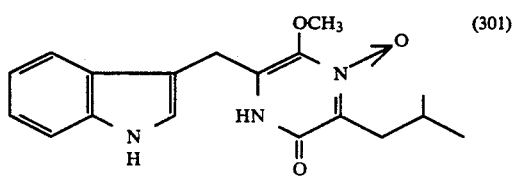

can be obtained by the following method at a high yield and a high purity on an industrial scale without using any troublesome separation means.

That is, the NF-1616-904 substance represented by the formula

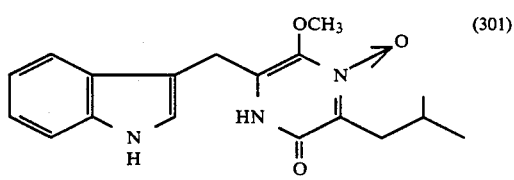

can be produced by cyclizing an indole derivative represented by the general formula

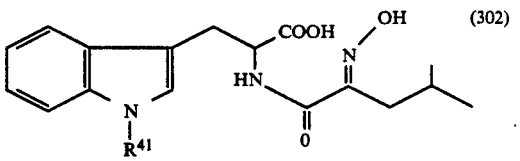

[in the formula, $R^{41}$ is a hydrogen atom, a lower alkoxycarbonyl group, a lower alkanoyl group or a benzoyl group]to obtain an indole derivative represented by the general formula

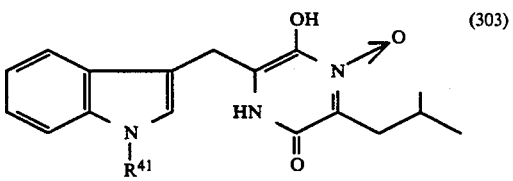

[in the formula, $R^{41}$ is the same as defined above], then protecting the oxo group of the derivative, subjecting the resulting derivative to methylation, and removing the protective group in the methylated indole derivative.

The indole derivative of the general formula (302) used as a starting material can be produced easily according to the following method.

[Reaction scheme C-1]

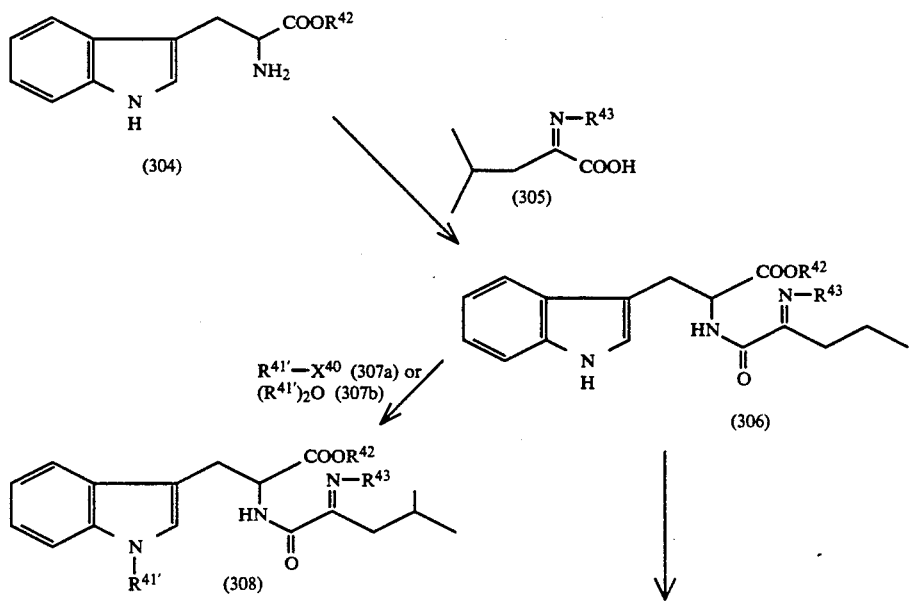

-continued
[Reaction scheme C-1]

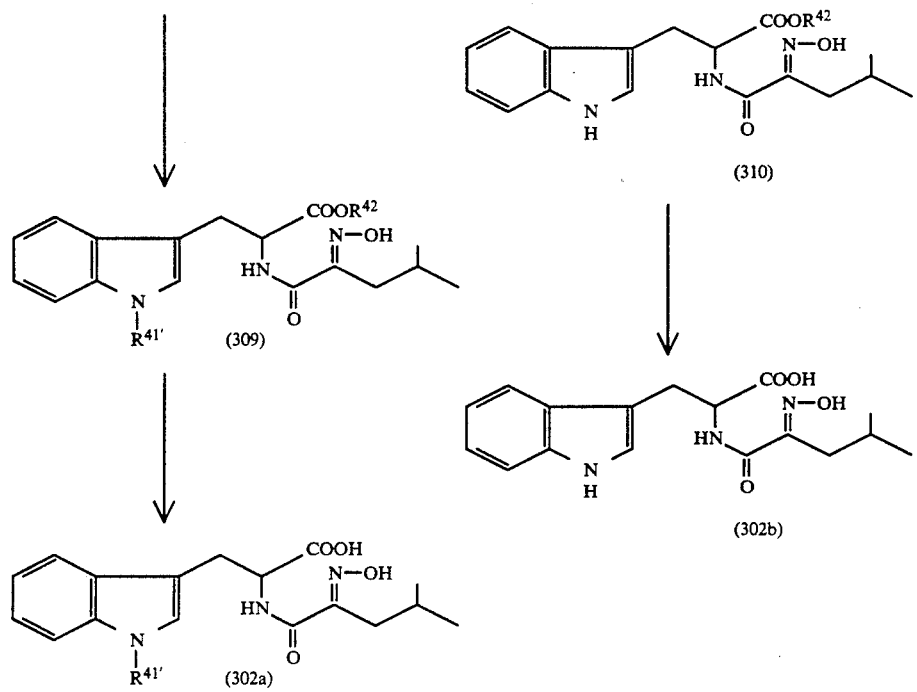

[in the formula, $R^{41'}$ is a lower alkoxycarbonyl group, a lower alkanoyl group or a benzoyl group; $X^{40}$ is a halogen atom; $R^{42}$ is a lower alkyl group or a phenyl-lower alkyl group which may have, on the phenyl ring, substituents selected from the group consisting of a halogen atom, a lower alkyl group, a lower alkoxy group, a nitro group and a cyano group; and $R^{43}$ is a hydroxy group, a phenyl-lower alkoxy group which may have, on the phenyl ring, substituents selected from the group consisting of a halogen atom, a lower alkyl group, a lower alkoxy group, a nitro group and an amino group, a tetrahydropyranyloxy group, a silyloxy group having 1 to 3 groups selected from the group consisting of a lower alkyl group and a phenyl group, or a lower alkoxy-lower alkoxy group.]

The halogen atom can be illustrated by a chlorine atom, a bromine atom, an iodine atom, a fluorine atom, etc.

The lower alkyl group can be illustrated by straight chain or branched chain alkyl groups of 1 to 6 carbon atoms such as methyl, ethyl, propyl, isopropyl, butyl, tert-butyl, pentyl, hexyl and the like.

The phenyl-lower alkoxy group which may have, on the phenyl ring, substituents selected from the group consisting of a halogen atom, a lower alkyl group, a lower alkoxy group, a nitro group and an amino group, can be illustrated by phenylalkoxy groups whose phenyl ring may have 1–3 substituents selected from the group consisting of a halogen atom, a straight chain or branched chain alkyl group of 1 to 6 carbon atoms, a nitro group, an amino group and a straight chain or branched chain alkoxy group of 1 to 6 carbon atoms and whose alkoxy portion is straight chain or branched chain alkoxy group of 1 to 6 carbon atoms and is substituted with 1 to 3 said phenyl groups, such as benzyloxy, 2-phenylethoxy, 1-phenylethoxy, 3-phenylpropoxy, 4-phenylbutoxy, 1,1-dimethyl-2-phenylethoxy, 5-phenylpentyloxy, 6-phenylhexyloxy, 2-methyl-3-phenylpropoxy, 2-chlorobenzyloxy, 2-(3-chlorophenyl)ethoxy, 1-(4-chlorophenyl)ethoxy, 3-(2-fluorophenyl)propoxy, 4-(3-fluorophenyl)butoxy, 1,1-dimethyl-2-(4-fluorophenyl)ethoxy, 5-(2-bromophenyl)pentyloxy, 6-(3-bromophenyl)hexyloxy, 2-methyl-3-(4-bromophenyl)propoxy, 3-iodobenzyloxy, 2-(4-iodophenyl)ethoxy, 1-(3,5-dichlorophenyl)ethoxy, 2-(3,4-dichlorophenyl)ethoxy, 3-(2,6-dichlorophenyl)propoxy, 4-(3,4-dichlorophenyl)butoxy, 1,1-dimethyl-2-(3,4-difluorophenyl)ethoxy, 5-(3,5-dibromophenyl)pentyloxy, 6-(3,4,5-trichlorophenyl)hexyloxy, 4-methylbenzyloxy, 2-(2-methylphenyl)ethoxy, 1-(3-methylphenyl)ethoxy, 3-(3-ethylphenyl)propoxy, 4-(2-ethylphenyl)butoxy, 5-(4-ethylphenyl)pentyloxy, 6-(3-isopropylphenyl)hexyloxy, 2-methyl-3-(4-hexylphenyl)propoxy, 2-(3,4-dimethylphenyl)ethoxy, 2-(2,5-dimethylphenyl)ethoxy, 2-(3,4,5-trimethylphenyl)ethoxy, 4-methoxybenzyloxy, 3,4-dimethoxybenzyloxy, 3,4,5-trimethoxybenzyloxy, 1-(3-methoxyphenyl)ethoxy, 2-(2-methoxyphenyl)ethoxy, 3-(2-ethoxyphenyl)propoxy, 4-(4-ethoxyphenyl)butoxy, 5-(3-ethoxyphenyl)pentyloxy, 6-(4-isopropoxyphenyl)hexyloxy, 1,1-dimethyl-2-(4-hexyloxyphenyl)ethoxy, 2-methyl-3-(3,4-dimethoxyphenyl)propoxy, 2-(3,4-dimethoxyphenyl)ethoxy, 2-(3,4-diethoxyphenyl)ethoxy, 2-(3,4,5-trimethoxyphenyl)ethoxy, 1-(2,5-dimethoxyphenyl)ethoxy, (2-chloro-4-methoxy)benzyloxy, 2-aminobenzyloxy, 1-(3-aminophenyl)ethoxy, 1-(4-aminophenyl)propoxy, 1-(2,3-diaminophenyl)butoxy, 1-(2,3,4-triaminophenyl)pentyloxy, 1-(2,4-diaminophenyl)hexyloxy, 2-nitrobenzyloxy, 1-(3-nitrophenyl)ethoxy, 1-(4-nitrophenyl)propoxy, 1-(2,4-dinitrophenyl)butoxy, 1-(2,4,6-trinitroiphenyl)pentyloxy, 1-(2-chloro-4-nitrophenyl)hexyloxy, (3-methyl-4-amino)benzyloxy, trityloxy, diphenylmethoxy and the like. Of these, there are particularly preferred phenyl-lower alkoxy groups wherein the 1-position of the alkyl portion has 1 to 3 substituted or unsubstituted phenyl groups as mentioned above, such as benzyloxy, 1-phenylethoxy, 1-(4- chlorophenyl)ethoxy, 1-(3,5-dichlorophenyl)ethoxy, 1-(3-methylphenyl)ethoxy, 1-(3-methoxyphenyl)ethoxy, 1-(2,5-dimethoxyphenyl)ethoxy, trityloxy, diphenylmethoxy and the like.

The silyloxy group having 1 to 3 groups selected from the group consisting of a lower alkyl group a phenyl group can be illustrated by trialkylsilyloxy groups whose alkyl portion is a straight chain or branched chain alkyl group of 1 to 6 carbon atoms, such as trimethylsilyloxy, triethylsilyloxy, tripropylsilyloxy, tributylsilyloxy, tert-butyldimethylsilyloxy, tert-butyldiphenylsilyloxy, tripentylsilyloxy, trihexylsilyloxy, dimethylethylsilyloxy and the like.

The lower alkoxy-lower alkoxy group can be illustrated by, for example, alkoxyalkoxy groups whose alkoxy portion is a straight chain or branched chain alkoxy group of 1 to 6 carbon atoms, such as methoxymethoxy, 2-methoxyethoxy, 1-ethoxyethoxy, 3-propoxypropoxy, 4-butoxybutoxy, 5-pentyloxypentyloxy, 6-hexyloxyhexyloxy, 1,1-dimethyl-2-methoxyethoxy, 2-methyl-3-methoxypropoxy and the like. Of these, particularly preferable are 1-lower alkoxy-lower alkoxy groups such as methoxymethoxy, 1-ethoxyethoxy and the like.

The phenyl-lower alkyl group which may have, on the phenyl ring, substituents selected from the group consisting of a halogen atom, a lower alkyl group, a lower alkoxy group, a nitro group and a cyano group, can be illustrated by phenylalkyl groups whose phenyl ring may have 1 to 3 substituents selected from the group consisting of a halogen atom, a straight chain or branched chain alkyl group of 1 to 6 carbon atoms, a nitro group, a cyano group and a straight chain or branched chain alkoxy group of 1 to 6 carbon atoms and whose alkyl portion is a straight chain or branched chain alkyl group of 1 to 6 carbon atoms and is substituted with 1 to 3 phenyl groups as mentioned above, such as benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, 2-chlorobenzyl, 2-(3-chlorophenyl)-ethyl, 1-(4-chlorophenyl)ethyl, 3-(2-fluorophenyl)propyl, 4-(3-fluorophenyl)butyl, 1,1-dimethyl-2-(4-fluorophenyl)ethyl, 5-(2-bromophenyl)pentyl, 6-(3-bromophenyl)hexyl, 2-methyl-3-(4-bromophenyl)propyl, 3-iodobenzyl, 2-(4-iodophenyl)ethyl, 1-(3,5-dichlorophenyl)ethyl, 2-(3,4-dichlorophenyl)ethyl, 3-(2,6-dichlorophenyl)propyl, 4-(3,4-dichlorophenyl)butyl, 1,1-dimethyl-2-(3,4-difluorophenyl)ethyl, 5-(3,5-dibromophenyl)pentyl, 6-(3,4,5-trichlorophenyl)hexyl, 4-methylbenzyl, 2-(2-methylphenyl)ethyl, 1-(3-methylphenyl)ethyl, 3-(3-ethylphenyl)propyl, 4-(2-ethylphenyl)butyl, 5-(4-ethylphenyl)pentyl, 6-(3-isopropylphenyl)hexyl, 2-methyl-3-(4-hexylphenyl)propyl, 2-(3,4-dimethylphenyl)ethyl, 2-(2,5-dimethylphenyl)ethyl, 2-(3,4,5-trimethylphenyl)ethyl, 4-methoxybenzyl, 3,4-dimethoxybenzyl, 3,4,5-trimethoxybenzyl, 1-(3-methoxyphenyl)ethyl, 2-(2-methoxyphenyl)ethyl, 3-(2-ethoxyphenyl)propyl, 4-(4-ethoxyphenyl)butyl, 5-(3-ethoxyphenyl)pentyl, 6-(4-isopropoxyphenyl)hexyl, 1,1-dimethyl-2-(4-hexyloxyphenyl)ethyl, 2-(methyl-3-(3,4-dimethoxyphenyl)propyl, 2-(3,4-dimethoxyphenyl)ethyl, 2-(3,4-diethoxyphenyl)ethyl, 2-(3,4,5-trimethoxyphenyl)ethyl, 1-(2,5-dimethoxyphenyl)ethyl, (2-chloro-4-methoxyphenyl)benzyl, 2-aminobenzyl, 1-(3-cyanophenyl)ethyl, 1-(4-cyanophenyl)propyl, 1-(2,3-dicyanophenyl)butyl, 1-(2,3,4-tricyanophenyl)pentyl, 1-(2,4-dicyanophenyl)hexyl, 2-nitrobenzyl, 1-(3-nitrophenyl)ethyl, 1-(4-nitrophenyl)propyl, 1-(2,4-dinitrophenyl)butyl, 1-(2,4,6-trinitrophenyl)pentyl, 1-(2-chloro-4-nitrophenyl)hexyl, (3-methyl-4-cyano)benzyl, trityl, diphenylmethyl and the like. Of these, particularly preferable are phenyl-lower alkyl groups wherein the 1-position of the alkyl portion is substituted with 1 to 3 substituted or unsubstituted phenyl groups as mentioned above, such as benzyl, 1-phenylethyl, 1-(4-chlorophenyl)ethyl, 1-(3,5-dichlorophenyl)ethyl, 1-(3-methylphenyl)ethyl, 1-(3-methoxyphenyl)ethyl, 1-(2,5-dimethoxyphenyl)ethyl, trityl, diphenylmethyl and the like.

The reaction between the compound (304) and the compound (305) is carried out according to an ordinary amide bond forming reaction. The amide bond forming reaction can be carried out by various known methods, for example, (a) a mixed acid anhydride method, for example, a method wherein a carboxylic acid (305) is reacted with an alkyl halocarboxylate and the resulting mixed acid anhydride is reacted with an amine (304); (b) an activated ester method, for example, a method wherein a carboxylic acid (305) is converted to an activated ester such as p-nitrophenyl ester, N-hydroxysuccinimide ester, 1-hydroxybenzotriazole ester or the like and the activated ester is reacted with an amine (304); (c) a carbodiimide method, that is, a method wherein a carboxylic acid (305) is condensed with an amine (304) in the presence of an activating agent such as dicyclohexylcarbodiimide, carbonyldiimidazole or the like; (d) other methods, for example, a method wherein a carboxylic acid (305) is converted into a corresponding carboxylic acid anhydride with a dehydrating agent such as acetic anhydride or the like and the carboxylic acid anhydride is reacted with an amine (304), a method wherein an ester between a carboxylic acid (305) and a lower alcohol is reacted with an amine (304) under a high pressure and a high temperature, and a method wherein an acid halide of a carboxylic acid (305), i.e. a carboxylic acid halide is reacted with an amine (304). The amide bond forming reaction can also be carried out by a method wherein a carboxylic acid (305) is activated by a phosphorus compound such as triphenylphosphine, diethyl chlorophosphate or the like and the activated carboxylic acid is reacted with an amine (304), a method wherein a carboxylic acid (305) is converted to N-carboxyaminoacid anhydride with phosgene, trichloromethyl chloroformate or the like and the anhydride is reacted with an amine (304), and so forth.

In the mixed acid anhydride method (a), the mixed acid anhydride used is obtained by an ordinary Schotten-Baumann reaction and is reacted with an amine (304) ordinarily without being isolated, whereby a compound of the general formula (306) can be produced. The Schotten-Baumann reaction is carried out in the presence of a basic compound. As the basic compound, there are used compounds conventionally used in the Schotten-Baumann raction. They are illustrated by, for example, organic bases such as triethylamine, trimethylamine, pyridine, dimethylaniline, N-methylmorpholine, 4-dimethylaminopyridine, 1,5-diazabicyclo[4,3,0]nonene-5 (DBN), 1,8-diazabicyclo[5,4,0]undecene-7 (DBU), 1,4-diazabicyclo[2,2,2]octane (DABCO) and the like, and inorganic bases such as potassium carbonate, sodium carbonate, potassium hydrogencarbonate, sodium hydrogencarbonate and the like. The reaction is carried out at about −20° to 100° C., preferably 0° to 50° C. for about 5 minutes to 10 hours, preferably about 5 minutes to 2 hours. The reaction of the mixed acid anhydride obtained, with an amine (304) is carried out at about −20° to 150° C., preferably 10° to 50° C. for about 5 minutes to 10 hours, preferably about 5 minutes to 5 hours. The mixed acid anhydride method is carried out generally in a suitable solvent conventionally used in the method, such as halogenated hydrocarbon (e.g. methylene chloride, chloroform, dichloroethane), aromatic hydrocarbon (e.g. benzene, toluene, xylene), ether (e.g. diethyl ether, dioxane, diisopropyl ether, tetrahydrofuran, dimethoxyethane), ester (methyl acetate, ethyl acetate), aprotic polar solvent (e.g. 1,1,3,3-tetramethylurea, N,N-dimethylformamide, dimethyl sulfoxide, hexamethylphosphoric triamide) or the like, or in a mixed solvent or in the absence of any solvent. As to examples of the alkyl halocarboxylate used in the production of the mixed acid anhydride, there can be mentioned methyl chloroformate, methyl bromoformate, ethyl chloroformate, ethyl bromoformate and isobutyl chloroformate. The alkyl halocarboxylate is used in an amount of generally at least 1 mole, preferably about 1 to 1.5 moles per mole of the amine (304). The preferable proportion of the carboxylic acid (305) used is generally at least 1 mole, preferably about 1 to 1.5 moles per mole of the amine (304).

The activated ester method (b), when there is used, for example, N-hydrocysuccinimide ester, is carried out in an appropriate solvent giving no adverse effect on the reaction, in the presence or absence of a basic compound. To the reaction system may be added a condensing agent such as dicyclohexylcarbodiimide, carbonyldiimidazole or the like. As to the basic compound, there can be used any basic compounds used in the Schotten-Baumann reaction. As to the solvent, there can be specifically mentioned, for example, halogenated hydrocarbons such as methylene chloride, chloroform, dichloroethane and the like; aromatic hydrocarbons such as benzene, toluene, xylene and the like; ethers such as diethyl ether, dioxane, tetrahydrofuran, dimethoxyethane and the like; esters such as methyl acetate, ethyl acetate and the like; aprotic polar solvents such as N,N-dimethylformamide, dimethyl sulfoxide, hexamethylphosphoric triamide and the like; and their mixed solvents. The reaction is completed in 5 to 30 hours at 0° to 150° C., preferably at 10 to 100° C. The desirable proportions of the amine (304) and N-hydroxysuccinimide ester used are each generally at least 1 mole, preferably 1 to 2 moles per mole of the compound (305). The compound (306) can also be obtained by reacting the amine (304) with the carboxylic acid (305) in the presence of a condensing agent which is a phosphorus compound such as triphenylphosphine, triphenylphosphine-2,2'-dipyridyl sulfide, diethyl chlorophosphate, diphenylphosphinyl chloride, phenyl N-phenylphosphoramide chloridate, diethyl cyanophosphate, bis(2-oxo-2-oxazolidinyl)phosphinic chloride or the like.

As to the basic compound, there can be used various known basic compounds; and there can be mentioned, for example, not only those basic compounds used in the Scotten-Baumann reaction, but also sodium hydroxide and potassium hydroxide. As to the solvent, there can be mentioned, besides the solvents used in the above-mentioned mixed acid anhydride method, for example, pyridine, acetone, acetonitrile and mixtures of two or more of the above.

The reaction is carried out generally at about −20° to 150° C., preferably at about 0° to 100° C., and is completed generally in about 5 minutes to 30 hours. The desirable amounts of the condensing agent and carboxylic acid (305) are each at least about 1 mole, preferably about 1 to 2 moles per mole of the amine (304).

The compound (306) can also be obtained by reacting the amine (304) and the carboxylci acid (305) in the presence of a condensing agent. The reaction is carried out in an appropriate solvent in the presence or absence of a catalyst. The solvent can be illustrated by halogenated hydrocarbons such as dichloromethane, dichloroethane, chloroform, carbon tetrachloride and the like; acetonitrile; dimethylformamide; etc. The catalyst can be illustrated by organic bases such as dimethylaminopyridine, 4-piperidinopyridine and the like; salts such as pyridinium tosylate and the like; camphorsulfonic acid; mercury oxide; etc. As to the condensing agent, there can be mentioned, for example, acetylene compounds such as trimethylsilylethoxyacetylene and the like. The desirable amount of the condensing agent used is generally 1 to 10 moles, preferably 2 to 6 moles per mole of the amine (304). The desirable amount of the carboxylic acid (305) used is generally at least about 1 mole, preferably about 1 to 2 moles per mole of the amine (304). The reaction is carried out generally at about 0° to 150° C., preferably at about room temperature to 100° C., and is completed generally in about 1 to 10 hours.

The reaction between the compound (306) and the compound (307a) or the compound (307b) is carried out generally in an appropriate inert solvent in the presence or absence of a basic compound. As to the inert solvent, there can be mentioned, for example, halogenated hydrocarbons such as dichloromethane, chloroform, carbon tetrachloride and the like; aromatic hydrocarbons such as benzene, toluene, xylene and the like; ethers such as dioxane, tetrahydrofuran, ethylene glycol dimethyl ether and the like; dimethyl sulfoxide; dimethylformamide; hexamethylphosphoric triamide; and their mixed solvents. As to the basic compound, there can be mentioned, for example, metal hydroxides such as sodium hydroxide, potassium hydroxide and the like; potassium and sodium; sodium amide and potassium amide; metal alcoholates such as sodium methylate, sodium ethylate, potassium tert-butoxide and the like; metal phenyl-lower alkoxides such as sodium benzyl oxide and the like; lower alkyl lithium compounds such as n-butyllithium, methyllithium and the like; sodium hydride; lithium diisopropylamide; and organic bases such as pyridine, ethyldiisopropylamine, dimethylaminopyridine, triethylamine, DBN, DBU, DABCO and the like. The proportions of the compound (306) and the compound (307a) or the compound (307b) used are not particularly restricted and can be selected appropriately each in a wide range; however, desirably the latter is used in an amount of generally at least about 1 mole, preferably about 1 to 5 moles per mole of the former. The reaction is carried out generally at about 0° to 120° C., preferably at 0° to 100° C., and is completed generally in about 30 minutes to 30 hours. In the reaction, there may be added a phase transfer catalyst such as quaternary ammonium halide (tetra-n-butylammonium bromide, phenyltriethylammonium chloride), crown ether (18-crown-6, benzo-18-crown-6, benzo-18-crown-6, dicyclohexano-18-crown-6, 12-crown-4, 15-crown-5) or the like.

The reaction for converting the compound (308) or the compound (306) into a compound (309) or a compound (310), respectively, is carried out by reducing the compound (308) or the compound (306), when the $R^{43}$ of the compound (308) or the compound (306) is a phenyl-lower alkoxy group. This reduction reaction can be carried out by, for example, effecting catalytic hydrogenation in an appropriate solvent in the presence of a catalyst. As to the solvent, there can be mentioned, for example, water; acetic acid; alcohols such as methanol, ethanol, isopropanol and the like; hydrocarbons such as hexane, cyclohexane and the like; ethers such as dioxane, tetrahydrofuran, diethyl ether, ethylene glycol dimethyl ether and the like; esters such as ethyl acetate, methyl acetate and the like; aprotic polar solvents such as dimethylformamide and the like; and their mixed solvents. As to the catalyst, there can be mentioned, for example, palladium, palladium-black, palladium-carbon, platinum, platinum oxide, copper chromite, Raney nickel, etc. The desirable amount of the catalyst used is generally about 0.02 to 1 time the weight of the compound (308) or the compound (306). The desirable reaction temperature is generally about $-20°$ to $100°$ C., preferably $0°$ to $80°$ C.; the desirable hydrogen pressure is generally 1 to 10 atm.; and the reaction is completed generally in about 0.5 to 20 hours.

The reaction for converting the compound (308) or the compound (306) into the compound (309) or the compound (310), respectively, is carried out by hydrolysis, when the $R^{43}$ of the compound (308) or the compound (306) is a tetrahydropyranyloxy group or a tri-lower alkylsilyloxy group. This hydrolysis is carried out in an appropriate solvent or in a solventless state in the presence of an acid. The solvent can be any as long as it gives no adverse effect on the reaction, and there can be mentioned, for example, water, halogenated hydrocarbons (e.g. dichloromethane, chloroform), lower alcohols (e.g. methanol, ethanol, isopropanol), ketones (e.g. acetone, methyl ethyl ketone), ethers (e.g. dioxane, tetrahydrofuran, ethylene glycol monomethyl ether, ethylene glycol dimethyl ether), fatty acids (e.g. formic acid, acetic acid), and their mixed solvents. As to the acid, there can be mentioned, for example, mineral acids such as hydrochloric acid, sulfuric acid, hydrobromic acid and the like, and organic acids such as formic acid, trifluoroacetic acid, acetic acid, aromatic sulfonic acid and the like. The amount of the acid used is not particularly restricted and can be selected appropriately from a wide range; however, desirably it is generally about 1 to 10 moles, preferably about 1 to 2 moles per mole of the compound (308) or (306). The reaction proceeds favorably generally at about $0°$ to $200°$ C., preferably at about room temperature to $150°$ C., and is completed generally in about 0.5 to 15 hours. When the $R^{43}$ is a tri-lower alkylsilyloxy group, the reaction may also be carried out using a fluorine compound such as tetra-n-butylammonium fluoride, hydrogen fluoride, cesium fluoride or the like.

When the $R^{43}$ is a lower alkoxy-lower alkoxy group, the reaction for converting the compound (308) or the compound (306) to the compound (309) or the compound (310), respectively, is carried out by treating the compound (308) or the compound (306) in a mixture of a mineral acid (e.g. hydrobromic acid, hydrochloric acid) or an organic acid (e.g. p-toluenesulfonic acid) and a solvent (e.g. water, methanol, ethanol, isopropanol) at $0°$ to $150°$ C., preferably at room temperature to $120°$ C., or by hydrolyzing the compound (308) or the compound (306). The hydrolysis is carried out in an appropriate solvent in the presence of an acid. As to the solvent, there can be mentioned, for example, water; lower alcohols such as methanol, ethanol, isopropanol and the like; ethers such as dioxane, tetrahydrofuran and the like; halogenated hydrocarbons such as dichloromethane, chloroform, carbon tetrachloride and the like; polar solvents such as acetonitrile and the like; and their mixed solvents. As to the acid, there can be mentioned, for example, mineral acids such as hydrochloric acid, sulfuric acid, hydrobromic acid and the like; fatty acids such as formic acid, acetic acid and the like; Lewis acids such as boron trifluoride, aluminum chloride, boron tribromide and the like; iodides such as sodium iodide, potassium iodide and the like; and mixtures of the above Lewis acid and the above iodide. The reaction proceeds favorably generally at $0°$ to $150°$ C., preferably at room temperature to $100°$ C., and is completed generally in about 0.5 to 15 hours.

The reaction for converting the compound (309) or the compound (310) into a compound (302a) or a compound (302b), respectively, is carried out by hydrolyzing the compound (309) or the compound (310) in the presence of a basic compound. The basic compound can be illustrated by sodium carbonate, potassium carbonate, sodium hydroxide, potassium hydroxide, barium hydroxide, etc. Desirably, the basic compound is used in an amount of generally about 1 to 15 moles, preferably about 1 to 10 moles per mole of the compound (309) or the compound (310). The solvent can be illustrated by water; alcohols such as methanol, ethanol, isopropanol and the like; ethers such as tetrahydrofuran, dioxane, dimethoxyethane and the like; dimethylformamide; dimethyl sulfoxide; hexamethylphosphoric triamide; their mixed solvents; and so forth. The reaction proceeds favorably generally at about $0°$ to $200°$ C., preferably at about room temperature to $150°$ C., and is completed generally in about 0.5 to 15 hours.

When the $R^{42}$ of the compound (309) or the compond (310) is a phenyl-lower alkyl group, the compound (302a) or the compound (302b) can also be obtained by reducing the compound (309) or the compound (310) under the same conditions as in the reduction reaction for converting the compound (308) or the compound (306) to the compound (309) or the compound (310), respectively.

In the process of the present invention, first the above-obtained compound (302) is cyclized to obtain a compound (303).

In this cyclization reaction, there can be employed the same reaction conditions as in the reaction between the compound (304) and the compound (305) in the reaction scheme C-1. Particularly preferable is a method using a phosphorus compound (e.g. triphenylphosphine-2,4'-dipyridyl disulfide) or an acetylene compound (e.g. trimethylsilylethoxyacetylene).

In the present invention, the oxo group of the compound (303) is then protected.

The protection of the oxo group is carried out by reacting the compound (303) with a compound represented by the general formula

$$R^{44}X^{44} \tag{311}$$

[in the formula, $X^{40}$ is the same as defined above; and $R^{44}$ is a lower alkoxycarbonyl group, a lower alkanoyl group, a benzoyl group or a phenyl-lower alkyl group which may have, on the phenyl ring, substituents selected from the group consisting of a halogen atom, a lower alkoxy group, a lower alkyl group, a nitro group and an amino group] or a compound represented by the general formula $(R^{45})_2O$ (312)

[in the formula, $R^{45}$ is a lower alkoxycarbonyl group, a lower alkanoyl group or a benzoyl group]. The reaction is carried out under the same conditions as in the reaction between the compound (306) and the compound (307a) or the compound (307b).

The lower alkanoyl group is illustrated by straight chain or branched chain alkanoyl groups of 1 to 6 carbon atoms such as formyl, acetyl, propionyl, butyryl, isobutyryl, pentanoyl, tert-butylcarbonyl, hexanoyl and the like.

The phenyl-lower alkyl group which may have, on the phenyl ring, substituents selected from the group consisting of a halogen atom, a lower alkyl group, a nitro group, an amino group and a lower alkoxy group, can be illustrated by, for example, phenylalkyl groups whose phenyl ring may have 1 to 3 substituents selected from the group consisting of a halogen atom, a straight chain or branched chain alkyl group of 1 to 6 carbon atoms, a nitro group, an amino group and a straight chain or branched chain alkoxy group of 1 to 6 carbon atoms and whose alkyl portion is a straight chain or branched chain alkyl group of 1 to 6 carbon atoms and is substituted with 1 to 3 phenyl groups as mentioned above, such as benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, 2-chlorobenzyl, 2-(3-chlorophenyl)ethyl, 1-(4-chlorophenyl)ethyl, 3-(2-fluorophenyl)propyl, 4-(3-fluorophenyl)butyl, 1,1-dimethyl-2-(4-fluorophenyl)ethyl, 5-(2-bromophenyl)pentyl, 6-(3-bromophenyl)hexyl, 2-methyl-3-(4-bromophenyl)propyl, 3-iodobenzyl, 2-(4-iodophenyl)ethyl, 1-(3,5-dichlorophenyl)ethyl, 2-(3,4-dichlorophenyl)ethyl, 3-(2,6-dichlorophenyl)propyl, 4-(3,4-dichlorophenyl)butyl, 1,1-dimethyl-2-(3,4-difluorophenyl)ethyl, 5-(3,5-dibromophenyl)pentyl, 6-(3,4,5-trichlorophenyl)hexyl, 4-methylbenzyl, 2-(2-methylphenyl)ethyl, 1-(3-methylphenyl)ethyl, 3-(3ethylphenyl)propyl, 4-(2-ethylphenyl)butyl, 5-(4-ethylphenyl)pentyl, 6-(3-isopropylphenyl)hexyl, 2-methyl-3-(4-hexylphenyl)propyl, 2-(3,4-dimethylphenyl)ethyl, 2-(2,5-dimethylphenyl)ethyl, 2-(3,4,5-trimethylphenyl)ethyl, 4-methoxybenzyl, 3,4-dimethoxybenzyl, 3,4,5-trimethoxybenzyl, 1-(3-methoxyphenyl)ethyl, 2-(2-methoxyphenyl)ethyl, 3-(2-ethoxyphenyl)propyl, 4-(4-ethoxyphenyl)butyl, 5-(3-ethoxyphenyl)pentyl, 6-(4-isopropoxyphenyl)hexyl, 1,1-dimethyl-2-(4-hexyloxyphenyl)ethyl, 2-methyl-3-(3,4-dimethoxyphenyl)propyl, 2-(3,4dimethoxyphenyl)ethyl, 2-(3,4-diethoxyphenyl)ethyl, 2-(3,4,5-trimethoxyphenyl)ethyl, 1-(2,5-dimethoxyphenyl)ethyl, 2-chloro-4-methoxy)benzyl, 2-aminobenzyl, 1-(3-aminophenyl)ethyl, 1-(4-aminophenyl)propyl, 1-(2,3-diaminophenyl)butyl, 1-(2,3,4-triaminophenyl)pentyl, 1-(2,4-diaminophenyl)hexyl, 2-nitropbenzyl, 1-(3-nitrophenyl)ethyl, 1-(4-nitriophenyl)propyl, 1-(2,4-dinitrophenyl)butyl, 1-(2,4,6-trinitrophenyl)pentyl, 1-(2-chloro-4-nitrophenyl)hexyl, 3-(methyl-4-amino)benzyl, trityl, diphenylmethyl and the like. Of these, particularly preferable are phenyl-lower alkyl groups wherein the 1-position of the alkyl portion is substituted with 1 to 3 substituted or unsubstituted phenyl groups as mentioned above, such as benzyl, 1-phenylethyl, 1-(4-chlorophenyl)ethyl, 1-(3,5-dichlorophenyl)ethyl, 1-(3-methylphenyl)ethyl, 1-(3-methoxyphenyl)ethyl, 1-(2,5-dimethoxyphenyl)ethyl, trityl, diphenylmethyl and the like.

In the present invention, the subsequent methylation reaction is carried out by reacting the above-obtained product with diazomethane in a suitable solvent in the presence or absence of a catalyst. The solvent can be illustrated by, for example, lower alcohols such as methanol, ethanol, propanol and the like; ethers such as dioxane, tetrahydrofuran, diethyl ether, ethylene glycol monomethyl ether and the like; halogenated hydrocarbons such as dichloromethane, chloroform, carbon tetrachloride and the like; and their mixed solvents. The catalyst can be illustrated by, for example, Lewis acids such as boron tribromide, boron trifluoride-diethyl ether and the like. The desirable amount of diazomethane used is generally a large excess, preferably about 10 to 20 equivalents relative to the starting material compound. The reaction is carried out generally at about −30° to 100° C., preferably at about −20° to 70° C., and is completed generally in about 0.5 to 20 hours.

In the present invention, the protective group of the thus obtained compound is removed. When the protective group of the oxo group is a lower alkanoyl group or a benzoyl group, or the $R^{41}$ is a lower alkoxycarbonyl group, a lower alkanoyl group or a benzoyl group, the compound is subjected to a hydrolysis treatment to remove the protective group. This hydrolysis is carried out under the same conditions as in the hydrolysis reaction of the compound (309) or the compound (310). When the $R^{41}$ is a lower alkoxycarbonyl group, it can also be carried out under the same conditions as in the hydrolysis reaction for converting the compound (308) or the compound (306) both having a tetrahdyropyranyloxy group as the $R^{43}$, to the compound (309) or the compound (310), respectively. When the protective group of the oxo group is a phenyl-lower alkyl group which may have, on the phenyl ring, substituents selected from the group consisting of a halogen atom, a lower alkoxy group, a lower alkyl group, a nitro group and an amino group, the compound is subjected to a reduction treatment to remove the protective. This reduction reaction can be carried out under the same conditions as in the reduction reaction for the compound (308) or the compound (306) both having a phenyl-lower alkoxy group as the $R^{43}$.

Specific examples for production according to the reaction scheme C-1 are described in Reference Examples C-1 to C-7 and Examples C-1 to C-10 all to appear later.

The known NF-1616-904 substance represented by the following formula (401)

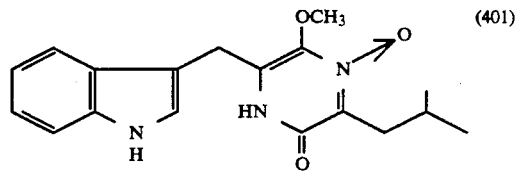

can be obtained at a high yield and a high purity on the industrial scale without using any troublesome separation means.

That is, the NF-1616-904 substance represented by the formula (401)

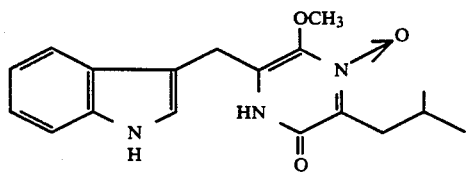

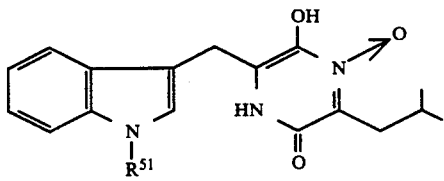

can be produced by cyclizing an indole derivative represented by the general formula

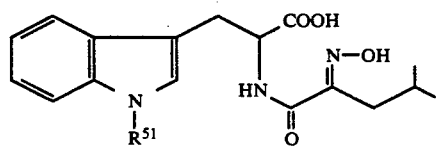

[in the formula, $R^{51}$ is a hydrogen atom, a lower alkoxycarbonyl group, a lower alkanoyl group a phenyl-lower alkoxycarbonyl group or a benzoyl group] to obtain an indole derivative represented by the general formula

[in the formula, $R^{51}$ is the same as defined above], then methylating the indole derivative, and when the $R^{51}$ of the methylated indole derivative is a group other than hydrogen atom, removing the protective group, or by oxidizing anindole derivative represented by the general formula (411)

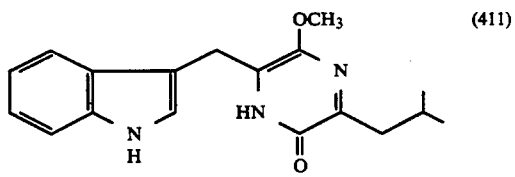

The indole derivative of the general formula (402) used as a starting material can be easily produced according to the following method.

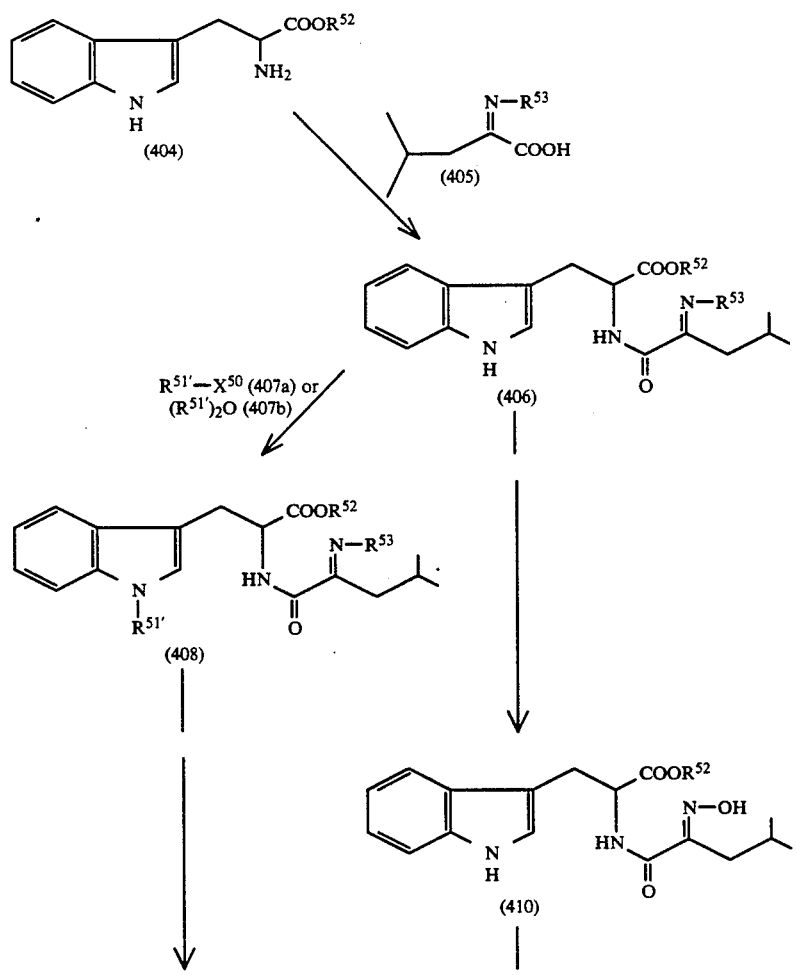

[Reaction scheme D-1]

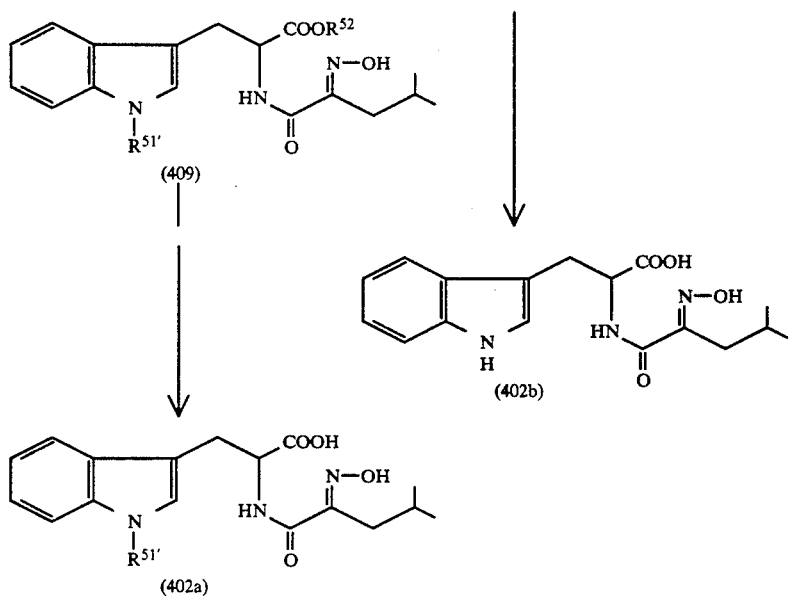

[in the formula, $R^{51'}$ is a lower alkoxycarbonyl group, a lower alkanoyl group, a phenyl-lower alkoxycarbonyl group or a benzoyl group; $X^{50}$ is a halogen atom; $R^{52}$ is a lower alkyl group or a phenyl-lower alkyl group which may have, on the phenyl ring, substituents selected from the group consisting of a halogen atom, a lower alkyl group, a lower alkoxy group, a nitro group and a cyano group; and $R^{53}$ is a hydroxy group, a phenyl-lower alkoxy group which may have, on the phenyl ring, substituents selected from the group consisting of a halogen atom, a lower alkyl group, a lower alkoxy group, a nitro group and an amino group, a tetraahydropyranyloxy group, a silyloxy group having 1 to 3 groups selected from the group consisting of a lower alkyl group and a phenyl group, or a lower alkoxy-lower alkoxy group.]

The halogen atom can be illustrated by a chlorine atom, a bromine atom, an iodine atom, a fluorine atom, etc.

The lower alkyl group can be illustrated by straight chain or branched chain alkyl groups of 1 to 6 carbon atoms such as methyl, ethyl, propyl, isopropyl, butyl, tert-butyl, pentyl, hexyl and the like.

The phenyl-lower alkoxy group which may have, on the phenyl ring, substituents selected from the group consisting of a halogen atom, a lower alkyl group, a lower alkoxy group, a nitro group and an amino group, can be illustrated by phenylalkoxy groups whose phenyl ring may have 1-3 substituents selected from the group consisting of a halogen atom, a straight chain or branched chain alkyl group of 1 to 6 carbon atoms, a nitro group, an amino group and a straight chain or branched chain alkoxy group of 1 to 6 carbon atoms and whose alkoxy portion is a straight chain or branched chain alkoxy group of 1 to 6 carbon atoms and is substituted with 1 to 3 said phenyl groups, such as benzyloxy, 2-phenylethoxy, 1-phenylethoxy, 3-phenylpropoxy, 4-phenylbutoxy, 1,1-dimethyl-2-phenylethoxy, 5-phenylpentyloxy, 6-phenylhexyloxy, 2-methyl-3-phenylpropoxy, 2-chlorobenzyloxy, 2-(3-chlorophenyl)ethoxy, 1-(4-chlorophenyl)ethoxy, 3-(2-fluorophenyl)propoxy, 4-(3-fluorophenyl)butoxy, 1,1-dimethyl-2-(4-fluorophenyl)ethoxy, 5-(2-bromophenyl)pentyloxy, 6-(3-bromophenyl)hexyloxy, 2-methyl-3-(4-bromophenyl)propoxy, 3-iodobenzyloxy, 2-(4-iodophenyl)ethoxy, 1-(3,5-dichlorophenyl)ethoxy, 2-(3,4-dichlorophenyl)ethoxy, 3-(2,6-dichlorophenyl)propoxy, 4-(3,4-dichlorophenyl)butoxy, 1,1-dimethyl-2-(3,4-difluorophenyl)ethoxy, 5-(3,5-dibromophenyl)pentyloxy, 6-(3,4,5-trichlorophenyl)hexyloxy, 4-methylbenzyloxy, 2-(2-methylphenyl)ethoxy, 1-(3-methylphenyl)ethoxy, 3-(3-ethylphenyl)propoxy, 4-(2-ethylphenyl)butoxy, 5-(4-ethylphenyl)pentyloxy, 6-(3-isopropylphenyl)hexyloxy, 2-methyl-3-(4-hexylphenyl)propoxy, 2-(3,4-dimethylphenyl)ethoxy, 2-(2,5-dimethylphenyl)ethoxy, 2-(3,4,5-trimethylphenyl)ethoxy, 4-methoxybenzyloxy, 3,4-dimethoxybenzyloxy, 3,4,5-trimethoxybenzyloxy, 1-(3-methoxyphenyl)ethoxy, 2-(2-methoxyphenyl)ethoxy, 3-(2-ethoxyphenyl)propoxy, 4-(4-ethoxyphenyl)butoxy, 5-(3-ethoxyphenyl)pentyloxy, 6-(4-isopropoxyphenyl)hexyloxy, 1,1-dimethyl-2-(4-hexyloxyphenyl)ethoxy, 2-methyl-3-(3,4-dimethoxyphenyl)propoxy, 2-(3,4-dimethoxyphenyl)ethoxy, 2-(3,4-diethoxyphenyl)ethoxy, 2-(3,4,5-trimethoxyphenyl)ethoxy, 1-(2,5-dimethoxyphenyl)ethoxy, (2-chloro-4-methoxy)benzyloxy, 2-aminobenzyloxy, 1-(3-aminophenyl)ethoxy, 1-(4-aminophenyl)propoxy, 1-(2,3-diaminophenyl)butoxy, 1-(2,3,4-triaminophenyl)pentyloxy, 1-(2,4-diaminophenyl)hexyloxy, 2-nitrobenzyloxy, 1-(3-nitrophenyl)ethoxy, 1-(4-nitrophenyl)propoxy, 1-(2,4-dinitrophenyl)butoxy, 1-(2,4,6-trinitrophenyl)pentyloxy, 1-(2-chloro-4-nitrophenyl)hexyloxy, (3-methyl-4-amino)benzyloxy, trityloxy, diphenylmethoxy and the like. Of these, there are particularly preferred phenyl-lower alkoxy groups wherein the 1-position of the alkyl portion has to 3 substituted or unsubstituted phenyl groups as mentioned above, such as benzyloxy, 1-phenylethoxy, 1-(4-chlorophenyl)ethoxy, 1-(3,5-dichlorophenyl)ethoxy, 1-(3-methylphenyl)ethoxy, 1-(3-methoxyphenyl)ethoxy, 1-(2,5-dimethoxyphenyl)ethoxy, trityloxy, diphenylmethoxy and the like.

The silyloxy group having 1 to 3 groups selected from the group consisting of a lower alkyl group and a phenyl group can be illustrated by trialkylsilyloxy groups whose alkyl portion is a straight chain or branched chain alkyl group of 1 to 6 carbon atoms, such as trimethylsilyloxy, triethylsilyloxy, tripropylsiloxy, tributylsilyloxy, tert-butyldimethylsilyloxy, tert-butyldiphenylsilyloxy, tripentylsilyloxy, trihexylsilyloxy, dimethylethylsilyloxy and the like.

The lower alkoxy-lower alkoxy group can be illustrated by, for example, alkoxyalkoxy groups whose alkoxy portion is a straight chain or branched chain alkoxy group of 1 to 6 carbon atoms, such as methoxymethoxy, 2-methoxyethoxy, 1-ethoxyethoxy, 3-propoxypropoxy, 4-butoxybutoxy, 5-pentyloxypentyloxy, 6-hexyloxyhexyloxy, 1,1-dimethyl-2-methoxyethoxy, 2-methyl-3-methoxypropoxy and the like. Of these, particularly preferable are 1-lower alkoxy-lower alkoxy groups such as methoxymethoxy, 1-ethoxyethoxy and the like.

The phenyl-lower alkyl group which may have, on the phenyl ring, substituents selected from the group consisting of a halogen atom, a lower alkyl group, a lower alkoxy group, a nitro group and a cyano group, can be illustrated by phenylalkyl groups whose phenyl ring may have 1 to 3 substituents selected from the group conssiting of a halogen atom, a straight chain or branched chain alkyl group of 1 to 6 carbon atoms, a nitro group, a cyano group and a straight chain or branched chain alkoxy group of 1 to 6 carbon atoms and whose alkyl portion is a straight chain or branched chain alkyl group of 1 to 6 carbon atoms and is substituted with 1 to 3 phenyl groups as mentioned above, such as benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, 2-chlorobenzyl, 2-(3-chlorophenyl)ethyl, 1-(4-chlorophenyl)ethyl, 3-(2-fluorophenyl)propyl, 4-(3-fluorophenyl)butyl, 1,1-dimethyl-2-(4-fluorophenyl)ethyl, 5-(2-bromophenyl)pentyl, 6-(3-bromophenyl)hexyl, 2-methyl-3-(4-bromophenyl)propyl, 3-iodobenzyl, 2-(4-iodophenyl)ethyl, 1-(3,5-dichlorophenyl)ethyl, 2-(3,4-dichlorophenyl)ethyl, 3-(2,6-dichlorophenyl)propyl, 4-(3,4-dichlorophenyl)butyl, 1,1-dimethyl-2-(3,4-difluorophenyl)ethyl, 5-(3,5-dibromophenyl)pentyl, 6-(3,4,5-trichlorophenyl)hexyl, 4-methylbenzyl, 2-(2-methylphenyl)ethyl, 1-(3-methylphenyl)ethyl, 3-(3-ethylphenyl)propyl, 4-(2-ethylphenyl)butyl, 5-(4-ethylphenyl)pentyl, 6-(3-isopropylphenyl)hexyl, 2-methyl-3-(4-hexylphenyl)propyl, 2-(3,4-dimethylphenyl)ethyl, 2-(2,5-dimethylphenyl)ethyl, 2-(3,4,5-trimethylphenyl)ethyl, 4-methoxybenzyl, 3,4-dimethoxybenzyl, 3,4,5-trimethoxybenzyl, 1-(3-methoxyphenyl)ethyl, 2-(2-methoxyphenyl)ethyl, 3-(2-ethoxyphenyl)propyl, 4-(4-ethoxyphenyl)butyl, 5-(3-ethoxyphenyl)pentyl, 6-(4-isopropoxyphenyl)hexyl, 1,1-dimethyl-2-(4-hexyloxyphenyl)ethyl, 2-(methyl-3-(3,4-dimethoxyphenyl)propyl, 2-(3,4-dimethoxyphenyl)ethyl, 2-(3,4-diethoxyphenyl)ethyl, 2-(3,4,5-trimethoxyphenyl)ethyl, 1-(2,5-dimethoxyphenyl)ethyl, (2-chloro-4-methoxy)benzyl, 2-aminobenzyl, 1-(3-cyanophenyl)ethyl, 1-(4-cyanophenyl)propyl, 1-(2,3-dicyanophenyl)butyl, 1-(2,3,4-tricyanophenyl)pentyl, 1-(2,4-dicyanophenyl)hexyl, 2-nitrobenzyl, 1-(3-nitrophenyl)ethyl, 1-(4-nitrophenyl)propyl, 1-(2,4-dinitrophenyl)butyl, 1-(2,4,6-trinitrophenyl)pentyl, 1-(2-chloro-4-nitrophenyl)hexyl, (3-methyl-4-cyano)benzyl, trityl, diphenylmethyl and the like. Of these, particularly preferable are phenyllower alkyl groups wherein the 1-position of the alkyl portion is substituted with 1 to 3 substituted or unsubstituted phenyl groups as mentioned above, such as benzyl, 1-phenylethyl, 1-(4-chlorophenyl)ethyl, 1-(3,5-dichlorophenyl)ethyl, 1-(3-methylphenyl)ethyl, 1-(3-methoxyphenyl)ethyl, 1-(2,5-dimethoxyphenyl)ethyl, trityl, diphenylmethyl and the like.

The reaction between the compound (404) and the compound (405) is carried out according to an ordinary amide bond forming reaction. The amide bond forming reaction can be carried out by various known methods, for example, (a) a mixed acid anhydride method, for example, a method wherein a carboxylic acid (405) is reacted with an alkyl halocarboxylate and the resulting mixed acid anhydride is reacted with an amine (404); (b) an activated ester method, for example, a method wherein a carboxylic acid (405) is converted into an activated ester such as p-nitrophenyl ester, N-hydroxysuccinimide ester, 1-hydroxybenzotriazole ester or the like and the activated ester is reacted with an amine (404); (c) a carbodiimide method, that is, a method wherein a carboxylic acid (405) is condensed with an amine (404) in the presence of an activating agent such as dicyclohexylcarbodiimide, carbonyldiimidazole or the like; (d) other methods, for example, a method wherein a carboxylic acid (405) is converted into a corresponding carboxylic acid anhydride with a dehydrating agent such as acetic anhydride or the like and the carboxylic acid anhydride is reacted with an amine (404), a method wherein an ester between a carboxylic acid (305) and a lower alcohol is reacted with an amine (404) under a high pressure and a high temperature, and a method wherein an acid halide of a carboxylic acid (405), i.e. a carboxylic acid halide is reacted with an amine (404). The amide bond forming reaction can also be carried out by a method wherein a carboxylic acid (405) is activated by a phosphorus compound such as triphenylphosphine, diethyl chlorophosphate or the like and the activated carboxylic acid is reacted with an amine (404), a method wherein a carboxylic acid (405) is converted into N-carboxyaminoacid anhydride with phosgene, trichloromethyl chloroformate or the like and the anhydride is reacted with an amine (404), and so forth.

In the mixed acid anhydride method (a), the mixed acid anhydride used is obtained by an ordinary Schotten-Baumann reaction and is reacted with an amine (404) ordinarily without being isolated, whereby a compound of the general formula (406) can be produced. The Schotten-Baumann reaction is carried out in the presence of a basic compound. As to the basic compound, there are used compounds conventionally used in the Schotten-Baumann reaction. They are illustrated by, for example, organic bases such as triethylamine, trimethylamine, pyridine, dimethylaniline, N-methylmorpholine, 4-dimethylaminopyridine, 1,5-diazabicyclo[4,3,0]nonene-5 (DBN), 1,8-diazabicyclo[5,4,0]undecene-7 (DBU), 1,4-diazabicyclo[2,2,2]octane (DABCO) and the like, and inorganic bases such as potassium carbonate, sodium carbonate, potassium hydrogencarbonate, sodium hydrogencarbonate and the like. The reaction is carried out at about $-20°$ to $100°$ C., preferably $0°$ to $50°$ C. for about 5 minutes to 10 hours, preferably about 5 minutes to 2 hours. The reaction of the mixed acid anhydride obtained, with an amine (404) is carried out at about $-20°$ to $150°$ C., preferably $10°$ to $50°$ C. for about 5 minutes to 10 hours, preferably about 5 minutes to 5 hours. The mixed acid anhydride method is carried out generally in a suitable solvent conventionally used in the method, such as halogenated hydrocarbon (e.g. methylene chloride, chloroform, dichloroethane), aromatic hydrocarbon (e.g. benzene, toluene, xylene), ether (e.g. diethyl ether, dioxane, diisopropyl ether, tetrahydrofuran, dimethoxyethane), ester (methyl acetate, ethyla cetate), aprotic polar solvent (e.g. 1,1,3,3-tetramethylurea, N,N-dimethylformamide, dimethyl sulfoxide, hexamethylphosphoric triamide) or the like, or in a mixed solvent or in the absence of any solvent. As to examples of the alkyl halocarboxylate used in the production of the mixed acid anhydride, there can be metnioned methyl chloroformate, methyl bromoformate, ethyl chloroformate, ethyl bromoformate and isobutyl chloroformate. The alkyl halocarboxylate is used in an amount of generally at least 1 mole, preferably about 1 to 1.5 moles per mole of the amine (404). The preferable proportion of the carboxylic acid (405) used is generally at least 1 mole, preferably about 1 to 1.5 moles per mole of the amine (404).

The activated ester method (b), when there is used, for example, N-hydroxysuccinimide ester, is carried out in an appropriate solvent giving no adverse effect on the reaction, in the presence or absence of a basic compound. To the reaction system may be added a condensing agent such as dicyclohexylcarbodiimide, carbonyldiimidazole 1-ethyl-3-(3'-dimethylaminopropyl)carbodiimide or the like. As to the basic compound, there can be used any basic compounds used in the Schotten-Baumann reaction. In addition to these, the basic compound can further be illustrated by, for example, alkali metal carboxylates such as sodium acetate, sodium benzoate, sodium formate, potassium acetate, lithium benzoate, cesium acetate and the like; and alkali metal halides such as potassium fluoride, cesium fluoride and the like. As to the solvent, there can be specifically mentioned, for example, halogenated hydrocarbons such as methylene chloride, chloroform, dichloroethane and the like; aromatic hydrocarbons such as benzene, toluene, xylene and the like; ethers such as diethyl ether, dioxane, tetrahydrofuran, dimethoxyethane and the like; esters such as methyl acetate, ethyl acetate and the like; aprotic polar solvents such as N,N-dimethylformamide, dimethyl sulfoxide, hexamethylphosphoric triamide and the like; and their mixed solvents. The reaction is completed in 5 to 30 hours at 0° to 150° C., preferably at 10° to 100° C. The desirable proportions of the amine (404) and N-hydroxysuccinimide ester used are each generally at least mole, preferably 1 to 2 moles per mole of the compound (405).

The compound (406) can also be obtained by reacting the amine (404) with the carboxylic acid (405) in the presence of a condensing agent which is a phosphorus compound such as triphenylphosphine, triphenylphosphine-2,2'-dipyridyl sulfide, diethyl chlorophosphate, diphenylphosphinyl chloride, phenyl N-phenylphosphoramide chloridate, diethyl cyanophosphate, bis(2-oxo-2-oxazolidinyl)phosphinic chloride or the like.

As to the basic compound, there can be used various known basic compounds; and there can be mentioned, for example, not only those basic compounds used in the Scotten-Baumann reaction, but also sodium hydroxide and potassium hydroxide. As to the solvent, there can be mentioned, besides the solvents used in the above-mentioned mixed acid anhydride method, for example, pyridine, acetone, acetonitrile and mixtures of two or more of the above.

The reaction is carried out generally at about −20° to 150° C., preferably at about 0° to 100° C., and is completed generally in about 5 minutes to 30 hours. The desirable amounts of the condensing agent and carboxylic acid (405) are each at least about 1 mole, preferably about 1 to 2 moles per mole of the amine (404).

The compound (406) can also be obtained by reacting the amine (404) and the carboxylic acid (405) in the presence of a condensing agent. The reaction is carried out in a suitable solvent in the presence or absence of a catalyst. The solvent can be illustrated by halogenated hydrocarbons such as dichloromethane, dichloroethane, chloroform, carbon tetrachloride and the like; acetonitrile; dimethylformamide; etc. The catalyst can be illustrated by organic bases such as dimethylaminopyridine, 4-piperidinopyridine and the like; salts such as pyridinium tosylate and the like; camphorsulfonci acid; mercury oxide; etc. As the condensing agent, there can be mentioned, for example, acetylene compounds such as trimethylsilylethoxyacetylene and the like. The desirable amount of the condensing agent used is generally 1 to 10 moles, preferably 2 to 6 moles per mole of the amine (404). The desirable amount of the carboxylic acid (405) used is generally at least about 1 mole, preferably about 1 to 2 moles per mole of the amine (404). The reaction is carried out generally at about 0° to 150° C., preferably at about room temperature to 100° C., and is completed generally in about 1 to 10 hours.

The reaction between the compound (406) and the compound (407a) or the compound (407b) is carried out generally in a suitable inert solvent in the presence or absence of a basic compound. As to the inert solvent, there can be mentioned, for example, halogenated hydrocarbons such as dichloromethane, chloroform, carbon tetrachloride and the like; aromatic hydrocarbons such as benzene, toluene, xylene and the like; ethers such as dioxane, tetrahydrofuran, ethylene glycol dimethyl ether and the like; dimethyl sulfoxide; dimethylformamide; hexamethylphosphoric triamide; and their mixed solvents. As to the basic compound, there can be mentioned, for example, metal hydroxides such as sodium hydroxide, potassium hydroxide and the like; potassium and sodium; sodium amide and potassium amide; metal alcoholates such as sodium methylate, sodium ethylate, potassium tert-butoxide and the like; metal phenyl-lower alkoxides such as sodium benzyl oxide and the like; lower alkyl lithium compounds such as n-butyllithium, methyllithium and the like; sodium hydride; lithium diisopropylamide; and organic bases such as pyridine, ethyldiisopropylamine, dimethylaminopyridine, triethylamine, DBN, DBU, DABCO and the like. The proportions of the compound (406) and the compound (407a) or the compound (407b) used are not particularly restricted and can be selected suitably from a wide range; and, desirably the later is used in an amount of generally at least about 1 mole, preferably about 1 to 5 moles per mole of the former. The reaction is carried out generally at about 0° to 120° C., preferably at 0° to 100° C., and is completed generally in about 30 minutes to 30 hours. In the reaction, there may be added a phase transfer catalyst such as quaternary ammonium halide (tetra-n-butylammonium bromide, phenyltriethylammonium chloride), crown ether (18-crown-6, benzo-18-crown-6, benzo-18-crown-6, dicyclohexano-18-crown-6, 12-crown-4, 15-crown-5) or the like.

The reaction for converting the compound (408) or the compound (406) into a compound (409) or a compound (410), respectively, is carried out by reducing the compound (408) or the compound (406), when the $R^{53}$ of the compound (408) or the compound (406) is a phenyl-lower alkoxy group. This reducing reaction can be carried out by, for example, effecting catalytic hydrogenation in a suitable solvent in the presence of a catalyst. As to the solvent, there can be mentioned, for example, water; acetic acid; alcohols such as methanol, ethanol, isopropanol and the like; hydrocarbons such as hexane, cyclohexane and the like; ethers such as dioxane, tetrahydrofuran, diethyl ether, ethylene glycol dimethyl ether and the like; esters such as ethyl acetate, methyl acetate and the like; aprotic polar solvents such as dimethylformamide and the like; and their mixed solvents. As to the catalyst, there can be mentioned, for example, palladium, palladium-black, palladium-carbon, platinum, platinum oxide, copper chromite, Raney nickel, etc. The desirable amount of the catalyst used is generally about 0.02 to 1 time the weight of the compound (408) or the compound (406). The desirable reaction temperature is generally about −20° to 100° C., preferably 0° to 80° C.; the desirable hydrogen pressure is generally 1 to 10 atm.; and the reaction is completed generally in about 0.5 to 20 hours.

The reaction for converting the compound (408) or the compound (406) into the compound (409) or the compound (410), respectively, is carried out by hydrolysis, when the $R^{53}$ of the compound (408) or the compound (406) is a tetrahydropyranyloxy group or a tri-lower alkylsilyloxy group. This hydrolysis is carried out in a suitable solvent or in the absence of a solvent and in the presence of an acid. The solvent can be any as long as it gives no adverse effect on the reaction, and there can be mentioned, for example, water, halogenated hydrocarbons (e.g. dichloromethane, chloroform), lower alcohols (e.g. methanol, ethanol, isopropanol), ketones (e.g. acetone, methyl ethyl ketone), ethers (e.g. dioxane, tetrahydrofuran, ethylene glycol monomethyl ether, ethylene glycol dimethyl ether), fatty acids (e.g. formic acid, acetic acid), and their mixed solvents. As to the acid, there can be mentioned, for example, mineral acids such as hydrochloric acid, sulfuric acid, hydrobromic acid and the like, and organic acids such as formic acid, trifluoroacetic acid, acetic acid, aromatic sulfonic acid and the like. The amount of the acid used is not particularly restricted and can be selected suitably from a wide range; and, desirably it is generally about 1 to 10 moles, preferably about 1 to 2 moles per mole of the compound (408) or (406). The reaction proceeds favorably generally at about 0° to 200° C., preferably at about room temperature to 150° C., and is completed generally in about 0.5 to 15 hours. When the $R^{53}$ is a tri-lower alkylsilyloxy group, the reaction may also be carried out using a fluorine compound such as tetra-n-butylammonium fluoride, hydrogen fluoride, cesium fluoride or the like.

When the $R^{53}$ is a lower alkoxy-lower alkoxy group, the reaction for converting the compound (408) or the compound (406) to the compound (409) or the compound (410), respectively, is carried out by treating the compound (408) or the compound (406) in a mixture of a mineral acid (e.g. hydrobromic acid, hydrochloric acid) or an organic acid (e.g. p-toluenesulfonic acid) and a solvent (e.g. water, methanol, ethanol, isopropanol) at 0° to 150° C., preferably at room temperature to 120° C., or by hydrolyzing the compound (408) or the compound (406). The hydrolysis is carried out in a suitable solvent in the presence of an acid. As to the solvent, there can be mentioned, for example, water; lower alcohols such as methanol, ethanol, isopropanol and the like; ethers such as dioxane, tetrahydrofuran and the like; halogenated hydrocarbons such as dichloromethane, chloroform, carbon tetrachloride and the like; polar solvents such as acetonitrile and the like; and their mixed solvents. As to the acid, there can be mentioned, for example, mineral acids such as hydrochloric acid, sulfuric acid, hydrobromic acid and the like; fatty acids such as formic acid, acetic acid and the like; Lewis acids such as boron trifluoride, aluminum chloride, boron tribromide and the like; iodides such as sodium iodide, potassium iodide and the like; and mixtures of the above Lewis acid and the above iodide. The reaction proceeds favorably generally at 0° to 150° C., preferably at room temperature to 100° C., and is completed generally in about 0.5 to 15 hours.

The reaction for converting the compound (409) or the compound (410) into a compound (402a) or a compound (402b), respectively, is carried out by hydrolyzing the compound (409) or the compound (410) in the presence of a basic compound. The basic compound can be illustrated by sodium carbonate, potassium carbonate, sodium hydroxide, potassium hydroxide, barium hydroxide, etc. Desirably, the basic compound is used in an amount of generally about 1 to 15 moles, preferably about 1 to 10 moles per mole of the compound (409) or the compound (410). The solvent can be illustrated by water; alcohols such as methanol, ethanol, isopropanol and the like; ethers such as tetrahydrofuran, dioxane, dimethoxyethane and the like; dimethylformamide; dimethyl sulfoxide; hexamethylphosphoric triamide; their mixed solvents; and so forth. The reaction proceeds favorably generally at about 0° to 200° C., preferably at about room temperature to 150° C., and is completed generally in about 0.5 to 15 hours.

When the $R^{52}$ of the compound (409) or the compound (410) is a phenyl-lower alkyl group, the compound (402a) or the compound (402b) can also be obtained by reducing the compound (409) or the compound (410) under the same conditions as in the reduction reaction for converting the compound (408) or the compound (406) to the compound (409) or the compound (410), respectively.

In the process of the present invention, first the above-obtained compound (402) is cyclized to obtain a compound (403).

In this cyclization reaction, there can be employed the same reaction conditions as in the reaction between the compound (404) and the compound (405) in the reaction scheme D-1.

Particularly preferable is the method (b) using an activated ester such as N-hydroxysuccinimide ester, 1-hydroxybenzotriazole ester or the like. As the basic compound used therein, alkali metal carboxylates, alkali metal halides, etc. are particularly preferable.

The compound (403) forms a salt with an organic amine (e.g. DBU, PBN, diisopropylethylamine), a salt of the alkali metal (e.g. sodium, potassium) or the like and thereby can have a higher purity and higher stability, and can be used advantageously in the subsequent reaction.

In the present invention, the subsequent methylation reaction is carried out by reacting the above-obtained compound with a methylating agent in a suitable solvent in the presence or absence of a catalyst. The methylating agent can be illustrated by diazomethane and trimethylsilyldiazomethane; methyl halides such as methyl iodide and the like; methyl sulfonates such as methyl fluorosulfonate, methyl trifluoromethyl sulfonate, dimethyl sulfate and the like; methyl oxonium salts such as $(CH_3)_3O^\oplus BF_4^\ominus$, $(CH_3)_3O^\oplus PF_6^\ominus$, $(CH_3)_3O^\oplus SbCl_6^\ominus$,

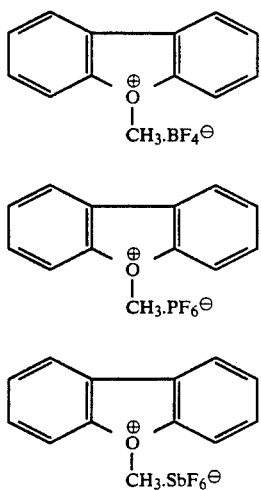

and the like; methyl sulfonium salts such as methyl diphenylsufonium tetrafluoroborate and the like; and so forth.

Of these, methyl oxonium salts are preferable, and $(CH_3)_3O^\oplus BF_4^\ominus$ is particularly preferable. The solvent can be illustrated by, for example, lower alcohols such as methanol, ethanol, propanol and the like; ethers such as dioxane, tetrahydrofuran, diethyl ether, ethylene glycol monomethyl ether and the like; halogenated hydrocarbons such as dichloromethane, chloroform, carbon tetrachloride and the like; aromatic hydrocarbons such as benzene, toluene, xylene and the like; dimethylformamide; acetonitrile; nitromethane; acetone; esters such as ethyl acetate; alkane acids such as trifluoroacetic acid and the like; and their mixed solvents. The catalyst can be illustrated by Lewis acids such as boron tribromide, boron trifluoride-diethyl ether and the like. The desirable amount of the methylating agent, when the agent is diazomethane, is generally a large excess, preferably about 10 to 20 equivalents relative to the raw material compound. The desirable amount of the methylating agent, when the agent is other methylating agent, is at least 1 mole, preferably 1 to 3 moles per mole of the raw material compound. The reaction is carried out generally at about $-30°$ to $100°$ C., preferably at about $-20°$ to $70°$ C., and is completed generally in about 0.5 to 20 hours.

In the present invention, the protective group of the thus obtained compound is removed. When the $R^{51}$ of the compound is a lower alkoxycarbonyl group, a lower alkanoyl group or a benzoyl group, the compound is subjected to a hydrolysis treatment to remove the protective group. This hydrolysis reaction can be carried out under the same conditions as in the hydrolysis reaction for the compound (409) or the compound (410). When the $R^{51}$ is a lower alkoxycarbonyl group, the hydrolysis reaction can also be carried out under the same conditions as in the hydrolysis reaction for converting the compound (408) or the compound (406) both having a tetrahydropyranyloxy group as the $R^{53}$, into the compound (409) or the compound (410), respectively. When the $R^{51}$ is a phenyl-lower alkoxycarbonyl group, the compound can be subjected to a reduction treatment to remove the protective group. This reduction reaction can be carried out under the same conditions as in the reduction reaction for the compound (408) or the compound (406) both having a phenyl-lower alkoxy group as the $R^{53}$.

In the present invention, the indole derivative of the general formula (411) used as a starting material can be produced easily according to the following method.

[Reaction scheme D-2]

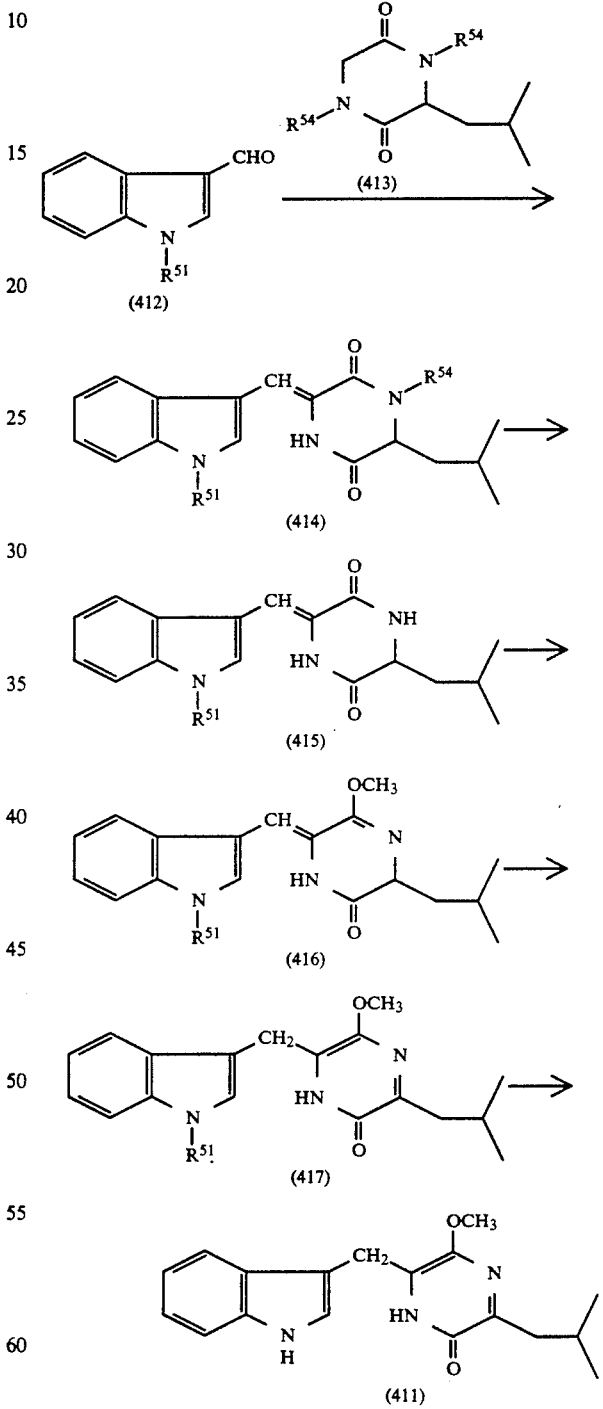

[in the formula, $R^{51}$ is the same as defined above; and $R^{54}$ is a lower alkanoyl group.]

The reaction between the compound (412) and the compound (413) can be carried out in a solvent in the presence of a basic compound. As to the solvent, there can be mentioned, for example, ethers such as THF, dioxane, diethyl ether and the like. As to the basic compound, there can be used alkali metal alcoholates such as potassium tert-butoxide, sodium methylate, sodium ethylate and the like; sodium amide; lower alkyl lithiums such as n-butyllithium, methyllithium and the like; lithium diisopropylamide; and so forth. The amount of the compound (413) used is not particularly restricted and can be selected appropriately from a wide range, and desirable is generally at least about 1 mole, preferably about 1 to 1.5 moles per mole of the compound (407). The reaction is carried out generally at about $-100°$ to $0°$ C., preferably at about $-80°$ to $0°$ C., and is completed in about 1 to 5 hours.

The reaction for obtaining a compound (415) is carried out by hydrolysis.

The hydrolysis is carried out in a suitable solvent or in the absence of a solvent, in the presence of an acid. The solvent can be any one as long as it gives no adverse effect to the reaction, and there can be mentioned, for example, water, halogenated hydrocarbons (e.g. dichloromethane, chloroform), lower alcohols (e.g. methanol, ethanol, isopropanol), ketones (e.g. acetone, methyl ethyl ketone), ethers (e.g. dioxane, tetrahydrofuran, ethylene glycol monomethyl ether, ethylene glycol dimethyl ether), fatty acids (e.g. formic acid), and their mixed solvents. As to the acid, there can be mentioned, for example, mineral acids such as hydrochloric acid, sulfuric acid, hydrobromic acid, and organic acids such as formic acid, trifluoroacetic acid, acetic acid, aromatic sulfonic acid and the like. The amount of the acid used is not particularly restricted and can be selected suitably from a wide range, and desirably is generally about 1 to 10 moles, preferably about 1 to 2 moles per mole of the compound (414). The reaction proceeds favorably generally at about room temperature to $200°$ C., generally at about room temperature to $150°$ C., and is completed generally in about 0.5 to 7 days.

The methylation reaction for the compound (415) is carried out in a solvent in the presence of a methylating agent. As the methylating agent, there can be mentioned methyl sulfonates such as methyl fluorosulfonate, methyl trifluoromethyl sulfonate, dimethyl sulfate and the like; methyl oxonium salts such as $(CH_3)_3O^+BF_4^-$ and the like; and so forth. The solvent can be of any one as long as it gives no adverse effect to the reaction, and there can be mentioned, for example, halogenated hydrocarbons such as dichloromethane, chloroform, carbon tetrachloride and the like. The amount of the alkylating agent used is not particularly restricted and can be selected suitably from a wide range, and desirably is generally at least about 1 mole, preferably about 1 to 5 moles per mole of the compound (415). The reaction is carried out generally at about $0°$ to $100°$ C., preferably at about $0°$ to $70°$ C., and is completed in about 1 to 40 hours.

The reaction for converting the compound of the general formula (416) into a compound (417) is carried out in a solvent in the presence of a basic compound. As to the basic compound, there can be used, besides the basic compounds used in the Schotten-Baumann reaction, for example, sodium hydroxide and potassium hydroxide; sodium hydride and potassium hydride; alkali metal alcoholates such as potassium tert-butoxide, sodium methylate, sodium ethylate and the like; sodium amide; and alkyl lithiums such as n-butyllithium, methyllithium and the like.

As to the solvent, there can be mentioned, besides the solvents used in the above-mentioned mixed acid anhydride method, for example, alcohols such as methanol, ethanol, propanol, butanol, 3-methoxy-1-butanol, ethyl cellosolve, methyl cellosolve and the like; pyridine; acetone; acetonitrile; and mixed solvents consisting of two or more of the above.

The reaction is carried out generally at about $0°$ to $100°$ C., preferably at about $0°$ to $70°$ C., and is completed generally in about 1 to 50 hours.

The reaction for converting the compound (417) having, as the $R^{51}$, a group other than hydrogen atom, into a compound (411) can be carried out under the same conditions as in the reaction for removing the protecting group.

In the present invention, the subsequent oxidation reaction can be carried out by culture of microorganism.

As to specific example of the microorganism strain used in the oxidation reaction, there can be mentioned a strain which belongs to a Thielavia genus and which has been named as *Thielavia minor* OFR-1561 (Deposition No. REFM BP-1908, deposited at the Fermentation Research Institute, Agency of Industrial Science and Technology, Ministry of International Trade and Industry, Japanese Government).

The intermediate substance for producing the substance of the present invention can be produced by culturing in an appropriate medium a microorganism (e.g. the above *Thielavia minor* OFR-1561 or its variant) belonging to the Thielavia genus and capable of producing the above NF-1616-904 substance. The culture of the microorganism is carried out principally in accordance with the general method for culturing microorganisms, and is conducted preferably under aerobic conditions, i.e. by shaking culture, aeration stirring culture or the like.

The medium used in the culture can be any as long as it contains nutrients utilized by the microorganisms belonging to the Thielavia genus. There can be used various synthetic media, semi-synthetic media and natural media. With respect to the formulation of the medium, the carbon source includes glucose, sucrose, fructose, glycerine, dextrine, starch, molasses, corn steep liquor, organic acids, etc., and they can be used alone or in combination. The nitrogen source includes organic nitrogen sources such as pharmadia, peptone, meat extract, yeast extract, soybean powder, casein, amino acids, urea and the like, as well as inorganic nitrogen sources such as sodium nitrate, ammonium sulfate and the like, and they can be used alone or in combination. There can also be used, as necessary, sodium salts, potassium salts, magnesium salts, phosphates, other heavy metal salts, etc. When there occurs severe foaming during the culture, various known anti-foaming agents can be added appropriately to the medium, and the addition must be made so as not to give any adverse effect to the production of intended substance.

The pH of the medium is preferably maintained within the optimum pH range of the microorganism, generally at about neutrality. The culture temperature is preferably maintained at a temperature at which the microorganism can grow normally, generally at $20°-40°$ C., particularly preferably at about $30°$ C. The culture period is generally about 1 to 5 days in the case of a liquid medium. An intended substance is formed and accumulated by the above culture. As a matter of course, the above culture conditions can be modified as necessary depending upon the kind and properties of the microorganism used, the external conditions, etc., and optimum conditions for each culture condition can be selected from the above ranges.

The isolation of the substance produced by the above culture can be carried out according to the general method(s) for collecting a fermentation product, for example, one or any combination (the order of combination has no restriction) of salting-out method (e.g. ammonium sulfate precipitation method), dialysis method, extraction, gel chromatography, ion exchange chromatography, absorption chromatography, etc.

A more specific explanation is made. Since the intended substance produced by the above culture is present mainly in the culture solution, the culture solution is first subjected to separation of culture filtrate and microorganism solid by filtration, centrifugation, etc.; the resulting filtrate is extracted with ethyl acetate or the like; the resulting extract layer containing an intended substance is concentrated; and the resulting concentrate is purified by silica gel chromatography, chromatography using a Sephadex LH 20 column (made by Pharmacia Co.) or the like.

Specific examples for production according to the reaction schemes D-1 to D-2 are described in Reference Examples D-1 to D-6 and Examples D-1 to D-4.

Of the compounds represented by the general formula (1) according to the present invention, those having a basic group can be easily converted into respective acid addition salts by reacting them with a pharmaceutically acceptable acid. As to the acid, there can be mentioned, for example, inorganic acids such as hydrochloric acid, sulfuric acid, phosphoric acid, hydrobromic acid and the like; and organic acids such as oxalic acid, acetic acid, malonci acid, methanesulfonic acid, maleic acid, fumaric acid, malic acid, tartaric acid, citric acid, benzoic acid and the like.

Of the compounds represented by the general formula (1) according to the present invention, those having an acidic group can be easily converted into respective salts by reacting them with a pharmaceutically acceptable basic compound. As to the basic compound, there can be mentioned, for example, sodium hydroxide, potassium hydroxide, calcium hydroxide, sodium carbonate and potassium hydrogencarbonate.

The intended compounds thus obtained in each step can be isolated and purified easily by conventional separation means. The separation means can be illustrated by, for example, solvent extraction, dilution, recrystallization, column chromatography and preparative thin layer chromatography.

The compounds of the present invention include optical isomers and stereoisomers.

The compounds of the present invention are generally used in the form of ordinary pharmaceutical preparations. The preparations are prepared using diluents or fillers conventionally used, such as filler, bulking agent, binder, humectant, disintegrator, surfactant, lubricant and the like. The compounds of the present invention can be made into various forms of pharmaceutical preparations depending upon the purpose of remedy of disease, and typical examples of such preparations are tablets, pills, a powder, a solution, a suspension, an emulsion, granules, capsules, suppositories and an injection (solution, suspension, etc.). In molding the present compounds into the form of tablets, there can be used various carriers conventionally known in the relevant field, such as filler (e.g. lactose, white sugar, sodium chloride, grape sugar, urea, starch, calcium carbonate, kaolin, crystalline cellulose, silicic acid), binder (e.g. water, ethanol, propanol, simple syrup, grape sugar solution, starch solution, gelatin solution, carboxymethyl cellulose, shellac, methyl cellulose, potassium phosphate, polyvinyl pyroolidone), disintegrator (e.g. dry starch, sodium alginate, agar powder, laminaran powder, sodium hydrogencarbonate, calcium carbonate, polyoxyethylene sorbitan-fatty acid ester, sodium laurylsulfate, stearic acid monoglyceride, starch, lactose), disintegration inhibitor (e.g. white sugar, stearin, cacao butter, hydrogenated oil), absorpiton promotor (e.g. quaternary ammonium base, sodium laurylsulfate), humectant (e.g. glycerine, starch), adsorbent (e.g. starch, lactose, kaolin, bentonite, colloidal silicic acid) and lubricant (e.g. refined talc, stearci acid salt, boric acid powder, polyethylene glycol). The tablets can be prepared, as necessary, as coated tablets such as sugar-coated tablets, gelatin-coated tablets, enteric-coated tablets and film-coated tablets, or as double layered tablets or multi layered tablets. In molding the present compounds into the form of pills, there can be used various carriers conventionally known in the relevant field, such as filler (e.g. grape sugar, lactose, starch, cacao fat, hardened vegetable oil, kaolin, talc), binder (e.g. gum arabic powder, tragacanth powder, gelatin, ethanol) and disintegrator (e.g. laminaran agar). In molding the present compounds into the form of suppositories, there can be used various carriers conventionally known, such as polyethylene glycol, cacao fat, higher alcohol, higher alcohol ester, gelatin and semi-synthesized glyceride. In preparing an injection from the present compounds, the prepared solution or suspension is preferably sterilized and made isotonic to the blood. In preparing a solution, an emulsion or a suspension from the present compounds, there can be used any diluents conventionally used in the relevant field, such as water, ethyl alcohol, propylene glycol, ethoxized isostearyl alcohol, polyoxidized isostearyl alcohol and polyoxyethylene sorbitan-fatty acid ester. In this case, the solution, emulsion or suspension as a cardiotonic may contain sodium chloride, glucose, or glycerin in an amount sufficient to make an isotonic solution, and may further contain a dissolution aid, a buffer agent, an analgesic, etc. all conventionally used. The above pharmaceutical preparations may furthermore contain, as necessary, a coloring agent, a preservative, a perfume, a flavoring agent, a sweetener and other drug.

The amount of the compound of the general formula (1) contained in the above pharmaceutical preparation is not particularly restricted and can be selected appropriately in a wide range, but is generally 1 to 7% by weight, preferably 1 to 30% by weight in the whole formulation.

The methods of administration of the above pharmaceutical preparation is not particularly restricted, and they are administered appropriately so as to meet the form of preparation, the age, sex and other conditions of patient, the degree of disease, etc. For example, oral administration is adopted in the cases of tablets, pills, solution, suspension, emulsion, granules and capsules. In the case of injection, the injection is administered intravenously alone or in admixture with an ordinary supplementary solution such as grape sugar, amino acid or the like, and is further administered alone, as necessary, intramuscularly, intracutaneously, subcutaneously or intraperitoneally. Suppositories are administered intrarectally.

The dose of the above pharmaceutical preparation is selected appropriately depending upon the age, sex and other conditions of patient, the degree of disease, etc., but desirably is generally about 0.5 to 30 mg per day per kg of body weight in terms of the compound of the general formula (1) contained as an activate ingredient. The compound (1) as an active ingredient is desirably allowed to be present in each unit form for administration in an amount of 10 to 1,000 mg.

EXAMPLES

Reference Examples, Examples, Pharmacological Tests and Examples of Pharmaceutical Preparation are illustrated as follows.

REFERENCE EXAMPLE A-1

Synthesis of methyl ester of N-tert-butoxycarbonyl-DL-phenylglycyl-N-methyl-L-tryptophan (Compound A-2a)

In 15 ml of $CH_2Cl_2$ were dissolved 1.5 g of N-tert-butoxycarbonyl-phenylglycine, 1.52 g of bis(2-oxo-3-oxazolinyl)phosphinic chloride (BOPC) and 0.89 ml of triethylamine. The mixture was stirred for 1 hour at 0°–5° C. Thereto was dropwise added at 0°–5° C. in 30 minutes, 5 ml of a solution of 0.99 g of methyl ester of L-tryptophan and 0.89 ml of triethanolamine dissolved in 5 ml of $CH_2Cl_2$. The mixture was stirred overnight at room temperature. Water was added to the reaction mixture, then extracted with $CH_2Cl_2$. The extract was dried with $Na_2CO_3$, subjected to a silica gel column chromatography, and crystallized from n-hexane-$Et_2O$ to obtain 1.8 g (91%) of the title compound as white crystals having a melting point of 69°–71° C.

$^1$H-NMR (250 MHz, $DCDl_3$) δ: 1.22–1.49 (9H, m), 2.69 (3H, d, J=4.7 Hz), 3.12–3.63 (2H, m), 3.68, 3.78 (3H, s), 5.21–5.38 (1H, m), 5.48 (1H, d, J=7.9 Hz), 5.87–6.02 (1H, m), 6.79 (1H, brs), 6.98–7.47 (8H, m), 7.52–7.65 (1H, m), 7.32–7.98 (1H, m).

MS (m/e): 465 (M+), 20 eV.

REFERENCE EXAMPLE A-2

Synthesis of methyl ester of N-tert-butoxycarbonyl-phenylglycyl-N-methyldehydrotryptophan (Compound A-3a)

In 30 ml of DMF were dissolved 1.41 g of the Compound A-2a and 0176 g of DDQ. The mixture was stirred for 1 hour in an argon gas atmosphere. The reaction mixture was poured into water, then extracted with ethyl acetate. The extract was washed with an aqueous solution saturated with $NaHCO_3$, washed with water, dried with $Na_2CO_3$, and subjected to a silica gel column chromatography to obtain 1.1 g (71%) of the title compound. Recrystallized from $Et_2O$-n-hexane to obtain white crystals having a melting point of 199°–200° C.

EXAMPLE A-1

Synthesis of (Z)-6-(indol-3-yl)methylidene-1-methyl-3-phenylpiperazine-2,5-dione (Compound A-4a)

The Compound A-3a was dissolved in 5 ml of 99% $HCO_2H$. Three drops of hydrochloric acid were added thereto, and the mixture was stirred overnight at room temperature. The reaction mixture was concentrated, and water was added thereto. To the mixture was added $K_2CO_3$ to make the pH of the mixture basic, then extracted with $CHCl_3$. The extract was dried with $Na_2CO_3$ and subjected to solvent removal. The resulting oily matter was dissolved in 10 ml of toluene. The solution was refluxed for 1 hour with heating and then concentrated. The concentrate was purified with a short silica gel column to obtain 0.4 g (56%) of the title compound. Recrystallized from $Et_2O$-n-hexane to obtain yellow crystals having a melting point of 120°–123° C.

$^1$H-NMR (200 MHz, $DCDl_3$) δ: 2.95 (3H, s), 5.26 (1H, d, J=3.5 Hz), 6.61 (1H, d, J=3.0 Hz), 7.00–7.52 (10H, m), 8.50 (1H, brs).

IR (KBr): 3246, 1676, 1624, 1458, 1420, 1365, 1339, 745 $cm^{-1}$.

EXAMPLE A-2

Synthesis of (Z)-6-(indol-3-yl)methylidene-5-methoxy-1-methyl-3-phenyl-1,2,3,6-tetrahydropyrazin-2-one (Compound A-5a)

One gram (3.0 mM) of Compound A-4a was dissolved in methylene chloride. Thereto was added 0.28 g of $FSO_3CH_3$ The mixture was stirred overnight at room temperature. The reaction mixture was poured into an aqueous $K_2CO_3$ solution, then extracted with ethyl acetate. The extract was dried with $Na_2CO_3$ and subjected to a silica gel column chromatography ($SiO_2$, ether) to obtain 214 mg (20%) of the title compound. Recrystallized from $Et_2O$-n-hexane to obtain a pale yellow powder having a melting point of 139°–141° C. (decomposed).

$^1$H-NMR (200 MHz, $CDCl_3$) δ: 2.92 (3H, s), 3.99 (3H, s), 5.55 (1H, s), 7.00–7.43 (11H, m), 8.43 (1H, brs)

EXAMPLE A-3

Synthesis of 6-(indol-3-yl)methyl-5-methoxy-1-methyl-3-phenyl-1,2-dihydropyrazin-2-one (Compound A-6a)

547 Milligrams of Compound A-5a was dissolved in 20 ml of THF. Thereto was added a catalytic amount of tert-BuOK. The mixture was stirred for 2 hours at room temperature in an argon gas atmosphere. The reaction mixture was concentrated. The concentrate was purified by a short silica gel column ($SiO_2$, ether) to obtain 410 g (75%) of the title compound. Recrystallized from ether to obtain orange-yellow prismatic crystals having a melting point of 150°–152° C. (decomposed).

$^1$H-NMR (200 MHz, $CDCl_3$) δ: 3.60 (3H, s), 4.03 (3H, s), 4.25 (2H, d, J=0.9Hz), 6.83–6.88 (1H, m), 7.11–7.48 (5H, m), 7.64 (1H, d, J=7.4 Hz), 8.13 (1H, brs), 8.49–8.57 (2H, m)

REFERENCE EXAMPLE A-3

The following compounds were obtained by the same manner as in Reference Example A-1.

Methyl ester of tert-butoxycarbonyl-L-leucyl-N-methyl-L-tryptophan (Compound A-2b). A white powdery substance.

$^1$H-NMR (200 MHz, $CDCl_3$) δ: 0.35–1.03 (6H, m), 1.18–1.56 (11H, m), 1.57–1.83 (1H, m), 2.85, 2.93 (3H, s), 3.13–3.67 (2H, m), 3.73, 3.75 (3H, s), 4.40–4.67 (1H, m), 5.08–5.47 (2H, m), 6.97–7.38 (4H, m), 7.53–7.63 (1H, m), 7.98–8.27 (1H, m)

Methyl ester of tert-butoxycarbonylglycyl-N-methyl-L-tryptophan (Compound A-2c), a white powdery substance.

$^1$H-NMR (200 MHz, $CDCl_3$) δ: 1.33–1.55 (9H, m), 2.75, 2.81 (3H, s), 3.10–3.63 (2H, m), 3.72, 3.74 (3H, s), 4.32–4.63 (2H, m), 5.13–5.54 (2H, m), 6.92–7.04 (1H, m), 7.05–7.25 (2H, m), 7.28–7.42 (1H, m), 7.53–7.62 (1H, m), 8.15–8.41 (1H, m)

REFERENCE EXAMPLE A-4

The following compounds were obtained by the same manner as in Reference Example A-2, using Compounds A-2b and 2c.

Methyl ester of N-tert-butoxycarbonyl-L-leucyl-N-methyldehydrotryptophan (Compound A-3b). A white powdery substance. Melting point: 130°–132° C. (recrystallized from Et$_2$O-n-hexane), Methyl ester of N-tert-butoxycarbonylglycyl-N-methyldehydrotryptophan (Compound A-3c). A yellow oily substance.

$^1$H-NMR (200 MHz, CDCl$_3$) δ: 1.33 (9H, s), 3.14 (3H, s), 3.76–3.85 (2H, m), 3.86 (1H, s), 5.32 (1H, brs), 7.22–7.32 (2H, m), 7.40–7.54 (2H, m), 7.70–7.82 (2H, m), 8.09 (1H, s), 9.93 (1H, brs)

EXAMPLE A-4

The following compounds were obtained by the same manner as in Example A-1, using Compounds A-3b and A-3c. (3S,Z)-6-(Indol-3-yl)methylidene-3-isobutyl-1-methylpiperazine-2,5-dione (Compound A-4b). A pale yellow powdery substance. Melting point: 98°–100° C. (recrystallized from Et$_2$O-n-hexane).

(Z)-6-(Indol-3-yl)methylidene-1-methyl-piperazine-3,6-dione (Compound A-4c). A light yellow powder. Melting point: 143°–144° C. (recrystallized from Et$_2$O-n-hexane).

EXAMPLE A-5

The following compounds were obtained by the same manner as in Example A-2, using Compounds A-4b and A-4c. (3S,Z)-6-(Indol-3-yl)methylidene-3-isobutyl-5-methoxy-1-methyl-1,2,3,6-tetrahydropyrazin-2-one (Compound A-5b). A white powdery substance. Melting point: 109°–110° C. (recrystallized from Et$_2$O-n-hexane)

(Z)-6-(Indol-3-yl)methylidene-5-methoxy-1-methyl-1,2,3,6-tetrahydropyrazin-2-one (Compound A-5c). A pale yellow powdery substance.

$^1$H-NMR (200 MHz, CDCl$_3$) δ: 2.97 (3H, s), 3.88 (3H, s), 4.33 (2H, s), 6.96 (1H, s), 7.16–7.32 (3H, m), 7 38–7.44 (1H, m), 7.58–7.65 (1H, m), 8.61 (1H, brs)

EXAMPLE A-6

The following compounds were obtained by the same manner as in Example A-3, using the Compounds A-5b and A-5c. 6-(Indol-3-yl)methyl-3-isobutyl-5-methoxy-1-methyl-1,2-dihydropyrazin-2-one (Compound A-6b). A light yellow powdery substance. Melting point: 164°–167° C. (decomposed) (recrystallized from ET$_2$O-n-hexane).

6-(Indol-3-yl)methyl-5-methoxy-1-methyl-1,2-dihydropyrazin-2-one (Compound A-6c). A yellow oily substance.

$^1$H-NMR (200 MHz, CDCl$_3$) δ: 3.52 (3H, s), 3.93 (3H, s), 4.20 (2H, s), 6.80–6.84 (1H, m), 7.11–7.30 (2H, m), 7.35–7.41 (1h, m), 7.57–7.63 (1H, m), 7.87 (1H, s), 8.23 (1H, brs)

EXAMPLE A-7

Synthesis of (Z)-5-ethoxy-6-(indol-3-yl)methylidene-1-methyl-3-phenyl-1,2,3,6-tetrahydropyrazin-2-one (Compound A-7a)

One gram of the Compound A-4a was dissolved in 20 ml of CH$_2$Cl$_2$. Thereto was dropwise added at room temperature 4.5 ml of a solution of 1 M of Et$_3$O$^⊕$BF$_4$$^⊖$ dissolved in CH$_2$Cl$_2$. The mixture was stirred overnight at room temperature and then poured into an aqueous K$_2$CO$_3$ solution, then extracted with CHCl$_3$. The extract was dried over Na$_2$CO$_3$ and subjected to a silica gel column chromatography (n-hexane:ether =3:1) to obtain 100 mg (9%) of the title compound as a pale brown powdery substance having a melting point of 192°–196° C. (decomposed) (recrystallized from Et$_2$O-n-hexane). Also, 600 mg of Compound A-4a (the starting material) was recovered.

$^1$H-NMR (200 MHz, CDC$_3$) δ: 1.49 (3H, t, J=7.1 Hz), 2.91 (3H, s), 4.41 (2H, q, J=7.1 Hz), 5.53 (1H, s), 7.00–7.45 (11H, m), 8.40 (1H, brs)

EXAMPLE A-8

The following compound was obtained by the same manner as in Example A-3, using the compound A-7a.

5-Ethoxy-6-(indol-3-yl)methyl-1-methyl-3-phenyl-1,2-dihdyropyrazine-2-one (Compound A-8a). A pale yellow powdery substance.

$^1$H-NMR (200 MHz, CDCl$_3$) δ: 1.40 (3H, t, J=7.0 Hz), 3.58 (3H, s), 4.28 (2H, d, J=0.9 Hz), 4.45 (2H, q, J=7.0 Hz), 6.83–6.86 (1H, m), 7.10–7.50 (6H, m), 7.66 (d, J=7.4 Hz, 1H), 8.25 (1H, brs), 8.48–8.54 (2H, m)

EXAMPLE A-9

Synthesis of 6-[(1-formyl)indol-3-yl]methyl-methoxy-1-methyl-3-phenyl-1,2-dihydropyrazin-2-one (Compound A-9a)

42 Milligrams of the Compound A-6a was dissolved in 1 ml of 99% HCO$_2$H. Thereinto was blown HCl gas for 10 minutes. The vessel was stoppered and the mixture therein was stirred overnight at room temperature. The mixture was then concentrated. The concentrate was purified with a short silica gel column chromatography (CHCl$_3$) to obtain 35 mg (80%) of the title compound as a pale yellow powdery substance (recrystallized from Et$_2$O) having a melting point of 209°–213° C. (decomposed).

$^1$H-NMR (250 MHz, CDCl$_3$) δ: 3.61 (3H, s), 4.04 (3H, s), 4.22 (2H, d, J=1.4 Hz), 7.32–7.76 (8H, m), 8.48–8.57 (2H, m), 9.02, 9.48 (1H, brs), IR (KBr): 1708, 1637, 1575, 1560, 1455 cm$^{-1}$.

EXAMPLE A-10

Synthesis of (Z)-3-[(1-methyl)indol-3-yl]methylidene-1,4-dimethyl-6-phenylpiperazine-2,5-dione (Compound A-10a)

0.9 Gram of KOH was dispersed in 10 ml of DMSO with fine grinding. The dispersion was stirred for 30 minutes at room temperature. Thereto was added 1.34 g of the Compound 4a, and the mixture was stirred for 30 minutes. Then, 0.6 ml of MeI was added. Stirring was effected for about 1 hour. The reaction mixture was mixed with water, then extracted with ethyl acetate. The extract was dried over Na$_2$CO$_3$ and subjected to a silica gel (Art-9385, manufactured by Merck & Co.) column chromatography (n-hexane: ethyl acetate=25:1) to obtain 0.5 mg (34%) of the title compound. Recrystallized from Et$_2$O-n-hexane to obtain a pale yellow powdery substance having a melting point of 217°–220° C. (decomposed).

REFERENCE EXAMPLE A-5

Synthesis of (6S,Z)-1-acetyl-3-[(1-benzyloxycarbonyl]indol-3-yl)methylidene-6-isobutylpiperazine-2,5-dione (Compound A-11)

12.7 Milliliters of a solution of 1.6 M of n-BuLi dissolved in n-hexane was added dropwise into 100 ml of a solution of 4.5 g of N-benzyloxycarbonyl-indole-3-carbaldehyde dissolved in anhydrous THF, at −78° C. with stirring. After the completion of the dropwise addition, stirring was effected for a further 30 minutes at the same temperature. Then, there was added dropwise 30 ml of a solution of 5.0 g of (3S)-1,4-diacetyl-3-isobutyl-2,5-diketopiperazine dissolved in anhydrous THF to the reaction mixture. After the completion of the dropwise addition, the mixture was heated to −60° C. in 30 minutes and mixed with water. The resulting mixture was subjected to extraction with $CH_2Cl_2$. The extract was washed with an aqueous solution saturated with NaCl, dried over $MgSO_4$, and the solvent was removed by evaporation to obtain 9 g of a yellow oily substance. It was dissolved in 100 ml of benzene. To the solution was added 2 ml of DBU, and the mixture was stirred for 10 minutes at room temperature. The solvent was removed by evaporation. The residue was purified by a silica gel column chromatography (n-hexane: ethyl acetate=3:1) to obtain 5.5 g (66%) of the title compound as light yellow prismatic crystals having a melting point of 95°-97° C.

EXAMPLE A-11

Synthesis of (6S,Z)-3-[(1-benzyloxycarbonylindol)-3-yl]methylidene-6-isobutylpiperazine-2,5-dione (Compound A-12)

80 Milliliters of 1 N hydrochloric acid was added to 400 ml of a solution of 4.0 g of the Compound A-11 dissolved in methanol. The mixture was refluxed for 2 hours. The mixture was cooled in an ice-bath and the resulting crude crystals (3.3 g, 91%) were collected by filtration. Colorless needle-like crystals. Melting point: 255°-257° C. (recrystallized from ethyl acetate-n-hexane).

$^1$H-NMR (250 MHz, $CDCl_3$) δ: 0.99 (3H, d, J=6 Hz), 1.02 (3H, d, J=6 Hz), 1.72-1.97 (3H, m), 4.16-4.26 (1H, m), 5.50 (2H, s), 6.42 (1h, brs), 7.07 (1H, s), 7.30-7.57 (7H, m), 7.64 (1h, d, J=7 Hz), 7.82 (1H, s), 7.88 (1H, brs), 8.21 (1H, d, J=8 Hz).

EXAMPLE A-12

9.5 Grams of Compound A-12 was suspended in 500 ml of dry $CH_2Cl_2$. Thereto was added 12.5 ml of $CF_3SO_2OCH_3$. The mixture was refluxed for 36 hours at 50°-60° C. with stirring. The mixture was allowed to cool, washed with an aqueous solution saturated with NaCl, dried over magnesium sulfate, and the solvent was removed by evaporation. The resulting residue was purified by a silica gel column chromatography (n-hexane:ethyl acetate=5:1→3:1→$CH_2Cl_2$:methanol=3:1) to obtain 7.0 g (71%) of the following Compound A-13 and 0.3 g (3%) of its dimethylated compound (Compound A-14). Also, there was recovered 1.8 g (18%) of the Compound A-12 (the starting material).

(3S,Z)-6-[(1-Benzyloxycarbonyl)indol-3-yl]-methylidene-3-isobutyl-5-methoxy-1,2,3,6-tetrahydropyrazin-2-one (Compound A-13). Colorless needle-like crystals. Melting point: 129°-131° C. (recrystallized from ethyl acetate-n-hexane).

3-[(1-Benzyloxycarbonylindol)-3-yl]methyl-6-isobutyl-2,5-dimethoxypyrazine (Compound A-14). Colorless needle-like crystals (recrystallized from ethyl acetate-n-hexane).

$^1$H-NMR (250 MHz, $CDCl_3$) δ: 0.91 (6H, d, J=6.5 Hz), 2.03-2.23 (1H, m), 2.54 (2H, d, J=7 Hz), 3.81 (3H, s), 3.91 (3H, s), 4.07 (2H, s), 5.43 (2H, s), 7.19-7.50 (7H, m), 7.52 (1H, s), 7.74 (1H, d, J=8 Hz), 8.15 (1H, brd, J=8 Hz).

EXAMPLE A-13

The following compound was obtained by the same manner as in Example A-2, using the Compound A-13.

6-[(1-Benzyloxycarbonyl)indol-3-yl]methyl-3-isobutyl-5-methoxy-1,2-dihydropyrazin-2-one (Compound A-15). Recrystallized from ethyl acetate-n-hexane. Colorless prismatic crystals. Melting point: 149°-151° C.

EXAMPLE A-14

Synthesis of 6-(indol-3-yl)methyl-3-isobutyl-2-methoxy-1,2-dihydropyrazin-2-one (Compound A-16)

0.62 Gram of Compound A-15 was dissolved in 20 ml of dioxane. Thereto was added 0.20 g of 10% Pd-C. The mixture was stirred for 1 hour at ambient temperature and under atmospheric pressure in a $H_2$ gas atmosphere. After the catalyst was removed by filtration, the filtrate was refluxed for 1 hour. The solvent was removed by evaporation under reduced pressure. The residue was purified by a silica gel column chromatography (n-hexane:ethyl acetate=4:1) to obtain 0.34 g (79%) of the title compound. Recrystallized from ethyl acetate-n-hexane to obtain colorless needle-like crystals having a melting point of 172°-173° C. (Compound A-16).

EXAMPLE A-15

The following compound was obtained by the same manner as in Example A-14, using the Compound A-13.

(3S,Z)-6-(Indol-3-yl)methylidene-3-isobutyl-5-methoxy-1,2,3,6-tetrahydropyrazin-2-one (Compound A-17). Colorless needle-like crystals (recrystallized from ethyl acetate-n-hexane). Melting point: 116°-117° C.;

REFERENCE EXAMPLE A-6

Synthesis of 2-acetoxy-6-[(1-benzyloxycarbonyl)indol-3-yl]methyl-3-isobutyl-5-methoxypyrazine (Compound A-18)

55 Microliters of dry pyridine, 40 μl of $Ac_2O$ and 4 mg of DMAP were added to a solution of 100 mg of the compound 15 dissolved in 2 ml of dry $CH_2Cl_2$. The mixture was allowed to stand for 15 hours at room temperature. A slight amount of methanol was added thereto. After 30 minutes, the solvent was removed by evaporation under reduced pressure. The residue was purified by a silica gel column chromatography (n-hexane: ethyl acetate=5:1) to obtain 110 mg (quant.) of the title compound as an orange oily substance.

$^1$H-NMR (250 MHz, $CDCl_3$) δ: 0.92 (6H, d, J=6.5 Hz), 2.07-2.27 (1H, m), 2.33 (3H, s), 2.45 (2H, d, J=7 Hz), 3.94 (3H, s), 4.12 (2H, s), 5.43 (2H, s), 7.17-7.53 (9H, m), 7.64 (1H, d, J=7 Hz), 8.12 (1H, brd, J=7.5 Hz).

EXAMPLE A-16

The following compounds were obtained by the same manner as in Example A-14, using the Compounds A-14 and A-18. 3-(Indol-3-yl)methyl-6-isobutyl-2,5-dimethoxypyrazine (Compound A-19). An orange oily substance.

$^1$H-NMR (250 MHz, CDCl$_3$) δ: 0.91 (6H, d, J=6.5 Hz), 2.05-2.23 (1H, m), 2.53 (2H, d, J=7 Hz), 3.88 (3H, s), 3.91 (3H, s), 4.15 (2H, s), 7.10 (1H, t, J=7.5 Hz), 7.10 (1H, d, J=2 Hz), 7.17 (1H, t, J=7.5 Hz), 7.32 (1H, d, J=7.5 Hz), 7.85 (1H, d, J=7.5 Hz), 7.93 (1H, brs)

2-Acetoxy-6-(indol-3-yl)methyl-3-isobutyl-5-methoxypyrazine (Compound A-20). An orange oily substance.

$^1$H-NMR (250 MHz, CDCl$_3$) δ: 0.92 (6H, d, J=6.5 Hz), 2.06-2.27 (1H, m), 2.33 (3H, s), 2.45 (2H, d, J=7 Hz), 3.94 (3H, s), 4.20 (2H, d), 7.03 (1H, d, J=2.5 Hz), 7.07-7.21 (2H, m), 7.31 (1H, d, J=6.5 Hz), 7.73 (1H, d, J=7.5 Hz), 7.98 (1H, brs).

EXAMPLE A-17

Synthesis of (3S,6S)-3-[(1-benzyloxycarbonyl)indol-3-yl]methyl-2,5-diethoxy-6-isobutyl-3,6-dihydroipyrazine (Compound A-21)

In 40 ml of dry CH$_2$Cl$_2$ was dispersed 2.86 g of (3S,6S)-3-(1-benzyloxycarbonylindol-3-yl)-methyl-6-isobutylpiperazine-2,5-dione. Thereto was added 3.76 g of Et$_3$O$^\oplus$BF$_4^\ominus$. The mixture was stirred for 24 hours at room temperature in an Ar gas atmosphere. 4 Grams of Et$_3$O$^\oplus$BF$_4^\ominus$ was further added, and the resulting mixture was stirred overnight. The mixture was then poured into a phosphate buffer solution (pH=7). The mixture was adjusted to pH 7 by adding Na$_2$CO$_3$, then extracted with CHCl$_3$. The extract was dried over Na$_2$SO$_4$ and subjected to a silica gel column chromatography (n-hexane:Et$_2$O=10:1) to obtain 2.5 g (78%) of the title compound as a yellow oily substance.

$^1$H-NMR (200 MHz, CDCl$_3$) δ: 0.00-0.17 (1H, m), 0.53 (3H, d, J=6.7 Hz), 0.69 (3H, d, J=6.6 Hz), 0.86-1.05 (1H, m), 1.18 (3H, d, J=7.1 Hz), 1.29 (3H, t, J=7.1 Hz), 1.37-1.57 (1H, m), 3.08-3.29 (2H, m), 3.70-3.85 (1H, m), 3.92-4.18 (4H, m), 4.28-4.43 (1H, m), 5.42 (2H, s), 7.16-7.58 (9H, m), 8.04-8.21 (1H, m).

EXAMPLE A-18

Synthesis of 3-[(1-benzyloxycarbonyl)indol-3-yl]methyl-2,5-diethoxy-6-isobutylpyrazine (Compound A-22)

In 50 ml of toluene were dissolved 1 g of compound A-21 and 1.16 g of DDQ. The mixture was stirred for 2 hours at 100° C. The reaction mixture was concentrated. The concentrate was purified by using a silica gel column chromatography (n-hexane:Et$_2$O=10:1) to obtain 0.3 g (30%) of the title compound as a colorless oily substance.

$^1$H-NMR (200 MHz, CDCl$_3$) δ: 0.82 (6H, d, J=6.6 Hz), 1.06-1.52 (6H, m), 1.87-2.20 (1H, m), 2.44 (2H, d, J=7.1 Hz), 3.97 (2H, s), 4.05-4.40 (4H, m), 5.35 (2H, s), 7.00-7.52 (8H, m), 7.62-7.73 (1H, m), 7.93-8.12 (1H, m).

EXAMPLE A-19

Synthesis of 3-[(1-benzyloxycarbonyl)indol-3-yl]methyl-2,5-dichloro-6-isobutylpyrazine (Compound A-24) and 3-(1-benzyloxycarbonylindole-3-yl)methyl-2-(or -5)-chloro-6-isobutylpyrazine [Compound A-25a (or A-25b)]

In 30 ml of POCl$_3$ was dispersed 5 g of (3S,6S)-3-(benzyloxycarbonylindol-3-yl)methyl-6-isobutylpiperazine-2,5-dione. The dispersion was heated to obtain a clear solution. The solution was then stirred for 1 hour at room temperature. Thereto was added 5.3 g of PCl$_5$, and the mixture was stirred overnight at room temperature. The reaction mixture was poured into ice water. The mixture was made basic by adding Na$_2$CO$_3$ thereto, then extracted with ethyl acetate. The extract was dried over Na$_2$CO$_3$ and subjected to a silica gel column chromatography (Art 9385, manufactured by Merck & Co., n-hexane:Et$_2$O=20:1) to obtain 1.67 g (31%) of a dichloro compound (Compound A-24) and 0.5 g (10%) of monochloro compounds (a mixture of Compound A-25a and Compound A-25b). Compound A-24. Colorless needle-like crystals. Melting point: 89°-91° C. (recrystallized from Et$_2$O-n-hexane).

$^1$H-NMR (200 MHz, CDCl$_3$) δ: 0.95 (6H, d, J=6.6 Hz), 2.08-2.34 (1H, m), 2.76 (2H, d, J=7.2 Hz), 4.29 (2H, s), 5.44 (2H, s), 7.21-7.57 (8H, m), 7.65-7.72 (1H, m), 8.10-8.20 (1H, m).

MS (m/e): 467 (M+).

Compound A-25a. A pale yellow oily substance.

$^1$H-NMR (200 MHz, CDCl$_3$) δ: 0.85 (6H, d, J=6.6 Hz), 1.92-2.13 (1H, m), 2.54 (2H, d, J=7.2 Hz), 4.26 (2H, s), 5.36 (2H, s), 7.12-7.45 (8H, m), 7.52-7.56 (1H, m), 8.13-8.18 (1H, m), 8.17 (1H, s).

MS (m/e): 433 (M+).

Compound 25b. A pale yellow oily substance.

$^1$H-NMR (200 MHz, CDCl$_3$) δ: 0.94 (6H, d, J=6.6 Hz), 2.05-2.32 (1H, m), 2.79 (2H, d, J=7.2 Hz), 4.18 (2H, s), 5.45 (2H, s), 7.18-7.54 (9H, m), 8.12-8.26 (1H, m), 8.31 (1H, s).

MS (m/e): 433 (M+).

EXAMPLE A-20

The following compounds were obtained by the same manner as in Example A-14, using the Compound A-22 and the Compound A-24.

3-(Indol-3-yl)methyl-2,5-diethoxy-6-isobutylpyrazine (Compound 23). A pale yellow oily substance.

$^1$H-NMR (250 MHz, CDCl$_3$) δ: 0.94 (6H, d, J=6.7 Hz), 1.36 (3H, t, J=7.0 Hz), 1.42 (3H, t, J=7.0 Hz), 2.07-2.27 (1H, m), 2.56 (2H, d, J=7.1 Hz), 4.18 (2H, s), 4.35 (2H, q, J=7.0 Hz), 4.36 (2H, q, J=7.0 Hz), 7.09-7.27 (3H, m), 7.34-7.38 (1H, m), 7.87-7.91 (1H, m), 7.92 (1H, brs).

MS (m/e): 353 (M+).

3-(Indol-3-yl)methyl-2,5-dichloro-6-isobutylpyrazine (Compound A-26). A white powdery substance. Melting point: 84°-85° C. (recrystallized from Et$_2$O-n-hexane).

$^1$H-NMR (200 MHz, CDCl$_3$) δ: 0.95 (6H, d, J=6.6 Hz), 2.03-2.36 (1H, m), 2.74 (2H, d, J=7.2 Hz), 4.36 (2H, s), 7.08-7.24 (3H, m), 7.32-7.39 (1H, m), 7.74-7.82 (1H, m), 8.04 (1H, brs).

MS (m/e): 333 (M+).

EXAMPLE A-21

Synthesis of 2-(indol-3-yl)methyl-5-isobutylpyrazine (Compound A-27)

0.6 Gram of the chloropyrazine compounds obtained in Example A-19 (a mixture of Compounds A-25a and A-25b) was dissolved in 12 ml of sodium acetate, 7 ml of methanol and 1.2 ml of water. Thereto were added 1.2 g of sodium acetate and 50 mg of 10% Pd-C. Nitrogen was purged into the reaction mixture. The mixture was stirred in a hydrogen gas atmosphere. After the disappearance of the raw materials used was confirmed by means of a thin layer chromatography, the catalyst was removed by filtration and the filtrate was concentrated. Water was added to the filtrate, then extracted with ethyl acetate. The extract was dried over $Na_2CO_3$ and subjected to a silica gel column chromatography (n-hexane:$Et_2O$=10:1) to obtain 320 mg (87%) of the title compound as a colorless oily substance.

$^1$H-NMR (200 MHz, $CDCl_3$) δ: 0.92 (6H, d, J=6.6 Hz), 1.97–2.18 (1H, m), 2.62 (2H, d, J=7.2 Hz), 4.28 (2H, s), 7.03–7.24 (3H, m), 7.32–7.40 (1H, m), 7.51–7.60 (1H, m), 8.12 (1H, brs), 8.33 (1H, d, J=1.4 Hz), 8.44 (1H, d, J=1.3 Hz).

REFERENCE EXAMPLE A-7

Synthesis of methyl ester of N-α-bromopropionyl-L-tryptophan (Compound A-28b)

In 150 ml of anhydrous methylene chloride were dissolved 20 g of methyl L-tryptophanate hydrochloride and 18 g of triethylamine. To the solution being ice cooled and stirred was dropwise added 50 ml of a solution of 17 g of α-bromopropionyl bromide dissolved in anhydrous methylene chloride. The resulting mixture was stirred for 1 hour with ice cooling and for 1 hour at room temperature, then washed with water, dried with magnesium sulfate, and concentrated. The residue was dissolved in ether-methanol. The insoluble matter was removed. The resulting solution was concentrated to obtain 27 g (95%) of the title compound as a pale brown oily substance.

$^1$H-NMR (200 MHz, $CDCl_3$) δ: 1.78 (1.5H, d, J=7 Hz), 1.82 (1.5H, d, J=7 Hz), 3.35 (2H, d, J=5.5 Hz), 3.69 (1.5H, s), 3.70 (1.5H, s), 4.32 (0.5H, ABq, J=7 Hz), 4.34 (0.5H, ABq, J=7 Hz), 4.83–4.95 (1H, m), 6.83 (1H, brt, J=10 Hz), 7.01 (0.5H, d, J=2.5 Hz), 7.03 (0.5H, d, J=2.5 Hz), 7.11 (1H, t, J=7 Hz), 7.19 (0.5H, t, J=7 Hz), 7.20 (0.5H, t, J=7 Hz), 7.35 (1H, d, J=7 Hz), 7.53 (0.5H, d, J=7 Hz), 7.56 (0.5H, d, J=7 Hz), 8.31 (1H, brs).

EXAMPLE A-22

Synthesis of (3S,6S)-1-hydroxy-3-(indol-3-yl)methyl-6-methylpiperazine-2,5-dione (Compound A-29b) and (3S,6S)-1-hydroxy-3-(indol-3-yl)methyl-6-methylpiperazine-2,5-dione (Compound A-30b)

1.0 Gram of hydroxylamine was added to 15 ml of a solution of 1.2 g of Compound A-28b dissolved in ethanol. The mixture was refluxed for 8 hours with stirring. After cooling to room temperature, the resulting crystals (Compound 29b) were collected by filtration. The filtrate was concentrated to dryness. The residue was mixed with methanol-$CH_2Cl_2$ (1:10) for crystallization. The resulting crystals (Compound 29b) were collected by filtration. Yield: 0.3 g (37%).

The filtrate was reconcentrated to dryness. The residue was purified by a silica gel column chromatography ($CH_2Cl_2$:MeOH=40:1) to obtain 0.15 g (19%) of Compound 30b. Compound A-29b. Recrystallized from ethanol-n-hexane. Colorless prismatic crystals. Melting point: 188°–190° C.

$^1$H-NMR (200 MHz, DMSO-$d_6$) δ: 0.35 (1.5H, d, J=6.5 Hz), 0.37 (1.5H, d, J=6.5 Hz), 2.98 (1H, d, J=14 Hz), 3.19 (1H, d, J-14 Hz), 3.72 (1H, q, J=6.5 Hz), 4.17 (1H, brs), 6.85–7.10 (3H, m), 7.26 (1H, d, J=8 Hz), 7.50 (1H, d, J=8 Hz), 10.87 (1H, brs).

Compound A-30b. Recrystallized from ethanol. Colorless prismatic crystals. Melting point: 207°–209° C.

$^1$H-NMR (200 MHz, DMSO-$d_6$) δ: 1.20 (1.5H, d, J=7 Hz), 1.21 (1.5H, d, J=7 Hz), 3.07 (1H, dt, J=14 Hz, 5 Hz), 3.19–3.38 (2H, m), 4.23 (1H, brs), 6.86–7.10 (3H, m), 7.27 (1H, d, J=7.5 Hz), 7.53 (1H, d, J=7 Hz), 8.16 (1H, s), 9.76 (H, s), 10.85 (1H, brs).

REFERENCE EXAMPLE A-8

Synthesis of methyl ester of N-α-bromoisocaproyl-L-tryptophan (Compound A-28a)

Reaction was effected by the same manner as in Reference Example A-7 except that α-bromoisocaproyl bromide was used in place of α-bromopropionyl bromide, to obtain the title compound as a pale yellow oily substance.

$^1$H-NMR (250 MHz, $CDCl_3$) δ: 0.80–0.97 (6H, m), 1.70–1.93 (3H, m), 3.35 (2H, d, J=5.5 Hz), 3.69 (3H, s), 4.24 (1H, dd, J=8.5 Hz, 5.5 Hz), 6.76 (1H, brt, J=8.5 Hz), 7.04 (1H, t, J=2.5 Hz), 7.08–7.30 (2H, m), 7.36 (1h, d, J=8 Hz), 7.55 (1H, dd, J=8Hz, 4 Hz), 8.16 (1H, brs).

EXAMPLE A-23

The following compounds were obtained by the same manner as in Example A-22, using Compound A-28a or suitable starting materials.

(3S,6S)-1-Hydroxy-3-(indol-3-yl)methyl-6-isobutyl-piperazine-2,5-dione (Compound A-29a). Recrystallized from ethanol. Pale yellow prismatic crystals. Melting point: 243°–245° C.

$^1$H-NMR (250 MHz, $CDCl_3$) δ: 0.20–0.44 (1H, m), 0.29 (3H, d, J=7 Hz), 0.32 (3H, d, J=7 Hz), 0.47–0.68 (1H, m), 1.10–1.35 (1H, m), 2.91 (2H, d, J=4.5 Hz), 3.55 (1H, t, J=6 Hz), 3.91 (1H, brs), 6.65 (1H, t, J=8 Hz), 6.70 (1H, s), 6.73 (1H, d, J=8 Hz), 6.98 (1H, d, J=8 Hz), 7.24 (1H, d, J=8 Hz), 7.30 (1H, brs), 9.27 (1H, brs), 9.93 (1H, brs).

(3S,6R)-1-Hydroxy-3-(indol-3-yl)methyl-6-isobutyl-piperazine-2,5-dione (Compound A-30a). Recrystallized from ethanol-n-hexane. Colorless needle-like crystals. Melting point: 234°–236° C.

$^1$H-NMR (250 MHz, $CDCl_3$, DMSO-$d_6$) δ: 0.89 (3H, d, J=6 Hz), 0.91 (3H, d, J=6 Hz), 1.70–1.95 (3H, m), 3.07 (1H, dd, J=14.5 Hz, 9 Hz), 3.67 (1H, dd, J=14.5 Hz, 3.5 Hz), 4.05 (1H, t, J=5.5 Hz), 4.33 (1h, dd, J=9 Hz, 3.5 Hz), 6.33 (1H, brs), 7.11 (1H, t, J=7.5 Hz), 7.13 (1H, s), 7.19 (1H, t, J=7.5 Hz), 7.41 (1H, d, J=7.5 Hz), 7.62 (1H, d, J=7.5 Hz), 9.45 (1H, brs), 9.68 (1H, brs).

(3S)-1-Hydroxy-3-(indol-3-yl)methylpiperazine-2,5-dione (Compound A-29c). Recrystallized from ethanol. Colorless needle-like crystals. Melting point: 247°–248° C. (decomposed).

¹H-NMR (200 MHz, DMSO-d₆) δ: 3.13–3.27 (3H, m), 3.69 (1H, d, J=16.6 Hz), 4.12–4.20 (1H, m), 6.87–7.04 (3H, m), 7.20–7.27 (1H, m), 7.43–7.59 (2H, m), 9.67 (1H, brs), 10.14 (1H, brs).
MS (m/e): 259 (M+).

REFERENCE EXAMPLE A-9

Synthesis of methyl ester of N-(α-hdyroxyimino)isocaproyl-L-tryptophan (Compound A-31)

In 220 ml of dry dioxane were dissolved 6.54 g of methyl L-tryptophanate, 4.35 g of α-hydroxy iminoisocaproic acid and 3.63 g of N-hydroxysuccinimide. Thereto was added 6.19 g of DCC. The mixture was stirred for 24 hours at room temperature. The insoluble matter was removed by filtration. The filtrate was concentrated to dryness in vacuo. The residue was purified by a silica gel column chromatography (n-hexane:ethyl acetate=4:1) to obtain 9.83 g (95%) of the title compound as colorless needle-like crystals having a melting point of 109°–110° C. (recrystallized from diethyl ether-n-hexane).

¹H-NMR (250 MHz, CDCl₃) δ: 0.91 (6H, d, J=6.5 Hz), 1.94–2.17 (1H, m), 2.52 (2H, d, J=7.5 Hz), 3.32 (2H, d, J=5.5 Hz), 3.67 (3H, s), 4.40–4.49 (1H, m), 6.98 (1H, d, J=2.5 Hz), 7.10 (1H, d, J=8 Hz), 7.13 (1H, d, J=8 Hz), 7.19 (1H, d, J=8 Hz), 7.53 (1H, d, J=8 Hz), 7.59 (1H, brs), 8.06 (1H, brs).

EXAMPLE A-24

Synthesis of Compound A-29a and Compound A-30a

150 Milliliters of 7 N HCl/ethanol was dropwise added at 20°–25° C. to 150 ml of a solution of 10.48 g of Compound A-31 and 3.33 g of BH₃:N—(CH₃)₃ in 150 ml of ethanol. After completion of the dropwise addition, the mixture was stirred for 16 hours at room temperature. The solvent was removed by evaporation under reduced pressure at room temperature. The residue was dissolved in CH₂Cl₂. The resulting solution was washed with a an aqueous solution saturated with NaHCO₃ dried over Na₂SO₄. The solvent was removed by evaporation. The residue was dissolved in 150 ml of toluene, and the solution was refluxed for 1 hour with stirring. The solvent was removed by evaporation under reduced pressure. The residue was subjected to a silica gel column chromatography (CH₂Cl₂:methanol=40:1→20:1). Each of the resulting crude crystals was ground with CH₂Cl₂ to obtain 2.10 g (16%) of pure Compound A-29a and 1.90 g (14%) of a Compound A-30a.

EXAMPLE A-25

Synthesis of (3S,6S)-3-(indol-3-yl)methyl-6-isobutyl-1-methoxypiperazine-2,5-dione (Compound A-32a)

A solution of CH₂N₂ dissolved in ether was added to a solution of 0.43 g of Compound A-29a dissolved in 20 ml of methanol. The mixture was allowed to stand for 2 hours at room temperature. The solvent was removed by evaporation under reduced pressure. The residue was purified by a silica gel column chromatography (CH₂Cl₂:methanol=40:1) to obtain 0.25 g (56%) of the title compound as a white powdery substance having a melting point of 100°–101° C.

¹H-NMR (250 MHz, CDCl₃) δ: 0.80 (3H, d, J=6.5 Hz), 0.83 (3H, d, J=7.5 Hz), 1.10–1.40 (2H, m), 1.64–1.,87 (1H, m), 3.21 (1H, dd, J=14.5 Hz, 8 Hz), 3.45 (1H, dd, J=14.5 Hz, 3.5 Hz), 4.15 (1H, t, J=6 Hz), 4.27–4.37 (1H, m), 6.10 (1H, brs), 7.08 (1H, d, J=2.5 Hz), 7.14 (1H, t, J=7.5 Hz), 7.13 (1H, d, J=8 Hz), 7.22 (1H, t, J=7.5 Hz), 7.37 (1H, d, J=7.5 Hz), 7.61 (1H, d, J=7.5 Hz), 8.22 (1H, brs).

EXAMPLE A-26

The follwoing compound was obtained by the same manner as in Reference Example A-2, using Compound A-32a. (6S,Z)-3-(Indol-3-yl)methylidene-6-isobutyl-1-methoxypiperazine-2,5-dione (Compound A-33a). A brown oily substance.

¹H-NMR (250 MHz, CDCl₃) δ: 0.98 (3H, d, J=6 Hz), 1.00 (3H, d, J=6 Hz), 1.75–2.10 (3H, m), 3.88 (3H, s), 4.45 (1H, t, J=6 Hz), 7.23 (1H, t, J=7.5 Hz), 7.29 (1H, t, J=7.5 Hz), 7.38 (1H, s), 7.44 (1H, d, J=7.5 Hz), 7.48 (1H, d, J=2.5 Hz), 7.71 (1H, d, J=7.5 Hz), 7.83 (1H, s), 9.11 (1H, brs).

EXAMPLE A-27

Synthesis of (Z,Z)-3-(indol-3-yl)methylidene-6-isobutylidenepiperazine-2,5-dione (Compound A-34)

0.15 Milliliter of DBU was added to a solution of 31.7 mg of the Compound A-33a dissolved in 1 ml of dry dioxane. The mixture was stirred for 30 minutes at 100° C. After cooling to room temperature, the resulting yellow crystals were collected by filtration to yield 28.9 mg (quant.) Melting point: over 300° C.

EXAMPLE A-28

Synthesis of (3S,6S)-1-benzyloxy-3-(indol-3-yl)methyl-6-methylpiperazine-2,5-dione (Compound A-35b)

0.27 Gram of the Compound A-29b was dissolved in 20 ml of anhydrous THF and 5 ml of anhydrous HMPA. To the resulting solution being ice cooled and stirred was added 0.12 g of t-BuOK. Then, a solution of 0.17 g of benzyl bromide dissolved in THF was dropwise added. The mixture was stirred for 1–2 hours at room temperature, and then washed with an aqueous NaCl solution twice. The THF layer was dried with MgSO₄ and concentrated. The residue was dissolved in 50 ml of ether. The solution was washed with water twice, washed with an aqueous NaCl solution, dried over MgSO₄, and subjected to a short silica gel column chromatography (methanol/CH₂Cl₂=1/50) to obtain 0.27 g (75%) of the title compound as a colorless powdery substance having a melting point of 172°–174° C. (recrystallized from ethyl acetate-n-hexane).

¹H-NMR (200 MHz, CDCl₃) δ: 1.06 (3H, d, J=7 Hz), 3.27 (1H, dd, J=14.5 Hz, 7 Hz), 3.41 (1H, dd, J=14.5 Hz, 3.5 Hz), 3.97 (1H, q, J=7 Hz), 4.30–4.40 (1H, m), 4.85 (2H, ABq, J=10.5 Hz), 6.49 (1H, brs), 7.04 (1H, d, J=2 Hz), 7.10–7.46 (8H, m), 7.65 (1H, d, J=7.5 Hz), 8.56 (1H, brs).

EXAMPLE A-29

The following compounds were obtained by the same manner as in Example A-28, using Compound A-30a and the Compound A-29c.

(3S,6R)-1-Benzyloxy-3-(indol-3-yl)methyl-6-isobutyl-piperazine-2,5-dione (Compound A-35a) Recrystallized from ethyl acetate-ether. Colorless needle-like crystals. Melting point: 109°–110° C.

¹H-NMR (200 MHz, CDCl₃) δ: 0.85 (3H, d, J=6 Hz), 0.87 (3H, d, J=6 Hz), 1.50–1.93 (3H, m), 3.05 (1H, dd,

J=14.5 Hz, 9.5 Hz), 3.69 (1H, dd, J=14.5 Hz, 3.5 Hz), 3.83 (1H, t, J=6.5 Hz), 4.27 (1H, dd, J=9.5 Hz, 3.5 Hz), 4.76 (1H, d, J=10.5 Hz), 4.93 (1H, d, J=10.5 Hz), 5.76 (1H, brs), 7.11 (1H, d, J=2.5 Hz), 7.14-7.50 (5H, m), 7.66 (1H, d, J=7.5 Hz), 8.24 (1H, brs)

(3S)-1-Benzyloxy-3-(indol-3-yl)methylpiperazine-2,5-dione (Compound A-35c). Recrystallized from Et$_2$O-n-hexane. A white powdery substance.

Melting point: 215°-218° C. (decomposed).

$^1$H-NMR (200 MHz, CDCl$_3$+DMSO-d$_3$) δ: 2.87 (1H, d, J=16.3 Hz), 3.01 (1H, dd, J=16.0 Hz, 3.7 Hz), 3.22 (1H, dd, J=14.6 Hz, 4.7 Hz), 3.39 (1H, d, J=16.2 Hz), 4.03-4.12 (1H, m), 4.13 (1H, d, J=10.7 Hz), 4.43 (1H, d, J=10.8 Hz), 6.83-6.94 (5H, m), 6.98-7.10 (3H, m), 7.12-7.19 (1H, m), 7.40-7.55 (2H, m), 9.91 (1H, brs)

The following compounds were obtained by the same manner, as in Example A-28 by using appropriate starting materials.

(3S,6S)-1-Benzyloxy-3-(indol-3-yl)methyl-6-isobutylpiperazine-2,5-dione (Compound A-35d). A pale yellow foamy solid.

$^1$H-NMR (200MHz, CDCl$_3$) δ: 0.77 (3H, d, J=6.5 Hz), 0.79 (3H, d, J=6.5 Hz), 1.08-1.24 (1H, m), 1.31-1.46 (1H, m), 1.63-1.92 (1H, m), 3.16 (1H, dd, J=14.5 Hz, 8.5 Hz), 3.49 (1H, dd, J=14.5 Hz, 3.5 Hz), 3.86 (1H, t, J=6 Hz), 4.27-4.37 (1H, m), 4.97 (2H, s), 5.96 (1H, brs), 7.07 (1H, d, J=2.5 Hz), 7.10-7.26 (2H, m), 7.32-7.48 (6H, m), 7.61 (1H, d, J=7.5 Hz), 8.19 (1H, brs).

(3S,6R)-1-Benzyloxy-3-(indol-3-yl)methyl-6-methylpiperazine-2,5-dione (Compound A-35e).

$^1$H-NMR (200 MHz, CDCl$_3$) δ: 1.47 (3H, d, J=8 Hz), 3.17 (1H, dd, J=14.5 Hz, 8.5 Hz), 3.57 (1H, dd, J=14.5 Hz, 3 Hz), 3.78 (1H, q, J=8 Hz), 4.26-4.39 (1H, m), 4.79 (2H, ABq, J=10.5 Hz), 6.01 (1H, brs), 7.07 (1H, s), 7.12-7.48 (8H, m), 7.67 (1H, d, J=7.5 Hz), 8.28 (1H, brs)

EXAMPLE A-30

Synthesis of (3S,6S)-1-benzyloxy-3-[(1-benzyloxycarbonyl)indol-3-yl]methyl-6-methylpiperazine-2,5-dione (Compound A-36b)

In 20 ml of anhydrous methylene chloride were dissolved 0.18 g of the Compound 35b, 40 mg of ground NaOH and 10 mg of n-tetrabutylammonium bromide (TEBA). To the resulting solution being stirred vigorously was dropwise added 0.13 g of benzyloxycarbonyl chloride. The mixture was stirred for 2 hours at room temperature, washed with water, dried over magnesium sulfate, and concentrated. The residue was subjected to thin layer chromatography (CHCl$_3$, silica gel) to obtain 0.18 g (75%) of the title compound as a white powdery substance having a melting point of 119°-120° C.

$^1$H-NMR (200 MHz, CDCl$_3$) δ: 0.81 (3H, d, J=7 Hz), 3.35 (1H, dd, J=14.5 Hz, 5.5 Hz), 3.47 (1H, dd, J=14.5 Hz, 4.5 Hz), 4.06 (1H, q, J=7 Hz), 4.78 (2H, ABq, J=10 Hz), 5.43 (2H, s), 7.22 (1H, d, J=1.5 Hz), 7.15-7.52 (13H, m), 8.17 (1H, d, J=8 Hz).

EXAMPLE A-31

The following compound was obtained by the same manner as in Example A-30, using the Compound A-35a.

(3S,6S)-1-Benzyloxy-3-[(1-benzyloxycarbonyl)indol-3-yl]methyl-6-isobutylpiperazine-2,5-dione (Compound A-36a). Recrystallized from CH$_2$Cl$_2$-n-hexane. A white powdery substance. Melting point: 171°-172° C.

$^1$H-NMR (200MHz, CDCl$_3$) δ: 0.86 (3H, d, J=6 Hz), 0.87 (3H, d, J=6 Hz), 1.55-1.90 (3H, m), 2.99 (1H, dd, J=15 Hz, 9.5 Hz), 3.63 (1H, dd, J=15 Hz, 4 Hz), 3.85 (1H, t, J-6.5 Hz), 4.27 (1H, dd, J=9.5 Hz, 4 Hz), 4.78 (1H, d, J=10.5 Hz), 4.94 (1H, d, J=10.5 Hz), 5.46 (2H, s), 5.62 (1H, brs), 7.26-7.55 (12H, m), 7.58 (1H, s), 7.60 (1H, d, J=8 Hz), 8.23 (1H, brd, J=8 Hz)

EXAMPLE A-32

The following compounds were obtained by the same manner as in Example A-30, using appropriate starting materials.

(3S,6S)-1-Benzyloxy-3-[(1-benzyloxycarbonyl)indol-3-yl]methyl-6-isobutylpiperazine-2,5-dione (Compound A-36d). A pale yellow foamy solid.

$^1$H-NMR (250MHz, CDCl$_3$) δ: 0.80 (3H, d, J=6.5 Hz), 0.82 (3H, d, J=6.5 Hz), 1.25-1.37 (1H, m), 1.45-1.57 (1H, m), 1.73-1.90 (1H, m), 3.12 (1H, dd, J=14.5 Hz, 8.5 Hz), 3.47 (1H, dd, J=14.5 Hz, 2.5 Hz), 3.92 (1H, t, J=5.5 Hz), 4.32-4.41 (1H, m), 4.99 (2H, s), 5.47 (2H, ABq, J=12 Hz), 6.01 (1H, brs), 7.28-7.57 (12H, m), 7.57 (1H, s), 7.61 (1H, d, J=7 Hz), 8.22 (1H, d, J=8 Hz)

(3S,6R)-1-Benzyloxy-3-[(1-benzyloxycarbonyl)indol-3-yl]methyl-6-methylpiperazine-2,5-dione (Compound A-36e).

$^1$H-NMR (200 MHz, CDCl$_3$) δ: 1.48 (3H, d, J=7 Hz), 3.06 (1H, dd, J=14.5 Hz, 9 Hz), 3.53 (1H, dd, J=14.5 Hz, 4 Hz), 3.88 (1H, q, J=7 Hz), 4.31 (1H, dd, J=9 Hz, 4 Hz), 4.84 (2H, ABq, J=10.5 Hz), 5.44 (2H, s), 5.85 (1H, brs), 7.26-7.54 (7H, m), 7.56 (1H, s), 7.59 (1H, d, J=8 Hz), 8.21 (1H, d, J=8 Hz).

EXAMPLE A-33

Synthesis of 1-benzyloxy-3-[(1-benzyloxycarbonyl)indol-3-yl]methyl-5-chloro-6-isobutyl-1,2-dihydropyrazin-2-one (Compound A-37)

5.5 Grams of the Compound A-36a was suspended in 11 ml of phosphorus oxychloride. To the suspension being stirred was added 2.1 g of phosphorus pentachloride, in small portions in 10 minutes. The mixture was stirred for 3 hours at the same temperature and then poured into a phosphate buffer solution (pH 7) being ice cooled, to cause decomposition. Then, the reaction mixture was extracted with ether (200 ml×two times). The insoluble matter (the starting material) was removed by filtration. The ether layer was washed with water and an aqueous solution saturated with NaCl in this order and dried over magnesium sulfate. The dried ether layer was concentrated. The residue was purified by a short column chromatography (developing solvent: CH$_2$Cl$_2$) and crystallized from methanol to obtain 1.2 g (yield: 43%) of the title compound as a pale brown powdery substance. 2.6 Grams of the starting material was recorded. MS (m/e): M$^+$ 555. Melting point: 134°-135° C.

EXAMPLE A-34

Synthesis of 5-chloro-1-hydroxy-3-(indol-3-yl)methyl-6-isobutyl-1,2-dihydropyrazin-2-one (Compound A-38) and 3-[(1-carboxy)indol-3-yl]methyl-5-chloro-1-hydroxy-6-isobutyl-1,2-dihydropyrazin-2-one (Compound A-39)

0.55 Gram of the Compound A-37 was dissolved in 30 ml of ethanol. Thereto was added 60 mg of 5% Pd/C. The mixture was subjected to hydrogenation at under atmospheric pressure. The mixture was stirred for 1 hour. The catalyst was removed by filtration. The filtrate was concentrated. The residue was crystallized with a small amount of methanol. The crystals were recrystallized from methanol to obtain 0.12 g (33%) of Compound A-39 as colorless needle-like crystals. Melting pont: 164°–165° C. MS (m/e): 375 (M+).

The filtrate was concentrated to dryness under reduced pressure. The residue was purified by a silica gel column chromatography ($CH_2Cl_2$ methanol=40:1) to obtain 0.16 g (50%) of Compound A-38. Recrystallized from methanol. Colorless needle-like crystals. Melting point: 167°–168° C. MS (m/e): 331 (M+).

EXAMPLE A-35

Synthesis of 5-chloro-3-(indol-3-yl)methyl-6-isobutyl-1-methoxy-1,2-dihydropyrazin-2-one (Compound A-45) and 3-chloro-5-(indol-3-yl)methyl-2-isobutyl-6-methoxypyrazine-1-oxide (Compound A-46)

A solution of $CH_2N_2$ dissolved in ether was added to 20 ml of a solution of 0.60 g of Compound A-38 dissolved in THF. The mixture was allowed to stand for 1 hour at room temperature. The solvent was removed by evaporation under reduced pressure. The residue was purified by a silica gel column chromatography to obtain the following compounds.

Compound A-45

Yield: 0.22 g (35%). Recrystallized from ethanol. A pale brown powdery substance. Melting point: 112°–114° C.

Compound A-46

Yield: 0.20 g (32%). Recrystallized from ethanol. Colorless needle-like crystals. Melting point: 137°–139° C.

EXAMPLE 36

The following compounds were obtained by the same manner as in Example 35, using Compound A-39.

5-Chloro-6-isobutyl-3-[(1-methoxycarbonyl)indol-3-yl]methyl-1-methoxy-12,-dihydropyrazin-2-one (Compound A-47). A white powdery substance. Melting point: 136°–137° C. (recrystallized from methanol).

3-Chloro-2-isobutyl-5-[(1-methoxycarbonyl)indol-3-yl]methyl-6-methoxypyrazineyl-oxide (Compound A-48). Colorless needle-like crystals. Melting point: 146°–147° C. (recrystallized from methanol).

EXAMPLE A-37

Synthesis of 1-benzyloxy-3-[(1-benzyloxycarbonyl-2-chloro)indol-3-yl]methyl-5-chloro-6-isobutyl-1,2-dihydropyrazin-2-one (Compound A-40)

2.3 Grams of $PCl_5$ was added to 20 ml of a solution of 2.0 g of Compound 36a dissolved in dry $CH_2Cl_2$. The mixture was stirred for 4 hours at room temperature. The reaction mixture was poured into a phosphate buffer solution (pH 7) with ice cooling. The reaction mixture was extracted with ether. The extract was dried over magnesium sulfate. The solvent was removed by evaporation under reduced pressure. The residue was subjected to preparative TLC ($CHCl_3$:n-hexane=3:2) to obtain 0.4 g (18%) of the title compound as a white powdery substance.

$^1$H-NMR (200MHz, $CDCl_3$) δ: 0.80 (6H, d, J=6.5 Hz), 2.00–2.20 (1H, m), 2.53 (2H, d, J=7.5 Hz), 4.29 (2H, d), 5.26 (2H, d), 5.50 (2H, d), 7.17–7.67 (13H, m), 8.08 (1H, dd, J=6.5 Hz, 2.5 Hz).

EXAMPLE A-38

The following compound was obtained by the same manner as in Example A-34, using Compound A-40.

5-Chloro-3-[(2-chloro)indol-3-yl]methyl-1-hydroxy-1,2-dihydropyrazin-2-one (Compound A-41).

$^1$H-NMR (200 MHz, $CDCl_3$) δ: 0.83 (6H, d, J=7 Hz), 1.95–2.25 (1H, m), 2.73 (2H, d, J=7.5 Hz), 4.15 (2H, s), 6.93–7.23 (3H, m), 7.55 (1H, d, J=8 Hz), 7.95 (1H, brs).

EXAMPLE A-39

The following compounds were obtained by the same manner as in Example A-35, using Compound A-41.

5-Chloro-3-[(2-chloro)indol-3-yl]methyl-6-isobutyl-1-methoxy-1,2-dihydropyrazin-2-one (Compound A-42). A colorless oily substance.

$^1$H-NMR (200 MHz, $CDCl_3$) δ: 0.98 (6H, d, J=6.5 Hz), 2.00–2.25 (1H, m), 2.65 (2H, d, J=7.5 Hz), 4.05 (3H, s), 4.25 (3H, s), 7.03–7.26 (3H, m), 7.64 (1H, dd, J=8 Hz, 2.5 Hz), 8.28 (1H, brs).

3-Chloro-5-[(2-chloro)indol-3-yl]methyl-2-isobutyl-6-methoxypyrazin-1-oxide (Compound A-43). A pale brown oily substance.

$^1$H-NMR (200 MHz, $CDCl_3$) δ: 0.97 (6H, d, J=6.5 Hz), 2.14–2.40 (1H, m), 2.90 (2H, d, J=7 Hz), 3.88 (3H, s), 4.21 (2H, s), 7.10 (1H, dt, J=6.5 Hz, 2 Hz), 7.17 (1H, dt, J=6.5 Hz, 1.5 Hz), 7.25 (1H, dd, J=6.5 Hz, 2 Hz), 7.63 (1H, dd, J=6.5 Hz, 1.5 Hz), 8.28 (1H, brs).

EXAMPLE A-40

Synthesis of 2-benzyloxy-5-chloro-3-[(2-chloro)indol-3-yl]methyl-6-isobutylpyrazine-1-oxide (Compound A-44)

To 5 ml of dry THF were added 20 mg of the compound 43, 5 mg of 18-crown-6-ether and 13 mg of sodium benzyl alcoholate. The mixture was stirred for 2 hours at 80° C., and then concentrated. The concentrate was subjected to preparative TLC ($CHCl_3$) to obtain the title compound as a yellow oily substance. Yield: 10 mg (40%).

MS (m/e): M+455.

$^1$H-NMR (200 MHz, $CDCl_3$) δ: 0.97 (6H, d, J=6.5 Hz), 2.20–2.45 (1H, m), 2.91 (2H, d, J=7.5 Hz), 4.02 (2H, s), 5.36 (2H, s), 7.07 (1H, d, J=8 Hz), 7.16 (1H, d, J=8 Hz), 7.22–7.42 (6H, m), 7.46 (1H, d, J=8Hz), 8.02 (1H, brs).

REFERENCE EXAMPLE A-10

Synthesis of O-benzyl-N-benzyloxycarbonyl-N$^{in}$tert-butoxycarbonyl-L-tryptophanohydroxamic acid (Compound A-49)

14.6 Grams of DCC was added to a solution of 29.3 g of N-benzyloxycarbonyl-N$^{in}$tert-butoxycarbonyltriptophane, 10.8 g of O-benzylhydroxylamine and 8.1 g of N-hydroxysuccinimide dissolved in 300 ml of dry dioxane. The mixture was stirred for 18 hours at room temperature. The insoluble matter was removed by filtration. The filtrate was concentrated to dryness under reduced pressure. The residue was purified by a silica gel column chromatography (n-hexane:ethyl acetate =4:1) to obtain 37.0 g (quant.) of Compound A-49 as a white foamy solid.

$^1$H-NMR (250 MHz, CDCl$_3$) δ: 1.62 (9H, s), 3.13 (2H, m), 4.10 (1H, m), 4.59 (1H, d, J=11.0 Hz), 4.75 (1H, d, J=11.0 Hz), 5.00 (2H, s), 5.48 (1H, brd, J=6.5 Hz), 7.13–7.35 (12H, m), 7.45 (1H, s), 7.52 (1H, d, J=8.0 Hz), 8.13 (1H, d, J=7.8 Hz), 8.68 (1H, brs).

REFERENCE EXAMPLE A-11

Synthesis of N$^{in}$tert-butoxycarbonyl-L-tryptophanohydroxamic acid (Compound A-50)

5 Grams of 10% Pd-C was added to a solution of 37.0 g of Compound A-49 dissolved in 300 ml of ethanol. The mixture was hydrogenated with the theoretical amount of hydrogen gas for 5 hours at 50° C. under atmospheric pressure. The catalyst was removed by filteration, then the solvent was removed by evaporation to obtain 20.0 g (96%) of pale yellow crystals.

$^1$H-NMR (250 MHz, CDCl$_3$-CD$_3$OD) δ: 1.68 (9H, s), 2.88 (1H, dd, J=8.3 Hz, 14.3 Hz), 3.20 (1H, dd, J=5.5 Hz, 15.5 Hz), 3.59 (1H, m), 7.26–7.36 (2H, m), 7.48 (1H, s), 7.61 (1H, d, J=7.0 Hz), 8.10 (1H, d, J=8.0 Hz).

EXAMPLE A-41

Synthesis of 3-[(1-tert-butoxycarbonyl)indol-3-yl]methyl-1-hydroxy-5,6-dimethyl-1,2-dihydropyrazin-2-one (Compound A-51)

2.1 Milliliters (21.5 mM) of 2,4-butanedione was dropwise added to a solution of 7.0 g (22.0 mM) of Compound A-50 dissolved in 70 ml of methanol. After 30 minutes, the mixture was diluted with CHCl$_3$, washed with water, dried over magnesium sulfate, then the solvent was removed by evaporation under reduced pressure. The residue was subjected to a silica gel column chromatography. From the 5% methanol/CHCl$_3$ fraction was obtained 6.8 g of an orange oily condensate. Thereto was added 50 ml of benzene and Molecular sieve 4A, the mixture was refluxed for 30 minutes with heating while removing water. The solvent was removed by evaporation under reduced pressure to obtain 4.88 g of Compound A-51 as an orange foamy substance.

$^1$H-NMR (250 MHz, CDCl$_3$) δ: 1.63 (9H, s), 2.36 (3H, s), 2.38 (3H, s), 4.19 (2H, s), 7.20–7.32 (2H, m), 7.54 (1H, s), 7.70 (1H, d, J=7.5 Hz), 8.05 (1H, d, J=7.5 Hz).

EXAMPLE A-42

Synthesis of 1-hydroxy-4-(indol-3-yl)methyl-5,6-dimethyl-1,2-dihydropyrazin-2-one (Compound A-52)

3 Milliliters of trifluoroacetic acid was added to a solution of 2.0 g (5.28 mM) of Compound A-51 dissolved in 30 ml of CH$_2$Cl$_2$, and the mixture was stirred for 1 day at room temperature. A small amount of methanol was added thereto and the resulting mixture was washed with an aqueous solution saturated with 10 NaCl. The CH$_2$Cl$_2$ layer was separated, and the crystals formed in the CH$_2$Cl$_2$ layer were collected by filtration. The filtrate was dried over magnesium sulfate and then the solvent was removed by evaporation under reduced pressure. The residue was combined with the above obtained crystals. The mixture was dissolved in 100 ml of methanol and refluxed for 1 hour with heating. The solvent was removed by evaporation under reduced pressure. The residue was dissolved in 10 ml of methanol and crystallized with Et$_2$O to obtain 970 mg (68%) of the title compound as orange crystals.

$^1$H-NMR (250 MHz, DMSO-d$_6$) δ: 2.32 (3H, s), 2.35 (3H, s), 4.17 (2H, s), 7.02 (1H, m), 7.24 (1H, s), 7.39 (1H, d, J=8.0 Hz), 7.72 (1H, d, J=7.5 Hz)

EXAMPLE A-43

The following compounds were obtained by the same manner as in Example A-35, using Compound A-52.

3-(Indol-3-yl)methyl-1-methoxy-5,6-dimethyl-1,2-dihydropyrazin-2-one (Compound A-53). A light yellow powdery substance (recrystallized from ethyl acetate-n-hexane). Melting point: 168° C. (decomposed).

3-(Indol-3-yl)methyl-2-methoxy-5,6-dimethylpyrazine 1-oxide (Compound A-54). A pale yellow powdery substance. Melting point: 148°–149° C. (recrystallized from Et$_2$O-n-hexane).

$^1$H-NMR (250 MHz, CDCl$_3$) δ: 2.42 (3H, s), 2.51 (3H, s), 3.91 (3H, s), 4.24 (2H, s), 7.05 (1H, m), 7.09–7.19 (2H, m), 7.31 (1H, dd, J=1.0 Hz, 7.0 Hz), 7.75 (1H, d, J=7.0 Hz), 8.35 (1H, brs)

EXAMPLE A-44

Synthesis of 1-hydroxy-6-(indol-3-yl)methyl-3-methyl-1,2,5,6-tetrahydropyrazin 2,5-dione (Compound A-55)

In 5 ml of tetramethylurea was dissolved 0.22 g of 2-hydroxylamino-3-(indol-3-yl)propionic acid amide. The solution was cooled to −5° to 0° C. Thereto was added 0.1 g of pyruvic acid chloride. Then, there was added 1 ml of a tetramethylurea solution containing 90 mg of pyridine. The mixture was stirred for 1.5 hours with ice cooling and for 1 hour at room temperature. The mixture was poured into ice water. The resulting mixture was subjected to extraction with CHCL$_3$. The extract was washed with water, dried over magnesium sulfate, and subjected to TLC (methanol/CH$_2$Cl$_2$=1/10). The fraction separated was heated for 10–20 minutes at 80° C. under vacuum. The residue was mixed with methanol for crystallization. The resulting crystals were recrystallized from methanol to obtain 40 mg of colorless needle-like cyrstals. Yield: 15%. MS (m/e):M$^{30}$ 271. Melting point: 166°–168° C.

REFERENCE EXAMPLE A-12

Synthesis of N-(α-hydroxyimino)isocaproyl-L-tryptophan (Compound A-56)

6 Milliliters of 1N NaOH was added to 20 ml of a solution of 0.68 g of Compound A-31 dissolved in ethanol. The mixture was stirred for 30 minutes at room temperature. Thereto was added 7 ml of 1N HCl with stirring under ice cooling, to make the mixture acidic. The reaction mixture was extracted with ethyl acetate. The extract was washed with an aqueous solution saturated with NaCl, and dried over magnesium sulfate to obtain 0.67 g of the title compound. Colorless needle-like crystals. Melting point: 97°–98° C. (recrystallized from dichloromethane).

$^1$H-NMR (250 MHz, CDCl$_3$) δ: 0.79 (3H, d, J=6.5 Hz), 0.80 (3H, d, J=6.5 Hz), 1.80–2.30 (1H, m), 2.40 (2H, d, J=7.5 Hz), 3.20 (2H, d, J=5.5 Hz), 4.85 (1H, dd,

J=14 Hz, 5.5 Hz), 5.70–6.90 (1H, br), 6.77 (1H, d, J=2 Hz), 7.00 (1H, t, J=7.5 Hz), 7.07 (1H, t, J=7.5 Hz), 7.16 (1H, d, J=7.5 Hz), 7.44 (1H, d, J=7.5 Hz), 8.00 (1H, brs).

EXAMPLE A-45

Synthesis of 5-hydroxy-6-(indol-3-yl)methyl-3-isobutyl-1,2-dihydropyrazin-2-one 4-oxide (Compound A-57)

There was stirred for 3 hours at room temperature, 5 ml of a solution of 66.2 mg of Compound A-56, 210 mg of triphenylphosphine and 170 mg of 2,2'-dipyridyl disulfide dissolved in anhydrous THF. Thereto was added 0.5 ml of methanol. The solvent was removed by evaporation under reduced pressure. The residue was purified by a silica gel column chromatography ($CH_2Cl_2$:methanol=20:1→8:1→4:1) to obtain 10.8 g of Compound A-57. A pale brown powdery substance.

$^1$H-NMR (200 MHz, $CDCl_3$-$CD_3OD$) δ: 0.92 (6H, d, J=6.5 Hz), 2.15–2.39 (1H, m), 2.76 (2H, d, J=7 Hz), 4.13 (2H, s), 6.99 (1H, t, J×7.5 Hz), 7.11 (1H, t, J=7.5 Hz), 7.14 (1H, s), 7.36 (1H, d, J=7.5 Hz), 7.61 (1H, d, J=7.5 Hz).

REFERENCE EXAMPLE A-13

Synthesis of 6-(indol-3-yl)methYl-3-isobutyl-5-methoxy-1,2-dihydropyrazin-2-one 4-oxide (NF-1616-904 substance) (Compound B-42)

The above-compound is described in Japanese Patent Application No. 200928/1988 and was synthesized as follows. (1) Culture of microbe In a 500-ml Erlenmeyer flask was placed 100 ml of medium consisting of 30 g/l of starch, 5 g/l of glucose, 5 g/l of a soybean powder, 1 g/l of an yeast extract, 1 g/l of a polypeptone, 3 g/l of $CaCO_3$ and 0.5 g/l of $MgSO_4$. Thereto was innoculated one platinum loop amount of microbe cells obtained by culturing *Thielavia Minor* OFR-1561 strain (deposited in the Fermentation Research Institute, the Agency of Industrial Science and Technology, Japan, under the Budapest Treaty with the accession No. FERM BP 1908) in a slamt medium (pH 6.5) containing 4% of maltose, 1% of a polypeptone and 2% of agar, at 30° C. for 1 week. The resulting medium was subjected to shaking or rotational culture for 96–120 hours at 28° C.

(2) Purification of NF-1616-902 substance

After the culture mentioned above (1), the culture medium was filtered to obtian 100 ml of a filtrate. then the filtrate was extracted with ethyl acetate, and was concentrated. The thus obtained concentrate was purified by means of a silcica gel column chromatography (eluant: chloroform:ethyl acetate=2:1). The active fraction was passed through a Sephadex LH-20 column (manufactured by Pharmacia Biotechnology Group.), and fractionated by eluting with chloroform : methanol = 1:1, The eluted fractions were combined together and then concentrated to obtain NF-1616-902 substance.

$^1$H-NMR (400 MHz, DMSO-$d_6$): 7.36 (2H, d, J=7.6 Hz), 7.12 (2H, s), 7.05 (2H, t, J=7.6 Hz), 6.67 (2H, t, J=7.6 Hz), 6.65 (2H, d, J=7.6 Hz), 6.03 (2H, s), 3.86 (2H, d, J=17.6 Hz), 3.72 (6H, s), 3.47 (2H, d, J=17.6 Hz), 2.61 (2H, dd, J=12.7 Hz, 1.2 Hz), 2.53 (2H, dd, J=12.7 Hz, 1.2 Hz), 2.05 (2H, m), 0.84 (12H, d, J=7.1 Hz)

MS (EI): $M^+$=327.

IR (KBr): 3352, 2950, 2852, 1680, 1610, 1480, 1452, 1371, 1330, 1315, 1255, 1240, 1182, 1092, 1018, 750 $cm^{-1}$.

(3) Preparation of 6-(indol-3-yl)methyl-3-isobutyl-5-methoxy-1,2-dihydropyrazin-2-one 4-oxide (NF-1616-904 substance) (Compound B-42)

NF-1616-902 substance obtained in (2) above was dissolved in methnaol-NaOH (2:2 volume/volume), and the mixture was allowed to stand at room temperature for 48 hours. Then the mixture was neutralized with 6 N-HCl, then was extracted with ethyl acetate. The ethyl acetate extract was concentrated to dryness, and the residue was chromatographed on a Sephadex LH-20 column and eluted with $chCl_3$: methanol (2:1) to give the desired NF-1616-904 substance (Compound B-42), which was crystallized from methanol.

Melting point: 223.5°–225.5° C.

Pale yellow crystals.

EXAMPLE A-46

Synthesis of 6-(indol-3-yl)methyl-3-isobutyl-5-methoxy-1-methyl-1,2-dihydropyrazin-2-one 4-oxide (Compound A-59) and 3-(indol-3-yl)methyl-6-isobutyl-2,5-dimethoxypyrazine 1-oxide (Compound A-60)

To a solution of 1.2 g of Compound B-42 dissolved in 60 ml of methylene dichloride and 60 ml of methanol was added a solution of $CH_2N_2$ dissolved in diethyl ether, until there was no disappearence of yellow color. The mixture was allowed to stand for 12 hours at room tmeperature. The solvent was removed by evaporation under reduced pressure. The residue was purified by a silica gel column chromatography (n-hexane:ethyl acetate =2:1) to obtain 0.74 g (55%) of Compound A-59 and 0.56 g (45%) of Compound A-60.

Compound A-59. A yellow powder.

$^1$H-NMR (250 MHz, $CDCl_3$) δ: 0.98 (6H, d, J=6.5 Hz), 2.21–2.41 (1H, m), 2.90 (2H, d, J=7.5 Hz), 3.43 (3H, s), 3.99 (3H, s), 4.21 (2H, s), 6.85 (1H, d, J=2.5 Hz), 7.17 (1H, t, J=8 Hz), 7.25 (1H, t, J=8 Hz), 7.41 (1H, d, J=8 Hz), 7.62 (1H, d, J=8 Hz), 8.65 (1H, brs)

Compound 60. Colorless needle-like crystals. Melting point: 177°–179° C. (recrystallized from ethyl acetate-n-hexane).

$^1$H-NMR (250 MHz, $CDCl_3$) δ: 0.91 (6H, d, J=6.5 Hz), 2.10–2.30 (1H, m), 2.74 (2H, d, J=7.5 Hz), 3.94 (3H, s), 3.95 (3H, s), 4.18 (2H, s), 7.10–7.25 (3H, m), 7.35 (1H, d, J=7.5 Hz), 7.85 (1H, d, J=7.5 Hz), 8.06 (1H, brs)

REFERENCE EXAMPLE A-14

Synthesis of 3-(indol-3-yl)-2-(o-hydroxyimino)isocaproylaminopropionitrile (Compound A-61)

5.86 Grams of DCC was added to a solution of 5.26 g of 2-amino-3-(indol-3-yl)propionitrile, 4.12 g of N-(hydroxyimino)isocaproic acid and 3.43 g of hydroxysuccinimide dissolved in 150 ml of dry $CH_2Cl_2$. The succinimide dissolved mixture was stirred for 9 hours at room temperature. The insoluble matter was removed by filtration. The filtrate was concentrated to dryness under reduced pressure. The residue was mixed with 150 ml of dry dioxane. The insoluble matter was removed by filtration. The filtrate was concentrated to dryness under reduced pressure. The residue was purified by a silica gel column chromatography (CH₂Cl₂:methanol=160:1) to obtain 9.03 g (quant.) of Compound A-61. Colorless needle-like crystals. Melting point: 106°–108° C., ¹H-NMR (250 MHz, CDCl₃) δ: 0.91 (3H, d, J=6.5 Hz), 0.92 (3H, d, J=6.5 Hz), 1.93–2.13 (1H, m), 2.51 (2H, d, J=7.5 Hz), 3.23–3.40 (2H, m), 5.20–5.32 (1H, m), 7.07–7.23 (2H, m), 7.24 (1H, s), 7.40 (1H, d, J=8 Hz), 7.62 (1H, d, J=8 Hz), 7.92 (1H, brs), 8.23 (1H, brs)

EXAMPLE A-47

Synthesis of 5-amino-6-(indol-3-yl)methyl-3-isobutyl-1,2-dihydropyrazin-2-one 4-oxide (Compound A-62) and 5-acetamino-6-(indol-3-yl)methyl-3-isobutyl1,2-dihydropyrazin-2-one 4-oxide (Compound A-63)

287 Milligrams of Compound A-61 was dissolved in 3 ml of acetic acid. The solution was stirred for 29 hours at 60°–70° C. The solvent was removed by evaporation under reduced pressure. The residue was dissolved in CH₂Cl₂. The solution was washed with an aqueous solution saturated with NaHCO₃ and dried with Na₂SO₄. The solvent was removed by evaporation. The residue was subjected to a silica gel column chromatography (n-hexane: ethyl acetate =1:1) to obtain 138 mg (59%) of Compound A-62 and 40 mg (15%) of a Compound A-63.

Compound A-62

Yellow powdery substance. Melting point: 194°–196° C. (ethyl acetate-n-hexane).

Compound A-63

Pale yellow needle-like crystals. Melting point: 144°–145° C. (ethyl acetate-ether).

EXAMPLE A-48

1.6 Milliliters of acetic anhdyride was added to 30 ml of a solution of 0.53 g of Compound A-62 dissolved in methanol. The mixture was allowed to stand for 2.5 hours at room temperature. The solvent was removed by evaporation under reduced pressure. The residue was recrystallized from ethyl acetate-ether to obtain 0.41 g (68%) of Compound A-63.

REFERENCE EXAMPLE A-15

Synthesis of α-tetrahydropyran-2-yloxyiminoisocaproic acid (Compound A-64)

9.6 Milliliters of 3,4-dihydro-2H-pyran and 0.29 g of p-TsOH.H₂O were added to 50 ml of a solution of 4.35 g of α-hydroxyimino-isocaproic acid dissolved in dry CH₂Cl₂. The mixture was stirred for 100 minutes at room temperature. The reaction mixture was added to an aqueous solution saturated with NaHCO₃ with ice cooling, and subjected to phase separation. An aqueous solution saturated with NaHCO₃ was covered with ethyl acetate, then concentrated hydrochloric acid was added thereto, with stirring under ice cooling, to make the reaction mixture weakly acidic. The ethyl acetate layer was separated, washed with an aqueous selection saturated with NaCl, and dried over magnesium sulfate to obtain 6.00 g (87%) of the title compound as a colorless oily substance.

¹H-NMR (250 MHz, CDCl₃) δ: 0.95 (3H, d, J=6.5 Hz), 0.96 (3H, d, J=6.5 Hz), 1.50–1.90 (6H, m), 2.00–2.20 (1H, m), 2.54 (2H, d, J=7.5 Hz), 3.63–3.77 (1H, m), 3.77–3.91 (1H, m), 5.40–5.47 (1H, m)

REFERENCE EXAMPLE A-16

The following compound was obtained by the same manner as in Reference Example A-14, using Compound A-64.

3-(Indol-3-yl)-2-(α-tetrahydropyran-2-yloxyimin) isocaproylaminopropionitrile (Compound A-65).

¹H-NMR (250 MHz, CDCl₃) δ: 0.87–0.97 (6H, m), 1.50–1.90 (6H, m), 1.90–2.14 (1H, m), 2.53 (1H, d, J=7.5 Hz), 2.54 (1H, d, J=7.5 Hz), 3.23–3.42 (2H, m), 3.55–3.72 (1H, m), 3.72–3.90 (1H, m), 5.12–5.32 (2H, m), 7.10–7.37 (4H, m), 7.39 (1H, d, J=8 Hz), 7.60 (0.5H, d, J=8 Hz), 7.67 (0.5H, d, J=7.5 Hz), 8.24 (1H, brs).

EXAMPLE A-49

Synthesis of 2-(α-hydroxyimino)isocaproylamino-3-[(1-p-toluenesulfonylindol)-3-yl]propionitrile (Compound A-66)

0.16 Gram of 60% NaH was added to a solution of 0.74 g of Compound A-65 dissolved in 10 ml of dry DMSO. The mixture was stirred for 30 minutes at room temperature. Thereto was added 0.72 g of p-toluenesulfonyl chloride, and the resulting mixture was stirred for 6.5 hours at room temperature. The mixture was added to an aqueous solution saturated with NH₄Cl under ice cooling. The reaction mixture was extracted with ethyl acetate. The extract was washed three times with an aqueous solution saturated with NaCl, and dried with MgSO₄. The solvent was removed by evaporation. The residue was dissolved in 20 ml of THF. Thereto was added 10 ml of 4N HCl. The mixture was stirred for 6.5 days at room temperature. CH₂Cl₂ and water were added to the mixture and subjected to phase separation. The organic layer was washed with an aqueous solution saturated with NaHCO₃ solution and dried over Na₂SO₄. The solvent was removed by evaporation. The residue was purified by silicon gel column chromatography (n-hxane:ethyl acetate=3:1) to obtain 0.39 g (52%) of the title compound. A pale yellow powdery substance. Melting point: 66°–68° C.

¹H-NMR (250 MHz, CDCl₃) δ: 0.90 (3H, d, J=6.5 Hz), 0.91 (3H, d, J=6.5 Hz), 1.92–2.12 (1H, m), 2.34 (3H, s), 2.51 (2H, d, J=7.5 Hz), 3.23 (2H, dABq, J=15 Hz, 6 Hz), 5.13–5.27 (1H, m), 7.16 (1H, brd, J=8.5 Hz), 7.22 (2H, d, J=8.5 Hz), 7.29 (1H, t, J=8 Hz), 7.35 (1H, t, J=7.5 Hz), 7.55 (1H, d, J=7.5 Hz), 7.60 (1H, s), 7.77 (2H, d, J=8.5 Hz), 7.97 (1H, d, J=8 Hz).

EXAMPLE A-50

The following compounds were obtained by the same manner as in Example A-47, using Compound A-66.

5-Amino-3-isobutyl-6-[(1-p-toluenesulfonyl)indol-3-yl]methyl-1,2-dihydropyrazin-2-one 4-oxide (Compound A-67). A yellow powdery substance. Melting point: 133°–135° C.

¹H-NMR (250 MHz, CDCl₃) δ: 0.90 (6H, d, J=6.5 Hz), 2.13–2.32 (1H, m), 2.30 (3H, s), 2.79 (2H, d, J=8 Hz), 4.02 (2H, s), 4.68 (2H, s), 7.18 (2H, d, J=8.5 Hz), 7.19 (1H, t, J=8 Hz), 7.33 (1H, t, J=7.5 Hz), 7.48 (1H, s), 7.50 (1H, d, J=7.5 Hz), 7.73 (2H, d, J=8.5 Hz), 7.97 (1H, d, J=8 Hz).

5-Acetamino-3-isobutyl-6-[(1-p-toluenesulfonyl)indol-3-yl]methyl-1,2-dihydropyrazin-2-one 4-oxide (Compound A-68). A yellow powdery substance. Melting point: 86°–88° C.

¹H-NMR (250 MHz, CDCl₃) δ: 0.90 (6H, d, J=6.5 Hz), 2.10-2.30 (1H, m), 2.23 (3H, s), 2.31 (3H, s), 2.72 (2H, d, J=7 Hz), 4.02 (2H, s), 7.20 (2H, d, J=8.5 Hz), 7.34 (1H, t, J=8 Hz), 7.38 (1H, t, J=8 Hz), 7.62 (1H, s), 7.76 (3H, d, J=8.5 Hz), 7.98 (1H, t, J=8 Hz).

EXAMPLE A-51

Synthesis of 2-amino-5-benzyloxy-6-isobutyl-3-[(1-p-toluenesulfonyl)indol-3-yl]methylpyrazine 1-oxide (Compound A-69)

9.6 Milligrams of 60% NaH was added to a solution of 93.2 mg of Compound A-67 dissolved 3 ml of in dry DMSO. The mixture was stirred for 1 hour at room temperature. Thereto was added 48 μl of BnBr, and the mixture was stirred for 5 hours at room temperature. The mixture was added to a saturated NH₄Cl solution under ice cooling. The reaction mixture was extracted with ethyl acetate. The extract was washed with an aqueous solution saturated with NaCl three times, and dried over magnesium sulfate. The solvent was removed by evaporation. The residue was purified by a silica gel column chromatography (n-hexane:ethyl acetate=4:1→2:1) to obtain 60.9 g (55%) of the title compound. A brown oily substance.

¹H-NMR (250 MHz, CDCl₃) δ: 0.94 (6H, d, J=6.5 Hz), 2.13-2.37 (1H, m), 2.30 (3H, s), 2.85 (2H, d, J=7.5 Hz), 4.06 (2H, s), 4.87 (2H, s), 5.27 (2H, s), 7.18 (2H, d, J=8.5 Hz), 7.10-7.40 (8H, m), 7.42 (1H, s), 7.73 (2H, d, J=8.5 Hz), 7.99 (1H, d, J=8 Hz).

EXAMPLE A-52

Synthesis of 5-acetamino-6-(indol-3-yl)carbonyl-3-isobutyl-1,2-dihydropyrazin-2-one 4-oxide (Compound A-70)

45.4 Milligrams of DDQ was added to a solution of 35.4 mg of Compound A-63 dissolved in 2 ml of 90% THF. The mixture was stirred for 2.5 hours at room temperature. The reaction mixture per se was subjected to 2 silica gel column chromatography (CH₂Cl₂:MeOH=8:1) to remove DDHQ (2,3-dichloro-5,6-dicyanohydroquinone). The solution obtained from the silcia gel column was concentrated to dryness. The residue was subjected to preparative TLC (CH₂Cl₂:methanol=20:1) to obtain 5.4 mg (15%) of Compound 70. A pale yellow powdery substance.

Melting point: 170°-172° C.

¹H-NMR (250 MHz, CDCl₃-CD₃OD) δ: 1.01 (6H, d, J=6.5 Hz), 1.99 (3H, s), 2.18-2.40 (1H, m), 2.87 (2H, d, J=7 Hz), 72.7-7.37 (2H, m), 7.47 (1H, dd, J=6.5 Hz, 2.5 Hz), 7.98 (1H, s), 8.29 (1H, dd, J=9.5 Hz, 3.5 Hz).

MS (m/e): 367 (M⁺−11),

EXAMPLE A-53

Synthesis of 5-amino-6-(indole-3-yl)carbonyl-3-isobutyl-1,2-dihydropyrazin-2-one 4-oxdie (Compound A-71)

0.1 Milliliter of 1N NaOH was added to a solution of 4.5 mg of Compound A-70 dissolved in 2 ml of methyl cellosolve. The mixture was refluxed for 2 hours with stirring. After cooling to room temperature, the mixture was made acidic by adding 1N HCl with stirring under ice cooling. The reaction mixture was extracted with ethyl acetate. The extract was washed with an aqueous solution saturated with NaCl, and dried over magnesium sulfate to obtain 3.3 mg (82%) of the title compound. A yellow powdery substance. Melting point: 228°-230° C.

¹H-NMR (250 MHz, CDCl₃-CD₃OD) δ: 1.03 (6H, d, J=6.5 Hz), 2.21-2.47 (1H, m), 2.94 (2H, d, J=7 Hz), 7.20-7.37 (2H, m), 7.42-7.53 (1H, m), 8.50-8.62 (1H, m), 9.15 (1H, s).

MS (m/e): 326 (M⁺).

REFERENCE EXAMPLE A-17

Synthesis of 2-amino-4-[(1-tert-butoxycarbonyl)indol-3-yl]butyronitrile (Compound A-72)

2.6 Grams of 60% NaH was suspended in 300 ml of DMSO. The suspension was stirred for 30 minutes at 60° C. in an argon gas stream. After colling to room temperature, the suspension was mixed with 12.8 g of diphenylmethyleneaminoacetonitrile, and the mixture was stirred for 30 minutes at room temperature. Thereto was added 18.8 g of 3-bromoethyl-1-tert-butoxycarbonylindole, and the mixture was stirred for 4 hours at room temperature. The mixture was then added to an aqueous solution saturated with NH₄Cl under ice cooling, then extracted with ethyl acetate. The extract was washed with an aqueous solution saturated with NaCl three times and dried over magnesium sulfate. The solvent was removed by evaporation. The residue was purified by a silica gel column chromatography (n-hexane:ethyl acetate=3:1) to obtain a condensate of 4-[(1-tert-butoxycarbonyl)indol-3-yl]-2-diphenylmethyleneaminobutyronitrile. This brown oily substance was dissolved in 280 ml of dioxane. Thereto was added 280 ml of 3N HCl. The mixture was stirred for 4 hours at room temperature. Ethyl acetate and water were added and shaken vigorously. The aqueous layer was made alkaline with an aqueous NaOH solution, then extracted with CH₂Cl₂. The extract was washed with an aqueous solution saturated with NaCl solution and dried over magnesium sulfate. The solvent was removed by evaporation. The residue was purified by a silica gel column chromatography (CH₂Cl₂:methanol=15:1) to obtain 5.6 g (31%) of Compound A-72. Yellow oily substance.

¹H-NMR (250 MHz, CDCl₃) δ: 1.63 (2H, s), 1.67 (9H, s), 2.14 (2H, q, J=7 Hz), 2.70-3.15 (2H, m), 3.70 (1H, t, J=7 Hz), 7.04-7.64 (4H, m), 8.13 (1H, d, J=7.5 Hz)

REFERENCE EXAMPLE A-18

The following compound was obtained by the same manner as in Reference Example A-14, using Compound A-72.

2-(α-Hydroxyimino)isocaproylamino-4-[(1-tert-butoxycarbonyl)indol-3-yl]butyronitrile (Compound A-73). A yellow oily substance.

¹H-NMR (250 MHz, CDCl₃) δ: 0.99 (6H, d, J=7 Hz), 1.67 (9H, s), 1.90-2.10 (1H, m), 2.22-2.32 (2H, m), 2.49 (2H, d, J=7 Hz), 2.90 (2H, t, J=7 Hz), 4.92 (1H, q, J=7 Hz), 7.15-7.36 (3H, m), 7.42-7.55 (2H, m), 8.13 (1H, d, J=8 Hz), 9.36 (1H, s).

EXAMPLE A-54

The following compound was obtained by the same manner as in Example A-47, using Compound A-73.

6-Amino-6-{2-[(1-tert-butoxycarbonyl)indol-3-yl]ethyl}-3-isobutyl-1,2-dihydropyrazin-3-one 4-oxide (Compound A-74). Yellow prismatic crystals. Melting point: 179.5°-181° C. (decomposed) (from ethylacetate-n-hexane).

EXAMPLE A-55

The following compound was obtained by the same manner as in Example A-51, using Compound A-74.

2-Amino-5-benzyloxy-3-{2-[(1-tert-butoxycarbonyl-)indol-3-yl]ethyl}-6-isobutylpyrazine 1-oxide (Compound A-75). A yellow oily substance.

$^1$H-NMR (250 MHz, CDCl$_3$) δ: 0.95 (6H, d, J=7 Hz), 1.66 (9H, s), 2.18–2.35 (1H, m), 2.85 (2H, d, J=7 Hz), 3.03 (2H, t, J=6 Hz), 3.15 (2H, t, J=6 Hz), 4.64 (2H, s), 5.32 (2H, s), 7.18–7.55 (9H, m), 8.12 (1H, d, J=8 Hz).

EXAMPLE A-56

Synthesis of 3-benzyloxy-6-chloro-5-{2-[(1-tert-butoxycarbonyl)indol-3-yl]ethyl}-2-isobutylpyrazine 1-oxide (Compound A-76)

To 15 ml of CH$_3$CN were added 0.49 g (0.95 mmol) of Compound 75 and 0.85 g (5 mmol) of CuCl$_2$.2H$_2$O. There was further added 0.4 ml (3 mmol) of isoamyl nitrite. The mixture was stirred for 30 minutes at room temperature. Then, CHCl$_3$ and 2N HCl were added.

The CHCl$_3$ layer was washed with an aqueous solution saturated with NaCl, and dried with magnesium sulfate. The solvent was removed by evaporation. The residue was purified by a silica gel column chromatography (n-hexane:CHCl$_3$:ethyl acetate=10:3:1) to obtain 132 mg (26%) of a yellow viscous oily substance.

$^1$H-NMR (250 MHz, CDCl$_3$) δ: 0.94 (6H, d, J=7 Hz), 1.66 (9H, s), 2.15–2.35 (1H, m), 2.84 (2H, d, J=7 Hz), 3.05–3.30 (4H, m), 5.34 (2H, s), 7.13–7.56 (9H, m), 8.14 (1H, d, J=8 Hz).

REFERENCE EXAMPLE A-19

Synthesis of (α-benzyloxyimino)isocaproic acid (Compound A-77)

52.2 Grams of sodium 2-oxoisocaproate and 61.2 g of O-benzylhydroxylamine hydrochloride were suspended in 600 ml of methanol and 900 ml of CHCl$_3$. The suspension was stirred for 20 hours at room temperature. The insoluble matter was removed by filtration. The filtrate was concentrated to dryness under reduced pressure. The residue was mixed with ether and diluted hydrochloric acid to effect phase separation. The ether layer was washed with an aqueous solution saturated with NaCl and dried with magnesium sulfate. The solvent was removed by evaporation under reduced pressure to obtain 63.0 g (70%) of the title compound as colorless needle-like crystals having a melting point of 83°–84° C.

$^1$H-NMR (250 MHz, CDCl$_3$) δ: 0.90 (6H, d, J=6.5 Hz), 1.90–2.15 (1H, m), 2.51 (2H, d, J=6.5 Hz), 5.26 (2H, s), 7.27–7.50 (5H, m).

REFERENCE EXAMPLE A-20

Synthesis of methyl ester of N-(α-benzyloxyimino)isocaproyl-L-tryptophan (Compound A-78)

At room temperature, 14 g (67.9 mM) of DCC was added to a suspension of 15 g (68.8 mM) of methyl L-tryptophanate, 15.4 g (65.4 mM) of α-benzyloxyiminoisocaproic acid and 7.9 g (68.6 mM) of N-hydroxysuccinimide in 200 ml of 1,4-dioxane. The mxiture was stirred for 18 hours at the same temperature. The reaction mixture was filtered. The solvent was removed from the filtrate by evaporation under reduced pressure. The residue was subjected to a silica gel column chromatography. From the ethyl acetate-n-hexane (1:2) fraction was obtained 27.73 g (98%) of a pale yellow oily substance.

$^1$H-NMR (250 MHz, CDCl$_3$) δ: 0.87 (6H, d, J=6.5 Hz), 1.99 (1H, m), 2.49 (2H, d, J=7.5 Hz), 3.32 (2H, m), 3.66 (3H, s), 4.91 (1H, m), 5.80 (2H, s), 6.87 (1H, d, J=2.5 Hz), 7.05–7.37 (8H, m), 7.54 (1H, d, J=8 Hz), 7.96 (1H, brs).

REFERENCE EXAMPLE A-21

Synthesis of N-(α-benzyloxyimino)isocaproyl-L-tryptophan (Compound A-79)

5.31 Grams (12.2 mmol) of Compound A-78 was dissolved in a mixed solvent consisting of 50 ml of an aqueous 5% KOH solution and 50 ml of methanol. The solution was stirred for 5 hours at room temperature. The solution was then made acidic with an aqueous 10% HCl solution. The solution was extracted with CHCl$_3$. The extract was washed with water and dried over magnesium sulfate. The solvent was removed by distillation under vacuum to obtain 4.98 g (97%) of the title compound as a pale yellow gum-like substance.

$^1$H-NMR (250 MHz, CDCl$_3$) δ: 0.84 (6H, d, J=6.5 Hz), 1.97 (1H, m), 2.46 (2H, d, J=7.5 Hz), 3.34 (2H, d, J=5.5 Hz), 4.90 (1H, m), 6.90 (1H, brs), 7.04–7.32 (8H, m), 7.58 (1H, d, J=8 Hz), 8.15 (1H, brs).

REFERENCE EXAMPLE A-22

Synthesis of 3-(2-benzyloxyimino-4-methyl)pentanoylamino-4-(indol-3-yl)butan-2-one (Compound A-80a)

1.99 Grams of Compound A-79 was dissolved in 20 ml of acetic anhydride and 10 ml of triethylamine. Thereto was added 0.10 g of DMAP. The mixture was stirred for 16 hours at room temperature. 20 Milliliters of methanol was added slowly, and the resulting mixture was allowed to stand for 30 minutes at room temperature, then diluted with ethyl acetate. The mixture was washed with an aqueous solution saturated with NaCl solution, 10% HCl and an aqueous solution saturated with NaCl in this order, and dried over magnesium sulfate. The solvent was removed by evaporation under reduced pressure. 2.51 Grams of the resulting black oily substance was dissolved in 20 ml of methanol. 0.20 gram of K$_2$CO$_3$ was added, then the mixture was stirred for 1 hour at room temperature. The solvent was removed by evaporation under reduced pressure. The residue was purified by a silica gel column chromatography (n-hexane:ethyl acetate=5:1) to obtain 1.18 g of a Compound 80a as a brown oily substance.

$^1$H-NMR (250 MHz, CDCl$_3$) δ: 0.85 (6H, d, J=6.5 Hz), 1.98 (1H, m), 2.09 (3H, s), 2.49 (2H, d, J=7.5 Hz), 3.26 (2H, d, J=6 Hz), 4.86 (1H, m), 5.09 (2H, s), 6.91 (1H, d, J=2.5 Hz), 7.08–7.36 (8H, m), 7.63 (1H, d, J=7.5 Hz), 8.01 (1H, brs).

The following compound was obtained by the same manner as mentioned above.

2-(2-Benzyloxyimino-4-methyl)pentanoylamino-1-(indol-3-yl)pentan-3-one (Compound A-80b). A yellow oily substance.

$^1$H-NMR (250 MHz, CDCl$_3$) δ: 0.85 (6H, d, J=6.5 Hz), 0.94 (3H, t, J=7 Hz), 1.98 (1H, m), 2.35 (2H, q, J=7 Hz), 2.48 (2H, d, J=7.5 Hz), 3.24 (2H, m), 4.87 (1H, m), 5.10 (2H, s), 6.89 (1H, d, J=2.5 Hz), 7.08–7.36 (8H, m), 7.60 (1H, d, J=8 Hz), 8.00 (1H, brs).

REFERENCE EXAMPLE A-23

Synthesis of 3-(2-hydroxyimino-4-methyl)pentanoylamino-4-(indol-3-yl)butan-2-one (Compound A-81a)

One gram of 10% Pd-C was added to a solution of 1.18 g (2.82 mM) of Compound 80a dissolved in 30 ml of ethanol. The mixture was hydrogenated to absorb a stoichiometric amount of hdyrogen gas for 14 hours at room temperature under normal pressure. The solvent was removed by evaporation under reduced pressure. The residue was subjected to a silica gel column chromatography. From the ethyl acetate-hexane fraction, there was obtained 710 mg (77%) of the title compound as a pale purple gum-like matter.

$^1$H-NMR (250 MHz, CDCl$_3$) δ: 0.90 (6H, d, J=6.5 Hz), 2.01 (1H, m), 2.10 (1H, s), 2.50 (2H, d, J=7.5 Hz), 3.25 (2H, d, J=6.5 Hz), 4.94 (1H, m), 6.97 (1H, s), 7.08–7.21 (2H, m), 7.32 (1H, d, J=8 Hz), 7.46 (1H, d, J=7 Hz), 7.58 (1H, d, J=7.5 Hz), 8.13 (2H, brs).

REFERENCE EXAMPLE A-24

The following compound was obtained by the same manner as in Reference Example A-23, using Compound A-80b.

2-(2-Hydroxyimino-4-methyl)pentanoylamino-1-(indol-3-yl)pentan-3-one (Compound A-81b). A pale yellow gum-like substance.

$^1$H-NMR (250 MHz, CDCl$_3$) δ: 0.88 (6H, d, J=6.5 Hz), 0.92 (3H, t, J=7 Hz), 2.01 (1H, m), 2.36 (2H, m), 3.17 (2H, d, J=7.0 Hz), 4.90 (1H, m), 6.90 (2H, d, J=2.5 Hz), 7.07–7.21 (2H, m), 7.30 (1H, d, J=7.5 Hz), 7.54 (2H, d, J=8 Hz), 8.02 (1H, brs), 8.95 (1H, brs).

EXAMPLE A-57

Synthesis of 6-(indol-3-yl)methyl-2-isobutyl-5-methyl-1,2-dihydropyrazin-3-one 4-oxide (Compound A-82a)

80 Milligrams of p-TsOH.H$_2$O was added to a solution of 820 mg of Compound 81a dissolved in 10 ml of methanol, and the mixture was refluxed for 17 hours. The solvent was removed by evaporation under reduced pressure. The residue was purified by a silica gel column chromatography (CHCl$_3$:methanol=30:1) to obtain 490 mg (63%) of Compound A-82a. A white powdery substance. Melting point: 209°–211° C. (from methanol).

$^1$H-NMR (250 MHz, CDCl$_3$) δ: 0.92 (6H, d, J=8.5 Hz), 2.23 (1H, m), 2.44 (3H, s), 2.76 (2H, d, J=8 Hz), 4.08 (2H, s), 7.09–7.26 (3H, m), 7.40 (1H, d, J=8.0 Hz), 7.49 (1H, d, J=8.0 Hz), 8.28 (1H, brs).

EXAMPLE A-58

The following compound was obtained by the same manner as in Example A-57, using Compound A-81b.

5-Ethyl-6-(indol-3-yl)methyl-3-isobutyl-1,2-dihydropyrazin-2-one 4-oxide (Compound 82b). A pale yellow powdery substance. Melting point: 212°–214° C. (from methanol).

$^1$H-NMR (250 MHz, CDCl$_3$) δ: 0.91 (6H, d, J=6.5 Hz), 1.19 (3H, t, J=7.5 Hz), 2.21 (1H, m), 2.75 (2H, d, J=7 Hz), 2.91 (2H, q, J=7.5 Hz), 4.06 (2H, s), 7.07 (1H, d, J=2.5 Hz), 7.14 (1H, ddd, J=1 Hz, 8 Hz, 8 Hz), 7.22 (1H, ddd, J=1 Hz, 8 Hz, 8 Hz), 7.36 (1H, d, J=8 Hz), 7.49 (1H, d, J=8 Hz), 8.43 (1H, brs).

REFERENCE EXAMPLE A-25

Synthesis of 2-(α-benzyloxyimino-4-methyl)pentanoylamino-3-(indol-3-yl)propanal (Compound A-83)

27.5 Milliliters of a solution of 1.5M of DIBAL dissolved in toluene was dropwise added to a solution of 6.0 g (13.8 mmol) of Compound A-78b dissolved in 100 ml of CH$_2$Cl$_2$, at around −100° C. in a N$_2$ gas stream. After 30 minutes, methanol was added to terminate the reaction. Thereto was slowly added 10 ml of an aqueous solution saturated with NH$_4$Cl. The mixture was filtered using Celite, and the filtrate was washed over an aqueous solution saturated with NaCl, and dried over magnesium sulfate. The solvent was removed by evaporation under reduced pressure. The residue was subjected to a silica gel column chromatography [Silicur (trade name), 200–425 mesh, Type 60A special]. From the ethyl acetate-hexane (1:3) fraction there was obtained 4.07 g (73%) of an orange oily substance.

$^1$H-NMR (250 MHz, CDCl$_3$) δ: 0.88 (6H, d, J=6.5 Hz), 2.01 (1H, m), 2.50 (2H, d, J=7.5 Hz), 3.26 (1H, dd, J=7 Hz, 8.5 Hz), 3.38 (1H, dd, J=6 Hz, 8.5 Hz), 4.75 (1H, m), 5.08 (2H, s), 6.93 (1H, d, J=2.5 Hz), 7.13–7.37 (8H, m), 7.62 (1H, d, J=8 Hz), 8.02 (1H, brs), 9.63 (1H, s).

EXAMPLE A-59

Synthesis of 6-(indol-3-yl)methyl-3-isobutyl-1,2-dihydropyrazin-2-one 4-oxide (Compound A-84)

4 Grams of 10% Pd-C was added to a solution of 4.01 g (0.99 mM) of the Compound A-83 dissolved in 50 ml of ethanol. The mixture was hydrogenated to absorb a stoichiometric amount of hydrogen gas for 8 hours at room temperature under atmospheric pressure. The resulting mixture was then filtered. The filtrate was subjected to vacuum evaporation to remove the solvent to obtain 3.04 g of a debenzylation product as a pale yellow foamy substance. 800 Milligrams of this product was dissolved in 10 ml of an aqueous 10% HCl solution and 10 ml of methanol. The solution was stirred for 2 hours at 70° C. The solution was extracted with CHCl$_3$, and the extract was dried over magnesium sulfate. The solvent was removed by evaporation under reduced pressure. The residue was subjected to a silica gel column chromatography. From the ethyl acetatehexane fraction was obtained 314 mg of a brown oily matter. Recrystallized from methanol to obtain 124 mg (16%) of pale yellow powdery crystals. Melting point: 226° C. (decomposed).

$^1$H-NMR (250 MHz, DMSO-d$_6$) δ: 0.93 (6H, d, J=6.5 Hz), 2.16 (1H, m), 2.64 (2H, d, J=7.5 Hz), 3.96 (2H, s), 7.04 (1H, s), 7.04–7.22 (2H, m), 7.45 (1H, s), 7.46 (1H, d, J=8.0 Hz), 7.68 (1H, d, J=7.5 Hz)

REFERENCE EXAMPLE B-1

To 290 ml of water were added 110 ml of 25–28% ammonia water, 51 g of ammonium chloride and 38 g of sodium cyanide. To the solution was dropwise added 56 g of α-allyloxyacetaldehyde in about 2 hours at room temperature. After completion of the dropwise addition, reaction mixture was stirred for 3 hours at the same temperature. Then, 150 ml of diethyl ether was added and the reaction was continued for a further 3 days. After completion of the reaction, the aqueous layer was extracted with diethyl ether. The extract was washed with an aqueous solution saturated with NaCl, and dried over magnesium sulfate. The solvent was removed by evaporation to obtain 52 g of 3-allyloxy-2-aminopropionitrile (Compound B-1) as a brown oily substance.

NMR (CDCl$_3$) δ: 1.81 (2H, br), 3.62 (2H, d, J=5 Hz), 3.86 (1H, br), 4.08 (2H, dt, J=6 Hz, 1 Hz), 5.23 (1H, ddd, J=10 Hz, 3 Hz, 1 Hz), 5.30 (1H, ddd, J=17 Hz, 3 Hz, 1 Hz), 5.88 (1H, ddt, J=17 Hz, 10 Hz, 6 Hz).

REFERENCE EXAMPLE B-2

In 750 ml of dioxane were dissolved 52 g of 3-allyloxy-2-aminopropionitrile, 40 g of α-hydroxyiminoisocaproic acid and 34.9 g of N-hdyroxysuccinimide. Thereto was added 59.7 g of N,N'-dicyclohexylcarbodiimide. The mixture was subjected to a reaction for 16 hours at room temperature. After completion of the reaction, N,N'-dicyclohexylurea was removed by filtration. The filtrate was concentrated to remove dioxane. The resulting residue was mixed with 800 ml of ethyl acetate. The mixture was washed with an aqueous sodium hydrogen carbonate solution and dried over magnesium sulfate. The solvent was removed by evaporation. The residue was purified by a silica gel column chromatography (eluting solvent: 40% by volume of ethyl acetate-n-hexane) to obtain 67 g of 3-allyloxy-2-(α-hydroxyiminoisocaproylamino)propionitrile (Compound B-2) as white crystals.

NMR (CDCl$_3$) δ: 0.91 (6H, d, J=7 Hz), 2.03 (1H, sept, J=7 Hz), 2.52 (2H, d, J=7 Hz), 3.65 (1H, dd, J=10 Hz, 4 Hz), 3.75 (2H, dd, J=10 Hz, 4 Hz), 4.10 (2H, dt, J=6 Hz, 1 Hz), 5.08 (1H, dt, J=9 Hz, 4 Hz), 5.25 (1H, ddd, J=10 Hz, 3 Hz, 1 Hz), 5.32 (1H, ddd, J=17 Hz, 3 Hz, 1 Hz), 5.88 (1H, ddt, J=17 Hz, 10 Hz, 3 Hz), 7.36 (1H, brd, J=9 Hz), 7.87 (1H, brs).

REFERENCE EXAMPLE B-3

To 220 ml of acetic acid was added 22 g of 3-allyloxy-2-(α-hydroxyiminoisocaproylamino)propionitrile. The mixture was subjected to a reaction for 1 hour at 85° C. After completion of the reaction, acetic acid was removed by evaporation under reduced pressure. The residue was purified by using Frorisil (60-100 mesh) (eluting solvent: 30 volume % ethyl acetate-n-hexane→60% volume of ethyl acetate-n-hexane), then washed with diethyl ether, followed by recrystallization from benzene, to obtain 5 g of 6-allyloxymethyl-5-amino-3-isobutyl-1,2-dihydropyrazin-2-one 4-oxide (Compound B-3) as pale yellow plate-like crystals having a melting point of 149°-151° C.

REFERENCE EXAMPLE B-4

In 25 ml of dimethylformamide were dissolved 2.00 g of 6-allyloxy-5-amino-3-isobutyl-1,2-dihydropyrazin-2-one 4-oxide and 570 mg of potassium carbonate. Thereto was added 1.05 ml of benzyl bromide. The mixture was stirred for 1.5 hours at room temperature. After completion of the reaction, 200 ml of ethyl acetate was added to the reaction mixture. The resulting mixture was washed with water. The aqueous layer was extracted with 50 ml of ethyl acetate twice. The extract was combined with the above ethyl acetate layer. The combined mixture was washed with an aqueous solution saturated with NaCl, and dried with magnesium sulfate, then the solvent was removed by evaporation. The residue was purified by a silica gel column chromatography (eluting solvent: 40% by volume of ethyl acetate-n-hexane), followed by recrystallization from n-hexane to obtain 1.57 g of 3-allyloxymethyl-2-amino-5-benzyloxy-6-isobutylpyrazine 1-oxide (Compound B-4) as white fine needle-like crystals having a melting point of 56.3°-57.2° C.

REFERENCE EXAMPLE B-5

352 Milligrams of cuprous chloride, 173 mg of cupric chloride and 3 ml of acetonitrile were added to 300 mg of 3-allyloxymethyl-2-amino-5-benzyloxy-6-isobutylpyrazine 1-oxide. Thereto was dropwise added 350 µl of isoamyl nitrite. After completion of the dropwise addition, the mixture was stirred for 20 minutes at room temperature. After completion of the reaction, there was effected purification by silica gel column chromatography (eluting solvent: 20% by volume of ethyl acetate-n-hexane), followed by purification by a silica gel thin layer chromatography (developing solvent: 20% by volume of ethyl acetate-n-hexane) to obtain 115 mg of 3-allyloxymethyl-5-benzyloxy-2-chloro-6-isobutylpyrazine 1-oxide (Compound B-5) as white needle-like crystals having a melting point of 34°-35° C.

REFERENCE EXAMPLE B-6

To 200 mg of 3-allyloxymethyl-5-benzyloxy-2-chloro-6-isobutylpyrazine 1-oxide were added 195 µl of diisopropylethylamine, 51 mg of a Wilkinson's catalyst

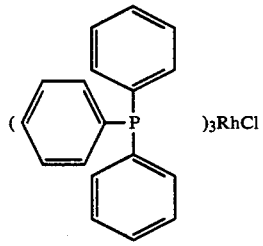

and 4 ml of water (10% volume)-ethanol. The mixture was reacted for 3 hours at 85°-90° C. The catalyst was removed by filtration to obtain 260 mg of 3-(1-propenyl)oxymethyl-5-benzyloxy-2-chloro-6-isobutylpyrazine 1-oxide (Compound B-6) [a cis/trans (about 4/3) mixture] as a colorless oily substance.

NMR (CDCl$_3$) δ: 0.93 (1H, d, J=6.8 Hz), 1.56 (3H, dd, J=6.8, 1.5 Hz), 1.61 (3H, dd, J=6.8, 1.5 Hz), 2.23 (1H, sept, J=7 Hz), 2.85 (2H, d, J=7 Hz), 4.92 (1H, six, J=6 Hz), 4.48 (1H, qui, J=6 Hz), 4.18 (2H, s), 4.88 (2H, s), 6.31 (1H, dq, J=12 Hz, 1.5 Hz), 6.08 (1H, dq, J=6 Hz, 1.5 Hz), 7.4 (5H, m).

REFERENCE EXAMPLE B-7

To 260 mg of the 3-(1-propenyl)oxy-5-benzyloxymethyl-2-chloro-6-isobutylpyrazine 1-oxide mixture obtained in Reference Example 6 were added in 5 ml of methanol and 5 drops of concentrated hydrochloric acid. The mixture was subjected to a reaction for 1.5 hours at room temperature. After completion of the reaction, the reaction mixture was neutralized with sodium hdyrogen carbonate. The solvent was removed by evaporation. The residue was purified by a silica gel thin layer chromatography (developing solvent: 30% by volume of ethyl acetate-n-hexane), followed by recrystallization from diethyl ether-n-hexane to obtain 151 mg of 3-benzyoxy-6-chloro-5-hydroxymethyl-2-isobutylpyrazine 1-oxide (Compound B-7) as colorless

REFERENCE EXAMPLE B-8

200 Milliliters of dioxane was added to 19.5 g of (α-hydroxyimino)isocaproic acid and 16.2 g of N-hydroxysuccinimide. Thereto was dropwise added, at 0° C., a solution of 29.1 g of N,N'-dicyclohexylcarbodiimide dissolved in 50 ml of dioxane. After completion of the dropwide addition, the mixture was stirred for 20 minutes at room temperature. Thereto were added 22 g of ethyl α-amino-α-cyanoacetate and 1.64 g of 4-dimethylaminopyridine. The mixture was subjected to a reaction for 14 hours at 50° C. N,N'-dicyclohexylurea was removed by filtration. The filtrate was subjected to evaporation to remove dioxane, then the residue was mixed with 500 ml of ethyl acetate. The mixture was washed with 150 ml of water, 250 ml of 10% hydrochloric acid, 150 ml of water, 300 ml of an aqueous solution saturated with sodium hydrogen carbonate and 50 ml of an aqueous solution saturated with NaCl in this order, and dried over magnesium sulfate. The solvent was removed by evaporation to obtain 35 g of ethyl 2-cyano-2-[(α-hydroxyimino)isocaproylamino]acetate (Compound B-8) as a brown oily substance.

NMR (CDCl$_3$) δ: 0.91 (6H, d, J=7 Hz), 1.36 (3H, t, J=7 Hz), 2.04 (1H, sept, J=7 Hz), 2.53 (2H, d, J=7 Hz), 4.36 (2H, q, J=7 Hz), 5.51 (1H, d, J=8 Hz), 7.49 (1H, brd, J=8 Hz), 7.8 (1H, brs).

REFERENCE EXAMPLE B-9

400 Milliliters of acetic acid was added to 35 g of ethyl 2-cyano-2-(α-hydroxyiminoisocaproylamino)acetate. The mixture was subjected to a reaction for 1 hour at 70° C. Acetic acid was removed by evaporation, then the residue was mixed with toluene, and toluene was removed by evaporation. This procedure was repeated several times. The residue was purified by a silica gel column chromatography (eluting solvent: 50% by volume of ethyl acetate-n-hexane), followed by recrystallization from ethanol to obtain 21.3 g of 5-amino-6-ethoxycarbonyl-3-isobutyl-1,2-dihydropyrazin-2-one 4-oxide (Compound B-9) as yellow needle-like crystals having a melting point of 179°–181° C.

REFERENCE EXAMPLE B-10

There were mixed 1.00 g of 5-amino-6-ethoxycarbonyl-3-isobutyl-1,2-dihydropyrazin-2-one 4-oxide, 1.18 g of potassium hydrogencarbonate (powder), 20 ml of dry dimethylformamide and 932 μl of benzyl bromide. The mixture was stirred for 16 hours at room temperature to effect a reaction. After completion of the reaction, the reaction mixture was poured into 50 ml of ethyl acetate. The resulting mixture was washed with 30 ml of water three times. The aqueous layer was extracted with 30 ml of ethyl acetate twice. The extract was combined with the above ethyl acetate layer. The combined solution was washed with 30 ml of water twice, and dried over magnesium sulfate. The solvent was removed by evaporation. The residue was recrystallized from ethanol to obtain 1.06 g of 2-amino-5-benzyloxy-3-ethoxycarbonyl-6-isobutylpyrazine 1-oxide (Compound B-10) as pale yellow fine needle-like crystals having a melting point of 114.5°–115.5° C.

REFERENCE EXAMPLE B-11

14 Milliliters of dry dichloromethane was added to 670 mg of 2-amino-5-benzyloxy-3-ethoxycarbonyl-6-isobutylpyrazine 1-oxide. The mixture was cooled to −35° C. Thereto was dropwise added in about 5 minutes 4.7 ml of a solution of 1 mol of diisobutylaluminum hydride dissolved in n-hexane. After completion of the dropwise addition, a reaction was effected for 40 minutes at −30° C., then the temperature of the reaction mixture was returned to room temperature by adding 1 ml of water to the reaction mixture. Further, 30 ml of 2% hydrochloric acid was added thereto and the reaction mixture was extracted with dichloromethane, and the extract was dried over magnesium sulfate. The solvent was removed by evaporation. The residue was purified by a silica gel column chromatography (eluting solvent: 70% by volume of methanol-dichloromethane), followed by recrystallization from benzene to obtain 385 mg of 2-amino-5-benzyloxy-3-hydroxymethyl-6-isobutylpyrazine 1-oxide (Compound B-11) as pale yellow fine needle-like crystals having a melting point of 129.0°–131.3° C.

REFERENCE EXAMPLE B-12

There were mixed 2.17 g of 2-amino-5-benzyloxy-3-hydroxymethyl-6-isobutylpyrazine 1-oxide, 2.89 g of cuprous chloride, 1.42 g of cupric chloride and 22 ml of acetonitrile, and the mixture was stirred for 10 minutes at room temperature. Thereto was added 2.88 ml of isoamyl nitrite at room temperature. The mixture was stirred for 30 minutes, whereby an exothermic reaction of 40°–45° C. was taken place. (No cooling was made.) To the reaction mixture were added 60 ml of 2% hydrochloric acid and 50 ml of diethyl ether to cause phase separation. The aqueous layer was extracted with 50 ml of diethyl ether twice. The extract was combined with the above diethyl ether layer. The combined mixture was dried over magnesium sulfate. The solvent was removed by evaporation. The residue was purified by a silica gel column chromatography (eluting solvent: 50% by volume of ethyl acetate-n-hexane), followed by recrystallization by diethyl ether-n-hexane to obtain 1.73 g of 3-benzyloxy-6-chloro-5-hydroxymethyl-2-isobutylpyrazine 1-oxide (Compound B-12) as pale yellow plate-like crystals having a melting point of 85.0°–88.0° C.

REFERENCE EXAMPLE B-13

4 Milligrams of p-toluenesulfonic acid hydrate was added at room temperature to a mixture of 65 mg of 3-benzyloxy-6-chloro-5-hydroxyemthyl- 2-isobutylpyrazine 1-oxide, 2 ml of dry dichloromethane and 40 μl of 3,4-dihydropyran. The resulting mixture was stirred for 1 hour at the same temperature. The reaction mixture was washed with an aqueous solution saturated with sodium hydrogen carbonate, then the solvent was removed by evaporation. The residue was purified by a silica gel thin layer chromatography (developing solvent: 25% by voluem of ethyl acetate-n-hexane) to obtain 78 mg of 3-benzyloxy-6-chloro-2-isobutyl-5-(2-tetrahydropyranyloxymethyl)pyrazine 1-oxide (Compound B-13) as a colorless oily substance.

NMR (CDCl$_3$) δ: 0.93 (6H, d, J=7 Hz), 1.5–1.9 (6H, m), 2.23 (1H, sept, J=7 Hz), 2.85 (2H, d, J=7 Hz), 3.56 (1H, m), 3.94 (1H, m), 4.64 (1H, ABq, J=12 Hz), 4.83 (1H, ABq, J=12 Hz), 4.83 (1H, brt, J=3 Hz), 5.42 (2H, s), 7.4 (5H, m).

REFERENCE EXAMPLE B-14

There was stirred, for 40 minutes at room temperature, a mixture of 170 mg of 3-benzyloxy-6-chloro-2- isobutyl-5-(2-tetrahydropyranyloxymethyl)pyrazine 1-oxide, 72 mg of tetrabutylammonium bromide, 1.5 ml of dry dimethylformamide, 230 μl of benzyl alcohol and 42.5 mg of 60% sodium hydride. The reaction mixture was stirred at room temperature for 40 minutes, diluted with diethyl ether, then the mixture was washed with water several times and dried over magnesium sulfate. The solvent was removed by evaporation, and the residue was purified by a silica gel thin layer chromatography (developing solvent: 10% by volume of ethyl acetatebenzene) to obtain 136 mg of 2,5-dibenzyloxy-6-isobutyl-3-(2-tetrahydropyranyloxymethyl)pyrazine 1-oxide (Compound B-14) as a colorless oily substance.

NMR (CDCl$_3$) δ: 0.94 (6H, d, J=7 Hz), 1.45–1.9 (6H, m), 2.28 (1H, sept, J=7 Hz), 2.85 (2H, d, J=7 Hz), 3.48 (1H, m), 3.88 (1H, m), 4.43 (1H, ABq, J=11 Hz), 4.62 (1H, ABq, J=11 Hz), 4.72 (1H, brt, J=3 Hz), 5.33 (2H, ABq, J=10 Hz), 5.38 (2H, s), 7.3–7.5 (10H, m).

REFERENCE EXAMPLE B-15

There was stirred, for 1 hour at room temperature, a mixture of 55 μl of methanol, 11 mg of 60% sodium hydride, 22 mg of tetra-n-butylammonium bromide, 50 μl of dimethylformamide and 65 mg of 2,5-dibenzyloxy-6-isobutyl-3-(2-tetrahydropyranyloxymethyl)pyrazine 1-oxide (Compound B-14). The reaction mixture was mixed with diethyl ether. The mixture was washed with water several times and dried with magnesium sulfate, then the solvent was removed by evaporation. The residue was purified by silica gel thin layer chromatography (developing solvent: 30 volume % ethyl acetate-n-hexane) to obtain 50 mg of 3-benzyloxy-2-isobutyl-6-methoxy-5-(2-tetrahydropyranyloxymethyl)pyrazine 1-oxide (Compound B-15) as a colorless oily substance.

NMR (CDCl$_3$) δ: 0.93 (6H, d, J=7 Hz), 1.5–1.9 (6H, m), 2.22 (1H, sept, J=7 Hz), 2.82 (2H, d, J=7 Hz), 3.55 (1H, m), 3.94 (1H, m), 4.05 (3H, s), 4.53 (1H, ABq, J=11 Hz), 4.76 (1H, ABq, J=11 Hz), 4.83 (1H, brt, J=3 Hz), 5.39 (2H, s), 7.4 (5H, m).

REFERENCE EXAMPLE B-16

There was stirred, for 30 minutes at room temperature, a mixture of 80 mg of 3-benzyloxy-2-isobutyl-6-methoxy-5-(2-tetrahydropyranyloxymethyl)pyrazine 1-oxide, 1 ml of methanol and one drop of concentrated hydrochloric acid. The reaction mixture was mixed with diethyl ether, then the mixture was washed with an aqueous solution saturated over sodium hydrogen carbonate, and dried over magnesium sulfate. The solvent was removed by evaporation. The residue was purified by a silica gel thin layer chromatography (developing solvent: 50% by volume of ethyl acetate-n-hexane), followed by recrystallization from diethyl ether-n-hexane to obtain 63 mg of 3-benzyloxy-5-hydroxymethyl-2-isobutyl-6-methoxypyrazine 1-oxide (Compound B-16) as colorless needle-like crystals having a melting point of 68.0°–69.2° C.

REFERENCE EXAMPLE B-17

At 0° C., 52 μl of mesyl chloride was added to a mixture of 210 mg of 3-benzyloxy-5-hydroxymethyl-6-methoxy-2-isobutylpyrazine 1-oxide, 2 ml of dichloromethane and 184 μl of triethylamine. The mixture was stirred for 30 minutes at the same temperature, then diethyl ether was added to the reaction mixture. The mixture was washed with water and dried over magnesium sulfate, then the solvent was removed by evaporation. The residue was purified by a silica gel column chromatography (eluting solvent: 50% by volume of ethyl acetate-n-hexane) to obtain 260 mg of 3-benzyloxy-2-isobutyl-6-methoxy-5-mesyloxymethylpyrazine 1-oxide (Compound B-17) as a colorless oily substance.

NMR (CDCl$_3$) δ: 0.94 (6H, d, J=7 Hz), 2.23 (1H, sept, J=7 Hz), 2.83 (2H, d, J=7 Hz), 3.01 (3H, s), 4.09 (3H, s), 5.24 (2H, s), 5.38 (2H, s), 7.4 (5H, m).

REFERENCE EXAMPLE B-18

There was stirred, for 1.5 hours at room temperature, a mixture of 140 mg of 3-benzyloxy-2-isobutyl-6-methoxy-5-methyloxymethylpyrazine 1-oxide, 7 ml of benzene and 200 mg of tetrabutylammonium iodide to effect a reaction. After completion of the reaction, the reaction mixture per se was subjected to a silica gel column chroamtography (eluting solvent: 30% by volume of ethyl acetate-n-hexane). Then, recrystallization from diethyl ether-n-hexane was effected to obtain 15 mg of 3-benzyloxy-5-iodomethyl-2-isobutyl-6-methoxypyrazine 1-oxide (Compound B-18) as colorless needle-like crystals having a melting point of 78.3°–79.5° C.

REFERENCE EXAMPLE B-19

4.5 Milliliters of 30% hydrogen peroxide was added to a solution of 0.49 g of 2-amino-5-benzyloxy-3ethoxycarbonyl-6-isobutylpyrazine 1-oxide dissolved in 15 ml of acetic acid. The mixture was stirred for 75 minutes at 90° C., then the reaction mixture was poured into ice water. The whole mixture was extracted with ethyl acetate, and the extract was washed with an aqueous selection saturated with NaCl three times, an aqueous sodium thiosulfate, an aqueous solution saturated with sodium hydrogen carbonate and an aqueous solution saturated with NaCl, in this order, and dried over magnesium sulfate. The solvent was removed by evaporation under reduced pressure. The residue was purified by a silica gel column chromatography (eluting solvent: dichloromethane) to obtain 0.23 g of 3-benzyloxy-5-ethoxycarbonyl-2-isobutyl-6-nitropyrazine 1-oxide (Compound B-19) as a colorless oily matter.

NMR (CDCl$_3$) δ: 0.94 (6H, d, J=6.5 Hz), 1.40 (3H, t, J=7 Hz), 2.23–2.37 (1H, m), 2.87 (2H, d, J=7 Hz), 4.45 (2H, q, J=7 Hz), 5.54 (2H, s), 7.32–7.52 (5H, m).

REFERENCE EXAMPLE B-20

1.50 grams of maleic anhydride was added to a solution of 1.50 g of an aqueous 70% hydrogen peroxide solution dissolved in 20 ml of chloroform, with stirring under ice cooling. The temperature of the mixture was returned to room temperature. Thereto was added 6 ml of a solution of 0.53 g of 2-amino-5-benzyloxy-3-ethoxycarbonyl-6-isobutylpyrazine 1-oxide dissolved in chloroform. The mixture was stirred for 12 hours at room temperature. The resulting crystals were removed by filtration. The filtrate was washed with an aqueous 5% sodium thiosulfate solution, an aqueous solution saturated with sodium hydrogen carbonate and an aqueous solution saturated with NaCl, in this order, and dried over magnesium sulfate. The solvent was removed by evaporation to obtain 0.59 g of 3-benzyloxy-5-ethoxycarbonyl-2-isobutyl-6-nitropyrazine 1-oxide (Compound B-20) as a colorless oily substance.

NMR (CDCl$_3$) δ: 0.94 (6H, d, J=6.5 Hz), 1.40 (3H, t, J=7 Hz), 2.23–2.37 (1H, m), 2.87 (2H, d, J≐7 Hz), 4.45 (2H, q, J=7 Hz), 5.54 (2H, s), 7.32–7.52 (5H, m).

REFERENCE EXAMPLE B-21

1.44 Grams of sodium methoxide was added to 200 ml of a solution of 10.0 g of 3-benzyloxy-5-ethoxycarbonyl-2-isobutyl-6-nitriopyrazine 1-oxide dissolved in anhydrous methanol. The mixture was stirred for 1.5 hours at room temperature, then the mixture was mixed with 28 ml of 1N hydrochloric acid with ice cooling, to make the mixture acidic. The while mixture was extracted with ethyl acetate, then the extract was washed with an aqueous solution saturated with NaCl solution and an aqueous solution saturated with sodium hydrogencarbonate, in this order, and dried with magnesium sulfate. The solvent was removed by evaporation. The residue was purified by a silica gel column chromatography (eluting solvent: chloroform) to obtain 5.20 g of 3-benzyloxy-2-isobutyl-6-methoxy-5-methoxycarbonylpyrazine 1-oxide (Compound B-21) as a pale yellow oily substance.

NMR (CDCl$_3$) δ: 0.94 (6H, d, J=6.5 Hz), 2.16–2.40 (1H, m), 2.85 (2H, d, J=7 Hz), 4.00 (3H, s), 4.10 (3H, s), 5.41 (2H, s), 7.30–7.50 (5H, m).

REFERENCE EXAMPLE B-22

4.1 Milliliters of 1N sodium hydroxide was added to a solution of 0.71 g of 3-benzyloxy-2-isobutyl-6-methoxy-5-methoxycarbonylpyrazine 1-oxide dissolved in 15 ml of methanol, then the mixture was stirred for 14 hours at room temperature. The reaction mixture was diluted with water, and then extracted with dichloromethane. The aqueous layer was made acidic with 6.0 ml of 1N hydrochloric acid with ice cooling, then extracted with ethyl acetate. The extract was washed with an aqueous solution saturated with NaCl twice and dried over magnesium sulfate. The solvent was removed by evaporation to obtain 0.62 g of 6-benzyloxy-5-isobutyl-3-methoxypyrazine-2-carboxylic acid 4-oxide (Compound B-22).

NMR (CDCl$_3$) δ: 0.97 (6H, d, J=6.5 Hz), 2.18–2.36 (1H, m), 2.88 (2H, d, J=7 Hz), 4.14 (3H, s), 4.71 (1H, s), 5.41 (2H, s), 7.28–7.50 (5H, m).

REFERENCE EXAMPLE B-23

2-Milliliters of a solution of 0.18 ml of ethyl chlorocarbonate dissolved in anhydrous tetrahydrofuran was dropwise added to 10 ml of a solution of 0.62 g of 6-benzyloxy-5-isobutyl-3-methoxypyrazine-2-carboxylic acid 4-oxide and 0.26 ml of triethylamine dissolved in anhdyrous tetrahydrofuran, with stirring at −15° to −10° C. After completion of the dropwise addition, the reaction mixture was stirred for 2 hours at −10° to −5° C. Thereto was dropwise added, at −5° C., 4 ml of a solution of 0.22 g of sodium boron hydride dissolved in anhydrous dimethylformamide. The mixture was stirred for 13.5 hours at room temperature, and 7.0 ml of 1N hydrochloric acid was added with ice cooling, to decompose excessive sodium boron hydride. The reaction mixture was extracted with ethyl acetate, then the extract was washed with an aqueous solution saturated with NaCl three times and dried over magnesium sulfate. The solvent was removed by evaporation under reduced pressure. The residue was purified by a silica gel column chromatography (eluting solvent: n-hexane ethyl acetate=3/1) to obtain 3-benzyloxy-5-hydroxymethyl-2-isobutyl-6-methxoypyrazine 1-oxide (Compound B-23) as colorless needle-like crystals having a melting point of 68.0°–69.2° C.

REFERENCE EXAMPLE B-24

2.4 Milligrams of lithium borohydride was added to 1 ml of a solution of 12.5 mg of 3-benzyloxy-2-isobutyl-6-methoxy-5-methoxycarbonylpyrazine 1-oxide dissolved in anhydrous diethyl ether. The mixture was refluxed for 6 hours in an argon gas stream with stirring, then 0.2 ml of 1N hydrochloric acid was added to the reaction mixture with ice cooling, and the mixture was diluted with water. The reaction mixture was extracted with ethyl acetate and the extract was washed with an aqueous solution saturated with NaCl solution and dried over magnesium sulfate, and the solvent was removed by evaporation. The residue was purified by a thin layer chromatography (developing solvent: dichloromethane/methanol=40/1) to obtain 3.5 mg of 3-benzyloxy-5-hydroxymethyl-6-methoxy-2-isobutylpyrazine 1-oxide (Compound B-24) as colorless needle-like crystals having a melting point of 68.0°–69.2° C.

REFERENCE EXAMPLE B-25

30 Milliliters of water and 7.0 g of sodium hydrogen carbonate were added to a suspension of 17.5 g of diethyl aminomalonate hydrochloride in 150 ml of dichloromethane. After 20 minutes, the dichloromethane layer was separated and dried over magnesium sulfate. The solvent was removed by evaporation under reduced pressure to obtain colorless oily diethyl aminomalonate. The diethyl aminomalonate was made into a solution of the diethyl aminomalonate, 10.0 g of α-hydroxyisocaproic acid and 8.7 g of N-hydroxysuccinimide dissolved in 200 ml of dioxane. To the solution was added 15.7 g of N,N'-dicyclohexylcarbodiimide. The mixture was stirred for 16 hours at room temperature and then filtered. The filtrate was subjected to removal of the solvent by evaporation. The residue was mixed with ethyl acetate, and the mixture was washed with 10% hydrochloric acid, water, an aqueous solution saturated with sodium hydrogen carbonate, and an aqueous solution saturated with NaCl solution in this order, and dried over magnesium sulfate. The solvent was removed by evaporation to obtain 29.19 g of diethyl N-(2-hydroxyimino-4-methylpentanoyl)aminomalonate (Compound B-25) as a colorless oily substance.

NMR (CDCl$_3$) δ: 0.91 (6H, d, J=6.5 Hz), 1.30 (6H, t, J=7.0 Hz), 2.04 (1H, m), 2.52 (1H, d, J=7.5 Hz), 4.30 (4H, m), 5.21 (1H, d, J=7.0 Hz), 7.76 (1H, brd, J=7.0 Hz), 8.71 (1H, s).

REFERENCE EXAMPLE B-26

A solution of 2.8 g of sodium hydroxide dissolved in 200 ml of water was added to a solution of 29.19 g of diethyl N-(2-hydroxyimino-4-methylpentanoyl)aminomalonate dissolved in 200 ml of ethanol. The mixture was stirred for 4 hours at room temperature, then the reaction mixture was neutralized with 10% hydrochloric acid and then concentrated. The residue was made acidic with 10% hydrochloric acid, and was extracted with ethyl acetate was effected. The extract was washed with water and an aqueous solution saturated with NaCl in this order, and dried over magnesium sulfate. The solvent was removed by distillation to obtain 23.0 g of monoethyl ester of N-(2-hydroxyimino-4-methylpentanoyl)aminomalonic acid (Compound B-26) as a pale yellow solid.

NMR (CDCl$_3$) δ: 0.91 (6H, d, J=6.5 Hz), 1.32 (3H, d, J=7.0 Hz), 2.56 (1H, m), 2.52 (2H, d, J=8.0 Hz), 4.31

(2H, q, J=7.0 Hz), 5.26 (1H, d, J=7.5 Hz), 7.85 (1H, brd, J=7.5 Hz).

REFERENCE EXAMPLE B-27

At 0° C., 15.2 g of 2,2'-dipyridyl disulfide was added to a solution of 23.0 g of monoethyl ester of N-(2-hdyroxyimino-4-methylpentanoyl)aminomalonic acid dissolved in 600 ml of dry dichloromethane. Thereto was added 18.1 g of triphenylphosphine, and the mixture was stirred for 1.5 hours at room temperature, and then washed with an aqueous 2.5% potassium hydrogen sulfate solution and an aqueous solution saturated with NaCl in this order. Then the reaction mixture was extracted with an aqueous solution saturated with sodium hydrogen carbonate, the extract was washed with ethyl acetate and then made it acidic with concentrated hydrochloric acid. The resulting crystals were collected by filtration to obtain 9.28 g of 6-ethoxycarbonyl-5-hydroxy-3-isobutyl-1,2-dihydropyrazin-2-one 4-oxide (Compound B-27) as a yellow solid having a melting point of 153°–155° C.

REFERENCE EXAMPLE B-28

To a suspension of 5.45 g of 6-ethoxycarbonyl-5-hydroxy-3-isobutyl-1,2-hydropyrazin-2-one 4-oxide in 100 ml of chloroform was dropwise added slowly at −15° C. a solution of diazomethane in diethyl ether in an amount about equivalent to that of the suspension. After 30 minutes, the reaction mixture was mixed with 0.5 ml of acetic acid. The mixture was allowed to stand for 30 minutes at room temperature, and then washed with water, then the solvent was removed by evaporation. The residue was mixed with 30 ml of chloroform, and the mixture was heated to obtain a solution. Thereto was slowly added 200 ml of diisopropyl ether to cause crystallization. The resulting crystals were collected by filtration. This procedure was repeated twice to obtain 3.10 g of 6-ethoxycarbonyl-3-isobutyl-5-methoxy-1,2-dihydropyrazin-2-one 4-oxide (Compound B-28) as a pale yellow solid having a melting point of 153°–155° C.

REFERENCE EXAMPLE B-29

There was stirred, for 16 hours at room temperature, a suspension of 926 mg of 6-ethoxycarbonyl-3-isobutyl-5-methoxy-1,2-dihydropyrazin-2-one 4-oxide, 0.66 ml of o-chlorobenzyl chloride and 950 mg of potassium carbonate in 20 ml of dry dimethylformamide. The reaction mixture was diluted with ethyl acetate, and the mixture was washed with water and dried over magnesium sulfate. The solvent was removed by evaporation to obtain 1.82 g of 3-(2-chloro)benzyloxy-5-ethoxycarbonyl-2-isobutyl-6-methoxypyrazine 1-oxide (Compound B-29) as a pale yellow oily substance.

NMR (CDCl₃) δ: 0.94 (6H, d, J=6.5 Hz), 1.45 (3H, t, J=7.0 Hz), 2.25 (1H, m), 2.85 (2H, d, J=7.0 Hz), 4.10 (3H, s), 4.45 (2H, q, J=7.0 Hz), 5.52 (2H, s), 7.26–7.58 (4H, m).

REFERENCE EXAMPLE B-30

2.0 Milliliters of 1N sodium hydroxide was added to a solution of 1.82 g 3-(2-chloro)benzyloxy-5-ethoxycarbonyl-2-isobutyl-6-methoxypyrazine 1-oxide dissolved in 20 ml of methanol. The mixture was stirred for 2 hours at room temperature, and the reaction mixture was diluted with ethyl acetate. The mixture was extracted with an aqueous 1N sodium hydroxide solution, and the extract was made acidic with concentrated hydrochloric acid, the extracted with ethyl acetate. The extract was washed with an aqueous solution saturated with NaCl, dried over magnesium sulfate. The solvent was removed by evaporation to obtain 1.09 g of 6-(2-chloro)benzyloxy-5-isobutyl-3-methoxypyrazine-2-carboxylic acid 4-oxide (Compound B-30) as a pale yellow oily substance.

NMR (CDCl₃) δ: 0.95 (6H, d, J=6.5 Hz), 2.27 (1H, m), 2.89 (2H, d, J=7.0 Hz), 4.14 (3H, s), 5.53 (2H, s), 7.30–7.53 (4H, m).

REFERENCE EXAMPLE B-31

1.09 Grams of 6-(2-chloro)benzyloxy-5-isobutyl-3-methoxypyrazine-2-carboxylic acid 4-oxide, 10 ml of tetrahydrofuran, 0.42 ml of triethylamine, 0.29 ml of ethyl chlorocarbonate, 340 mg of sodium borohydride and 6 ml of dimethylformamide were subjected to the same treatment as in Reference Example 23, to obtain 524 mg of 3-(2-chloro)benzyloxy-5-hydroxymethyl-2-isobutyl-6-methoxypyrazine 1-oxide (Compound B-31) as a colorless oily substance.

NMR (CDCl₃) δ: 0.95 (6H, d, J=6.5 Hz), 2.24 (1H, m), 2.86 (2H, d, J=7.0 Hz), 3.07 (1H, t, J=5.5 Hz), 4.05 (3H, s), 4.69 (2H, d, J=5.5 Hz), 7.26–7.32 (2H, m), 7.41–7.50 (2H, m).

REFERENCE EXAMPLE B-32

421 Milligrams of 3-(2-chlorobenzyloxy)-5-hydroxymethyl-2-isobutyl-6-methoxypyrazine 1-oxide, 10 ml of dichloromethane, 0.24 ml of triethylamine and 0.106 ml of mesyl chloride were subjected to the same treatment as in Reference Example B-17 to obtain 520 mg of 3-(2-chloro)benzyloxy-2-isobutyl-5-mesyloxymethyl-6-methoxypyrazine 1-oxide (Compound B-32) as a colorless oily substance.

NMR (CDCl₃) δ: 0.95 (6H, d, J=6.5 Hz), 2.25 (1H, m), 2.85 (2H, d, J=7.0 Hz), 3.06 (3H, s), 4.11 (3H, s), 5.27 (2H, s), 5.48 (2H, s), 7.26–7.33 (2H, m), 7.40–7.51 (2H, m).

REFERENCE EXAMPLE B-33

520 Milligrams of 3-(2-chloro)benzyloxy-2-isobutyl-5-mesyloxymethyl-6-methxoypyrazine 1-oxide, 10 ml of benzene and 630 mg of tetrabutylammonium iodide were subjected to the same treatment as in Reference Example B-18 to obtain 492 mg of 3-(2-chloro)benzyloxy-5-iodomethyl-2-isobutyl-6-methoxypyrazine 1-oxide (Compound B-33) as a pale yellow oily substance.

NMR (CDCl₃) δ: 0.94 (6H, d, J=6.5 Hz), 2.23 (1H, m), 2.81 (2H, d, J=7.0 Hz), 4.16 (3H, s), 4.45 (2H, s), 5.47 (2H, s), 7.25–7.32 (2H, m), 7.38–7.54 (2H, m).

REFERENCE EXAMPLE B-34

A solution of 932 mg of 6-ethoxycarbonyl-3-isobutyl-5-methoxy-1,2-dihydropyrazine-2-one 4-oxide dissolved in 21 ml of methanol and 10 ml of an aqueous 1N sodium hydroxide solution was stirred for 4 hours at room temperature. The reaction mixture was made acidic with 10% hdyrochloric acid. The resulting crystals were collected by filtration and dissolved in chloroform-methanol. The solvent was removed by evaporation to obtain 830 mg of 3-isobutyl-5-methoxy-1,2-dihydropyrazin-2-one-6-carboxylic acid 4-oxide (Compound B-34) as a white solid.

NMR (CDCl₃) δ: 0.98 (6H, d, J=6.5 Hz), 2.28 (1H, m), 2.84 (2H, d, J=7.0 Hz), 4.04 (3H, s).

REFERENCE EXAMPLE B-35

0.70 Milliliters of ethyl chlorocarbonate was added, at −15° C., to a solution of 730 mg of 3-isobutyl-5-methoxy-1,2-dihydropyrazin-2-one-6-carboxylic acid 4-oxide and 1.0 ml of triethylamine dissolved in 20 ml of tetrahydrofuran, and the mixture was stirred for 2 hours at the same temperature. Thereto was added 330 mg of lithium borohydride, and the mixture was stirred for 18 hours at room temperature. To the reaction mixture was added 5 ml of 10% hydrochloric acid, and the mixture was diluted with ethyl acetate with stirring, and the resulting mixture was dried over magnesium sulfate, then the solvent was removed by evaporation. The residue was purified by a silica gel column chromatography (eluting solvent: 10% by volume of methanol-chloroform) to obtain 467 mg of 6-hydroxymethyl-3-isobutyl-5-methoxy-1,2-dihydropyrazin-2-one 4-oxide (Compound B-35) as a pale yellow oily substance.

NMR (CDCl$_3$) δ: 0.95 (6H, d, J=6.5 Hz), 2.22 (1H, m), 2.77 (2H, d, J=7.0 Hz), 3.97 (3H, s), 4.70 (2H, s).

REFERENCE EXAMPLE B-36

There was stirred, for 1 day at room temperature, a suspension of 50.1 mg of 6-hydroxymethyl-3-isobutyl-5-methoxy-1,2-dihydroxypyrazin-2-one 4-oxide, 40 μl of benzyl bromide and 61 mg of potassium carbonate in 20 ml of tetrahydrofuran and 8 ml of hexamethylphosphoric triamide. The reaction mixture was diluted with ethyl acetate, and the mixture was washed with water and dried over magnesium sulfate. The solvent was removed by evaporation, and the residue was purified by a thin layer chromatography (developing solvent: ethyl acetate/n-hexane=2/1), followed by recrystallization from diethyl ether-n-hexane to obtain 41.1 mg of 3-benzyloxy-5-hydroxymethyl-2-isobutyl-6-methoxypyrazine 1-oxide (Compound B-36) as colorless needle-like crystals having a melting point of 68.0°–69.2° C.

EXAMPLE B-1

300 Microliters of toluene and 3.7 mg of 60% sodium hydride were added to a mixture of 10.0 mg of 3-benzyloxy-5-iodomethyl-2-isobutyl-6-methxoypyrazine 1-oxide and 8.2 mg of indole. The resulting mixture was stirred for 14 hours at room temperature, and the reaction mixture was mixed with diethyl ether, then the mixture was dried over magnesium sulfate. The solvent was removed by evaporation, and the residue was purified by a silica gel thin layer chromatography (developing solvent: 50 volume % ethyl acetate-n-hexane), followed by recrystallization from diethyl ether-n-hexane to obtain 7.7 mg of 3-benzyloxy-5-(indol-3-yl)methyl-2-isobutyl-6-methoxypyrazine 1-oxide (Compound B-37) as colorless prismatic crystals having a melting point of 139.6°–141.9° C.

EXAMPLE B-2

400 Microliters of toluene and 14.2 mg of indole were added to 13 mg of 3-benzyloxy-5-iodomethyl-2-isobutyl-6-methxoypyrazine 1-oxide. Thereto was added 12 mg of potassium t-butoxide at 0° C. After gradual temperature elevation to room temperature, the mixture was stirred for 3 hours at room temperature. Then, the mixture was subjected to the same post-treatment as in Example B-1 to obtain 8.5 mg of 3-benzyloxy-5-(indol-3-yl)methyl-2-isobutyl-6-methoxypyrazine 1-oxide (Compound B-38) as colorless prismatic crystals having a melting point of 139.6°–141.9° C.

EXAMPLE B-3

To 117 mg of indole were added 320 mg of bis-[tri-n-butyltin (IV)] oxide [(Bu$_3$Sn)$_2$O] and 2 ml of toluene. The mixture was refluxed for 3 hours with heating, then water was removed by using a Dean-Stark trap. 200 Microliters of the reaction mixture was taken from the reaction mixture and added to a solution of 20 mg of 3-benzyloxy-5-iodomethyl-2-isobutyl-6-methoxypyrazine 1-oxide dissolved in 800 μl of toluene. The mixture was subjected to a reaction for 14 hours at 80°–85° C., then the reaction mixture was subjected to the same post-treatment as in Example 1 to obtain 14.5 mg of 3-benzyloxy-5-(indol-3-yl)methyl-2-isobutyl-6-methoxypyrazine 1-oxide (Compound B-39) as colorless prismatic crystals having a melting point of 139.6°–141.9° C.

EXAMPLE B-4

To 117 mg of indole were added 1 ml of tetrahydrofuran and 685 μl of a solution of 1.46M of butyllithium dissolved in n-hexane, and the mixture was stirred for 80 minutes at room temperature. Thereto was added 136 mg of zinc chloride, and the mixture was stirred for 1 hour at the same temperature. Tetrahydrofuran was removed by evaporation and the reside was mixed with 2 ml of toluene, then 300 μl was taken from the mixture and added to a solution of 20 mg of 3-benzyloxy-5-iodomethyl-2-isobutyl-6-methoxypyrazine 1-oxide dissolved in 700 μl of toluene. The mixture was stirred for 30 minutes at room temperature and then subjected to the same post-treatment as in Example B-1 to obtain 17.7 mg of 3-benzyloxy-5-(indol-3-yl)methyl-2-isobutyl-6-methoxypyrazine 1-oxide (Compound B-40) as colorless prismatic crystals having a melting point of 39.6°–14.19° C.

EXAMPLE B-5

300 Microliters of toluene and 3.7 mg of 60% sodium hydride were added to a mixture of 8.8 mg of 3-benzyloxy-5-mesyloxymethyl-2-isobutyl-6-methoxypyrazine 1-oxide and 8.2 mg of indole. The mixture was stirred for 16 hours at room temperature, and the reaction mixture was subjected to the same post-treatment as in Example B-1 to obtain 5.8 mg of 3-benzyloxy-5-(indol-3-yl)methyl-2-isobutyl-6-methoxypyrazine 1-oxide (Compound B-41) as colorless prismatic crystals having a melting point of 139.6°–141.9° C.

EXAMPLE B-6

5.0 Milligrams of 3-benzyloxy-5-(indol-3-yl)methyl-2-isobutyl-6-methoxypyrazine 1-oxide, 500 μl of ethanol and 2 mg of 10% Pd-C were subjected to hydrogenation for 30 minutes at room temperature. After the completion of the reaction, the catalyst was removed by filtration, and the filtrate was concentrated. The residue was purified by a silica gel thin layer chromatography (developing solvent: 7% by volume of methanol-chloroform), followed by recrystallization from methanol-chloroform to obtain 3.9 mg of 6-(indol-3-yl)methyl-3-isobutyl-5-methoxy-1,2-dihydro(1)pyrazin-2-one 4-oxide (Compound B-42) (NF-1616-904 substance) as pale yellow prismatic crystals having a melting point of 222°–224° C.

EXAMPLE B-7

170 Milligrams of sodium hydride was added to a solution of 498 mg of indole dissolved in 20 ml of toluene, and the mixture was heated for 30 minutes at 110° C. After cooling, the reaction mixture was mixed with a solution of 492 mg of 3-(2-chloro)benzyloxy-2-isobutyl-5-iodomethyl-6-methoxypyrazine 1-oxide dissolved in 10 ml of toluene, and was stirred for 2 days at room temperature. The reaction mixture was diluted with ethyl acetate, and the mixture was washed with water and dried with magnesium sulfate, then the solvent was removed by evaporation. The residue was purified by a silica gel column chromatography (eluting solvent: ethyl acetate/n-hexane=1/5) to obtain 334.6 mg of 3-(2-chloro)benzyloxy-5-(3-indol-3-yl)methyl-2-isobutyl-6-methoxypyrazine 1-oxide (Compound B-43) as a pale yellow oily substance.

NNR (CDCl$_3$) δ: 0.93 (6H, d, J=6.5 Hz), 2.22 (1H, m), 2.80 (2H, d, J=7.0 Hz), 4.18 (2H, s), 5.49 (2H, s), 7.07–7.76 (8H, m), 7.78 (1H, d, J=8.0 Hz), 8.19 (H, brs).

EXAMPLE B-8

20 Milligram of 10% Pd-C was added to a suspension of 250.5 mg of 3-(2-chloro)benzyloxy-5-indol-3-yl)methyl-2-isobutyl-6-methoxypyrazine 1-oxide in 10 ml of methanol and 1 ml of 1N sodium hydroxide. The mixture was subjected to hydrogenation for 4 hours at room temperature, then the catalyst was removed by filtration. The filtrate was subjected to evaporation to remove the solvent, and the residue was recrystallized from methanol-dichloromethane to obtain 128 mg of 6-(indole-3-yl)methyl-3-isobutyl-5-methoxy-1,2-dihydro(1)-pyrazin-2-one 4-oxide (NF-1616-904 substance) (Compound B-42) as pale yellow prismatic crystals having a melting point of 222°–224° C.

REFERENCE EXAMPLE C-1

Synthesis of methyl ester of
N-(α-hydroxyimino)isocaproyl-L-tryptophan
(Compound C-1)

In 220 ml of dry dioxane were dissolved 6.54 g of methyl L-tryptophanate, 4.35 g of (α-hydroxyimino)isocaproic acid and 3.63 g of N-hdyroxysuccinimide. Thereto was added 6.19 g of dicyclohexylcarbodiimide. The mixture was stirred for 24 hours at room temperature. The insoluble matter was removed by filtration. The filtrate was concentrated to dryness under vacuum reduced pressure. The residue was purified by a silica gel column chromatography (n-hexane:ethyl acetate =4:1) to obtain 9.83 g (95%) of the title compound as colorless needle-like crystals having a melting point of 109°–110° C. (recrystallized from diethyl ether-n-hexane).

$^1$H-NMR (250 MHz, CDCl$_3$) δ: 0.91 (6H, d, J=6.5 Hz), 1.94–2.17 (1H, m), 2.52 (2H, d, J=7.5 Hz), 3.32 (2H, d, J=5.5 Hz), 3.67 (3H, s), 4.40–4.49 (1H, m), 6.98 (1H, d, J=2.5 Hz), 7.10 (1H, d, J=8 Hz), 7.13 (1H, d, J=8 Hz), 7.19 (1H, d, J=8 Hz), 7.53 (1H, d, J=8 Hz), 7.59 (1H, brs), 8.06 (1H, brs).

REFERENCE EXAMPLE C-2

Synthesis of
N-(α-hydroxyimino)isocaproyl-L-tryptophan
(Compound C-2)

6 Milliliters of an aqueous 1N sodium hydroxide solution was added to 20 ml of a solution of 0.68 g of methyl ester of N-(α-hydroxyimino)isocaproyl-L-tryptophan dissolved in ethanol. The mixture was stirred for 30 minutes at room temperature. Then, the mixture was made acidic with 7 ml of 1N hydrochloric acid, with stirring under ice cooling. The reaction mixture was extracted with ethyl acetate, then the extract was washed with an aqueous solution saturated with NaCl, and dried over magnesium sulfate to obtain 0.67 g of the title compound as colorless needle-like crystals having a melting point of 97°–98° C. (recrystallized from dichloromethane).

$^1$H-NMR (250 MHz, CDCl$_3$) δ: 0.79 (3H, d, J=6.5 Hz), 0.80 (3H, d, J=6.5 Hz), 1.80–2.30 (1H, m), 2.40 (2H, d, J=7.5 Hz), 3.20 (2H, d, J=5.5 Hz), 4.85 (1H, dd, J=14 Hz, 5.5 Hz), 5.70–6.90 (1H, br), 6.77 (1H, d, J=2 Hz), 7.00 (1H, t, J=7.5 Hz), 7.07 (1H, t, J=7.5 Hz), 7.16 (1H, d, J=7.5 Hz), 7.44 (1H, d, J=7.5 Hz), 8.00 (1H, brs).

REFERENCE EXAMPLE C-3

Synthesis of methyl ester of
N-(α-benzyloxyimino)isocaproyl-L-tryptophan
(Compound C-3)

At room temperature, 14.0 g of dicyclohexylcarbodiimide was added to a suspension of 15.0 g of methyl L-tryptophanate, 15.4 g of (α-benzyloxyimino)isocaproic acid and 7.9 g of N-hydroxysuccinimide in 200 ml of 1,4-dioxane. The mixture was stirred for 18 hours at the same temperature. The reaction mixture was filtered, and the filtrate was subjected to vacuum evaporation to remove the solvent. The residue was subjected to silica gel column chromatography, and from the ethyl acetate-n-hexane (1:2) fraction was obtained 27.7 g of a pale yellow oily substance.

$^1$H-NMR (250 MHz, CDCl$_3$) δ: 0.87 (6H, d, J=6.5 Hz), 1.99 (1H, m), 2.49 (2H, d, J=7.5 Hz), 3.32 (2H, m), 3.66 (3H, s), 4.91 (1H, m), 5.80 (2H, s), 6.87 (1H, d, J=2.5 Hz), 7.05–7.37 (8H, m), 7.54 (1H, d, J=8 Hz), 7.96 (1H, brs).

REFERENCE EXAMPLE C-4

Synthesis of (α-Benzyloxyimino)isocaproic acid
(Compound C-4)

52.2 Grams of sodium 2-oxo-isocaproate and 61.2 g of O-benzylhydroxylamine hydrochloride were suspended in 600 ml of methanol and 900 ml of chloroform. The suspension was stirred for 20 hours at room temperature. The insoluble matter was removed by filtration. The filtrate was concentrated to dryness under reduced pressure. The residue was mixed with diethyl ether and diluted hydrochloric acid for phase separation. The diethyl ether layer was washed with an aqueous solution saturated with NaCl and dried with magnesium sulfate. The solvent was removed by evaporation under reduced pressure to obtain 63.0 g of the title compound as colorless needle-like crystals having a melting point of 83°–84° C.

REFERENCE EXAMPLE C-5

Synthesis of methyl ester of
N-(α-benzyloxyimino)isocaproyl-N$^{in}$-tert-butoxycarbonyl-L-tryptophan (Compound C-5)

To 200 ml of a solution of 17.6 g of methyl ester of N-(α-benzyloxyimino)isocaproyl-1-tryptophan dissolved in anhdyrous dichloromethane were added 5.7 ml of triethylamine, 5.0 g of 4-dimethylaminopyridine and 9.3 ml of di-tert-butyl dicarbonate. The mixture was stirred for 24 hours at room temperature, then the reaction mixture was washed with an aqueous solution saturated with potassium hydrogen sulfate and an aqueous solution saturated with NaCl in this order, and the mixture was dried with sodium sulfate. The solvent was removed by evaporation under reduced pressure. The residue was purified by a silica gel column chromatography (n-hexane:ethyl acetate=8:1) to obtain 21.0 g of the title compound as a pale yellow oily substance.

$^1$H-NMR (250 MHz, CDCl$_3$) δ: 0.86 (6H, d, J=6.5 Hz), 1.65 (9H, s), 1.88-2.07 (1H, m), 2.48 (2H, d, J=7.5 Hz), 3.27 (2H, d, J=5.5 Hz), 3.69 (3H, s), 4.94 (1H, dt, J=8 Hz, 5.5 Hz), 5.10 (2H, s), 7.20 (1H, t, J=7.5 Hz), 7.23-7.46 (7H, m), 7.42 (1H, s), 7.50 (1H, d, J=7.5 Hz), 8.11 (1H, d, J=8 Hz).

REFERENCE EXAMPLE C-6

Synthesis of methyl ester of N$^{in}$-tert-butoxycarbonyl-N-(α-hydroxyimino)isocaproyl-L-tryptophan (Compound C-6)

In 220 ml of ethanol was dissolved 21.0 g of methyl ester of N-(α-benzyloxyimino)isocaproyl-N$^{in}$-tert-butoxycarbonyl-L-tryptophan. Thereto was added 3.5 g of 10% Pd-C, and the mixture was stirred for 3.5 hours at 40° C. under a hydrogen gas atmosphere. The catalyst was removed by filtration, and the filtrate was concentrated under reduced pressure. The residue was purified by a silica gel column chromatography (n-hexane:ethyl acetate=4:1) to obtain 12.6 g of the title compound as a pale yellow oily substance.

$^1$H-NMR (200 MHz, CDCl$_3$) δ: 0.91 (6H, d, J=6.5 Hz), 1.66 (9H, s), 1.93-2.15 (1H, m), 2.52 (2H, d, J=7.5 Hz), 3.25 (2H, d, J=5.5 Hz), 3.67 (3H, s), 4.96 (1H, dt, J=8 Hz, 5.5 Hz), 7.20 (1H, t, J=7.5 Hz), 7.31 (1H, t, J=7 Hz), 7.40 (1H, s), 7.47 (1H, d, J=7 Hz), 7.78 (1H, s), 8.08 (1H, d, J=8.5 Hz).

REFERENCE EXAMPLE C-7

Synthesis of N$^{in}$-tert-butoxycarbonyl-N-(α-hydroxyimino)isocaproyl-L-tryptophan (Compound C-7)

284 Milliliters of an aqueous 1 N sodium hydroxide solution was added to 600 ml of a solution of 12.6 g of methyl ester of N$^{in}$-tert-butoxycarbonyl-N-(α-hydroxyimino)isocaproyl-L-tryptophan dissolved in methanol. The mixture was stirred for 12 hours at room temperature, then, the mixture was made acidic with 25 ml of concentrated hydrochloric acid under ice cooling. The reaction mixture was subjected to extraction with ethyl acetate. The extract was washed with an aqueous solution saturated with NaCl three times and dried with magnesium sulfate. The solvent was removed by evaporation under reduced pressure. The residue was purified by a silica gel column chromatography (methylene chloride:methanol=8:1→4:1) to obtain 9.7 g of the title compound as a white powdery substance.

$^1$H-NMR (250 MHz, CDCl$_3$-CD$_3$OD=1:1) δ: 0.85 (6H, d, J=6.5 Hz), 1.66 (9H, s), 1.84-2.03 (1H, m), 2.41 (1H, dd, J=12.5 Hz, 7.5 Hz), 2.47 (1H,d d, J=12.5 Hz, 7.5 Hz), 3.18 (1H, dd, J=14.5 Hz, 7 Hz), 3.30-3.44 (1H, m), 4.72 (1H, dd, J=7 Hz, 5 Hz), 7.18 (1H, t, J=7.5 Hz), 7.26 (1H, t, J=7.5 Hz), 7.42 (1H, s), 7.58 (1H, d, J=7 Hz), 8.04 (1H, d, J=8 Hz).

EXAMPLE C-1

Synthesis of 5-hydroxy-6-(indol-3-yl)methyl-3-isobutyl-1,2-dihydropyrazin-2-one 4-oxide (Compound C-8)

(a) To 180 ml of acetonitrile were added 2.1 g of methyl ester of N-(α-hydroxyimino)isocaproyl-L-tryptophan and 5.3 ml of trimethylsilylethoxyacetylene, and the mixture was stirred for 7 hours at 60° C. The reaction mixture was concentrated under reduced pressure by using an evaporator and further concentrated for 1 hour at 40° C. by using a vacuum pump under reduced pressure (0.3 mmHg). The resulting yellow tar-like substance was purified by silica gel column chromatography (dichloromethane:methanol=20:1→4:1) to obtain 0.30 g of the title compound as a pale yellow powdery substance.

(b) There was stirred, for 3 hours at room temperature, 5 ml of a solution of 66.2 mg of methyl ester of N-(α-hydroxyimino)isocaproyl-L-tryptophan, 210 mg of triphenylphosphine and 170 mg of 2'-dipyridyl disulfide dissolved in anhydrous THF. Thereto was added 0.5 ml of methanol, then the solvent was removed by evaporation under reduced pressure. The residue was purified by a silica gel column chromatography (methylene chloride:methanol=20:1→8:1→4:1) to obtain 10.8 mg of the title compound as a light yellow powdery substance.

The NMR spectrum of the title compound obtained in (a) and (b) above was as follows.

$^1$H-NMR (200 MHz, CDCl$_3$-CD$_3$OD=1:1) δ: 0.92 (6H, d, J=6.5 Hz), 2.15-2.39 (1H, m), 2.76 (2H, d, J=7 Hz), 4.13 (2H, s), 6.99 (1H, t, J=7.5 Hz), 7.11 (1H, t, J=7.5 Hz), 7.14 (1H, s), 7.36 (1H, d, J=7.5 Hz), 7.61 (1H, d, J=7.5 Hz).

EXAMPLE C-2

Synthesis of 3-tert-butoxycarbonyloxy-6-hydroxy-5-(indol-3-yl)methyl-2-isobutylpyrazine 1-oxide (Compound C-9)

In 5 ml of anhydrous dimethylformamide were dissolved, in a nitrogen gas stream, 247 mg of 5-hydroxy-6-(indol-3-yl)methyl-3-isobutyl-1,2-dihdyropyrazin-1-one 4-oxide and 25 ml of anhydrous dichloromethane. Thereto were added, under ice cooling, 189 mg of di-tert-butyl dicarbonate, 10 mg of 4-dimethylaminopyridine and 0.12 ml of triethylamine. The mixture was stirred for 80 minutes, then the reaction mixture was mixed with 10 ml of an aqueous solution saturated with ammonium chloride, and the organic layer was separated and the aqueous layer was extracted twice with 10 ml of dichloromethane. The organic layers were combined, and washed with an aqueous solution saturated with NaCl three times, and dried with sodium sulfate. The solvent was removed by evaporation under reduced pressure. The residue was purified by a silica gel column chromatography (dichloromethane:methanol=20:1→10:1) to obtain 153 mg of the title compound as a pale brown solid substance.

$^1$H-NMR (500 MHz, CDCl$_3$) δ: 0.85 (6H, d, J=6.5 Hz), 1.56 (9H, s), 2.10-2.25 (1H, m), 2.70 (2H, d, J=7 Hz), 4.19 (2H, s), 6.93-7.18 (4H, m), 7.72 (1H, d, J=7.5 Hz), 8.11 (1H, brs).

IR $ν_{max}$(CHCl$_3$): 1755, 1605, 1535, 1500, 1255, 1155, 1130 cm$^{-1}$.

EXAMPLE C-3

Synthesis of 3-tert-butoxycarbonyloxy-5-(indol-3-yl)methyl-2-isobutyl-6-methoxypyrazine 1-oxide (Compound C-10)

In 0.5 ml of dichloromethane-methanol (3:1) was dissolved 10 mg of 3-tert-butoxycarbonyloxy-6-hydroxy-5-(indol-3-yl)methyl-2-isobutylpyrazine 1-oxide. Thereto were added, under ice cooling, a solution of diazomethane dissolved in diethyl ether and 4-5 drops of a solution of 0.1 M of boron tribromide dissolved in methylene chloride. The container was cook-stoppered and the contents were stirred for 12 hours at room temperature. The contents were then diluted with 5 ml of dichloromethane, and the mixture was washed with an aqueous sodium hydrogen carbonate solution and dried over sodium sulfate. The solvent was removed by evaporation under reduced pressure. The residue was purified by a silica gel thin layer chromatography (dichloromethane:methanol=40:1) to obtain 3.6 mg of the title compound as a pale brown solid substance.

$^1$H-NMR (250 MHz, CDCl$_3$) δ: 0.94 (6H, d, J=6.5 Hz), 1.55 (9H, s), 2.10–2.33 (1H, m), 2.71 (2H, d, J=7 Hz), 3.89 (3H, s), 4.23 (4H, s), 7.08 (1H, d, J=2.5 Hz), 7.10–7.23 (2H, m), 7.33 (1H, d, J=9 Hz), 7.73 (1H, d, J=7.5 Hz), 8.12 (1H, brs).

IR $\nu_{max}$ (CHCl$_3$): 1770 cm$^{-1}$.

EXAMPLE C-4

Synthesis of 6-(indol-3-yl)methyl-3-isobutyl-5-methoxy-1,2-dihdyropyrazin-2-one 4-oxide (NF-1616-904 substance) (Compound B-42)

In a nitrogen gas stream, 0.1 ml of trifluoroacetic acid was dropwise added to 0.4 ml of 2.2 mg of 3-tert-butoxycarbonyloxy-5-(indol-3-yl)methyl-2-isobutyl-6-methoxypyrazine 1-oxide dissolved in 0.4 ml of anhydrous dichloromethane, and the mixture was stirred for 30 minutes at room temperature. The solvent was removed by evaporation under reduced pressure at room temperature, and the residue was purified by a silica gel thin layer chromatography (dichloromethane:methanol=15:1), followed by recrystallization from methanol-chloroform to obtain 1.2 mg of the title compound as pale yellow prism-like crystals having a melting point of 222°–224° C.

EXAMPLE C-5

Synthesis of 6-[(1-tert-butoxycarbonyl)indol-3-yl]methyl-5-hydroxy-3-isobutyl-1,2-dihydropyrazin-2-one 4-oxide (Compound C-11)

To 200 ml of acetonitrile were added 1.87 g of N$^{in}$-tert-butoxycarbonyl-N-(α-hydroxyimino)isocaproyl-L-tryptophan and 4.4 ml of trimethylsilylethoxyacetylene, and the mixture was stirred for 2 hours at 60° C. The reaction mixture was concentrated under reduced pressure by using an evaporator and then using a vacuum pump (40° C., 1 hour). The resulting yellow tar-like substance was purified by a silica gel column chromatography (methylene chloride:methanol=30:1→7:1) to obtain 0.30 g of the title compound as a yellow solid substance.

$^1$H-NMR (500 MHz, CDCl$_3$-CD$_3$OD=10:1) δ: 0.83 (6H, d, J=6 Hz), 1.65 (9H, s), 2.05–2.17 (1H, m), 2.70 (2H, d, J=7.5 Hz), 4.07 (2H, s), 7.11 (1H, t, J=8 Hz), 7.26 (1H, t, J=8 Hz), 7.51 (1H, s), 7.57 (1H, d, J=8 Hz), 8.06 (1H, d, J=8 Hz).

EXAMPLE C-6

Synthesis of 3-benzyloxy-5-[(1-tert-butoxycarbonyl)indol-3-yl]methyl-6-hydroxy-2-isobutylpyrazine 1-oxide (Compound C-12)

In a nitrogen gas stream, 5.4 ml of oily 60% sodium hydride was placed in a dried eggplant-shaped flask and washed with anhydrous n-hexane (1 ml×2) to remove the oil. Thereto was added 0.5 ml of anhydrous dimethylformamide, and under ice cooling, thereto was added a solution of 13.7 ml of 6-[(1-tert-butoxycarbonyl)indol-3-yl]methyl-5-hydroxy-3-isobutyl-1,2-dihydropyrazin-2-one 4-oxide dissolved in 0.5 ml of anhydrous dimethylformamide. After about 2 minutes later, there was added 0.03 ml of benzyl bromide, and the mixture was stirred for 40 minutes under the same conditions. The reaction mixture was mixed with 10 ml of an aqueous solution saturated with ammonium chloride, to terminate the reaction, and the reaction mixture was subjected to extraction with dichloromethane (10 ml×2). The organic layers were combined, washed with 10 ml of an aqueous solution saturated with NaCl, dried with sodium sulfate, and concentrated under reduced pressure. The residue was further concentrated by using a vacuum pump (0.3 mmHg) to remove partially remaining dimethylformamide (50° C., 15 minutes). The residue was purified by a silica gel column chromatography (dichloromethane:methanol=30:1) to obtain 12 mg of the title compound as a pale yellow solid substance.

$^1$H-NMR (500 MHz, CDCl$_3$) δ: 0.89 (6H, d, J=6 Hz), 1.64 (9H, s), 2.15–2.26 (1H, m), 2.82 (2H, d, J=7 Hz), 4.24 (2H, s), 4.92 (1H, brs), 5.19 (2H, s), 7.15–7.40 (7H, m), 7.71 (1H, d, J=7 Hz), 8.06 (1H, d, J=8 Hz).

IR $\nu_{max}$ (CHCl$_3$): 1720 cm$^{-1}$.

EXAMPLE C-7

Synthesis of 3-benzyloxy-5-[(1-tert-butoxycarbonyl)indol-3-yl]methyl-2-isobutyl-6-methxoypyrazine 1-oxide (Compound C-12)

To a solution of 8.5 mg of 3-benzyloxy-5-[(1-tert-butoxycarbonyl)indol-3-yl]methyl-6-hydroxy-2-isobutylpyrazine 1-oxide dissolved in 0.5 ml of dichloromethane-methanol (3:1) were added, under ice-cooling, a diethyl ether solution containing diazomethane (10–20 equivalents) and 0.015 ml of a dichloromethane solution containing 0.1 M of boron tribomide, in this order, and the container was sealed with cork and the contents were stirred for 3 hours at room temperature. Then, a diethyl ether solution of diazomethane and a dichloromethane solution of 0.1 M of boron tribromide were added in the same amounts as above, respectively. The mixture was stirred overnight. Nitrogen gas was bubbled through the reaction mixture with heating, to remove the solvent. The residue was purified by a silica gel thin layer chromatography (dichloromethane:methanol=40:1) to obtain 3.0 mg of the title compound as a pale brown solid substance.

$^1$H-NMR (500 MHz, CDCl$_3$) δ: 0.92 (6H, d, J=6.5 Hz), 1.66 (9H, s), 2.17–2.27 (1H, m), 2.79 (2H, d, J=7.5 Hz), 3.99 (3H, s), 4.10 (2H, s), 5.31 (2H, s), 7.21 (1H, t, J=8 Hz), 7.26–7.52 (6H, m), 7.48 (1H, s), 7.66 (1H, d, J=8 Hz), 8.10 (1H, d, J=8 Hz),

IR $\nu_{max}$ (CHCl$_3$): 1725 cm$^{-1}$.

EXAMPLE C-8

Synthesis of 3-benzyloxy-5-[(1-methoxycarbonyl)indol-3-yl]methyl-2-isobutyl-6-methoxypyrazine 1-oxide (Compound C-13)

In a nitrogen gas stream, and at −40° C., 0.17 ml of a dichloromethane solution of 0.1 M of boron tribromide was added to a solution of 7 mg of 3-benzyloxy-5-[(1-tert-butoxycarbonyl)indol-3-yl]methyl-6-hydroxy-2-isobutylpyrazine 1-oxide dissolved in 0.5 ml of anhydrous dichloromethane. The mixture was stirred for 20 minutes under the same conditions, and 5 ml of ice water was added, then the mixture was subjected to extraction with dichloromethane (5 ml×3). The organic layers were combined, washed with 5 ml of an aqueous solution saturated with NaCl, and dried with sodium sulfate. The solvent was removed by evaporation under reduced pressure to obtain 6.6 mg of a yellow solid substance.

6.6 Milligrams of the above-mentioned crude product was dissolved in 0.5 ml of dichloromethane-methanol (3:1), thereto was added, under ice cooling, a diethyl ether solution of azomethane (10–20 equivalents). The mixture was stirred for 3 hours at room temperature, and nitrogen gas was bubbled through the reaction mixture with heating, to remove the solvent to obtain 6.5 mg of the title compound.

$^1$H-NMR (500 MHz, CDCl$_3$) δ: 0.92 (6H, d, J=7 Hz), 1.56 (9H, s), 2.15–2.27 (1H, m), 2.79 (2H, d, J=7.5 Hz), 3.98 (3H, s), 4.03 (3H, s), 4.10 (2H, s), 5.32 (2H, s), 7.23 (1H, t, J=8 Hz), 7.32 (5H, s), 7.33 (1H, t, J=8 Hz), 7.46 (1H, s), 7.66 (1H, d, J=8 Hz), 8.16 (1H, d, J=8 Hz).

IR $\nu_{max}$ (CHCl$_3$): 1730 cm$^{-1}$.

EXAMPLE C-9

Synthesis of 3-benzyloxy-5-(indol-3-yl)methyl-2-isobutyl-6-methoxypyrazine 1-oxide (Compound C-14)

(a) 0.1 Milliliter of trifluoroacetic acid was added, in a nitrogen gas stream, to a solution of 2.3 mg of 3-benzyloxy-5-[(1-tert-butoxycarbonyl)indol-3-yl]methyl-2-isobutyl-6-methoxypyrazine 1-oxide dissolved in 0.4 ml of anhydrous dichloromethane, and the mixture was stirred for 1.5 hours at room temperature. The reaction mixture was concentrated under reduced pressure at room temperature. The residue was purified by a silica gel thin layer chromatography (dichloromethane:methanol= 25:1) to obtain 1.0 mg of the title compound as a white solid substance having a melting point of 140°–142° C.

(b) In 0.4 ml of methanol-tetrahydrofuran (3:1) was dissolved 6.5 mg of 3-benzyloxy-5-[(1-methoxycarbonyl)indol-3-yl]methyl-2-isobutyl-6-methoxypyrazine 1-oxide, (Compound C-14), and thereto was added 0.1 ml of an aqueous 1 N potassium hydroxide solution. The mixture was stirred for 1 hour at 30° C. and then concentrated under reduced pressure at room temperature to remove the solvent. The residue was mixed with 5 ml of methylene chloride and 2 ml of 1 N hydrochloric acid, and the organic layer was separated. The aqueous layer was extracted with dichloromethane (5 ml×2), and the organic layers were combined, washed with an aqueous solution saturated with NaCl, dried over sodium sulfate, and concentrated under reduced pressure. The residue was purified by a silica gel thin layer chromatography (dichloromethane:methanol=50:1) to obtain 1.3 mg of the title compound as a white solid substance having a melting point of 140°–142° C.

The NMR spectrum and mass spectrum of the compounds obtained in (a) and (b) above were as follows.

$^1$H-NMR (250 MHz, CDCl$_3$) δ: 0.92 (6H, d, J=6.5 Hz), 2.12–2.32 (1H, m), 2.78 (2H, d, J=7 Hz), 3.93 (3H, s), 4.18 (2H, s), 5.37 (2H, s), 7.05 (1H, d, J=2 Hz), 7.13 (1H, t, J=8 Hz), 7.19 (1H, t, J=8 Hz), 7.35 (5H, s), 7.36 (1H, d, J=8 Hz), 7.76 (1H, d, J=8 Hz), 8.06 (1H, brs).

MS SPECTRUM:

m/z: 418 (13%), 417 (M$^+$, 31%), 401 (22%), 400 (51%), 358 (10%), 193 (100%).

EXAMPLE C-10

Synthesis of 6-(indol-3-yl)methyl-3-isobutyl-5-methoxy-1,2-dihydropyrazin-2-one 4-oxide (NF-1616-904 substance) (Compound B-42)

In 140 ml of methanol was dissolved 2.69 g of 3-benzyloxy-5-(indol-3-yl)methyl-2-isobutyl-6-methoxypyrazine 1-oxide, thereto was added 10% palladium-carbon, and the mixture was stirred for 1 hour at room temperature in a hydrogen gas atmosphere. 150 Milliliters of dichloromethane was added, and the mixture was stirred for 20 minutes, then the catalyst was removed by filtration, and the filtrate was subjected to recrystallization from methanol-chloroform to obtain 1.94 g of the title compound as pale yellow prism-like crystals having a melting point of 222°–224° C.

REFERENCE EXAMPLE D-1

6 Kilograms of methyl L-tryptophanate hydrochloride and 3,280 ml of triethylamine were added to 48 liters of dimethylformamide, and the mixture was stirred at room temperature for 30 minutes. Then, at below 10° C., 3,035 g of 1-hydroxybenzotriazole and 3,760 g of 2-oxoisocaproic acid oxime were added. The mixture was stirred for 1 hour, then thereto was dropwise added, at below 10° C., a solution of 5,345 g of dicyclohexylcarbodiimide dissolved in 12 liters of dimethylformamide. The resulting mixture was stirred for 1 hour at the same temperature and for 3 hours at room temperature. To the reaction mixture were added 60 liters of an aqueous solution saturated over sodium hydrogencarbonate and 60 liters of ethyl acetate, then the organic layer was separated and the insoluble matter was removed by filtration, and the filtrate was dried with magnesium sulfate. The solvent was removed by evaporation, and the residue was recrystallized from methanol to obtain 7,750 g of methyl ester of N-(α-hydroxyimino)isocaproyl-L-tryptophan (Compound D-1). Melting point: 116°–118° C.

$^1$H-NMR (CDCl) δ: 0.89 (6H, d, J=6.8 Hz), 1.9–2.1 (1H, m), 2.51 (2H, d, J=7.2 Hz), 3.28 (2H, d, J=5.6 Hz), 3.65 (3H, s), 4.9–5.0 (1H, m), 6.92 (1H, d, J=2.2 Hz), 7.06–7.20 (2H, m), 7.27–7.55 (2H, m), 8.12 (1H, br), 8.29 (1H, brs).

REFERENCE EXAMPLE D-2

In 53 liters of methanol was dissolved 7,530 g of methyl ester of (N-α-hydroxyimino)isocaproyl-L-tryptophan. Thereto was added, at below 10° C., a solution of 1,125 g of sodium hydroxide dissolved in 53 l of water and the mixture was stirred for 2 hours at room temperature and for 1 hour at 50°–60° C. Methanol was removed by evaporation, and the residue was made acidic with hydrochloric acid. The resulting crystals were collected by filtration and recrystallized from ethyl acetatedichloromethane to obtain 5,810 g of N-(α-hydroxyimino)isocaproyl-L-tryptophan (Compound D-2). Melting point: 97°–98° C.

$^1$H-NMR (DMSO-d$_6$) δ: 0.78 (6H, d, J=6.8 Hz), 1.8–2.0 (1H, m), 2.32 (2H, d, J=7.4 Hz), 3.21 (2H, d, J=6.2 Hz), 4.5–4.6 (1H, m), 6.90–7.06 (3H, m), 7.30 (1H, d, J=7.8 Hz), 7.46 (1H, d, J=7.2 Hz), 7.62 (1H, d,

J=7.8 Hz), 10.8 (1H, d, J=1 Hz), 11.6 (1H, s), 12.7–13.0 (1H, br, s).

REFERENCE EXAMPLE D-3

Synthesis of (6S,Z)-1-acetyl-3-[(1-benzyloxycarbonyl)indol-3-yl]methylidene-6-isobutylpiperazine-2,5-dione (Compound D-3)

12.7 Milliliters of a solution of 1.6 M of n-BuLi dissolved in n-hexane was dropwise added, at −78° C. with stirring, to a solution of 4.5 g of N-benzyloxycarbonylindol-3-carbaldehyde dissolved in 100 ml of anhydrous THF. The mixture was stirred for 30 minutes at the same temperature. Thereto was dropwise added 30 ml of a solution of 5.0 g of (3S)-1,4-diacetyl- 3-isobutyl-2,5-diketopiperazine dissolved in anhydrous THF. After completion of the dropwise addition, the temperature of the mixture was elevated to −60° C. in 30 minutes, then water was added, and the reaction mixture was subjected to extraction with $CH_2Cl_2$. The extract was washed with an aqueous solution saturated with NaCl and then dried with $MgSO_4$, then the solvent was removed by evaporation. The resulting yellow oily substance (9 g) was dissolved in 100 ml of benzene, and 2 ml of DBU was added thereto, then the mixture was stirred for 10 minutes at room temperature. The solvent was removed by evaporation under vacuum reduced pressure, and the residue was purified by a silica gel column chromatography (n-hexane:ethyl acetate=3:1) to obtain 5.5 g (66%) of the title compound as pale yellow prism-like crystals having a melting point of 95°–97° C.

REFERENCE EXAMPLE D-4

Synthesis of (6S,Z)-3-[(1-benzyloxycarbonyl)indol-3-yl]methylidene-6-isobutylpiperazine-2,5-dione (Compound D-4)

80 Milliliters of 1 N hydrochloric acid was added to 400 ml of a solution of 4.0 g of the Compound 14 dissolved in methanol, and the mixture was refluxed for 2 hours. The mixture was then ice cooled, and the resulting crude crystals (3.3 g, 91%) were collected by filtration to obtain colorless needle-like crystals having a melting point of 255°–257° C. (recrystallized from ethyl acetate-n-hexane).

REFERENCE EXAMPLE D-5

(3S,Z)-6-[(1-Benzyloxycarbonyl)indol-3-yl]-methylidene-3-isobutyl-5-methoxy-1,2,3,6-tetrahydro(1H)-pyrazin-2-one (Compound D-5)

9.5 Grams of Compound 15 was suspended in 500 ml of $CH_2Cl_2$, and thereto. Thereto was added 12.5 ml of $CH_3SO_2OCH_3$, and the mixture was refluxed for 36 hours at 50°–60° C. with stirring. The mixture was then allowed to cool to room temperature, then washed with an aqueous solution saturated with NaCl, and dried with magnesium sulfate, and the solvent was removed by evaporation. The residue was purified by a silica gel column chromatography (n-hexane:ethyl acetate=5:1→3:1→$CH_2Cl_2$:methanol=3:1) to obtain 7.0 g (71%) of a Compound D-5 and 0.3 g (3%) of its dimethyl form product (Compound D-6). Further, there was collected 1.8 g (18%) of the starting material (Compound D-4).

Compound D-5: Colorless needle-like crystals. Melting point: 129°–131° C. (from ethyl acetate-n-hexane).

3-[(1-Benzyloxycarbonyl)indol-3-yl]methyl-6-isobutyl-2,5-dimethoxypyrazine (Compound D-7): Colorless needle-like crystals (recrystallized from ethyl acetate-n-hexane).

$^1$H-NMR (250 MHz, $CDCl_3$) δ: 0.91 (6H, d, J=6.5 Hz), 2.03–2.23 (1H, m), 2.54 (2H, d, J=7 Hz), 3.81 (3H, s), 3.91 (3H, s), 4.07 (2H, s), 5.43 (2H, s), 7.19–7.50 (7H, m), 7.52 (1H, s), 7.74 (1H, d, J=8 Hz), 8.15 (1H, brd, J=8 Hz).

REFERENCE EXAMPLE D-6

6-[(1-Benzyloxycarbonyl)indol-3-yl]methyl-3-isobutyl-5-methoxy-1,2-dihydro(1H)pyrazin-2-one (Compound D-6)

4.5 Grams of Compound D-5 was dissolved in 200 ml of THF, then thereto was added 10 drops of DBU, and the mixture was stirred for 3 hours at room temperature. The solvent was removed by evaporation under reduced pressure and the residue was dissolved in $CH_2Cl_2$, and the solution was washed with 1 N hydrochloric acid, an aqueous solution saturated with NaCl, an aqueous solution saturated with $NaHCO_3$, and an aqueous solution saturated with NaCl, in this order, and dried with $MgSO_4$. The solvent was removed by evaporation, and the resulting crude crystals were recrystallized from AcOEt-n-hexane to obtain 4.0 g (89%) of the title compound (Compound D-6) as colorless prims-like crystals having a melting point of 149°–151° C.

6-(Indol-3-yl)methyl-3-isobutyl-4-methoxy-1,2-dihydro(1H)pyrazin-2-one (Compound D-8).

0.62 Gram of Compound D-6 was dissolved in 20 ml of dioxane, and thereto was added 0.20 g of 10% Pd-C, and the mixture was stirred for 1 hour at room temperature under atmospheric pressure in a $H_2$ gas atmosphere. The catalyst was removed by filtration, and the filtrate was refluxed for 1 hour. The solvent was removed by evaporation under reduced pressure, and the residue was purified by a silica gel column chromatography (n-hexane:ethyl acetate=4:1) to obtain 0.34 g (79%) of the title compound (compound D-8). Recrystallized from ethyl acetate-n-hexane to obtain colorless needle-like crystals having a melting point of 172°–173° C.

EXAMPLE D-1

In 7.5 l of dioxane were dissolved 500 g of N-(α-hydroxyimino)isocaproyl-L-tryptophan and 191 g of N-hydroxysuccinimide, thereto was dropwise added, at below 20° C., a solution of 374 g of dicyclohexylcarbodiimide dissolved in 2.5 liters of dioxane. The mixture was stirred for 1 hour, then the resulting dicyclohexylurea was removed by filtration. To the filtrate was added 124 g of sodium acetate, and the mixture was subjected to a reaction for 2–3 hours at room temperature. Water was added to the reaction mixture, and the resulting crystals were collected by filtration, washed thoroughly with water, and dissolved in dimethylformamide, then thereto was added an equal mole of 1,8-diazabicyclo[5.4.0]undecene-7 (DBU). The resulting crystals were collected by filtration and washed with dichloromethane to obtain 351 g of DBU salt of 5-hydroxy-6-(indol-3-yl)methyl-3-isobutyl-1,2-dihydropyrazin- 2-one 4-oxide (Compound D-7). Melting point: 160°–170° C. (decomposed).

$^1$H-NMR ($D_3OD/CDCl_3$=1/1) δ: 0.92 (6H, d, J=8 Hz), 1.6–1.85 (6H, br, s), 1.9–2.05 (2H, m), 2:28 (1H, m), 2.6–2.7 (2H, m), 2.77 (2H, d, J=9 Hz), 3.3–3.4 (2H, m), 3.4–3.55 (4H, m), 4.18 (2H, s), 6.98–7.2 (2H, m), 7.18 (1H, s), 7.39 (1H, d, J=10 Hz), 7.60 (1H, d, J=10 Hz).

EXAMPLE D-2

In 6 liters of dichloromethane was suspended 600 g of DBU salt of 5-hydroxy-6-(indol-3-yl)methyl-3-isobutyl-1,2-dihydro(1H)-pyrazin-2-one 4-oxide, then the suspension was cooled to −10° C. Thereto was added 286 g of trimethyloxonium tetrafluoroborate, and the mixture was stirred for 1–2 hours. 5% NaHCO$_3$ aqueous solution was added thereto and the organic layer was separated, washed with water, and dried over magnesium sulfate. The solvent was removed by evaporation and the residue was dissolved in a dimethylformamide (DMF)ethyl acetate mixture and allowed to stand, to obtain 98 g of dimethylformamide complex of 6-(indol-3-yl)methyl-3-isobutyl-5-methoxy-1,2-dihydropyrazin-2-one-4-oxide (Compound D-8). Melting point: 230° C. (decomposed).

$^1$H-NMR (CDCl$_3$/CD$_3$D=1/1) δ: 0.95 (6H, d, J=6.8 Hz), 2.12–2.32 (1H, m), 2.76 (2H, d, J=7.2 Hz), 2.89 (3H, s), 3.00 (3H, s), 3.89 (3H, s), 4.08 (2H, s), 7.02–7.20 (3H, m), 7.40 (1H, d, J=8 Hz), 7.60 (1H, d, J=7.6 Hz), 7.97 (1H, br, s), 10.3 (1H, br, s).

EXAMPLE D-3

366 Grams of dimethylformamide complex of 6-(indol-3-yl)methyl-3-isobutyl-5-methxoy-1,2-dihydro(1H)-pyrazin-2-one 4-oxide was recrystallized from ethanol to obtain 257 g of 6-(indol-3-yl)methyl-3-isobutyl-5-methoxy-1,2-dihydro(1H)pyrazin-2-one 4-oxide (NF-1616-904 substance) (Compound B-42). Melting point: 225° C. Pale yellow prism-like crystals.

EXAMPLE D-4

6-(Indol-3-yl)methyl-3-isobutyl-5-methoxy-1,2-dihydropyrazin-2-one 4-oxide (NF-1616-904 substance) (Compound B-42)

In a 500-ml Erlenmeyer flask was palced 100 ml of a culture medium consisting of 30 g/liter of starch, 5 g/liter of glucose, 5 g/liter of a soybean powder, 1 g/liter of an yeast extract, 1 g/liter of a polypeptone, 3 g/liter of CaCO$_3$ and 0.5 g/liter of MgSO$_4$. The culture medium was innoculated with one platinum loop amount of microbe cells obtained by culturing *Thielavia Minor*-OFR- 1561 strain (Deposition No. 1908 at Fermentation Research Institute, Agency of Industrial Science and Technology) for 1 week at 30° C. on a slant medium (pH 6.5) containing 4% of maltose, 1% of a polypeptone and 2% of agar, then 100 mg of Compound 17 was added. The resulting mixture was subjected to shaking or rotational culture for 96–120 hours at 28° C. The culture mixture was filtered, and the filtrate was extracted with ethyl acetate. The extract was concentrated, and the concentrate was purified by a silica gel column chromatography (CH$_2$Cl$_2$:MeOH=80:1) to obtain 10 mg of the title compound. Melting point: 225° C., Pale yellow prism-like crystals.

EXAMPLE E-1

Compound E-66 was obtained in the same manner as in Example A-51 using the compound E-10 [the same as the compound B-42].

3-Benzyloxy-5-(indol-3-yl)methyl-2-isobutyl-6-methoxypyrazine 1-oxide (Compound E-66).

Colorless prism-like crystals (from Et$_2$O-n-hexane). Melting point: 139.6°–141.9° C.

REFERENCE EXAMPLE E-1

Compounds E-3a to E-3i, and E-3k were obtained by the same manner as in Reference Example A-9.

Methyl ester of N-(2-hydroxyimino)-propionyl-L-tryptophan (E-3a).

Pale yellow oily substance.

$^1$H-NMR (250 MHz, CDCl$_3$) δ: 2.0 (3H, s), 2.28 (2H, d, J=5.5 Hz), 3.66 (3H, s), 4.96 (1H, m), 6.89 (1H, d, J=2.5 Hz), 7.06–7.20 (2H, m), 7.25–7.37 (2H, m), 7.50 (1H, d, J=7.5 Hz), 8.22 (1H, s), 8.81 (1H, s).

Methyl ester of N-(2-hydroxyimino)butyryl-L-tryptophan (Compound E-3b).

Pale yellow oily substance.

$^1$H-NMR (250 MHz, CDCl$_3$) δ: 1.16 (3H, t, J=7.5 Hz), 2.59 (2H, q, J=7.5 Hz), 3.29 (2H, d, J=5.5 Hz), 3.66 (3H, s), 4.96 (1H, m), 6.93 (1H, d, J=2.5 Hz), 7.06–7.21 (2H, m), 7.28 (1H, d, J=7.0 Hz), 7.51 (1H, d, J=7.5 Hz), 8.14 (1H, s), 8.25 (1H, s).

Methyl ester of N-(2-hydroxyimino-3-phenyl)-propionyl-L-tryptophan (Compound E-3d).

Pale yellow oily substance.

$^1$H-NMR (250 MHz, CDCl$_3$) δ: 2.27 (2H, d, J=5.5 Hz), 3.63 (3H, s), 3.90–4.01 (2H, m), 4.93 (1H, m), 6.77 (1H, d, J=2.5 Hz), 7.00–7.34 (8H, m), 7.43 (1H, d, J=8 Hz), 7.99 (1H, s), 8.43 (1H, s).

Methyl ester of N-(2-hydroxyimino-4-phenyl)butyryl-L-tryptophan (Compound E-3e).

Pale yellow oily substance.

$^1$H-NMR (250 MHz, CDCl$_3$) δ: 2.72–2.97 (4H, m), 3.26 (2H, d, J=5.5 Hz), 3.65 (3H, s), 4.94 (1H, m), 6.86 (1H, d, J=2.5 Hz), 7.05–7.33 (9H, m), 7.49 (1H, d, J=7.5 Hz), 8.14 (1H, s), 8.71 (1H, s).

Methyl ester of N-(3-cyclohexyl-2-hydroxyimino)-propionyl-L-tryptophan (Compound E-3f).

Pale yellow oily substance.

$^1$H-NMR (250 MHz, CDCl$_3$) δ: 0.95–1.23 (5H, m), 1.54–1.70 (6H, m), 2.51 (2H, d, J=7 Hz), 3.28 (2H, d, J=5.5 Hz), 3.65 (3H, s), 4.95 (1H, m), 6.92 (1H, d, J=2.5 Hz),7.06–7.20 (2H, m), 7.27–7.37 (2H, m), 7.50 (1H, d, J=7.5 Hz), 8.15 (1H, s), 8.34 (1H, s).

Methyl ester of N-[2-hydroxyimino-3-(indol-3-yl)]propionyl-L-tryptophan (Compound E-3g).

Pale yellow oily substance. $^1$H-NMR (250 MHz, CDCl$_3$) δ: 3.19 (2H, d, J=5.5 Hz), 3.59 (3H, s), 3.98–4.08 (2H, m), 4.84–4.92 (1H, m), 6.43 (1H, d, J=2.5 Hz), 6.93–7.23 (7H, m), 7.36 (1H, d, J=7.0 Hz), 7.71 (1H, s), 7.78 (1H, d, J=7.5 Hz), 7.91 (1H, s), 8.83 (1H, s).

Methyl ester of N-[3-(4-benzyloxy)phenyl-2-hydroxyimino]propionyl-L-tryptophan (Compound E-3h).

Pale yellow oily substance.

$^1$H-NMR (250 MHz, CDCl$_3$) δ: 3.28 (2H, d, J=5.5 Hz), 3.64 (3H, s), 3.82–3.96 (2H, m), 4.89–4.97 (1H, m), 5.01 (2H, s), 6.78 (1H, d, J=2.4 Hz), 6.87 (2H, d, J=8.7 Hz), 7.04 (1H, t, J=6.9 Hz), 7.15 (1H, t, J=7.1 Hz), 7.21–7.45 (9H, m), 7.97 (1H, s), 8.15 (1H, s).

Methyl ester of N-(2-hydroxyimino)cyclohexylacetyl-L-tryprophan (Compound E-3i).

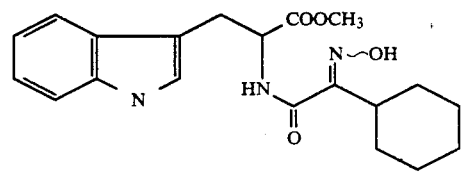

¹H-NMR (250 MHz, CDCl₃) δ: 1.20-1.40 (3H, m), 1.50-2.04 (7H,m), 3.06-3.24 (3H, m), 3.31 (2H, d, J=5.6 Hz), 3.66 (3H, s), 4.87-4.97 (1H, m), 6.97 (1H, d, J=2.3 Hz), 7.06-7.23 (3H, m), 7.31 (1H, d, J=7.8 Hz), 7.51 (1H, d, J=7.7 Hz), 8.00 (1H, brs), 8.13 (1H, s).

Methyl ester of N-(2-hydroxyimino-3-methyl)butyryl-L-tryptophan (Compound E-3k).

Pale yellow oily substance.

¹H-NMR (250 MHz, CDCl₃) δ: 1.24 (6H, d, J=7 Hz), 3.31 (2H, d, J=5.5 Hz), 3.34-3.53 (1H, m), 3.66 (3H, s), 4.88-5.00 (1H, m), 6.97 (1H, d, J=2.5 Hz), 7.05-7.25 (2H, m), 7.31 (1H, d, J=8.0 Hz), 7.52 (1H, d, J=7.5 Hz), 7.90 (1H, s), 8.13 (1H, brs).

REFERENCE EXAMPLE E-2

Compounds E-4a to -4i, 4k were obtained by the same manner as in Reference Example A-12. The compounds E-4a, -4b, -4d to -4i were used as they were, in the subsequent reactions.

N-(2-Hydroxyimino-3-methyl)pentanoyl-L-tryptophan (Compound E-4c).

White powdery substance.

¹H-NMR (250 MHz, CDCl₃) δ: 0.78 (1.5H, t, J=7.5 Hz), 0.81 (1.5H, t, J=7.5 Hz), 1.14 (1.5H, d, J=7.5 Hz), 1.17 (1.5H, d, J=7.5 Hz), 1.45-1.90 (2H, m), 3.10-3.40 (3H, m), 4.84-4.95 (1H, m), 6.24 (1H, brs), 6.84 (1H, d, J=2 Hz), 6.99-7.25 (4H, m), 7.50 (1H, d, J=7.5 Hz), 8.25 (1H, s).

N-(2-Hydroxyimino-3-methyl)butyryl-L-tryptophan (Compound E-4k).

White powdery substance.

¹H-NMR (250 MHz, CDCl₃) δ: 1.18 (3H, d, J=7 Hz), 1.21 (3H, d, J=7 Hz), 3.24-3.47 (3H, m), 4.84-4.96 (1H, m), 6.89 (1H, d, J=2 Hz), 7.02-7.20 (2H, m), 7.25 (1H, d, J=6.5 Hz), 7.53 (1H, d, J=7.5 Hz), 8.22 (1H, brs).

EXAMPLE E-2

Synthesis of 3-cyclohexylmethyl-5-hydroxy-6-(indol-3-yl)methyl-1,2-dihydropyrazin-2-one 4-oxide (Compound E-5f).

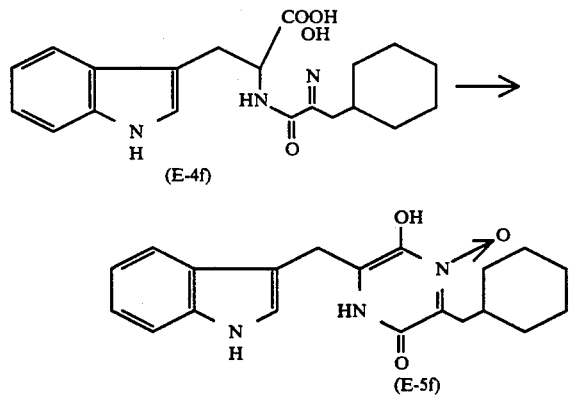

62 Millimoles of Compound E-4f and 7.48 g (65 mM) of N-hydroxysuccinimide were dissolved in 250 ml of dioxane, and thereto was added 13.41 g (65 mM) of DCC, then the mixture was stirred for 2 hours at room temperature. The reaction mixture was filtered. To the filtrate was added 5.33 g (65 mM) of AcONa, and the mixture was stirred for 3 hours at room temperature, then the reaction mixture was poured into 750 ml of water, and the resulting crystals were collected by filtration, washed with Et₂O, and suspended in 200 ml of CH₂Cl₂. The suspension was filtered and the crystals collected were dried under reduced pressure over P₂O₅ in a dark cool place to obtain 18.18 g (83%) of yellow powdery crystals. (Compound E-5f).

¹H-NMR (250 MHz, DMSO-d₆) δ: 0.95-1.25 (5H, m), 1.46-1.90 (6H, m), 2.64 (2H, d, J=7 Hz), 4.01 (2H, s), 6.96 (1H, t, J=7.5 Hz), 7.06 (1H, t, J=7.0 Hz), 7.19 (1H, d, J=2.5 Hz), 7.34 (1H, d, J=8.0 Hz), 7.60 (1H, d, J=7.5 Hz), 10.88 (1H, s).

EXAMPLE E-3

Compounds E-5a to E-5e, E-5g to E-5i and E-5k were obtained by the same manner as for the Compound E-5f.

5-Hydroxy-6-(indol-3-yl)methyl-3-methyl-1,2-dihydropyrazin-2-one 4-oxide (Compound E-5a).

Yellow powdery substance.

¹H-NMR (250 MHz, DMSO-d₆) δ: 2.23 (3H, s), 4.01 (2H, s), 6.96 (1H, t, J=7.5 Hz), 7.07 (1H, t, J=7.5 Hz), 7.19 (1H, s), 7.34 (1H, d, J=8 Hz), 7.61 (1H, d, J=7.5 Hz), 10.88 (1H, s).

3-sec-Butyl-5-hydroxy-6-(indol-3-yl)methyl-1,2-dihydropyrazin-2-one 4-oxide (Compound E-5c).

Yellow powdery substance.

¹H-NMR (250 MHz, DMSO-d₆) δ: 0.76 (3H, t, J=7.5 Hz), 1.25 (3H, d, J=7 Hz), 1.70-2.02 (1H, m), 3.25-3.55 (2H, m), 4.01 (2H, s), 6.97 (1H, t, J=7 Hz), 7.07 (1H, t, J=7 Hz), 7.19 (1H, d, J=2.5 Hz), 7.34 (1H, d, J=8.0 Hz), 7.60 (1H, d, J=8 Hz), 10.88 (1H, s),

3-Benzyl-5-hydroxy-6-(indol-3-yl)methyl-1,2-dihydropyrazin-2-one 4-oxide (Compound E-5d).

Yellow powdery substance.

¹H-NMR (250 MHz, DMSO-d₆) δ: 4.02 (2H, s), 4.07 (2H, s), 6.96 (1H, t, J=7.5 Hz), 7.07 (1H, t, J=7.5 Hz), 7.16-7.30 (6H, m), 7.34 (1H, d, J=8.0 Hz), 7.60 (1H, d, J=7.5 Hz), 10.87 (1H, s).

5-Hydroxy-6-(indol-3-yl)methyl-3-(2-phenyl)ethyl-1,2-dihydropyrazin-2-one 4-oxide (Compound E-5e).

Yellow powdery substance.

¹H-NMR (250 MHz, DMSO-d6) δ: 2.77-2.90 (2H, m), 2.96-3.10 (2H, m), 4.02 (2H, s), 6.97 (1H, t, J=7 Hz), 7.07 (1H, t, J=7 Hz), 7.14-7.32 (6H, m), 7.34 (1H, d, J=8 Hz), 7.60 (1H, d, J=7.5 Hz), 10.87 (1H, s).

3,6-Di(indol-3-yl)methyl-5-hydroxy-1,2-dihydropyrazin-2-one 4-oxide (Compound E-5g).

Yellow powdery substance.

¹H-NMR (250 MHz, DMSO-d₆) δ: 3.99 (2H, s), 4.15 (2H, s), 6.94 (2H, t, J=7.5 Hz), 7.01-7.10 (2H, m), 7.14-7.21 (2H,m), 7.37-7.46 (2H, m), 7.57 (1H, d, J=7.5 Hz), 7.73 (1H, d, J=7.5 Hz), 10.86 (2H, s).

3-(4-Benzyloxy)benzyl-5-hydroxy-6-indol-3-yl)methyl-1,2-dihydropyrazin-2-one 4-oxide (Compound E-5h).

Yellow powdery substance.

¹H-NMR (250 MHz, DMSO-d₆) δ: 3.99 (2H, s), 4.00 (2H, s), 5.04 (2H, s), 6.98 (2H, d, J=8.5 Hz), 6.95 (1H, t, J=7 Hz), 7.05 (1H, t, J=7 Hz), 7.15-7.25 (3H, m), 7.30-7.50 (6H, m), 7.60 (1H, d, J=7.5 Hz), 10.85 (1H, s).

3-Cyclohexylmethyl-5-hydroxy-6-(indol-3-yl)methyl-1,2-dihydropyrazin-2-one 4-oxide (Compound E-5i).

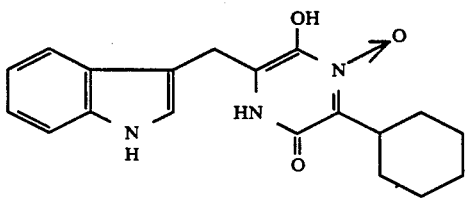

$^1$H-NMR (250 MHz, DMSO-d$_6$) δ: 0.95–1.40 (3H, m), 1.40–1.86 (5H, m), 1.95–2.20 (2H, m), 3.23–3.48 (1H, m), 4.00 (2H, s), 6.97 (1H, t, J=7.5 Hz), 7.07 (1H, t, J=7.5 Hz), 7.20 (1H, d, J=2.0 Hz), 7.34 (1H, d, J=7.5 Hz), 7.63 (1H, d, J=7.5 Hz), 10.88 (1H, s).

5-Hydroxy-6-(indol-3-yl)methyl-3-isobutyl-1,2-dihydropyrazin-2-one 4-oxide (Compound E-5k).

Yellow powdery substance.

$^1$H-NMR (250 MHz, DMSO-d$_6$) δ: 1.28 (6H, d, J=7 Hz), 3.57–3.77 (1H, m), 4.00 (2H, s), 6.98 (1H, t, J=7.5 Hz), 7.08 (1H, t, J=8 Hz), 7.20 (1H, d, J=2 Hz), 7.35 (1H, d, J=8 Hz), 7.64 (1H, d, J=7.5 Hz).

EXAMPLE E-4

Synthesis of 3-ethyl-6-(indol-3-yl)methyl-5-methoxy-1,2-dihydropyrazin-2-one 4-oxide (Compound E-6b).

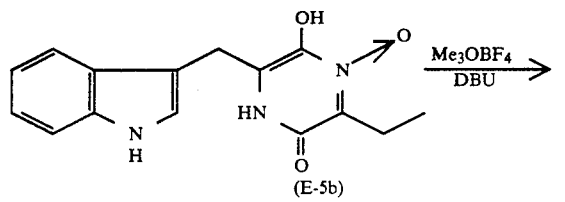

(E-5b)

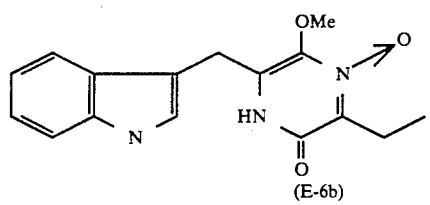

(E-6b)

2.0 Grams (7 mM) of Compound E-5b was suspended in 200 ml of CHCl$_3$, to the suspension were added 1.05 ml (7 mM) of DBU and 3.1 g (21 mM) of Me$_3$OBF$_4$, and the mixture was stirred for 2 hours at room temperature. An aqueous solution saturated with NaHCO$_3$ was added to the reaction mixture and the organic layer was collected, washed once with an aqueous solution saturated with NaHCO$_3$ and twice with water, then dried over MgSO$_4$. The solvent was removed by evaporation, and the residue was purified by a silica gel column chromatography (CH$_2$Cl$_2$→CH$_2$Cl$_2$:MeOH=40:1). The resulting crude crystals were recrystallized from MeOH to obtain 0.24 g (11%) of yellow prism-like crystals (Compound 6b) having a melting point of 202°–204° C. (decomposed).

$^1$H-NMR (250 MHz, DMSO-d$_6$) δ: 1.03 (3H, t, J=7.5 Hz), 2.71 (2H, q, J=7.5 Hz), 3.80 (3H, s), 3.93 (2H, s), 7.01 (J=7.5 Hz), 7.09 (1H, t, J=7.5 Hz), 7.28 (1H, d, J=2 Hz), 7.36 (1H, d, J=8 Hz), 7.61 (1H, d, J=7.5 Hz), 10.97 (1H, s), 12.00 (1H, brs).

EXAMPLE E-5

Compounds E-6a, -6c to -6e were obtained by the same manner as for the compound E-6b.

6-(Indol-3-yl)methyl-5-methxoy-3-methyl-1,2-dihydropyrazin-2-one 4-oxide (Compound E-6a).

Pale yellow prism-like crystals (from MeOH).

$^1$H-NMR (250 MHz, DMSO-d$_6$) δ: 2.16 (3H, s), 3.79 (3H, s), 3.93 (2H, s), 7.00 (1H, t, J=7.5 Hz), 7.09 (1H, t, J=7.5 Hz), 7.27 (1H, s), 7.36 (1H, d, J=8 Hz), 7.60 (1H, d, J=7.5 Hz), 10.97 (1H, s), 11.97 (1H, brs).

3-sec-Butyl-6-(indol-3-yl)methyl-5-methoxy-1,2-dihydropyrazin-2-one 4-oxide (Compound E-6c).

Pale yellow prism-like crystals (from MeOH).

Melting point: 218.5°–219.5° C. (decomposed).

$^1$H-NMR (250 MHz, DMSO-d$_6$) δ: 0.75 (3H, t, J=7.5 Hz), 1.21 (3H, d, J=7.0 Hz), 1.53–1.73 (1H, m), 1.80–2.01 (1H, m), 3.45–3.62 (1H, m), 3.79 (3H, s), 3.92 (2H, s), 7.00 (1H, t, J=7.5 Hz), 7.09 (1H, t, J=7.5 Hz), 7.28 (1H, s), 7.36 (1H, d, J=7.5 Hz), 7.61 (1H, d, J=7.5 Hz), 10.98 (1H, s), 11.90 (1H, brs).

3-Benzyl-6-(indol-3-yl)methyl-5-methoxy-1,2-dihydropyrazin-2-one 4-oxide (Compound E-6d).

Pale yellow prism-like crystals (from MeOH).

Melting point: 222°–222.5° C. (decomposed).

$^1$H-NMR (250 MHz, DMSO-d$_6$) δ: 3.78 (3H, s), 3.95 (2H, s), 4.03 (2H, s), 7.00 (1H, t, J=7.5 Hz), 7.09 (1H, t, J=7.5 Hz), 7.15–7.35 (6H, m), 7.36 (1H, d, J=8 Hz), 7.60 (1H, d, J=8 Hz), 10.99 (1H, s), 12.12 (1H, brs).

6-(Indol-3-yl)methyl-5-methoxy-3-(2-phenyl)ethyl-1,2-dihydropyrazin-2-one 4-oxide (Compound E-6e).

Pale yellow prism-like crystals (from MeOH).

Melting point: 231.5°–232° C. (decomposed).

$^1$H-NMR (250 MHz, DMSO-d$_6$) δ: 2.74–2.88 92H, m), 2.90–3.08 (2H, m), 3.79 (3H, s), 3.94 (2H, s), 7.02 (1H, t, J=7 Hz), 7.10 (1H, t, J=7 Hz), 7.14–7.32 (6H, m), 7.37 (1H, d, J=8 Hz), 7.60 (1H, d, J=7.5 Hz), 11.00 (1H, s), 12.03 (1H, brs).

EXAMPLE E-6

3-Cyclohexylmethyl-6-(indol-3-yl)methyl-5-methoxy-1,2-dihydropyrazin-2-one 4-oxide (Compound E-6f).

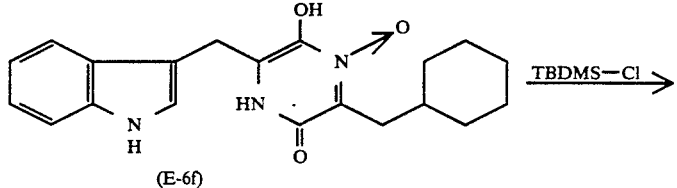

(E-6f)

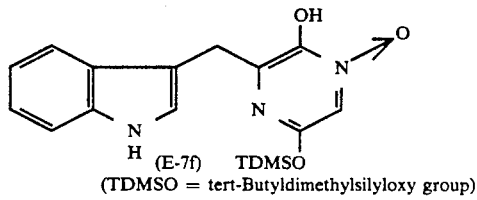

(E-7f)   TDMSO (TDMSO = tert-Butyldimethylsilyloxy group)

In 140 ml of DMF were dissolved 7.07 g (20 mM) of Compound E-6f, 2.72 g (40 mM) of imidazole and 3.62 g (24 mM) of TBDMS-Cl, then the solution was stirred for 3.5 hours at room temperature. The resulting mixture was poured into 500 ml of AcOEt, and the mixture was washed four times with water and twice with an aqueous solution saturated with NaCl, and dried on $MgSO_4$, and the solvent was removed by evaporation. The residue was allowed to stand for 2 days at room temperature, and then subjected to 2 silica gel chromatography ($CH_2Cl_2$:MeOH=40:1) to obtain 7.8 g of a Compound E-7f as a brown oily substance.

3-tert-Butyldimethylsilyloxy-2-cyclohexylmethyl 6-hydroxy-5-(indol-3-yl)methylpyrazine 1-oxide (Compound E-7f).

$^1$H-NMR (250 MHz, $CDCl_3$) δ: 0.10 (6H, s), 0.91 (9H, s), 1.1–2.0 (11H, m), 2.72 (2H, d, J=7 Hz), 4.00 (2H, s), 6.88–7.27 (4H, m), 7.44 (1H, d, J=8 Hz), 7.58 (1H, brs).

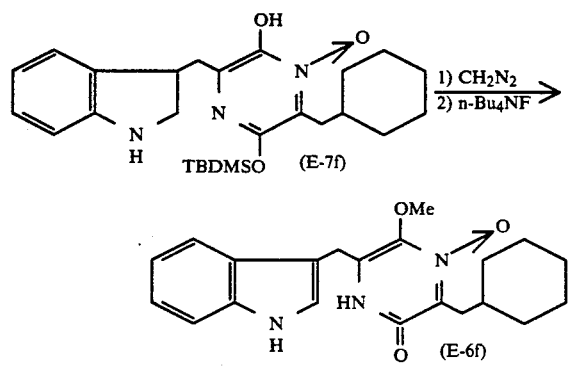

The Compound E-7f was dissolved in 300 ml of $CH_2Cl_2$, and thereto was added about 5 times equivalents of $CH_2N_2$ dissolved in $Et_2O$, and the mixture was stirred for 48 hours at room temperature. The solvent was removed by evaporation, and the residue was purified by a silica gel chromatography ($CH_2Cl_2$:MeOH=40:1) to obtain about 3 g of a brown oily substance, then it was dissolved in 100 ml of THF. Thereto was added 0.8 g of n-BuNF, and the mixture was stirred for 10 minutes at room temperature. The solvent was removed by evaporation, and the residue was dissolved in AcOEt, the solution was washed with an aqueous solution saturated with NaCl, then dried over $MgSO_4$. The solvent was removed by evaporation, and the residue was purified by silica gel chromatography ($CH_2Cl_2$:MeOH=40:1) to obtain a brown oily substance, and it was dissolved in a small amount of MeOH, the solution was allowed to stand overnight at room temperature to obtain 0.55 g of a Compound E-6f as yellow prism-like crystals having a melting point of 200.5°–201° C. (decomposed).

$^1$H-NMR (250 MHz, DMDO-$d_6$) δ: 0.90–1.30 (5H, m), 1.45–1.71 (5H, m), 1.71–1.90 (1H, m), 2.63 (2H, d, J=7 Hz), 3.79 (3H, s), 3.93 (2H, s), 7.00 (1H, t, J=7.5 Hz), 7.10 (1H, t, J=7.5 Hz), 7.28 (1H, d, J=2.0 Hz), 7.37 (1H, d, J=8.0 Hz), 7.60 (1H, d, J=7.5 Hz), 10.97 (1H, s), 11.95 (1H, brs).

EXAMPLE E-7

Using the compound E-5g, there was obtained Compound E-6g by the same manner as for the Compound E-6f, via compounds E-7g and E-8g.

3,6-Di(indol-3-yl)methyl-5-methoxy-1,2-dihydropyrazin-2-one 4-oxide (Compound E-6g).

$^1$H-NMR (250 MHz, DMSO-$d_6$) δ: 3.78 (3H, s), 3.92 (2H, s), 4.10 (2H, s), 6.90–7.15 (4H, m), 7.15–7.40 (6H, m), 7.57 (1H, d, J=7.5 Hz), 7.74 (1H, d, J=7.5 Hz), 10.85 (1H, s), 10.97 (1H, s), 11.98 (2H, brs).

3-tert-Butyldimethylsilyloxy-2,5-di(indol-3-yl)methyl-6-hydroxypyrazine 1-oxide (Compound E-7g).

Brown oily substance.

$^1$H-NMR (250 MHz, $CDCl_3$) δ: 0.13 (6H, s), 0.84 (9H, s), 4.01 (4H, brs), 6.80–7.20 (10H, m), 7.66 (2H, brs).

3-(4-Benzyloxy)benzyl-6-(indol-3-yl)methyl-5-methoxy-1,2-dihydropyrazin-2-one 4-oxide (Compound E-6h).

3-Cyclohexyl-6-(indol-3-yl)methyl-5-methoxy-1,2-dihydropyrazin-2-one 4-oxide (Compound E-6i).

$^1$H-NMR (250 MHz, DMSO-$d_6$) δ: 3.78 (3H, s), 3.92 (2H, s), 4.10 (2H, s), 6.90–7.15 (4H, m), 7.15–7.40 (6H, m), 7.57 (1H, d, J=7.5 Hz), 7.74 (1H, d, J=7.5 Hz), 10.85 (1H, s), 10.97 (1H, s), 11.98 (2H, brs).

By using the Compound E-5g, there was obtained the below Compound E-7g by the same manner as in Example E-6.

3-tert-Butyldimethylsilyloxy-2,5-di(indol-3-yl)methyl-6-hydroxypyrazine 1-oxdie (Compound E-7g).

Brown oily substance.

$^1$H-NMR (250 MHz, $CDCl_3$) δ: 0.13 (6H, s), 0.84 (9H, s), 4.01 (4H, brs), 6.80–7.20 (10H, m), 7.66 (2H, brs).

3-(4-Benzyloxy)benzyl-6-(indol-3-yl)methyl-5-methoxy-1,2-dihydropyrazine-2-one 4-oxide (Compound E-6h).

3.2 Grams (7 mM) of Compound E-5h was suspended in 200 ml of $CHCl_3$, then to this suspension was assed 1.05 ml (7 mM) of DBU and 3.1 g (21 mM) of Me-$_3OBF_4$, and the whole mixture was stirred at room temperature for 2 hours. To this reaction mixture was added an aqueous solution saturated with $NaHCO_3$, and the organic layer was separated, then this organic layer was washed once with an aqueous solution saturated with $NaHCO_3$, then washed twice with water, and dried over anhydrous $MgSO_4$. The solvent was removed by evaporation and the residue thus obtained was purified by means of a silica gel chromatography (eluent: $CH_2Cl_2 \rightarrow CH_2CH_2$:MeOH=40:1), the crude crystals was recrystallized from MeOH to obtain 0.36 g of the objective product (Compound E-6h).

IR (KBr): 1680 cm$^{-1}$.

| Elemental analysis for $C_{28}H_{25}N_3O_4$ | | | |
|---|---|---|---|
| | C | H | N |
| Calculated (%): | 71.93 | 5.39 | 8.99 |
| Found (%): | 71.43 | 5.01 | 9.22 |

3-Cyclohexyl-6-(indol-3-yl)methyl-5-methoxy-1,2-dihydropyrazin-2-one 4-oxide (Compound E-6i).

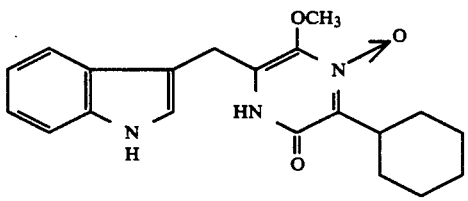

$^1$H-NMR (250 MHz, DMSO-$d_6$) δ: 0.98–1.90 (8H, m), 2.03–2.30 (2H, m), 3.30–3.60 (1H, m), 3.80 (3H, s), 3.90 (2H, s), 7.01 (1H, t, J=7.5 Hz), 7.09 (1H, t, J=7.5 Hz), 7.30 (1H, s), 7.36 (1H, d, J=7.5 Hz), 7.62 (1H, d, J=7.5 Hz), 11.00 (1H, s), 11.93 (1H, brs).

REFERENCE EXAMPLE E-3

By using the Compound E-6h, there was obtained Compound E-6j by the same manner as in Reference Example A-23.

3-(4-Hydroxy)benzyl-6-(indol-3-yl)methyl-5-methoxy-1,2-dihydropyrazin-2-one 4-oxide (Compound E-6j).

One gram of 10% Pd-C was added in a solution prepared by dissolving 2.82 mM of Compound E-6h in 30 ml of ethanol, then this mixture was hydrogenated by using the theoretical amount of hydrogen under ambient pressure at room temperature for 14 hours. After the reaction was finished, the catalyst was removed from the reaction mixture by filtration, then the filtrated was concentrated to dryness and the residue thus obtained was purified by means of a silica gel column chromatography (eluent:ethyl acetate:n-hexane=1:2) to obtain 810 mg of the objective product (Compound E-6j).

| Elemental analysis for $C_{21}H_{19}N_3O_4$ | | | |
|---|---|---|---|
| | C | H | N |
| Calculated (%): | 66.83 | 5.07 | 11.13 |
| Found (%): | 66.53 | 5.39 | 10.91 |

EXAMPLE E-8

By using Compound A-57, there was obtained Compound E-11 by the same manner as for the Compound E-6b.

5-Hydroxy-3-(indol-3-yl)methyl-6-isobutyl-1-methoxy-1,2-dihdyropyrazin-2-one (Compound E-11).

Yellow prism-like crystals.

Melting point: 163°–165° C. (decomposed).

$^1$H-NMR (250 MHz, DMSO-d$_6$) δ: 0.86 (6H, d, J=6.5 Hz), 1.84-2.06 (1H, m), 2.48 (2H, d, J=7 Hz), 3.97 (3H, s), 4.06 (2H, s), 6.93 (1H, t, J=7.5 Hz), 7.00 (1H, t, J=7.5 Hz), 7.15 (1H, d, J=2.5 Hz), 7.31 (1H, d, J=7.5 Hz), 7.57 (1H, d, J=7.5 Hz), 9.80 (1H, brs), 10.82 (1H, brs).

EXAMPLE E-9

By using Compound A-57, there was obtained Compound E-12 by the same manner as for the compound E-6b example that $(C_2H_5)_3O^{\oplus}OBF_4^{\ominus}$ was used in place of $(CH_3)_3O^{\oplus}BF_4^{\ominus}$.

5-Ethoxy-6-(indol-3-yl)methyl-3-isobutyl-1,2-dihydropyrazin-2-one 4-oxide (Compound E-12).

Pale yellow prism-like crystals (from MeOH). Melting point: 192°–193° C.

REFERENCE EXAMPLE E-4

Compounds E-15a and E-15c were obtained by the same manner as in Reference Example A-9.

Methyl ester of (2RS,3RS)-N-(2-hydroxyimino-4-methyl)pentanoyl-β-methyltryptophan (Compound E-15a).

Pale yellow oily substance.

$^1$H-NMR (250 MHz, CDCl$_3$) δ: 0.89 (3H, d, J=6.5 Hz), 0.90 (3H, d, J=6.5 Hz), 1.46 (3H, d, J=7 Hz), 1.91-2.10 (1H, m), 2.50 (2H, d, J=7.5 Hz), 3.58-3.73 (1H, m), 4.96 (1H, dd, J=9 Hz, 6 Hz), 7.01 (1H, d, J=2 Hz), 7.10 (1H, dt, J=7.5 Hz, 1 Hz), 7.18 (1H, dt, J=7.5 Hz, 1 Hz), 7.34 (1H, d, J=7.5 Hz), 7.61 (1H, d, J=7.5 Hz), 7.85 (1H, brs), 8.04 (1H, brs).

Ethyl ester of N-(2-hydroxyimino)-4-methylpentanoyl homotryptophan (Compound E-15c).

Pale yellow oily substance.

$^1$H-NMR (250 MHz, CDCl$_3$) δ: 0.92 (6H, d, J=7 Hz), 1.22 (3H, t, J=7 Hz), 2.0-2.3 (3H, m), 2.55 (2H, t, J=7 Hz), 2.80 (2H, t, J=7 Hz), 4.13 (2H, q, J=7 Hz), 4.6-4.8 (1H, m), 6.91 (1H, brs), 7.07 (1H, t, J=7 Hz), 7.17 (1H, t, J=7 Hz), 7.31 (1H, d, J=7 Hz), 7.51 (2H, brs, J=7 Hz), 8.03 (1H, brs), 8.86 (1H, brs).

REFERENCE EXAMPLE E-5

Compounds E-16a and E-16c were obtained by the same manner as in Reference Example A-12.

(2RS,3SR)-N-(2-Hydroxyimino-4-methyl)pentanoyl β-methyltryptophan (Compound E-16a).

Colorless needle-like crystals (recrystallized from CHCl$_3$).

Melting point: 131°–133° C.

$^1$H-NMR (250 MHz, CDCl$_3$) δ: 0.88 (6H, d, J=6.5 Hz), 1.45 (3H, d, J=7 Hz), 1.90-2.08 (1H, m), 2.49 (2H, d, J=7.5 Hz), 3.65-3.79 (1H, m), 4.97 (1H, dd, J=8.5 Hz, 5.5 Hz), 6.93 (1H, d, J=2.5 Hz), 7.09 (1H, t, J=7.5 Hz), 7.17 (1H, t, J=8 Hz), 7.22 (1H, d, J=8.5 Hz), 7.30 (1H, d, J=7.5 Hz), 7.60 (1H, d, J=8 Hz), 8.10 (1H, s).

N-(2-Hydroxyimino-4-methyl)pentanoyl homotryptophan (Compound E-16c).

Pale yellow oily substance.

$^1$H-NMR (250 MHz, CDCl$_3$) δ: 0.88 (3H, d, J=7 Hz), 0.91 (3H, d, J=7 Hz), 1.9-2.3 (3H, m), 2.4-2.7 (2H, m), 2.7-3.0 (2H,m), 4.82 (1H, br), 6.63 (1H, brs), 7.01 (1H, t, J=7 Hz), 7.16 (1H, t, J=7 Hz), 7.41 (1H, d, J=7 Hz), 7.61 (1H, d, J=7 Hz), 10.5-11.5 (1H, br).

EXAMPLE E-10

Using compounds E-16a and E-16c, there were obtained compounds E-17a and E-17c by the same manner as for compound E-5f.

5-Hydroxy-6-[1-(indol-3-yl)ethyl]-3-isobutyl-1,2-dihydropyrazin-2-one 4-oxide (Compound E-17a).

Pale yellow needle-like crystals.

Melting point: 165°–167° C.

$^1$H-NMR (250 MHz, DMSO-d$_6$) δ: 0.98 (3H, d, J=6.5 Hz), 0.99 (3H, d, J=6.5 Hz), 1.77 (3H, d, J=7.5 Hz), 2.17-2.38 (1H, m), 2.83 (2H, d, J=7.5 Hz), 4.76 (1H, q, J=7.5 Hz), 7.09 (1H, t, J=7.5 Hz), 7.20 (1H, t, J=7.5 Hz), 7.33 (1H, d, J=2 Hz), 7.36 (1H, d, J=8 Hz), 7.53 (1H, d, J=8 Hz), 9.13 (1H, s).

5-Hydroxy-6-[2-(indol-3-yl)ethyl]-3-isobutyl-1,2-dihydropyrazin-2-one 4-oxide (Compound E-17c).

Yellow powdery substance.

$^1$H-NMR (250 MHz, DMSO-d$_6$) δ: 0.90 (6H, d, J=7 Hz), 2.13 (1H, sept, J=7 Hz), 2.65 (2H, d, J=7 Hz), 2.8-3.1 (4H, m), 3.97 (1H, t, J=7 Hz), 7.07 (1H, t, J=7 Hz), 7.13 (1H, d, J=2 Hz), 7.34 (1H, d, J=7 Hz), 7.52 (1H, d, J=7 Hz), 10.80 (1H, br).

EXAMPLE E-11

Using Compounds E-17a and E-17c, there were obtained Compounds E-18a and E-18c by the same manner as for the Compound E-6b.

6-[1-(Indol-3-yl)ethyl]-3-isobutyl-5-methoxy-1,2-dihydropyrazin-2-one 4-oxide (Compound E-18a).

Colorless needle-like crystals (from ethanol).

Melting point: 238°–240° C.

6-[2-(Indol-3-yl)ethyl]-3-isobutyl-5-methoxy-1,2-dihydropyrazin-2-one 4-oxide (Compound E-18c).

Yellow powdery substance.

Melting point: 222°–224° C.

REFERENCE EXAMPLE E-6

Compound E-21 was obtained by the same manner as in Reference Example A-20.

Ethyl ester of N-(2-Benzyloxyimino-4-methyl)pentanoylphenylglycine (Compound E-21).

Pale yellow oily substance.

¹H-NMR (250 MHz, CDCl₃) δ: 0.87 (6H, d, J=6.5 Hz), 1.21 (3H, t, J=7 Hz), 1.90–2.12 (1H, m), 2.50 (2H, d, J=7.5 Hz), 4.08–4.32 (2H, m), 5.14 (2H, s), 5.83 (1H, d, J=7 Hz), 7.12–7.32 (7H, m), 7.39 (1H, d, J=8 Hz), 7.57 (1H, d, J=7.5 Hz), 7.72 (1H, d, J=8 Hz), 8.33 (1H, brs).

REFERENCE EXAMPLE E-7

Ethyl ester of N-(2-benzyloxyimino-4-methyl)pentanoyl-N$^{in}$-tert-butoxycarbonylphenylglycine (Compound E-22).

(E-21)

(E-22)
(Bn = Benzyl group)

In 60 ml of CH₂Cl₂ were dissolved 5.67 g (13 mM) of Compound E-21, 4.36 g (20 mM) of (Boc)₂O and 0.18 g (1.5 mM) of DMAP, then the solution was stirred for 23 hours at room temperature. The solvent was removed by evaporation, and the residue was purified by a silica gel chromatography (AcOEt:n-hexane=1:3) to obtain 5.64 g (81%) of a pale yellow oily substance (Compound E-22).

¹H-NMR (250 MHz, CDCl₃) δ: 0.87 (6H, d, J=6.5 Hz), 1.23 (3H, t, J=7 Hz), 1.66 (9H, s), 1.90–2.12 (1H, m), 2.49 (2H, d, J=7.5 Hz), 4.10–4.36 (2H, m), 5.16 (2H, s), 5.81 (1H, d, J=7.5 Hz), 7.20–7.44 (6H, m), 7.55–7.70 (3H, m), 8.16 (1H, d, J=8 Hz).

REFERENCE EXAMPLE E-8

N-(2-Benzyloxyimino-4-methyl)pentanoyl N$^{in}$-tert-butoxycarbonylphenylglycinamide (Compound E-23).

(E-22)

(E-23)
(Bn = Benzyl group)

0.58 Gram (1.1 mM) of Compound E-22 was dissolved in 10 ml of an ethanol solution saturated with NH₃, then the solution was stirred for 17 hours at room temperature and then for 8 hours at 50° C., in an autoclave. The solvent was removed by evaporation, and the residue was purified by a silica gel chromatography (AcOEt:n-hexane=1:2) to obtain 0.30 g of a colorless oily substance (Compound E-23).

¹H-NMR (250 MHz, CDCl₃) δ: 0.85 (3H, d, J=6.5 Hz), 0.86 (3H, d, J=6.5 Hz), 1.66 (9H, s), 1.88–2.04 (1H, m), 2.46 (2H, d, J=7.5 Hz), 5.17 (2H, s), 5.63 (1H, brs), 5.78 (1H, d, J=7.0 Hz), 5.97 (1H, brs), 7.25 (1H, d, J=7.5 Hz), 7.30–7.44 (5H, m), 7.58 (1H, d, J=7.5 Hz), 7.75 (1H, s), 7.81 (1H, d, J=7 Hz), 8.17 (1H, d, J=8 Hz),

REFERENCE EXAMPLE E-9

Compound E-24 was obtained by the same manner as in Reference Example A-23, by using Compound E-23.

N$^{in}$-tert-Butoxycarbonyl-N-(2-hdyroxyimino-4-methyl)pentanoylphenylglycinamide (Compound E-24).

Colorless oily substance.

¹H-NMR (250 MHz, CDCl₃) δ: 0.89 (6H, d, J=6.5 Hz), 1.62 (9H, s), 1.94–2.13 (1H, m), 2.45–2.60 (2H, m), 5.83 (1H, d, J=7.5 Hz), 5.86 (1H, brs), 6.12 (brs), 7.07 (1H, t, J=7.0 Hz), 7.19 (1H, t, J=7.5 Hz), 7.51 (1H, d, J=7.5 Hz), 7.67 (1H, s), 7.95 (1H, d, J=7.5 Hz), 8.02 (1H, d, J=8 Hz), 9.06 (1H, s).

REFERENCE EXAMPLE E-10

1-[(1-tert-Butoxycarbonyl)indol-3-yl]-1-[2-hydroxyimino-4-methyl)pentanoylamino]acetonitrile (Compound E-25)

(E-24)

(E-25)
(Bn = Benzyl group)

125 Milligrams (0.3 mM) of Compound E-24 was dissolved in 4 ml of CH₂Cl₂, thereto was added 240 mg (1 mM) of Burgess Reagent in four portions in 1 hour. 3.5 Hours later, 120 mg (0.5 mM) of the same reagent was added in two portions, and 5 hours later, the mixture was washed with water and dried over MgSO4. The solvent was removed by evaporation, and the residue was purified by a silica gel chromatography (AcOEt:n-hexane=1:2) to obtain 92 mg of a colorless oily substance.

$^1$H-NMR (250 MHz, CDCl$_3$) δ: 0.94 (6H, d, J=6.5 Hz), 1.68 (9H, s), 2.00–2.15 (1H, m), 2.58 (2H, d, J=7.5 Hz), 6.35 (0.5H, d, J=8.5 Hz), 6.36 (0.5H, d, J=8.5 Hz), 7.18 (1H, d, J=8.5 Hz), 7.26 (1H, t, J=7.5 Hz), 7.39 (1H, t, J=7 Hz), 7.50 (1H, d, J=7.5 Hz), 7.86 (1H, s), 8.18 (1H, d, J=8 Hz).

EXAMPLE E-12

Using Compound E-25, Compound E-26 was obtained by the same manner as in Example A-47.

5-Amino-6-[(1-t-butoxycarbonyl)indol-3-yl]-3-isobutyl-1,2-dihydropyrazin-2-one 4-oxide (Compound E-26).

Yellow powdery substance.

$^1$H-NMR (250 MHz, CDCl$_3$) δ: 1.13 (6H, d, J=6.5 Hz), 1.69 (9H, s), 2.28–2.42 (1H, m), 2.93 (2H, d, J=7 Hz), 4.99 (2H, s), 7.19 (1H, t, J=7 Hz), 7.33 (1H, t, J=7.5 Hz), 7.62 (1H, d, J=7.5 Hz), 7.77 (1H, s), 8.08 (1H, d, J=8 Hz).

EXAMPLE E-13

Using Compound E-26, Compound E-27 was obtained by the same manner as in Example A-51.

2-Amino-5-benzyloxy-3-[1-(tert-butoxycarbonyl)indol-3-yl]-6-isobutylpyrazine 1-oxide (Compound E-27).

Yellow oily substance.

$^1$H-NMR (250 MHz, CDCl$_3$) δ: 1.02 (6H, d, J=6.5 Hz), 1.71 (9H, s), 2.25–2.46 (1H, m), 2.97 (2H, d, J=7 Hz), 5.37 (2H, s), 5.44 (2H, s), 7.26 (1H, t, J=7.5 Hz), 7.31–7.50 (6H, m), 7.91 (1H, d, J=8 Hz), 8.10 (1H, s), 8.21 (1H, d, J=8 Hz).

EXAMPLE E-14

Using Compound E-27, there was obtained Compound E-28 by the same manner as in Example A-56.

3-Benzyloxy-6-chloro-5-[1-(tert-butoxycarbonyl)indol-3-yl]-2-isobutylpyrazine 1-oxide (Compound E-28).

Pale yellow oily substance.

$^1$H-NMR (250 MHz, CDCl$_3$) δ: 1.01 (6H, d, J=6.5 Hz), 1.71 (9H, s), 2.25–2.46 (1H, m), 2.95 (2H, d, J=7 Hz), 5.52 (2H, s), 7.26 (1H, t, J=7.5 Hz), 7.30–7.50 (6H, m), 7.97 (1H, d, J=8.0 Hz), 8.11 (1H, d, J=8 Hz), 8.36 (1H, s).

EXAMPLE E-15

3-Benzyloxy-6-chloro-5-(indol-3-yl)-2-isobutylpyrazine 1-oxide (Compound E-29)

In to a methanol solution (15 ml) of containing 0.53 g of Compound E-28, was added 0.27 g of CH$_3$ONa, then the mixture was refluxed for 5 minutes. The solvent was removed by evaporation, then to the residue thus obtained was added chloroform and a diluted hydrochloric acid, and the organic layer was separated. The organic layer was washed with an aqueous solution saturated with sodidum chloride, and dried over anhydrous magnesium sulfate. The solvent was removed by evaporation and the residue thus obtained was recrystallized from methanol to obtain 0.42 g (99%) of Compound E-29.

Yellow needle-like crystals (from MeOH).
Melting point: 189°–191° C. (decomposed).

REFERENCE EXAMPLE E-11

Using the compound E-29, there was obtained Compound E-30 was by the same manner as in Reference Example A-23.

5-Chloro-6-(indol-3-yl)-3-isobutyl-1,2-dihydropyrazin-2-one 4-oxide (Compound E-30).

Yellow needle-like crystals (recrystallized from MeOH).

Melting point: 203°–205° C. (decomposed).

$^1$H-NMR (250 MHz, CDCl$_3$) δ: 0.95 (6H, d, J=6.5 Hz), 2.13–2.30 (1H, m), 2.76 (2H, d, J=7.5 Hz), 7.10–7.30 (2H, m), 7.51 (1H, d, J=7.5 Hz), 8.04 (1H, brs), 11.85 (1H, s), 12.12 (1H, brs).

REFERENCE EXAMPLE E-12

Using the compound E-32 (the same as the product of Reference Example A-18, there were obtained Compounds E-33a to -33i, E-33k, -33i, -33m by the same manner as in Example A-1 or A-2.

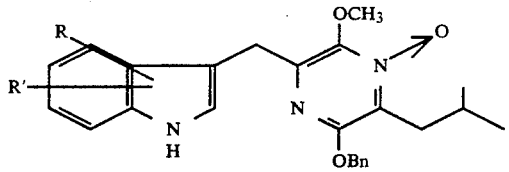

(E-33a/-33m)

Compound E-33a to -33m

| Compound E-33 | R | R' | Melting point | Crystal form (Recrystallization solvent) |
|---|---|---|---|---|
| a | 5-F | H | 140–141°0 C. | Colorless needle-like (Et$_2$O-n-hexane) |
| b | 5-Cl | H | 135–15.5° C. | Colorless prism-like (Et$_2$O-n-hexane) |
| c | 5-Br | H | 124–125° C. | Colorless needle-like (Et$_2$O-n-hexane) |
| d | 2-CH$_3$ | H | 164.5–165.5° C. | Pale yellow prism-like (EtOH) |
| e | 5-CH$_3$ | H | 128–129° C. | Colorless needle-like (Et$_2$O-Colorless |
| f | 7-CH$_3$ | H | 121.5–123.5° C. | COlorless needle-like (Et$_2$O-n-hexane) |
| g | 2-Ph | H | 180–182° C. | Pale yellow needle-like (EtOH) |
| h | 5-OCH$_3$ | H | 118–119° C. | Colorless needle-like (CH$_2$Cl$_2$-n-hexane) |
| i | 5-OBn | H | 93–94.5° C. | Colorless needle-like (CH$_2$Cl$_2$-n-hexane) |
| k | 2-CH$_3$ | 5-OCH$_3$ | 137–138.5° C. | Colorless needle-like (CH$_2$Cl$_2$-n-hexane) |
| l | 5-OCH$_3$ | 6-OCH$_3$ | 151–153° C. | Pale yellow needle-like (AcOEt) |
| m | 4-COOC$_2$H$_5$ | H | 142–142.5° C. | White powder (CH$_2$Cl$_2$-n-hexane) |

| Compound | Chemical Name |
|---|---|
| E-33a | 3-Benzyloxy-5-[(5-fluoroindol-3-yl]- |

-continued

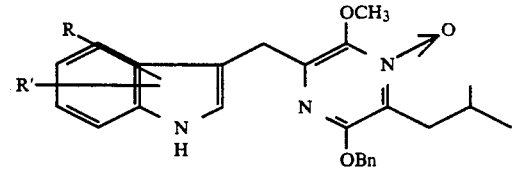

(E-33a/-33m)

Compound E-33a to -33m

| | |
|---|---|
| E-33b | methyl-2-isobutyl-6-methoxypyrazine 1-oxide<br>3-Benzyloxy-5-[(5-chloroindol-3-yl]methyl-2-isobutyl-6-methoxypyrazine 1-oxide |
| E-33c | 3-Benzoyloxy-5-[(5-bromo)indol-3-yl]methyl-2-isobutyl-6-methoxypyrazine 1-oxide |
| E-33d | 3-Benxyloxy-2-isobutyl-6-methoxy-5-[(2-methyl)indol-3-yl]methylpyrazine 1-oxide |
| E-33e | 3-Benzyloxy-2-isobutyl-6-methoxy-5-[(5-methyl)indol-3-yl]methylpyrazine 1-oxide |
| E-33f | 3-Benzyloxy-2-isobutyl-6-methoxy-5-[(7-methyl)indol-3-yl]methylpyrazine 1-oxide |
| E-33g | 3-Benzyloxy-2-isobutyl-6-methoxy-5-[(2-phenyl)indol-3-yl]methylpyrazine 1-oxide |
| E-33h | 3-Benzyloxy-2-isobutyl-6-methoxy-5-[(5-methoxy)indol-3-yl]methylpyrazine 1-oxide |
| E-33i | 3-Benzyloxy-5-[(5-benzyloxy)indol-3-yl]-methyl-2-isobutyl-6-methoxypyrazine 1-oxide |
| E-33k | 3-Benzyloxy-2-isobutyl-6-methoxy-5-[(5-methoxy-2-methyl)indol-3-yl]methylpyrazine 1-oxide |
| E-33l | 3-Benzyloxy-5-[(5,6-dimethyoxy)indol-3-yl]-methyl-2-isobutyl-6-methoxypyrazine 1-oxide |
| E-33m | 3-Benzyloxy-5-[(4-ethoxycarbonyl)indol-3-yl]-methyl-2-isobutyl-6-methoxypyrazine 1-oxide |

(Ph = Phenyl group, Bn = Benzyl geoup)

REFERENCE EXAMPLE E-13

Using Compounds E-33a to E-33i, E-33k, E-33l and E-33m there were obtained, Compounds E-34a to E-33h, E-33j to E-33m by the same manner as in Reference Example A-23.

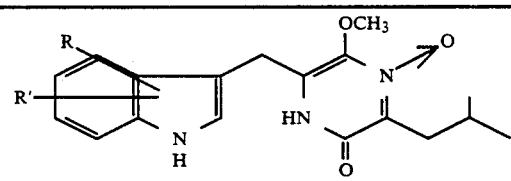

(E-34a/34m)

| Compound<br>E-34 | R | R' | Melting point | Crystal form<br>(Recrystallization solvent) |
|---|---|---|---|---|
| a | 5-F | H | 209–210° C. | Pale yellow prism-like (EtOH) |
| b | 5-Cl | H | 200–203.5° C. | Pale yellow prsim-like (EtOH) |
| c | 5-Br | H | 199.5–203.5° C. | Pale yellow prism-like (EtoH) |
| d | 2-CH$_3$ | H | 218–219.5° C. | Plae yellow prism-like (EOH) |
| e | 5-CH$_3$ | H | 195.5–197° C. | Pale yellow prism-like (EtOH) |
| f | 7-CH$_3$ | H | 200–201° C. | Pale yellow prsim-like (EOH) |
| g | 2-Ph | H | 194–195.5° C. | Pale yellow needle-like (EtOH) |
| h | 5-OCH$_3$ | H | 209–210° C. | Pale yellow needle-like (EtOH) |
| j | 5-OH | H | 207.5–208° C. | COlorless needle-like (EtOH) |
| k | 2-CH$_3$ | 5-OCH$_3$ | 190–19° C. | Pale yellow powdery (EOH) |
| l | 5-OCH$_3$ | 6-OCH$_3$ | 204° C. (decomposed) | Pale yellow prism-like (EtOH) |
| m | 4-COOC$_2$H$_5$ | H | 147.5–149° C. | Pale yellow needle-like (CH$_2$Cl$_2$—Et$_2$O) |

| Compound | |
|---|---|
| E-34a | 6-[(5-Fluoro)indol-3-yl]methyl-3-isobutyl-5-methoxy-1,2-dihydropyrazin-2-one 4-oxide |
| E-34b | 6-[(5-Chloro)indol-3-yl]methyl-3-isobutyl-5-methoxy-1,2-dihydropyrazin-2-one 4-oxide |
| E-34c | 6-[(5-Bromo)indol-3-yl]methyl-3-isobutyl-5-methoxy-1,2-dihydropyrazin-2-one 4-oxide |
| E-34d | 3-Isobutyl-5-methoxy-6-[(2-methyl)indol-3-yl]methyl-1,2-dihydropyrazin-2-one 4-oxide |
| E-34e | 3-Isobutyl-5-methoxy-6-[(5-methyl)indol-3-yl]methyl-1,2-dihydropyrazin-2-one 4-oxide |
| E-34f | 3-Isobutyl-5-methoxy-6-[(7-methyl)indol-3-yl]methyl-1,2-dihydropyrazin-2-one 4-oxide |

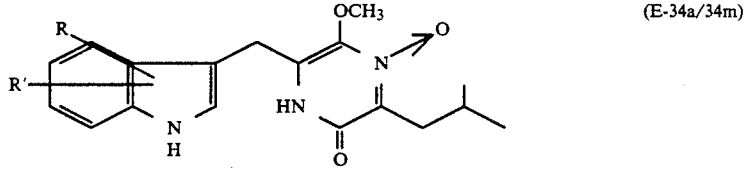

(E-34a/34m)

| | |
|---|---|
| E-34g | 3-Isobutyl-5-methoxy-6-[(2-phenyl)indol-3-yl]methyl-1,2-dihydropyrazin-2-one 4-oxide |
| E-34h | 3-Isobutyl-5-methoxy-6-[(5-methoxy)indol-3-yl]methyl-1,2-dihydropyrazin-2-one 4-oxide |
| E-34j | 6-[(5-Hydroxy)indol-3-yl]methyl-3-isobutyl-5-methoxy-1,2-dihydropyrazin-2-one 4-oxide |
| E-34k | 3-Isobutyl-5-methoxy-6-[(5-methoxy-2-methyl)indol-3-yl]methyl-1,2-dihydropyrazin-2-one 4-oxide |
| E-34l | 6-[(5,6-Dimethoxy)indol-3-yl]methyl-3-isobutyl-5-methoxy-1,2-dihydropyrazin-2-one 4-oxide |
| E-34m | 6-[(4-Ethoxycarbonyl)indol-3-yl]methyl-3-isobutyl-5-methoxy-1,2-dihydropyrazin-2-one 4-oxide |

(Ph = Phenyl group, Bn = Benzyl group)

REFERENCE EXAMPLE E-14

6-[(4-Carboxy)indol-3-yl]methyl-3-isobutyl-5-methoxy-1,2-dihydropyrazin-2-one 4-oxide To 500 mg of the Compound E-34m were added 5 ml of MeOH and 7.5 ml of an aqueous 1M NaOH solution, the mixture was subjected to a reaction for 5 hours at room temperature, then 50 ml of diethyl ether was added thereto. The reaction mixture was extracted with an aqueous 0.5M NaOH solution, then the aqueous NaOH layer was made acidic with an aqueous 2M HCl solution and then extracted with EtOAc, and the EtOAc layer was dried with $MgSO_4$. The solvent was removed by evaporation and the residue was recrystallized from $CH_2Cl_2$-n-hexane to obtain 250 mg of a pale yellow powder substance (Compound E-34n) having a melting point of 160.5°–163.5° C.

REFERENCE EXAMPLE E-15

3-Benzyloxy-5-(indol-3-yl)methyl-2-isobutyl-6-methoxy-pyrazine 1-oxide (Compound E-35p)

1.0 Gram of Compound E-32 and 550 mg of indole were dissolved in 20 ml of DMSO, thereto was added oily 60% NaH at 0° C., then the mixture was subjected to a reaction for 20 minutes at room temperature. After the completion of the reaction, 200 ml of diethyl ether was added, and the resulting mixture was washed with water (100 ml×3), and the diethyl ether layer was dried over $MgSO_4$. The solvent was removed by evaporation, and the residue was purified by a silica gel column chromatography (EtOAC-n-hexane) to obtain 880 mg of the title compound (Compound E-35p) as a colorless oily substance.

$^1$H-NMR (250 MHz, $CDCl_3$) δ: 0.91 (6H, d, J=7 Hz), 2.18 (1H, sept., J=7 Hz), 2.77 (2H, d, J=7 Hz), 3.90 (3H, s), 5.28 (2H, s), 5.31 (2H, s), 6.53 (1H, d, J=3 Hz), 7.10 (1H, t, J=7 Hz), 7.18 (1H, t, J=7 Hz), 7.23 (1H, d, J=3 Hz), 7.31 (5H, m), 7.48 (1H, d, J=7 Hz), 7.62 (1H, d, J=7 Hz).

REFERENCE EXAMPLE E-16

Compounds E-35o and E-38 were obtained by the same manner as for compound E-35p.

3-Benzyloxy-5-[(5-cyano)indol-1-yl]methyl-2-isobutyl-6-methoxypyrazine 1-oxide (Compound E-35o).

Colorless needle-like crystals (from ether-n-hexane).
Melting point: 97°–99° C.
3-Benzyloxy-2-isobutyl-6-methoxy-5-(oxindol-3-yl)methylpyrazine 1-oxide (Compound E-38).

White powdery substance. $^1$H-NMR (250 MHz, $CDCl_3$) δ: 0.90 (3H, d, J=7 Hz), 0.91 (3H, d, J=7 Hz), 2.21 (1H, sept., J=7 Hz), 2.79 (2H, d, J=7 Hz), 3.32 (1H, dd, J=16 Hz, 7 Hz), 3.53 (1H, dd, J=16 Hz, 5 Hz), 3.97 (3H, s), 4.00 (1H, br., t, J=6 Hz), 5.18 (2H, ABq, J=13 Hz), 6.78 (1H, d, J=7 Hz), 6.86 (1H, t, J=7 Hz), 6.91 (1H, d, J=7 Hz), 7.16 (1H, t, J=7 Hz), 7.33 (5H, m), 7.59 (1H, br., s).

REFERENCE EXAMPLE E-17

Using Compounds E-35o, E-35p and E-38, there were obtained Compounds F-36o, E-36p and E-39 by the same manner as in Reference Example A-23.

6-[(5-cyano)indol-1-yl]methyl-3-isobutyl-5-methoxy-1,2-dihydropyrazin-2-one 4-oxide (compound E-36o).

Colorless needle-like crystals (from EtOH).
Melting point: 205°–207° C.
6-(Indol-1-yl)methyl-3-isobutyl-5-methoxy-1,2-dihydropyrazin-2-one 4-oxide (Compound E-36p).

Pale yellow needle-like crystals (from EtOH).
Melting point: 179.5°–180.5° C.
2-Isobutyl-5-methxoy-6-(oxindol-3-yl)methyl-1,2-dihydropyrazin-2-one 4-oxide (Compound E-39).

Colorless powdery substance (from EtOH).
Melting point: 200.0°–201.5° C.

REFERENCE EXAMPLE E-18

Using the Compound E-40 [the same as the starting material used in Reference Example A-15], there were obtained Compounds E-42a, E-42b, E-42c and E-42d by the same manner as in Reference Example A-15, and then in the same manner as in Reference Example A-16.

3-Benzyloxy-5-hydroxymethyl-2-isobutyl-6-isopropoxypyrazine 1-oxide (Compound E-42a).

Pale yellow oily substance.
$^1$H-NMR (250 MHz, $CDCl_3$) δ: 0.94 (6H, d, J=7 Hz), 1.33 (6H, d, J=6 Hz), 2.44 (1H, sept., J=7 Hz), 2.83 (2H, d, J=7 Hz), 3.19 (1H, t, J=6 Hz), 4.67 (2H, d, J=6 Hz), 5.07 (1H, sept., J=6 Hz), 5.39 (2H, s), 7.3–7.5 (5H, m)

3-Benzyloxy-6-n-butoxy-5-hydroxymethyl-2-isobutylpyrazine 1-oxide (Compound E-42b).

Pale yellow oily substance.
¹H-NMR (250 MHz, CDCl₃) δ: 0.95 (6H, d, J=7 Hz), 0.97 (3H, d, J=7 Hz), 1.49 (2H, six, J=7 Hz), 1.78 (2H, qui., J=7 Hz), 2.24 (1H, sept., J=7 Hz), 2.83 (2H, d, J=7 Hz), 3.12 (1H, t, J=6 Hz), 4.25 (2H, t, J=7 Hz), 4.69 (2H, d, J=6 Hz), 5.40 (2H, s), 7.3-7.5 (5H, m).

3-Benzyloxy-5-hydroxymethyl-2-isobutyl-6-(2-phenyl)ethoxy-pyrazine 1-oxide (Compound E-42c).

Pale yellow oily substance.
¹H-NMR (250 MHz, CDCl₃) δ: 0.94 (6H, d, J=7 Hz), 2.23 (1H, sept., J=7 Hz), 2.82 (2H, d, J=7 Hz), 2.85 (1H, br), 3.11 (2H, t, J=7 Hz), 4.34 (2H, d, J=6 Hz), 4.51 (2H, t, J=7 Hz), 5.36 (2H, s), 7.2-7.4 (10H, m).

3-Benzyloxy-6-cyclohexyloxy-5-hydroxymethyl-2-isobutylpyrazine 1-oxide (Compound E-42d).

Pale yellow oily substance.
¹H-NMR (250 MHz, CDCl₃) δ: 0.95 (6H, d, J=7 Hz), 1.2-1.4 (3H, m), 1.4-1.6 (3H,m), 1.7-1.9 (2H, m), 1.9-2.1 (2H, m), 2.26 (1H, sept., J=7 Hz), 2.83 (2H, d, J=7 Hz), 3.15 (1H, t, J=5 Hz), 4.69 (2H,d, J=5 Hz), 4.65-4.75 (1H, m), 5.39 (2H, s), 7.3-7.5 (5H, m).

REFERENCE EXAMPLE E-19

Compounds E-43a, E-43b, E-43c and E-43d were obtained by the same manner as in Reference Example A-17.

3-Benzyloxy-2-isobutyl-6-isopropoxy-5-methyloxymethylpyrazine 1-oxide (Compound E-43a).

Pale yellow oily substance.
¹H-NMR (250 MHz, CDCl₃) δ: 0.94 (6H, d, J=7 Hz), 1.37 (6H, d, J=6 Hz), 2.25 (1H, sept., J=7 Hz), 2.84 (2H, d, J=7 Hz), 3.04 (3H, s), 5.12 (1H, qui., J=6 Hz), 5.21 (2H, s), 5.39 (2H, s), 7.3-7.5 (5H, m), 3-Benzyloxy-6-n-butoxy-2-isobutyl-5-mesyloxymethylpyrazine 1-oxide (Compound E-43b).

Pale yellow needle-like crystals (from Et₂O-n-hexane). Melting point: 70°-73° C.

3-Benzyloxy-2-isobutyl-6-(2-phenyl)ethoxy-5-mesyloxymethylpyrazine 1-oxide (Compound E-43c).

Pale yellow oily substance.
¹H-NMR (250 MHz, CDCl₃) δ: 0.94 (6H, d, J=7 Hz), 2.24 (1H, sept., J=7 Hz), 2.83 (2H, d, J=7 Hz), 2.89 (3H, s), 3.16 (2H, t, J=7 Hz), 4.55 (2H, t, J=7 Hz), 4.98 (2H, s), 5.37 92H, s), 7.3-7.5 (10H, m).

3-Benzyloxy-6-cyclohexyloxy-2-isobutyl-5-mesyloxymethylpyrazine 1-oxide (Compound E-43d).

Pale yellow needle-like crystals (from Et₂O-n-hexane)
Melting point: 114°-115.5° C.

REFERENCE EXAMPLE E-20

Compounds E-44a, E-44b, E-44c and E-44d were obtained by the same manner as in Reference Example A-18.

3-Benzyloxy-5-iodomethyl-2-isobutyl-6-isopropoxypyrazine 1-oxide (Compound E-44a).

Pale yellow oily substance.
¹H-NMR (250 MHz, CDCl₃) δ: 0.93 (6H, d, J=7 Hz), 1.40 (6H, d, J=6 Hz), 2.23 (1H, sept., J=7 Hz), 2.79 (2H, d, J=7 Hz), 4.46 (2H, s), 5.16 (1H, qui., J=6 Hz), 5.37 (2H, s), 7.3-7.5 (5H, m).

3-Benzyloxy-6-n-butoxy-5-iodomethyl-2-isobutylpyrazine 1-oxide (Compound E-44b).

Pale yellow needle-like crystals (from ether-n-hexane).
Melting point: 64.5°-65.5° C.

3-Benzyloxy-5-iodomethyl-2-isobutyl-6-(2-phenyl)ethoxypyrazine 1-oxide (Compound E-44c).

Pale yellow oily substance.
¹H-NMR (250 MHz, CDCl₃) δ: 0.92 (6H, d, J=7 Hz), 2.24 (1H, sept., J=7 Hz), 2.78 (2H, d, J=7 Hz), 3.20 (2H, t, J=7 Hz), 4.16 (2H, s), 4.60 (2H, t, J=7 Hz), 5.35 (2H, s), 7.3-7.5 (10H, m).

3-Benzyloxy-6-cyclohexyloxy-5-iodomethyl-2-isobutylpyrazine 1-oxide (Compound E-44d).

Pale yellow needle-like crystals (from Et₂O-n-hexane)
Melting point: 80.5°-81.5° C.

EXAMPLE E-16

Compounds E-45a, E-45b, E-45c and E-45d were obtained by the same manner as in Example A-1 or A-2.

3-Benzyloxy-5-(indol-3-yl)methyl-2-isobutyl-6-isopropoxypyrazine 1-oxide (Compound E-45a). Colorless prism-like crystals (from Et₂O-n-hexane).
Melting point: 106°-107° C.

3-Benzyloxy-6-butoxy-5-(indol-3-yl)methyl-2-isobutylpyrazine 1-oxide (Compound E-45b).

Pale yellow oily substance.
¹H-NMR (250 MHz, CDCl₃) δ: 0.93 (6H, d, J=7 Hz), 1.01 (3H, t, J=7 Hz), 1.54 (2H, sex., J=7 Hz), 1.88 (2H, qui., J=7 Hz), 2.23 (1H, sept., J=7 Hz), 2.79 (2H, d, J=7 Hz), 4.37 (2H, t, J=7 Hz), 4.45 (2H, s), 5.37 (2H, s), 7.3-7.5 (5H, m).

3-Benzyloxy-5-(indol-3-yl)methyl-2-isobutyl-6-(2-phenyl)ethoxypyrazine 1-oxide (Compound E-45c).

Pale yellow needle-like crystals (from CH₂Cl₂-n-hexane).
Melting point: 115°-116.5° C.

3-Benzyloxy-6-cyclohexyloxy-5-(indol-3-yl)methyl-2-isobutylpyrazine 1-oxide (Compound E-45d).

Pale yellow prism-like crystals (from CH₂Cl₂-n-hexane).
Melting point: 99°-100.5° C.

REFERENCE EXAMPLE E-21

Using Compounds E-45a, E-45b, E-45c and E-45d, there were obtained Compounds E-46a, E-46b, E-46c and E-46d by the same manner as in Reference Example A-23.

6-(Indol-3-yl)methyl-3-isobutyl-5-isopropoxy-1,2-dihydroipyrazin-2-one 4-oxide (Compound E-46a).

Pale yellow prism-like crystals (from EtOH).
Melting point: 182°-183° C.

5-n-Butoxy-6-(indol-3-yl)methyl-3-isobutyl-1,2-dihydropyrazin-2-one 4-oxide (Compound E-46b).

Pale yellow needle-like crystals (from EtOH).
Melting point: 185°-187° C.

6-(Indol-3-yl)methyl-3-isobutyl-5-(2-phenyl)ethoxy-1,2-dihydropyrazin-2-one 4-oxide (Compound E-46c).

Light yellow prism-like crystals.
Melting point: 167°-169° C.

5-Cyclohexyloxy-6-(indl-3-yl)methyl-3-isobutyl-1,2-dihydropyrazin-2-one 4-oxide (Compound E-46d).

Pale yellow needle-like crystals.
Melting point: 125°-128° C.

REFERENCE EXAMPLE E-22

The followings are additional data to Reference Examples A-22, A-23 and A-24 and Examples A-57 and A-58. Using Compound A-79, there were obtained Compounds E-48a and E-48b by the same manner as in Reference Example A-22.

2-(2-Benzyloximino-4-methyl)pentanoylamino-1-(indol-3-yl)hexan-3-one (Compound E-48a).

Yellow oily substance.

$^1$H-NMR (250 MHz, CDCl$_3$) δ: 0.80 (3H, t, J=7.5 Hz), 0.86 (6H, d, J=6.5 Hz), 1.43–1.52 (1H, m), 1.87–2.08 (1H, m), 2.33 (1H, t, J=7 Hz), 2.34 (1H, t, J=7 Hz), 2.48 (2H, d, J=7.5 Hz), 3.24 (2H, d, J=6.5 Hz), 4.87 (1H, dd, J=14 Hz, 6.5 Hz), 5.09 (2H, s), 6.90 (1H, d, J=2.5 Hz), 7.11 (1H, dt, J=7.5 Hz, 1 Hz), 7.20 (1H, dt, J=7.5 Hz, 1Hz), 7.26–7.44 (6H, m), 7.61 (1H, d, J=7.5 Hz), 7.97 (1H, brs).

2-(2-Benzyloxyimino-4-methyl)pentanoylamino-1-(indol-3-yl)-4-methylpentan-3-one (Compound E-48b).

REFERENCE EXAMPLE E-23

Using the Compounds E-48a and E-48b, there were obtained Compounds E-49a and E-49b by the same manner as in Reference Example A-23.

2-(2-Hydroxyimino-4-methyl)pentanoylamino-1-(indol-3-yl)hexan-3-one (Compound E-49a).

Pale yellow oily substance.

$^1$H-NMR (250 MHz, CDCl$_3$) δ: 0.79 (3H, t, J=7.5 Hz), 0.89 (6H, d, J=6.5 Hz), 1.51 (1H, sextet, J=7.5 Hz), 1.52 (1H, sextet, J=75. Hz), 1.92–2.15 (1H, m), 2.34 (1H, t, J=7.5 Hz), 2.38 (1H, t, J=7.5 Hz), 2.51 (2H, d, J=7.5 Hz), 3.48 (1H, d, J=6.5 Hz), 3.49 (1H, d, J=6.5 Hz), 4.95 (1H, dd, J=14 Hz, 6.5 Hz), 6.95 (1H, d, J=2.5 Hz), 7.11 (1H, dt, J=7.5 Hz, 1.5 Hz), 7.19 (1H, dt, J=7.5 Hz, 1.5 Hz), 7.34 (1H, dt, J=7.5 Hz, 1.5 Hz), 7.44 (0.5H, s), 7.48 (0.5H, s), 7.58(1H, d, J=7 Hz), 8.11 (1H, brs).

2-(2-Hydroxyimino-4-methyl)pentanoylamino-1-(indol-3-yl)-4-methylpentan-3-one (Compound E-49b).

EXAMPLE E-17

Using the compounds E-49a, there was obtained Compound E-50a by the same manner as in Example A-57.

6-(Indol-3-yl)methyl-3-isobutyl-5-n-propyl-1,2-dihydropyrazin-2-one 4-oxide (Compound E-50a).

Pale yellow plate like crystals (recrystallized from methanol).

Melting point: 229°–231° C.

EXAMPLE E-18

Compound E-52a [the same as the product of Reference Example A-17] was obtained by the same manner as in Example A-56.

3-Benzyloxy-6-chloro-5-hydroxymethyl-2isobutyl-pyrazine 1-oxide (Compound E-52a).

Pale yellow needle-like crystals (from Et$_2$O-n-hexane).

Melting point: 85°–88° C.

EXAMPLE E-19

Using Compound E-51, there was obtained Compound E-52b by the same manner as in Example A-56, except that CuBr$_2$ was used in place of CuCl$_2$.2H$_2$O.

3-Benzyloxy-6-bromo-5-hydroxymethyl-2-isobutyl-pyrazine 1-oxide (Compound E-52b).

Colorless needle-like crystals (from CH$_2$Cl$_2$-n-hexane).

Melting point: 74.5°–76° C.

EXAMPLE E-20

3-Benzyloxy-5-hydroxymethyl-2-isobutyl-6-methylthiopyrazine 1-oxide (Compound E-52c)

4.55 Grams of 6-amino-5-hydroxymethyl-3-benzyloxy-2-isobutyl isobutylpyrazine 1-oxide and 6.75 ml of dimethyl disulfide were dissolved in 50 ml of CH$_3$CN, and thereto was added 3.02 ml of isoamyl nitrite. The mixture was subjected to a reaction for 20 minutes at 70°–80° C., and the reaction mixture was cooled to room temperature, and mixed with 150 ml of diethyl ether. The resulting mixture was washed with water (100 ml×3), and the ether layer was dried over MgSO$_4$. The solvent was removed by evaporation. The residue was purified by a silica gel chromatography (30% EtOAc-hexane), followed by recrystallization from isopropyl ether-n-hexane to obtain 2.17 g of colorless needle-like crystals (Compound E-52c) having a melting point of 88.5°–86.5° C.

EXAMPLE E-21

3-Benzyloxy-5-hydroxymethyl-2-isobutyl-6-methylsulfonylpyrazine 1-oxide (Compound E-52d).

1.10 Grams of the Compound E-52c was dissolved in 33 ml of CH$_2$Cl$_2$, thereto was added 1.56 g of 80% m-CPBA, and the mixture was subjected to a reaction for 15 hours at room temperature. To the reaction mixture was added 50 ml of aqueous solution saturated with NaHCO$_3$, and the resulting mixture was extracted with CH$_2$Cl$_2$ (50 ml×3), then the CH$_2$Cl$_2$ layer was dried over MgSO$_4$. The solvent was removed by evaporation, and to the residue was added a small amount of diethyl ether. The mixture was allowed to stand, then the resulting crystals were recrystallized from CH$_2$Cl$_2$-hexane to obtain 1.10 g of a yellow powdery substance (Compound E-52d) having a melting point of 97.5°–98.5° C.

REFERENCE EXAMPLE E-24

Compounds E-53a, E-53b, E-53c, and E-53d were obtained by the same manner as in Reference Example A-17.

3-Benzyloxy-6-chloro-2-isobutyl-5-mesyloxymethyl-pyrazine 1-oxide (Compound E-53a).

Pale yellow oily substance.

$^1$H-NMR (200 MHz, CDCl$_3$) δ: 0.93 (6H, d, J=7 Hz), 2.23 (1H, sept., J=7 Hz), 2.86 (2H, d, J=7 Hz), 3.04 (3H, s), 5.32 (2H, s), 5.43 (2H, s), 7.3–7.5 (5H, m).

3-Benzyloxy-6-bromo-2-isobutyl-5-mesyloxymethyl-pyrazine 1-oxide (Compound E-53b).

Pale yellow needle-like crystals (from CH$_2$Cl$_2$-n-hexane).

Melting point: 98.5°–100° C.

3-Benzyloxy-2-isobutyl-5-mesyloxymethyl-6-methylthiopyrazine 1-oxide (Compound E-53c).

Pale yellow needle-like crystals (from CH$_2$Cl$_2$-ether).

Melting point: 89°–89.5° C.

3-Benzyloxy-2-isobutyl-5-mesyloxymethyl-6-methylsulfonylpyrazine 1-oxide (Compound E-53d).

Colorless needle-like crystals (from CH$_2$Cl$_2$-Et$_2$O).

Melting point: 126°–126.5° C.

REFERENCE EXAMPLE E-25

Compounds E-54a, E-54b, E-54c and E-54d were obtained by the same manner as in Reference Example A-18.

3-Benzyloxy-6-chloro-5-iodomethyl-2-isobutylpyrazine 1-oxide (Compound E-54a).

Colorless needle-like crystals.

$^1$H-NMR (200 MHz, CDCl$_3$) δ: 0.92 (6H, d, J=7 Hz), 2.22 (1H, sept., J=7 Hz), 2.82 (2H, d, J=7 Hz), 4.48 (2H, s), 5.40 (2H, s), 7.3–7.5 (5H, m).

3-Benzyloxy-6-bromo-5-iodomethyl-2-isobutylpyrazine 1-oxide (Compound E-54b).

Colorless needle-like crystals (from CH$_2$Cl$_2$-n-hexane).

Melting point: 106.5°–107° C.
3-Benzyloxy-5-iodomethyl-2-isobutyl-6-methylthiopyrazine 1-oxide (Compound E-54c).
Pale yellow needle-like crystals (from $CH_2Cl_2$-n-hexane).
Melting point: 85°–86° C.
3-Benzyloxy-5-iodomethyl-2-isobutyl-6-methyl-sulfonylpyrazine 1-oxide (Compound E-54d).
Colorless needle-like crystals (from ethyl acetate-n-hexane).
Melting point: 125.5°–126.5° C.

EXAMPLE E-22

Compounds E-56a, E-56b, E-56c and E-56d were obtained by the same manner as in Example B-1 or B-2.

3-Benzyloxy-6-chloro-5-(indol-3-yl)methyl-2-isobutylpyrazine 1-oxide (Compound E-56a).

Colorless needle-like crystals (from $CH_2Cl_2$-n-hexane).

$^1$H-NMR (200 MHz, $CDCl_3$) δ: 0.90 (6H, d, J=7 Hz), 2.20 (1H, sept., J=7 Hz), 2.80 (6H, d, J=7 Hz), 4.29 (2H, s), 5.36 (2H, s), 7.08 (1H, t, J=8 Hz), 7.09 (1H, s), 7.19 (1H, t, J=8 Hz), 7.31 (5H, s), 7.37 (1H, d, J=8 Hz), 7.76 (1H, d, J=8 Hz), 8.03 (1H, br).

3-Benzyloxy-6-bromo-5-(indol-3-yl)methyl-2-isobutylpyrazine 1-oxide (Compound E-56b).

Colorless needle-like crystals (from $CH_2Cl_2$-n-hexane).

Melting point: 143°–143.5° C.

3-Benzyloxy-5-(indol-3-yl)methyl-2-isobutyl-6-methylthiopyrazine 1-oxide (Compound E-56c).

Colorless powdery substance (from $CH_2Cl_2$-n-hexane).

Melting point: 156°–158° C.

3-Benzyloxy-5-(indol-3-yl)methyl-2-isobutyl-6-methylsulfonylpyrazine 1-oxide (Compound E-56d).

Colorless powdery substance (from $CH_2Cl_2$-n-hexane).

Melting point: 154°–155° C.

REFERENCE EXAMPLE E-56

Using the Compounds E-56a, E-56b and E-56d, there were obtained Compounds E-57a, E-57b and E-57d by the same manner as in Reference Example A-23.

5-Chloro-6-(indol-3-yl)methyl-3-isobutyl-1,2-dihydropyrazin-2-one 4-oxide (Compound E-57a).

Pale yellow needle-like crystals (from EtOH).
Melting point: 208° C. (decomposed).

5-Bromo-6-(indol-3-yl)methyl-3-isobutyl-1,2-dihydripopyrazin-2-one 4-oxide (Compound E-57b).

Pale yellow needle-like crystals (from EtOH),
Melting point: 190° C. (decomposed)

6-(Indol-3-yl)methyl-3-isobutyl-5-methylsulfonyl-1,2-dihydropyrazin-2-one 4-oxide (Compound E-57d).

Colorless needle-like crystals (from $CH_2Cl_2$-n-hexane).

Melting point: 190°–191° C.

EXAMPLE E-23

6-(Indol-3-yl)methyl-3-isobutyl-5-methylthio-1,2-dihydropyrazin-2-one 4-oxide (Compound E-57c)

50 Milliliters of $CH_2Cl_2$ and 25 ml of TFA were added to 2.50 g of the compound E-56c, then the mixture was subjected to a reaction for 1 hour at room temperature. Thereto was added 300 ml of water, and the resulting mixture was extracted with $CH_2Cl_2$ (100 ml×3), then the $CH_2Cl_2$ layer was washed with water (200 ml×2) and dried over $MgSO_4$. The solvent was removed by evaporation, and the residue was purified by a silica gel chromatography (20% EtOAc-$CH_2Cl_2$), followed by recrystallization from EtOH to obtain 900 mg of pale yellow needle-like crystals (Compound E-57c) having a melting point of 203° C. (decomposed).

EXAMPLE E-24

6-(Indol-3-yl)methyl-3-isobutyl-5-methylsulfinyl-1,2-dihydropyrazin-2-one 4-oxide (Compound E-58)

260 Milligrams of the Compound E-57 was dissolved in 11 ml of MeOH-$CH_2Cl_2$ (1:10), thereto was added at −10° C. 170 mg of 80% mCPBA. The mixture was subjected to a reaction for 20 minutes, then 50 ml of EtOAc was added. The mixture was washed with an aqueous solution saturated with $NaHCO_3$ (30 ml×3), and the EtOAC layer was dried over $MgSO_4$. The solvent was removed by evaporation, and the resulting oil was subjected to crystallization from $CH_2Cl_2$-ether to obtain 170 mg of a colorless powdery substance (Compound E-58) having a melting point of 209° C. (decomposed).

REFERENCE EXAMPLE E-27

3-Benzyloxy-5-formyl-2-isobutyl-6-methoxypyrazine 1-oxide (Compound E-60)

28 milliliters of $CHCl_3$ and 5.4 g of $MnO_2$ were added to 2.80 g of the alcohol form compound (Compound E-59). The mixture was subjected to a reaction for 3 hours at room temperature. The insoluble matter was removed by means of silica gel chromatography (EtOAc), and the solvent was removed by evaporation. The residue was purified by silica gel chromatography (35% EtOAc-hexane), followed by recrystallization from $Et_2O$-n-hexane to obtain 1.04 g of colorless needle-like crystals (Compound E-60) having a melting point of 64.5°–66° C.

Also, 1.38 g of 6-methoxy-5-hydroxymethyl-3-benzyloxy-2-isobutylpyrazine 1-oxide was recovered.

EXAMPLE E-25

3-Benzyloxy-5-[1-hydroxy-1-(indol-3-yl)methyl-isobutyl-6-methoxypyrazine 1-oxide (Compound E-61)

2.15 Grams of the aldehyde form compound (Compound E-60) and 960 mg of indole were dissolved in 22 ml of $H_2O$-MeOH (1:50), thereto was added 76 mg of tert-BuOK. The mixture was subjected to a reaction for 12 hours at room temperature, and the resulting crystals were collected by filtration and then recrystallized from EtOH to obtain 2.69 g of colorless needle-like crystals (Compound E-61) having a melting point of 161.5°–163.5° C.

EXAMPLE E-26

3-Benzyloxy-5-(indol-3-yl)carbonyl-2-isobutyl-6-methoxypyrazine 1-oxide (Compound E-62)

3.73 Grams of the alcohol form compound (Compound E-61) was dissolved in 15 ml of DMF with heating, thereto were added 120 ml of $CHCl_3$ and 7.5 g of $MnO_2$. The mixture was subjected to a reaction for 1 hour at room temperature. The insoluble matter was removed by a silica gel chromatography (EtOAc), and the solvent was removed by evaporation. The residue was purified by a silica gel chromatography (50% EtOAc-n-hexane), followed by recrystallization from $CH_2Cl_2$-ether to obtain 1.63 g of light yellow needle-like crystals (Compound E-62) having a melting point of 166.5°–167.5° C. Also, 2.09 g of the alcohol form compound (Compound E-61) was recovered by using 5% MeOH-CH$_2$Cl$_2$.

Using Compound E-62 prepared in Example E-26 as mentioned above, and by procedure as in Reference Example A-23, there was obtained Compound E-63 as follows.

6-(Indol-3-yl)carbonyl-3-isobutyl-5-methoxy-1,2-dihydropyrazin-2-one 4-oxide (EtOH adduct) (Compound (E-63).

Yellow needle-like crystals (from EtOH).
Melting point: 176°–178.5° C.

EXAMPLE E-27

6-[1-Hydroxy-1-(indol-3-yl)]methyl-3-isobutyl-5-methoxy-1,2-dihydropyrazin-2-one 4-oxide (Compound E-64)

1.24 Grams of the ketone form compound (Compound E-63) was dissolved in 62 ml of EtOH with heating, thereto was added 840 mg of NaBH$_4$, and the mixture was subjected to a reaction for 2 hours at room temperature, next 500 ml of EtOAc was added. The resulting mixture was washed with water (200 ml×3) and dried over MgSO$_4$. The solvent was removed by evaporation, and the residue was purified by silica gel chromatography (8% MeOH-CH$_2$Cl$_2$) to obtain 870 mg of Compound E-64 as in the form of a pale yellow oily substance.

$^1$H-NMR (250 MHz, CDCl$_3$) δ. 0.81 (3H, d, J=7 Hz), 0.82 (3H, d, J=7 Hz), 2.07 (1H, sept., J=7 Hz), 2.59 (2H, d, J=7 Hz), 3.64 (3H, s), 6.19 (1H, s), 6.93 (1H, d, J=7 Hz), 7.06 (1H, t, J=7 Hz), 7.16 (1H, t, J=7 Hz), 7.28 (1H, d, J=7 Hz), 7.62 (1H, d, J=7 Hz), 8.68 (1H, br, s).

REFERENCE EXAMPLE E-28

Using compound E-10 [the same as the Compound B-42], Compound E-65 was obtained by the same manner as in Reference Example A-6.

3-Acetoxy-5-(indol-3-yl)methyl-2-isobutyl-6-methoxypyrazine 1-oxide (Compound E-65).

Colorless needle-like crystals (from Et$_2$O-n-hexane).
Melting point: 105°–106° C.

EXAMPLE E-28

Using the Compound E-66 [the same as the product obtained Example A-49], there were obtained Compounds (E-67a, E-67b, E-67c, E-67d and E-67e by the same manner as in Example A-49.

3-Benzyloxy-2-isobutyl-5-[(1-methyl)indol-3-yl]methyl-6-methoxypyrazine 1-oxide (Compound E-67a).

Colorless needle-like crystals (from AcOEt-n-hexane).
Melting point: 83°–84.5° C.

5-[(1-Benzyl)indol-3-yl]methyl-3-benzyloxy-2-isobutyl-6-methoxypyrazine 1-oxide (Compound E-67b).

Yellow oily substance.

$^1$H-NMR (250 MHz, CDCl$_3$) δ: 0.92 (6H, d, J=6.5 Hz), 2.12–2.31 (1H, m), 2.78 (2H, d, J=7 Hz), 3.88 (3H, s), 4.17 (2H, s), 5.26 (2H, s), 5.35 (2H, s), 6.98 (1H, s), 6.93 (1H, d, J=7 Hz), 7.05–7.13 (3H, m), 7.17 (1H, dt, J=7.5 Hz, 1Hz), 7.23–7.40 (9H, m), 7.76 (1H, d, J=7.5 Hz).

3-Benzyloxy-5-[(1-ethyl)indol-3-yl]methyl-2-isobutyl-6-methoxypyrazine 1-oxide (Compound E-67c).

Yellow oily substance.

$^1$H-NMR (250 MHz, CDCl$_3$)δ: 0.92 (6H, d, J=6.5 Hz), 1.42 (3H, t, J=7.5 Hz), 2.11–2.30 (1H, m), 2.78 (2H, d, J=7 Hz), 3.93 (3H, s), 4.11 (2H, q, J=7.5 Hz), 4.16 (2H, s), 5.38 (2H, s), 6.97 (1H, s), 7.08 (1H, dt, J=7.5 Hz, 1Hz), 7.20 (1H, dt, J=7.5 Hz, 1Hz), 7.30–7.43 (6H, m), 7.75 (1H, d, J=7.5 Hz)

3-Benzyloxy-2-isobutyl-5-[(1-isobutyl)indol-3-yl]methyl-6-methoxypyrazine 1-oxide (Compound E-67d).

Yellow oily substance.

$^1$H-NMR (250 MHz, CDCl$_3$) δ: 0.90 (6H, d, J=6.5 Hz), 0.92 (6H, d, J=6.5 Hz), 2.07–2.30 (2H, m), 2.78 (2H, d, J=7 Hz), 3.84 (2H, d, J=7.5 Hz), 3.93 (3H, s), 4.16 (2H, s), 5.37 (2H, s), 6.94 (1H, s), 7.07 (1H, t, J=7 Hz), 7.18 (1H, J=7 Hz), 7.29 (1H, d, J=7.5 Hz), 7.32–7.43 (5H, m), 7.75 (1H, d, J=7.5 Hz).

5-[(1-Acetyl)indol-3-yl]methyl-3-benzyloxy-2-isobutyl-6-methoxypyrazine 1-oxide (Compound E-67e).

Pale yellow oily substance.

1H-NMR (250 MHz, CDCl$_3$)δ: 0.92 (6H, d, J=6.5 Hz), 2.13–2.31 (1H, m), 2.57 (2H, s), 2.80 (2H, d, J=7 Hz), 4.00 (3H, s), 4.11 (2H, s), 5.31 (2H, s), 7.13–7.33 (7H, m), 7.36 (1H, t, J=7.5 Hz), 7.66 (1H, d, J=7.5 Hz), 8.42 (1H, d, J=7.5 Hz),

REFERENCE EXAMPLE E-29

Using Compounds E-67a, E-67b, E-67c, E-67d and E-67e, there were obtained Compounds E-68a, E-68b, E-68c, E-68d and E-68e were obtained by the same manner as in Reference Example A-23.

3-Isobutyl-6-[(1-methyl)indol-3-yl]methyl-5-methoxy-1,2-dihydropyrazin-2-one 4-oxide (Compound E-68a).

Pale yellow needle-like crystals (from EtOH).
Melting point: 186°–187° C.

6-[(1-Benzyl)indol-3-yl]methyl-3-isobutyl-5-methoxy-1,2-dihydropyrazin-2-one 4-oxide (Compound E-68b).

Colorless needle-like crystals.
1 Melting point: 195°–196° C. (recrystallized from ethanol)

6-[(1-Ethyl)indol-3-yl]methyl-3-isobutyl-5-methoxy-1,2-dihydropyrazin-2-one 4-oxide (Compound E-68c).

Colorless needle-like crystals (recrystallized from ethanol).
Melting point: 165°–166° C.

3-Isobutyl-6-[(1-isobutyl)indol-3-yl]methyl-5-methoxy-1,2-dihydropyrazin-2-one 4-oxide (Compound E-68).

Colorless needle-like crystals (recrystallized from ethanol).
Melting point: 152°–153° C.

6-[(1-Acetyl)indol-3-yl]methyl-3-isobutyl-5-methoxy-1,2-dihydropyrazin-2-one 4-oxide (Compound E-68e).

Pale yellow prism-like crystals (recrystallized from ethanol).
Melting point: 219°–220° C.

1 Compound E-69b is the same as Compound A-35d.

EXAMPLE E-29

(3S,6S)-1-Benzyloxy-3-(indol-3-yl)methyl-6-isobutyl-4-methylpiperazine-2,5-dione (Compound E-70b)

$^1$H-NMR (250 MHz, CDCl$_3$) δ: 0.16–0.31 (1H, m), 0.42–0.50 (1H, m), 0.52 (3H, d, J=6.5 Hz), 0.55 (3H, d, J=6.5 Hz), 1.39–1.60 (1H, m), 3.04 (3H, s), 3.33 (1H, dd, J=15 Hz, 4.5 Hz), 3.56 (1H, dd, J=15 Hz, 4 Hz), 3.70–3.81 (1H, m), 4.27 (1H, t, J=4 Hz), 4.82 (1H, d,

J=10.5 Hz), 4.90 (1H, d, J=10.5 Hz), 6.97 (1H, d, J=2.5 Hz), 7.08–7.13 (2H, m), 7.31–7.45 (6H, m), 7.57 (1H, d, J=7.5 Hz), 8.36 (1H, br., s)

EXAMPLE E-30

(3S,6S)-1-Benzyloxy-6-isobutyl-4-methyl-3-[(1-methyl-)indol-3-yl]methylpiperazine-2,5-dione (Compound E-71b)

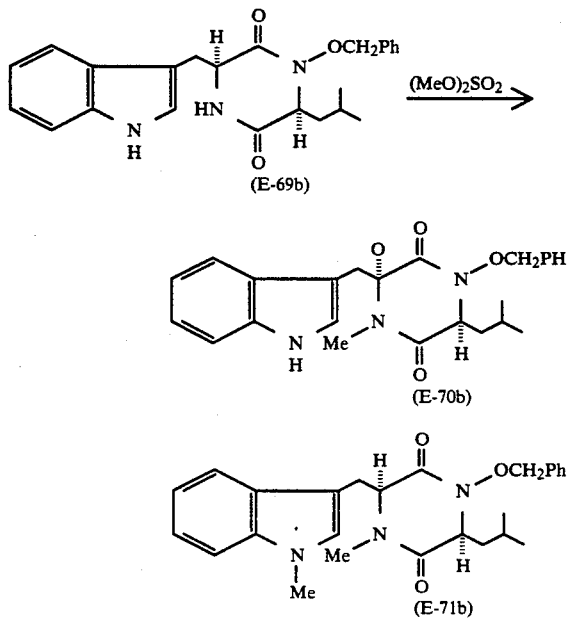

A mixture consisting of 1.18 g (3 mM) of Compound E-69b, 2.4 ml of an aqueous 50% NaOH solution, 15 ml of benzene, 0.05 g of PhCH$_2$(Et)$_3$N$\oplus$Cl$\ominus$ and 0.85 ml (9 mM) of (MeO)$_2$SO$_2$ was stirred at room temperature for 15 hours. The reaction mixture was poured into AcOEt and water, then the AcOEt layer was washed with an aqueous solution saturated with NaCl and dried over anhydrous MgSO$_4$. The solvent was removed by evaporation, and the residue was purified by a silica gel column chromatography (CH$_2$Cl$_2$:MeOH =40:1) to obtain 0.18 g (15%) of Compound E-70b as a brown oily substance and 0.94 g (74%) of Compound E-71b as a brown oily substance.

$^1$H-NMR (250 MHz, CDCl$_3$) δ: 0.14–0.27 (1H, m), 0.37–0.49 (1H, m), 0.51 (3H, d, J=6.5 Hz), 0.55 (3H, d, J=6.5 Hz), 1.39–1.58 (1H, m), 3.04 (3H, s), 3.30 (1H, dd, J=15 Hz, 4.5 Hz), 3.55 (1H, dd, J=15.0 Hz, 4 Hz), 3.68–3.80 (4H, m), 4.24 (1H, t, J=4 Hz), 4.76 (1H, d, J=10.5 Hz), 4.90 (1H, d, J=10.5 Hz), 6.84 (1H, s), 7.07–7.55 (8H, m), 7.56 (1H, d, J=8 Hz).

EXAMPLE E-31

Using Compound E-69a [the same as Compound A-35a] there were obtained Compounds E-70a and E-71a by the same manner as for the Compound E-69b.

(3S,6R)-1-Benzyloxy-3-(indol-3-yl)methyl-6-isobutyl-4-methylpiperazine-2,5-dione (Compound E-70a)

Brown oily substance .

$^1$H-NMR (250 MHz, CDCl$_3$) δ: 0.70 (3H, d, J=6.5 Hz), 0.76 (3H, d, J=6.5 Hz), 1.65–1.72 (3H, m), 3.12 (3H, s), 3.26–3.40 (2H, m), 3.60 (1H, d, J=10.5 Hz), 3.72 (1H, dd, J=15 Hz, 3 Hz), 4.21 (1H, d, J=10.5 Hz), 4.31 (1H, t, J=3 Hz), 6.83–6.95 (3H, m), 7.10–7.26 (5H, m), 7.36 (1H, d, J=9 Hz), 7.74 (1H, d, J=9 Hz), 8.22 (1H, s).

(3S,6R)-1-Benzyloxy-6-isobutyl-4-methyl-3-[(1-methyl)indol-3-yl]methylpiperazine-2,5-dione (Compound E-71a).

Brown oily substance.

$^1$H-NMR (250 MHz, CDCl$_3$) δ: 0.69 (3H, d, J=6.5 Hz), 0.76 (3H, d, J=6.5 Hz), 1.55–1.75 (3H, m), 3.11 (3H, s), 3.21–3.46 (2H,m), 3.63 (1H, d, J=10.5 Hz), 3.69 (1H, dd, J=15 Hz, 3.5 Hz), 3.75 (3H, s), 4.22–4.33 (2H, m), 6.78 (1H, s), 6.80–6.90 (2H, m), 7.10–7.25 (5H, m), 7.26–7.35 (1H, m), 7.21 (1H, dd, J=7 Hz, 1.5 Hz)

REFERENCE EXAMPLE E-30

Using Compounds E-70a, E-70b, E-71a and E-71b, there were obtained Compounds E-72a, E-72b, E-73a and E-73b by the same manner as in Reference Example A-23.

(3S,6R)-1-Hydroxy-3-(indol-3-yl)methyl-6-isobutyl-4-methylpiperazine-2,5-dione (Compound E-72a).

White powdery substance (from diisopropyl ether).

Melting point: 117°–119° C.

$^1$H-NMR (250 MHz, CDCl$_3$) δ: 0.70 (3H, d, J=6.5 Hz), 0.74 (3H, d, J=6.5 Hz), 1.50–1.75 (3H, m), 2.69–2.78 (1H, s), 3.09 (3H, s), 3.31 (1H, d-d, J=15 Hz, 4.5 Hz), 3.59 (1H, d, J=15 Hz), 4.35 (1H, s), 6.90 (1H, s), 7.09–7.25 (2H, m), 7.34 (1H, d, J=7.5 Hz), 7.53 (1H, d, J=7.5 Hz), 7.68 (1H, brs), 8.20 (1H, brs).

(3S,6S)-1-Hydroxy-3-(indol-3-yl)methyl-6-isobutyl-4-methylpiperazine-2,5-dione (Compound E-72b).

White powdery substance.

Melting point: 170.5°–171.5° C.

$^1$H-NMR (250 MHz, CDCl$_3$) δ: 0.12–0.27 (1H, m), 0.27–0.45 (1H, m), 0.56 (3H, d, J=6.5 Hz), 0.61 (3H, d, J=6.5 Hz), 1.35–1.46 (1H, m), 3.09 (3H, s), 3.25–3.40 (1H, m), 3.50–3.64 (1H, m), 4.02 (1H, s), 4.31 (1H, s), 6.97 (1H, s), 7.05–7.42 (3H, m), 7.54 (1H, d, J=7.5 Hz), 8.27 (1H, brs).

(3S,6R)-1-Hydroxy-6-isobutyl-4-methyl-3-[(1-methyl)indol-3-yl]methylpiperazine-2,5-dione (Compound E-73a).

White powdery substance (from diisopropyl ether).

Melting point: 130°–131° C.

$^1$H-NMR (250 MHz, CDCl$_3$) δ: 0.71 (3H, d, J=6.5 Hz), 0.75 (3H, d, J=6.5 Hz), 1.50–1.80 (3H, m), 2.81 (1H, s), 3.08 (3H, s), 3.29 (1H, d-d, J=15.0 Hz, 4.5 Hz), 3.55 (1H, d-d, J=15.0 Hz, 2.5 Hz), 3.73 (3H, s), 4.31 (1H, s), 6.78 (1H, s), ( 7.06–7.40 (3H, m), 7.50 (1H, d, J=8 Hz), 8.10 (1H, brs.

(3S,6S)-1-Hydroxy-6-isobutyl-4-methyl-3-[(1-methyl-)indol-3-yl]methylpiperazine-2,5-dione (Compound E-73b).

White powdery substance.

Melting point: 81°–83° C. .

$^1$H-NMR (250 MHz, CDCl$_3$) δ: 0.14–0.40 (2H, m), 0.57 (3H, d, J=6.5 Hz), 0.61 (3H, d, J=6.5 Hz), 1.39–1.58 (1H, m), 3.08 (3H, s), 3.29 (1H, d-d, J=15.0 Hz, 4.5 Hz), 3.54 (1H, d, J=15.0 Hz), 3.73 (3H, s), 4.01 (1H, t, J=6 Hz), 4.28 (1H, s), 6.81 (1H, s), 7.05–7.35 (4H, m), 7.51 (1H, d, J=8 Hz).

EXAMPLE E-32

Compounds E-77a, E-77b and E-77c were obtained by the same manner as in Example A-41, then by the same manner as in Example A-45.

3-[(1-tert-Butoxycarbonyl)indol-3-yl]methyl-6-isobutyl-2-methoxypyrazine 1-oxide (Compound E-77a).

$^1$H-NMR (250 MHz, CDCl$_3$) δ: 0.94 (6H, d, J=6.5 Hz), 1.65 (9H, s), 2.03-2.20 (1H, m), 2.54 (2H, d, J=7.0 Hz), 3.98 (3H, s), 4.20 (2H, s), 7.2-7.3 (2H, m), 7.43 (1H, s), 7.66 (1H, d, J=7.5 Hz), 7.83 (1H, s), 8.12 (1H, brd, J=7.5 Hz).

3-[(1-tert-Butoxycarbonyl)indol-3-yl]methyl-6-isobutyl-2-methoxy-5-methylpyrazine 1-oxide (Compound E-77b).

$^1$H-NMR (250 MHz, CDCl$_3$) δ: 0.97 (6H, d, J=6.5 Hz), 1.65 (9H, s), 2.17-2.37 (1H, m), 2.52 (3H, s), 2.78 (2H, d, J=7.0 Hz), 3.97 (3H, s), 4.16 (2H, s), 7.2-7.3 (2H, m), 7.45 (1H, s), 7.69 (1H, d, J=7.0 Hz), 8.10 (1H, brd, J=8.5 Hz).

3-[(1-tert-Butoxycarbonyl)-indol-3-yl]methyl-5-isobutyl-2-methoxy-6-methylpyrazine 1-oxide (Compound E-77c).

$^1$H-NMR (250MHz, CDCl$_3$) δ: 0.97 (6H, d, J=6.5 Hz), 1.65 (9H, s), 15 2.06-2.23 (1H, m), 2.44 (3H, s), 2.67 (2H, d, J=7.0 Hz), 3.97 (3H, s), 4.18 (2H, s), 7.2-7.3 (2H, m), 7.42 (1H, s), 7.69 (1H, d, J=7.0 Hz), 8.10 (1H, brd, J=8.0 Hz).

EXAMPLE E-33

Using Compounds E-77a, E-77b and E-77c, there were obtained Compounds E-78a, E-78b and E-78c by the same manner as in Example A-42.

3-(Indol-3-yl)methyl-6-isobutyl-2-methoxypyrazine 1-oxide (Compound E-78a).

Brown powdery substance (from Et$_2$O-disopropyl ether).

Melting point: 126°-130° C.

$^1$H-NMR (250 MHz, CDCl$_3$) δ: 0.95 (6H, d, J=6.5 Hz), 2.02-2.23 (1H, m), 2.53 (2H, d, J=7.0 Hz), 3.90 (3H, s), 4.28 (2H, s), 7.1-7.2 (3H, m), 7.34 (1H, d, J=8.0 Hz), 7.73 (1H, d, J=8.0 Hz), 7.80 (1H, s), 8.10 (1H, brs).

3-(Indol-3-yl)methyl-6-isobutyl-2-methoxy-5-methylpyrazine 1-oxide (Compound E-78b).

Brown powdery substance (from diisopropyl ether-n-hexane).

Melting point: 148° C. (decomposed).

3-(Indol-3-yl)methyl-5-isobutyl-2-methoxy-6-methylpyrazine 1-oxide (Compound E-78c).

Pale brown prism-like crystals (from diisopropyl ether-n-hexane).

Melting point: 107°-108° C.

Pharmacological Test—1

Inhibitory effect against superoxide radicals (O$_2$-) released from the peritoneal macrophage cells of guinea pig by stimulation Mineral oil (15 ml) was intraperitoneally administered to a guinea pig, then 96 hours after the administration, the peritoneal macrophage cells were samples.

Superoxide redicals (O$_2$-) were determined by means of reduction of cytochrome C method according to the procedure described in an article by T. Matsumoto, K. Takeshige and S. Minakami: Biochemical and Biophysical Research Communications, Vol. 88, No. 3, pp. 974-979, (1979).

The peritoneal macrophage cells were added to make the final concentration of 2×10$^6$ cells/ml into 1 ml of 80 μM-cytochome C solution, and the test compound of indole derivative of the present invention was added thereto to make the test group sample. On the other hand, water was added in place of the indole derivative of the present invention to make the control group sample. Each of the test group sample and the control group sample was subjected to pure incubaiton at 37° C. for 1 minute.

As to the stimulating agent for releasing superoxide radicals (O$_2$-), FMLP (formylmethionyl leucyl phenylalanine) was added to make the final concentration thereof to 10$^{-7}$M, to each of the test group sample and the control group sample. Then both samples were subjected to additional reaction by incubation for 1 minute.

Difference of the optical absorbances measured at 550 nm (OD$_{550}$) of both test group and control group samples were determined, and the 50% inhibitory concentration (IC$_{50}$) was obtained by calculating as the ratio of OD$_{550}$ of the test group sample to that of the control group sample. The IC$_{50}$ (×10$^{-5}$ g/ml) values obtained from the test are shown in Table 1 as follows:

TABLE 1

| Test compound No. | IC$_{50}$ (× 10$^{-5}$ g/ml) |
|---|---|
| A-16 | 5.0 |
| A-17 | 1.5 |
| A-29a | 5.0 |
| A-30a | 1.0 |
| A-38 | 0.6 |
| A-46 | 3.0 |
| A-47 | 2.5 |
| A-62 | 1.2 |
| A-63 | 3.0 |
| A-82b | 1.2 |
| E-6d | 0.5 |
| E-6f | 0.4 |
| E-6g | 0.15 |
| E-12 | 0.8 |
| E-30 | 0.8 |
| E-34a | 1.0 |
| E-34c | 0.5 |
| E-34f | 0.7 |
| E-34h | 0.5 |
| E-34j | 1.0 |
| E-34k | 0.2 |
| E-36p | 0.8 |
| E-46a | 0.3 |
| E-57a | 1.0 |
| E-57c | 1.0 |
| E-57d | 1.0 |
| E-58 | 0.6 |
| E-67a | 1.0 |
| E-72a | 0.08 |
| E-73a | 0.2 |

PHARMACOLOGICAL TEST—2

Inhibitory effect against the releasing of lysosome from the neutrocytes of rat

The neutrocytes of rat were samples from the abdominal cavity of the reat 16 hours after the administration of 10 ml of 1%-casein solution (physiological saline solution).

Reaction of the releasing of lysosome from the neutrocytes of rat was determined by means of the method described in an article by T. Matsumoto, K. Takeshige and S. Minakami: Biochemical and Biophysical Research Communications, Vol. 88, No. 3, pp. 974-979, (1979).

The neutrocytes being sampled were added to Hank's soluiton so as to make the concentraiton thereof as 5×10$^5$ cells/ml, and the test compound of indole derivative of the present invention was added thereto to make the test group sample. On the other hand, water was added in place of the indole derivative of the present invention to make the control group sample. Each of the test group sample and the control group sample was subjected to pre-incubation at 37° C. for 1 minute.

As to the stimulating agents, $10^{-6}$M of FMLP (formylmethionyl leucyl phenylalanine) and 5 μg/ml of cytochalasin B were added to the solution. Thus, obtained mixture of the solution was reacted by incubating for 15 minutes. After the incubation, the mixture of the solution was subjected to centrifugation at 2,000 rpm for 10 minutes. The supernatant (0.2 ml) was admixed with 0.5 ml of 0.1M-acetic acid buffer solution (pH 4.5) in which 0.2 mM of phenolphthalein glucuronic acid was dissolved. Then the resulting mixture of the solutions was reacted at 37° C. for 5 hours by incubation. After the reaction, 1N-NaOH solution was added to the reaction mixture so as to make the pH thereof to pH 8-9, and the optical absorbance of both test group samples and control group samples were determined at 550 nm ($OD_{550}$).

The 50% inhibitory concentration ($IC_{50}$) values were obtained by calculating as the ratio of $OD_{550}$ of the test group samples to that of the control group samples. The $IC_{50}$ ($\times 10^{-5}$ g/ml) values obtained from the test are shown in Table 2 as follows:

TABLE 2

| Test compound No. | $IC_{50}$ ($\times 10^{-5}$ g/ml) |
|---|---|
| A-6a | 3.0 |
| A-6b | 3.0 |
| A-5b | 2.5 |
| A-4b | 3.0 |
| A-4a | 3.5 |
| A-29c | 5.0 |
| A-23 | 5.0 |
| A-27 | 2.5 |
| A-26 | 1.0 |
| A-35d | 5.0 |
| A-20 | 2.0 |
| A-19 | 2.5 |
| A-34 | 5.0 |
| A-48 | 5.0 |
| A-45 | .2.0 |
| A-59 | 2.0 |
| A-60 | 2.0 |
| A-82a | 2.0 |
| A-84 | 5.0 |
| A-53 | 4.3 |
| E-34g | 0.8 |
| E-34 | 1.4 |
| E-36o | 1.2 |
| E-39 | 5.0 |
| E-65 | 0.9 |

EXAMPLE OF PHARMACEUTICAL PREPARATION

A pharmaceutical composition containing an indole derivative of the present invention as the active ingredient was prepared with the following formulation.

| | |
|---|---|
| Compound A-4a of the present invention | 150.0 g |
| Citric acid | 1.0 g |
| Lactose | 33.5 g |
| Dicalcium phosphate | 70.0 g |
| Pluronic F-68 (Trademark for a polyoxyalkylene glycol, manufactured by BASF-Wyandott Corp., N.J. U.S.A.) | 30.0 g |
| Sodium laurylsulfate | 15.0 g |
| Polyvinylpyrrolidone | 15.0 g |
| Carbowax 1500 (Trademark for a polyethylene glycol manufactured by Union Carbide Corp., N.Y., U.S.A.) | 4.5 g |
| Carbowax 6000 (Trademark for a polyethylene glycol manufacture by Union Carbide Corp., N.Y., U.S.A.) | 45.0 g |
| Corn starch | 30.0 g |
| Dried sodium laurylsulfate | 3.0 g |
| Dried magnesium stearate | 3.0 g |
| Ethanol | q.s. |

Compound A-4a of the present invention, citric acid, lactose, dicalcium phsphate, Pluronic F-68 and sodium laurylsulfate were admixed together thoroughly to obtain a mixture. The mixture thus obtained was sieved through a screen of No. 60, then such sieved powder of the mixture was subjected to wet-granulation with an ethanolic solution containing polyvinylpurrolidone, Carbowax 1500 and Carbowax 6000. The powder of mixture was shaped into a paste-like lump by adding an adequate amount of ethanol, if necessary. Corn starch was added to this lump and well kneaded to form the lump into granules having uniform particle size. The granules thus obtained were sieved through a screen of No. 10, then the sieved granules were placed on a tray and dried in an oven at 100° C. for 12-14 hours. The dried granules were sieved through a screen of No. 16, and were added thereto dried sodium laurylsulfate and dried magnesium stearate, then the whole mixture was mixed well and was compressed into the desired form by using a tablet machine to obtain tablets to be used for the core portions of coated tablets. The cored portions were treated with a varnish, and further the treated surface thereof were coated with talc for preventing the surface from the adsorption of moisture. The treated surface of core portions were further coated with a primary coating layer, and further coated with a varnish to make a sufficient number of layers for preventing coated tablets for oral administration. In order to make the coated core portions of tablets into complete spherical form and to make the treated surface smoothly, the coated tablets were further coated with primary coating layers and smoothing the coating layers. The coated tablets were color coated until the desired color of the surface was obtained. After the coated tablets were dried, the surface thereof were polished to make them uniform gloss.

What is claimed is:

1. Indole compounds or pharmaceutically acceptable salts thereof of the formula:

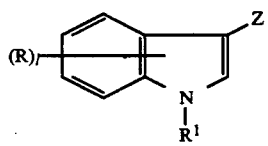

wherein R is a hydrogen atom, a cyano group, a phenyl-lower alkoxy group, a carboxy group, a phenyl group, a lower alkoxycarbonyl group, a lower alkyl group, a lower alkoxy group, a hydroxy group or a halogen atom;

l is an integer of 1 to 2;

$R^1$ is a hydrogen atom, a lower alkyl group, a phenyl-lower alkyl group, a lower alkanoyl group, a lower alkoxycarbonyl group, a phenyl-lower alkoxycarbonyl group, a carboxy group, a benzoyl group, a phenylsulfonyl group, which may have lower alkyl group as substituents on the phenyl ring, or a ring group of the formula

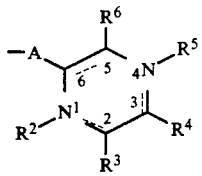

wherein A is a single bond, a group of the formula

a group of the formula —CH=, a group of the formula

or a lower alkylene group; $R^2$ is a hydrogen atom, a lower alkyl group, a hydroxyl group or a lower alkoxy group; $R^3$ is a hydrogen atom; an oxo group; a halogen atom; a lower alkoxy group; a lower alkanoyloxy group; a lower alkyl group; a silyloxy group having 1 to 3 substituents selected from the group consisting of a benzoyloxy group, a lower alkoxycarbonyloxy group, a lower alkyl group and a phenyl group; a phenyl-lower alkoxy group which may have, on the phenyl ring, substituents selected from the group consisting of a halogen atom, a lower alkyl group, a nitro group, an amino group and a lower alkoxy group; or a hydroxyl group; $R^4$ is a hydrogen atom; a lower alkyl group; a phenyl group; a phenyl-lower alkyl group which may have, on the phenyl ring, substituents selected from the group consisting of a hydroxyl group and a phenyl-lower alkoxy group; a cycloalkyl group; a cycloalkyl-lower group; an indolyl-lower alkyl group or a lower alkenylene group; $R^5$ is a hydrogen atom; an oxide group; a hydroxyl group; a phenyl-lower alkoxy group; a lower alkoxy group or a lower alkyl group; $R^6$ is a lower alkoxy group; an oxo group; a hydrogen atom; a hydroxyl group; a halogen atom; a lower alkyl group; an amino group which may have a lower alkanoyl group as a substituent; a lower alkylthio group; a lower alkylsulfinyl group; a lower alkylsulfonyl group; a cycloalkyloxy group; or a phenyl-lower alkoxy group; the bondings between the 1 and 2, 2 and 3, 3 and 4, 4 and 5, 5 and 6, and 6 and 1 positions of the ring group being single bonds or double bonds with a maximum of 3 double bonds; and Z is a hydrogen atom or a ring group of the formula

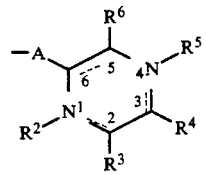

wherein A, $R^2$, $R^3$, $R^4$, $R^5$ and $R^6$ are the same as defined above and the bondings between the 1 and 2, 2 and 3, 3 and 4, 4 and 5, 5 and 6, and 6 and 1 positions in the ring group are single bonds or double bonds with a maximum of 3 double bonds, provided that:

(i) when Z is a ring group, A is a lower alkylene group and $R^3$ and $R^6$ are each an oxo group and the bond between the 4 and 5 positions is a single bond, then each of $R^2$ and $R^5$ should not be a hydrogen atom or a lower alkyl group;

(ii) when Z is a ring group, A is a methylene group, R, $R^1$ and $R^2$ are each a hydrogen atom, $R^3$ is an oxo group, $R^5$ is an oxide group and $R^6$ is a methoxy group, then $R^4$ should not be an isobutyl group;

(iii) when Z is a hydrogen atom, then $R^1$ is a ring group;

(iv) when $R^1$ is a hydrogen atom or a methyl group; l is 1; R is an isopropyl group which is bonded at the 8-position of the indole skeleton; Z is a ring group; $R^6$ is a methoxy group; $R^4$ is a methyl group; $R^3$ is a methoxy group or an acetyloxy group; and A is a methylene group; then none of the bondings between the 1 and 2, 2 and 3, 3 and 4, 4 and 5, 5 and 6, and 6 and 1 positions of the ring group of Z should be double bonds;

(v) when $R^1$ is a hydrogen atom; l is 1; R is an isopentyl group which is bonded at the 8-position of the indole skeleton; Z is a ring group; $R^2$ is a hydrogen atom, $R^6$ is a methoxy group; $R^4$ is a methyl group; $R^3$ is an oxo group; A is a methylene group; and the bondings between the 3 and 4 positions and between the 5 and 6 positions of th ring group of Z are both double bonds or only the bonding between the 4 and 5 positions of the ring group of Z is a double bond, then $R^5$ should be an oxide group;

(vi) when $R^1$ is a hydrogen atom; l is 1; R is an isopentyl group which is bonded at the 8-position of the indole skeleton; Z is a ring group, $R^4$ is a methyl group; $R^3$ is an oxo group; $R^2$, $R^5$ and $R^6$ are each a hydrogen atom; and A is a methylene group; then the bonding between the 5 and 6 positions of the ring group of Z should not be a single bond;

(vii) when $R^1$ is a lower alkoxycarbonyl group; R is a hydrogen atom; Z is a ring group; $R^3$ and $R^6$ are each a methoxy group; $R^4$ is an isopropyl group; and A is a methylene group; then the bondings between the 1 and 2 and between the 4 and 5 positions of the ring group of Z should not be double bonds;

(vii) when $R^1$ is a hydrogen atom or a lower alkyl group; R is a hydrogen atom, a lower alkyl group or a phenyl group; Z is a ring group; $R^2$ and $R^5$ are each a hydrogen atom or a lower alkyl group; $R^3$ and $R^6$ are oxo groups, $R^4$ is a lower alkyl group or an indolyl-lower alkyl group; then A should not be a lower alkylene group; and (ix) when $R^1$ and R are each a hydrogen atom; Z is a ring group; $R^2$ is a methyl group; $R^3$ and $R^6$ are oxo groups; $R^4$ is a propylene group; and $R^5$ is a hydrogen atom; A should not be a methylene group.

2. The indole compounds of claim 1, wherein Z is a hydrogen atom and $R^1$ is a ring group.

3. The indole compounds of claim 2, wherein $R^2$ is a hydrogen atom; $R^3$ is an oxo group or a halogen atom; $R^4$ is a lower alkyl group; $R^5$ is an oxide group or a hydroxy group; $R^6$ is an oxo group, a hydroxy group, a lower alkoxy group or a lower alkyl group.

4. The indole compounds of claim 3, wherein $R^3$ is an oxo group, $R^5$ is an oxide group; and $R^6$ is a lower alkoxy group.

5. The indole compounds of claim 4, wherein R is a hydrogenn atom.

6. The indole compounds of claim 4, wherein R is a cyano group, a phenyl-lower alkoxy group, a carboxy group, a phenyl group, a lower alkoxycarbonyl group, a lower alkyl group, a lower alkoxy group, a hydroxy group or a halogen atom.

7. The indole compounds of claim 1, wherein Z is a ring group.

8. The indole compounds of claim 7, wherein A in the ring group of Z is a lower alkylene group.

9. The indole compounds of claim 7, wherein A in the ring group of Z is a group of the formula —CH=.

10. The indole compounds of claim 7, wherein A in the ring group of Z is a single bond, a group of the formula

or a group of the formula

11. The indole compounds of claim 10, wherein in the ring group of Z, $R^2$ is a hydrogen atom; $R^3$ is an oxo group or a halogen atom; $R^4$ is a lower alkyl group; $R^5$ is an oxide group or a hydrogen atom; and $R^6$ is an oxo group, a hydroxy group, a lower alkyl group or a lower alkoxy group.

12. The indole compounds of claim 8, wherein $R^2$ in the ring group of Z is a hydrogen atom.

13. The indole compounds of claim 8, wherein $R^2$ in the ring group of Z is a lower alkyl group, a hydroxyl group or a lower alkoxy group.

14. The indole compounds of claim 11, wherein R is a hydrogen atom, a lower alkyl group or a halogen atom.

15. The indole compounds of claim 11, wherein R is a cyano group, a phenyl-lower alkoxy group, a carboxy group, a phenyl group, a lower alkoxycarbonyl group, a lower alkoxy group or a hydroxy group.

16. The indole compounds of claim 12, wherein $R^3$ in the ring group of Z is an oxo group or a halogen atom.

17. The indole compounds of claim 12, wherein $R^3$ in the ring group of Z is a hydrogen atom; a lower alkoxy group; a lower alkanoxyloxy group; a lower alkyl group; a silyloxy group having 1 to 3 substituents selected from the group consisting of a benzoyloxy group, a lower alkoxycarbonyloxy group; a lower alkyl group and a phenyl group; a phenyl-lower alkoxy group; which may have, on the phenyl ring, substituents selected from the group consisting of a halogen atom, a lower alkyl group, a nitro group, an amino group and a lower alkoxy group; or a hydroxyl group.

18. The indole compounds of claim 13, wherein $R^3$ in the ring group of Z is an oxo group or a halogen atom.

19. The indole compounds of claim 13, wherein $R^3$ in the ring group of Z is a hydrogen atom; a lower alkoxy group, a lower alkanoyloxy group, a lower alkanoyloxy group, a lower alkyl group; a silyloxy group having 1 to 3 substituents selected from the group consisting of a benzoyloxy group, a lower alkoxycarbonyloxy group, a lower alkyl group and a phenyl group; a phenyl-lower alkoxy group; phenyl-lower alkoxy group which may have, on the phenyl ring, substituents selected from the group consisting of a halogen atom, a lower alkyl group, a nitro group, an amino group and a lower alkoxy group; or a hydroxyl group.

20. The indole compounds of claim 14, wherein $R^1$ is a hydrogen atom.

21. The indole compounds of claim 14, wherein $R^1$ is a lower alkyl group; a phenyl-lower alkyl group; a lower alkanoyl group; a lower alkoxycarbonyl group; a phenyl-lower alkoxycarbonyl group; a carboxy group; a benzoyl group or a phenylsulfonyl group which may have lower alkyl groups as substituents on the phenyl ring.

22. The indole compounds of claim 16, wherein $R^4$ in the ring group of Z is a lower alkyl group.

23. The indole compounds of claim 16, wherein $R^4$ in the ring group of Z is a hydrogen atom; a phenyl group; a phenyl-lower alkyl group which may have, on the phenyl ring, substituents, selected from the group consisting of a hydroxy group and a phenyl-lower alkoxy group; a cycloalkyl group; a cycloalkyl-lower alkyl group, an indolyl-lower alkyl group; or a lower alkenylene group.

24. The indole compounds of claim 18, wherein $R^4$ in the ring group of Z is a lower alkyl group; $R^5$ is an oxide group or a hydroxyl group; and $R^6$ is an oxo group, a hydroxyl group, a lower alkoxy group or a lower alkyl group.

25. The indole compounds of claim 23, wherein $R^5$ in the ring group Z is an oxide group or a hydroxyl group.

26. The indole compounds of claim 22, wherein $R^5$ in the ring group of Z is a hydrogen atom, a phenyl-lower alkoxy group, a lower alkoxy group or a lower alkyl group.

27. The indole compounds of claim 25, wherein $R^6$ in the ring group of Z is an oxo group, a hydroxy group, a lower alkoxy group or a lower alkyl group.

28. The indole compounds of claim 25, wherein $R^6$ in the ring group of Z is a hydrogen atom; a halogen atom; an amino group, which may have a lower alkanoyl group as a substituent; a lower alkylthio group, a lower alkylsulfinyl group; a lower alkylsulfonyl group; a cycloalkyloxy group; or a phenyl-lower alkoxy group.

29. The indole compounds of claim 27, wherein R is a hydrogen atom, a lower alkyl group or a halogen atom.

30. The indole compounds claim 27, wherein R is a cyano group, a phenyl-lower alkoxy group, a carboxy group, a phenyl group, a lower alkoxycarbonyl group, a lower alkoxy group or a hydroxy group.

31. The indole compounds of claim 27 or claim 30, wherein $R^1$ is a hydrogen atom.

32. The indole compounds of claim 27 or claim 30, wherein $R^1$ is a lower alkyl group, a phenyl-lower alkyl group, a lower alkanoyl group, a lower alkoxycarbonyl group, a phenyl-lower alkoxycarbonyl group, a carboxy group, a benzoyl group, or a phenylsulfinyl group which may have lower alkyl groups as substituents on the phenyl ring.

33. The indole compounds of claim 7, wherein the bonding between the 1- and 2-positions in the ring group of Z is a single bond, and the bondings between 3- and 4-positions, and the 5- and 6-positions in the ring group of Z are double bonds.

34. The indole compounds of claim 7, wherein the bondings between the 1- and 2-positions, 3- and 4-positions, and 5- and 6-positions in the ring group of Z are double bonds.

35. The indole compound of claim 7, wherein the bondings between the 1- and 2-positions, 3- and 4-positions, and 5- and 6-positions in the ring group of Z are single bonds.

36. The indole compounds of claim 33, wherein $R^2$ in the ring group of Z is a hydrogen atom; $R^3$ is an oxo group or a halogen atom; $R^4$ is a lower alkyl group; $R^5$ is an oxide group or a hydroxy group; and $R^6$ is a hydrogen group, a lower alkoxy group or a lower alkyl group.

37. The indole compounds of claim 34, wherein $R^3$ in the ring group of Z is a halogen atom; $R^4$ is a lower alkyl group; $R^5$ is an oxide group or a hydroxyl group and $R^6$ is a hydroxyl group, a lower alkoxy group or a lower alkyl group.

38. The indole compounds of claim 35, wherein $R^2$ in the ring group of Z is a hydrogen atom; $R^3$ is an oxo group or a halogen atom; $R^4$ is a lower alkyl group; $R^5$ is an oxide group or a hydroxyl group; and $R^6$ is an oxo group, a hydroxyl group, a lower alkoxy group or a lower alkyl group.

39. The indole compounds of claim 33, wherein $R^2$ in the ring group of Z is a hydrogen atom; $R^3$ is an oxo group or a halogen atom; $R^4$ is a lower alkyl group; $R^5$ is an oxide group; and $R^6$ is a hydroxyl group, a lower alkoxy group or a lower alkyl group.

40. The indole compounds of claim 35, wherein $R^5$ in the ring group of Z is a hydroxyl group, a phenyl-lower alkoxy group or a lower alkoxy group.

41. The indole compounds of claim 1, wherein $R^1$ is a hydrogen atom, a lower alkyl group, a lower alkoxycarbonyl group, or a ring group and wherein Z is a ring group and in the ring group of Z, A is a single bond, a group of the formula —CH=, a group of the formula

or a lower alkylene group; $R^2$ is a hydrogen atom or a lower alkyl group; $R^3$ is a hydrogen atom, an oxo group, a halogen atom, a lower alkoxy group, a lower alkanoyloxy group, a lower alkyl group, a phenyl-lower alkoxy group which may have, on the phenyl ring, substituents selected from the group consisting of a halogen atom, a lower alkyl group, a nitro group, an amino group and a lower alkoxy group; or a hydroxyl group; and $R^5$ is a hydrogen atom, an oxide group, a hydroxyl group, a phenyl-lower alkoxy group or a lower alkoxy group.

42. The indole compounds of claim 41, wherein in the ring group of Z, A is a single bond, a group of the formula —CH=, or a lower alkylene group.

43. An agent fro preventing and treating nephritis, which comprises, as the active ingredient, an effective amount of an indole compound of claim 1 and a pharmaceutically acceptable carrier.

44. (3S, 6R)-1-Hydroxy-3-(indole-3-yl)methyl-6-isobutylpiperazine-2,5-dione.

45. 6-(Indol-3-yl)methyl-3-isobutyl-5-ethyl-1,2-dihydropyrazin-2-one 4-oxide.

46. 6-(5-Chloroindol-3-yl)methyl-3-isobutyl-5-methoxy- 1,2-dihydropyrazin-2-one 4-oxide.

47. 6-(5-Methylindol-3-yl)methyl-3-isobutyl-5-methoxy-1,2-dihydropyrazin-2-one 4-oxide.

48. 2-Chloro-6-(indol-3-yl)methyl-3-isobutyl-5-hydroxypyrazine 4-oxide.

49. 6-(Indol-1-yl)methyl-3-isobutyl-5-methoxy-1,2-dihydropyrazin-2-one 4-oxide.

50. 6-(Indol-3-yl)methyl-3-isobutyl-5-ethoxy-1,2-dihydropyrazin-2-one 4-oxide.

51. 6-(Indol-3-yl)methyl-3-sec-butyl-5-methoxy-1,2-dihydropyrazin-2-one 4-oxide.

* * * * *

UNITED STATES PATENT AND TRADEMARK OFFICE
CERTIFICATE OF CORRECTION

PATENT NO. : 5,238,938
DATED : August 24, 1993
INVENTOR(S) : Hitoshi Tone et al..

It is certified that error appears in the above-indentified patent and that said Letters Patent is hereby corrected as shown below:

Claim 1, column 182, line 63, change "1" (first occurrence) to --$l$--;

Claim 1, column 183, line 49, after "cycloalkyl-lower" insert --alkyl--;

Claim 1, column 184, line 29, change "1 is 1" to --$l$ is 1--;

Claim 1, column 184, line 37, change "1 is 1" to --$l$ is 1--; and

Claim 1, column 184, line 47, change "1 is 1" to --$l$ is 1--.

UNITED STATES PATENT AND TRADEMARK OFFICE
CERTIFICATE OF CORRECTION

PATENT NO. : 5,238,938
DATED : August 24, 1993
INVENTOR(S) : Hitoshi Tone, et al It is certified that error appears in the above-indentified patent and that said Letters Patent is hereby corrected as shown below:

Claim 25, column 186, line 42, change "claim 23" to --claim 22--.
Claim 36, column 187, line 22, change "hydroxy" to --hydroxyl--.

Signed and Sealed this

Twenty-seventh Day of September, 1994

Attest:

BRUCE LEHMAN

Attesting Officer　　Commissioner of Patents and Trademarks